(12) United States Patent
Kato et al.

(10) Patent No.: US 10,756,275 B2
(45) Date of Patent: Aug. 25, 2020

(54) COMPOUND, MATERIAL FOR ORGANIC ELECTROLUMINESCENCE DEVICES, ORGANIC ELECTROLUMINESCENCE DEVICE, AND ELECTRONIC EQUIPMENT

(71) Applicant: IDEMITSU KOSAN CO., LTD., Chiyoda-ku (JP)

(72) Inventors: Tomoki Kato, Ichihara (JP); Nobuhiro Yabunouchi, Sodegaura (JP); Masakazu Funahashi, Chiba (JP); Takahiro Fujiyama, Kisarazu (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 140 days.

(21) Appl. No.: 14/910,596

(22) PCT Filed: Jul. 13, 2015

(86) PCT No.: PCT/JP2015/070044
§ 371 (c)(1),
(2) Date: Feb. 5, 2016

(87) PCT Pub. No.: WO2016/006708
PCT Pub. Date: Jan. 14, 2016

(65) Prior Publication Data
US 2016/0197277 A1    Jul. 7, 2016

(30) Foreign Application Priority Data

Jul. 11, 2014   (JP) .................. 2014-143244

(51) Int. Cl.
*H01L 51/00* (2006.01)
*C07D 333/76* (2006.01)
(Continued)

(52) U.S. Cl.
CPC .......... *H01L 51/006* (2013.01); *C07C 211/61* (2013.01); *C07D 209/86* (2013.01);
(Continued)

(58) Field of Classification Search
CPC ..... H01L 51/006–0062; H01L 51/0071–0074; H01L 51/50;
(Continued)

(56) References Cited

U.S. PATENT DOCUMENTS

2007/0278938 A1   12/2007 Yabunouchi et al.
2010/0033081 A1    2/2010 Yamada et al.
(Continued)

FOREIGN PATENT DOCUMENTS

CN   101878241 A   11/2010
CN   103755574 A    4/2014
(Continued)

OTHER PUBLICATIONS

International Search Report dated Oct. 6, 2015, in PCT/JP2015/070044 filed Jul. 13, 2015.
(Continued)

*Primary Examiner* — Ruiyun Zhang
(74) *Attorney, Agent, or Firm* — Oblon, McClelland, Maier & Neustadt, L.L.P.

(57) ABSTRACT

A compound represented by formula (1) is useful as a material for organic EL devices which realizes an organic EL device exhibiting high emission efficiency even when driving at a low voltage and has a long lifetime:

(Continued)

(1)

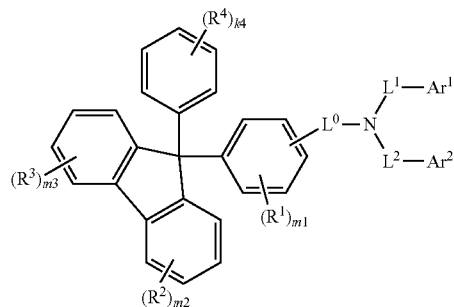

wherein $R^1$ to $R^4$, $L^0$ to $L^2$, $Ar^1$ to $Ar^2$, m1 to m3, and k4 are as defined in the description.

16 Claims, 1 Drawing Sheet

(51) Int. Cl.
| | |
|---|---|
| *C07C 211/61* | (2006.01) |
| *C07D 405/12* | (2006.01) |
| *C07D 307/91* | (2006.01) |
| *C09K 11/06* | (2006.01) |
| *H01L 51/50* | (2006.01) |
| *C07D 209/86* | (2006.01) |

(52) U.S. Cl.
CPC ......... *C07D 307/91* (2013.01); *C07D 333/76* (2013.01); *C07D 405/12* (2013.01); *C09K 11/06* (2013.01); *H01L 51/0061* (2013.01); *H01L 51/50* (2013.01); *C07C 2603/18* (2017.05); *H01L 51/0052* (2013.01); *H01L 51/0058* (2013.01); *H01L 51/0072* (2013.01); *H01L 51/0073* (2013.01); *H01L 51/0074* (2013.01); *H01L 51/5056* (2013.01); *H01L 51/5088* (2013.01)

(58) Field of Classification Search
CPC ............... H01L 51/5056; C07C 211/61; C07C 2503/18; C09K 11/06; C07D 209/86; C07D 307/91; C07D 33/76; C07D 405/12
USPC .................. 428/690, 917; 257/40, E51.027, 257/E51.032; 564/308
See application file for complete search history.

(56) References Cited

U.S. PATENT DOCUMENTS

| | | |
|---|---|---|
| 2010/0230666 A1 | 9/2010 | Ohuchi et al. |
| 2010/0301744 A1 | 12/2010 | Osaka et al. |
| 2012/0146014 A1 | 6/2012 | Kato |
| 2013/0105771 A1 | 5/2013 | Ryu et al. |
| 2014/0042411 A1 | 2/2014 | Fukuzaki et al. |
| 2014/0191214 A1 | 7/2014 | Kim |
| 2015/0280136 A1* | 10/2015 | Ryu ............... C09K 11/06 257/40 |
| 2016/0372666 A1 | 12/2016 | Ryu et al. |

FOREIGN PATENT DOCUMENTS

| | | |
|---|---|---|
| CN | 104086447 A | 10/2014 |
| CN | 106164061 A | 11/2016 |
| EP | 2 216 356 A1 | 8/2010 |
| JP | 11-144875 A | 5/1999 |
| JP | 2003-261472 A | 9/2003 |
| JP | 2005-85599 A | 3/2005 |
| JP | 2005-120030 A | 5/2005 |
| JP | 2005120030 A * | 5/2005 |
| JP | 3983215 B2 | 9/2007 |
| JP | 2009-149850 A | 7/2009 |
| JP | 2011-6405 A | 1/2011 |
| KR | 10-2011-0029831 A | 3/2011 |
| KR | 1389527 | 4/2014 |
| WO | 2010/137601 A1 | 12/2010 |
| WO | 2011/021520 A1 | 2/2011 |
| WO | 2013/087142 A1 | 6/2013 |
| WO | 2014/015935 A2 | 1/2014 |
| WO | 2014/034795 A1 | 3/2014 |
| WO | WO-2014104514 A1 * | 7/2014 ............. C09K 11/06 |
| WO | WO 2015/174640 A1 | 11/2015 |

OTHER PUBLICATIONS

Extended European Search Report dated Dec. 20, 2016 in Patent Application No. 15819775.6.
Office Action dated Nov. 7, 2018 in European Patent Application No. 15 819 775.6 filed Jul. 13, 2015.
Office Action dated Apr. 26, 2018 in connection with Chinese Patent Application No. 201580001553.1.
Japanese Office Action dated Jan. 29, 2019 in Patent Application No. 2015-560882 (with English translation), 7 pages.
Chinese Office Action dated Feb. 26, 2019 in Chinese Patent Application No. 201580001553.1, 6 pages.
Office Action (Notice of Reasons for Refusal) dated Aug. 27, 2019 in Japanese Patent Application No. 2015-560882 with machine English translation.
Office Action dated Apr. 28, 2020 in EPC Application No. 15819775.6.
Office Action dated Jun. 17, 2020 in Chinese Application No. 201580001553.1 (w/ English translation).

* cited by examiner

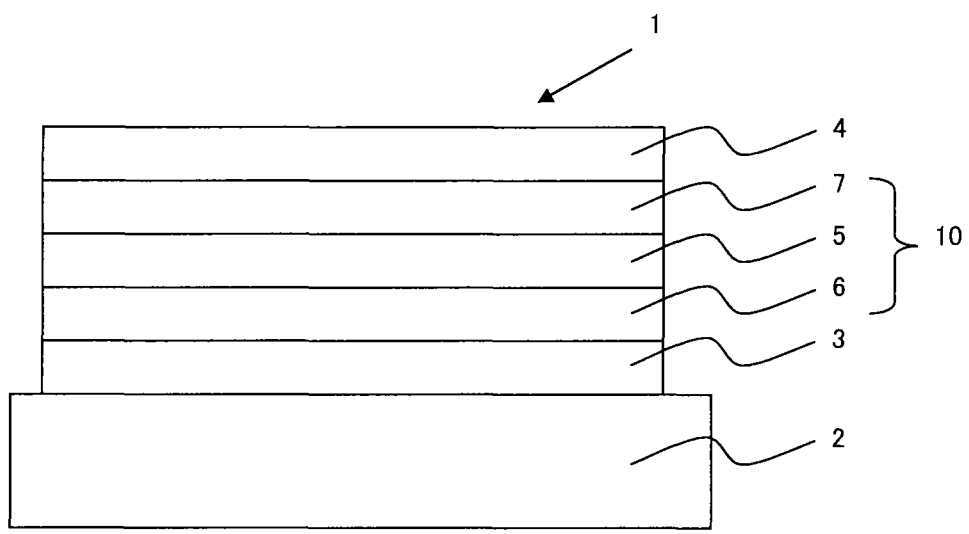

COMPOUND, MATERIAL FOR ORGANIC ELECTROLUMINESCENCE DEVICES, ORGANIC ELECTROLUMINESCENCE DEVICE, AND ELECTRONIC EQUIPMENT

TECHNICAL FIELD

The present invention relates to compounds, materials for organic electroluminescence devices comprising the compounds, organic electroluminescence devices comprising the compounds, and electronic equipment comprising the organic electroluminescence devices.

BACKGROUND ART

An organic electroluminescence device (also referred to as "organic EL device") is generally composed of an anode, a cathode, and one or more organic thin film layers which comprise a light emitting layer and are sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light. Therefore, it is important for increasing the efficiency of an organic EL device to develop a compound which transports electrons or holes into a light emitting zone efficiently and facilitates the recombination of electrons and holes.

The lower voltage drive of an organic EL device is effective for reducing the power consumption and also effective for improving the emission efficiency and the device lifetime. To reduce the driving voltage, a charge transporting material having a high mobility to electrons and/or holes is required, and many proposals have been made on such a charge transporting material.

CITATION LIST

Patent Literature

Patent Literature 1: WO 2010/137601
Patent Literature 2: JP 3983215B
Patent Literature 3: WO 2011/021520

SUMMARY OF INVENTION

Technical Problem

An object of the present invention is to provide an organic EL device which exhibits high emission efficiency even when driving at a lower voltage and has a long lifetime and also provide a material for organic EL devices which realizes such an organic EL device.

Solution to Problem

As a result of extensive research in view of achieving the above object, the inventors have found that a compound represented by formula (1) has a high hole mobility, and further found that an organic EL device which is capable of driving at a lower voltage and has high emission efficiency and a long lifetime is obtained by using the compound.

In an aspect of the invention, the following (1) to (4) are provided:
(1) a compound represented by formula (1):

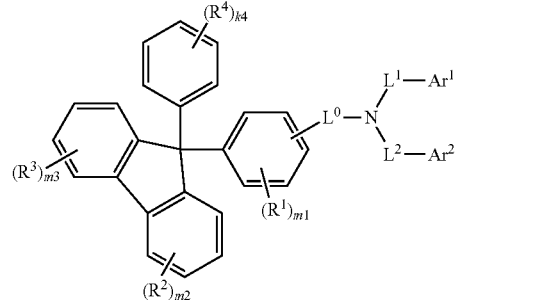

wherein $R^1$ to $R^4$ each independently represent a substituted or unsubstituted alkyl group having 1 to 20 carbon atoms, a substituted or unsubstituted aryl group having 6 to 50 ring carbon atoms, a substituted or unsubstituted heteroaryl group having 5 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group, and when $R_1$ to $R^4$ each are plurality in number, groups $R^1$ to groups $R^4$ may be the same or different, respectively;

m1 to m3 each independently represent an integer of 0 to 4, and k4 represents an integer of 0 to 5;

$L^0$ to $L^2$ each independently represent a single bond, a substituted or unsubstituted arylene group having 6 to 50 ring carbon atoms, or a substituted or unsubstituted heteroarylene group having 5 to 50 ring atoms;

$Ar^1$ represents a monovalent residue of a compound represented by formula (2):

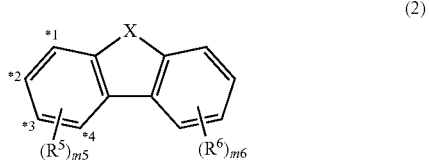

wherein X represents $-C(R^A)(R^B)-$, $-O-$, $-S-$, or $-NH-$;

$R^A$ and $R^B$ may be the same or different and each independently represent a substituted or unsubstituted aryl group having 6 to 50 ring carbon atoms or a substituted or unsubstituted heteroaryl group having 5 to 50 ring atoms;

$R^5$ and $R^6$ are each independently the same as defined with respect to $R^1$;

m5 and m6 each independently represent an integer of 0 to 4;

two selected from $R^5$ and $R^6$ may be bonded to each other to form a ring structure;

when X in formula (2) is $-C(R^A)(R^B)-$, $-O-$, or $-S-$, the hydrogen atom or $R^5$ attached to one of carbon atoms *1 to *4 is eliminated and a remaining carbon atom is bonded to $L^1$ or the nitrogen atom in formula (1);

when X in formula (2) is $-NH-$, the hydrogen atom of $-NH-$ is eliminated and a remaining nitrogen atom is bonded to $L^1$ or the nitrogen atom in formula (1); and $Ar^2$ represents a substituted or unsubstituted aryl group having 6 to 50 ring carbon atoms or a substituted or unsubstituted heteroaryl group having 5 to 40 ring atoms;
(2) a material for organic electroluminescence devices comprising the compound according to (1);
(3) an organic electroluminescence device which comprises a cathode, an anode, and at least one organic thin film layer disposed between the cathode and the anode, wherein the at least one organic thin film layer comprises a light emitting layer and at least one layer of the at least one organic thin film layer comprises the compound according to (1); and
(4) an electronic equipment comprising the organic electroluminescence device according to (3).

Advantageous Effects of Invention

An organic EL device which exhibits high emission efficiency even when driving at a lower voltage and has a long lifetime is obtained by using the compound represented by formula (1) as the material for organic EL devices.

BRIEF DESCRIPTION OF DRAWINGS

FIG. 1 is a schematic illustration of the structure of an organic EL device in an aspect of the present invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The number of "ring carbon atoms" referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The definition of "hydrogen atom" used herein includes isotopes different in the neutron numbers, i.e., light hydrogen (protium), heavy hydrogen (deuterium), and tritium.

The terms of "heteroaryl group" and "heteroarylene group" used herein means a group having at least one hetero atom as a ring atom. The hetero atom is preferably at least one selected from a nitrogen atom, an oxygen atom, a sulfur atom, a silicon atom, and a selenium atom.

The optional substituent referred to by "substituted or unsubstituted" used herein is preferably selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth)acryloyl group; an epoxy group; and an oxetanyl group.

The optional substituent may further has the substituent mentioned above. The optional substituents may be bonded to each other to form a ring.

The term of "unsubstituted" referred to by "substituted or unsubstituted" used herein means that no hydrogen atom in a group is substituted by a substituent.

Of the above substituents, more preferred are an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; a heteroaryl group having 5 to 50, preferably 5 to 24, more preferably 5 to 13 ring atoms; a halogen atom; and a cyano group.

In the present invention, those which are defined as being preferred can be selected arbitrarily and a combination thereof is a more preferred embodiment.

Compound

In an aspect of the invention, a compound represented by formula (1) (also referred to as "compound (1)") is provided. The compound (1) is useful as a material for organic electroluminescence devices.

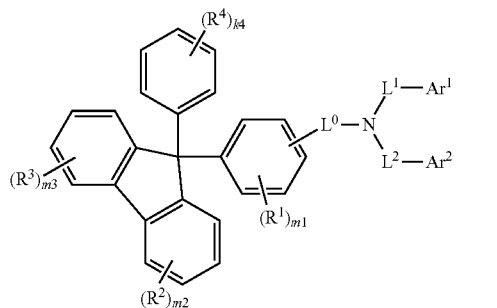

(1)

$R^1$ to $R^4$ in formula (1)

In formula (1), $R^1$ to $R^4$ each represent a substituent which is bonded to a carbon atom of each benzene ring in formula (1).

$R^1$ to $R^4$ each independently represent a substituted or unsubstituted alkyl group having 1 to 20, preferably 1 to 8, and more preferably 1 to 3 carbon atoms; a substituted or unsubstituted aryl group having 6 to 50, preferably 6 to 25, more preferably 6 to 18, and still more preferably 6 to 12 ring carbon atoms; a substituted or unsubstituted heteroaryl group having 5 to 50, preferably 5 to 10, more preferably 5 to 8, and still more preferably 5 or 6 ring atoms; a halogen atom, a substituted or unsubstituted fluoroalkyl group having 1 to 20, preferably 1 to 5, and more preferably 1 to 4 carbon atoms; a substituted or unsubstituted alkoxy group having 1 to 20, preferably 1 to 5, and more preferably 1 to 4 carbon atoms; a substituted or unsubstituted fluoroalkoxy group having 1 to 20, preferably 1 to 5, and more preferably 1 to 4 carbon atoms; a substituted or unsubstituted aryloxy group having 6 to 50, preferably 6 to 25, more preferably 6 to 18, and still more preferably 6 to 12 ring carbon atoms; or a cyano group.

Preferably, $R^1$ to $R^4$ each independently represent a group selected from a substituted or unsubstituted alkyl group having 1 to 20 carbon atoms, a substituted or unsubstituted heteroaryl group having 5 to 50 ring atoms, and a halogen atom, with a substituted or unsubstituted alkyl group having 1 to 20 carbon atoms is more preferred.

When $R^1$ to $R^4$ each are plurality in number, groups $R^1$ to groups $R^4$ may be the same or different, respectively.

In an embodiment of the invention, two selected from $R^1$ to $R^4$ are not bonded to each other, thereby failing to form a ring structure.

The subscripts m1 to m3 each independently represent an integer of 0 to 4, preferably an integer of 0 to 2, more preferably 0 or 1, and still more preferably 0.

The subscript k4 represents an integer of 0 to 5, preferably an integer of 0 to 2, more preferably 0 or 1, and still more preferably 0.

When m1, m2, m3, and k4 are each 0, each benzene ring has no substituent.

Examples of the alkyl group having 1 to 20 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups).

Of the above, preferred are a methyl group, an ethyl group, a n-propyl group, an isopropyl group, a n-butyl group, an isobutyl group, a s-butyl group, a t-butyl group, and a pentyl group (inclusive of isomeric groups), with a methyl group, an ethyl group, a n-propyl group, an isopropyl group, a n-butyl group, an isobutyl group, a s-butyl group, and a t-butyl group being more preferred, and a methyl group and a t-butyl group being still more preferred.

Examples of the aryl group having 6 to 50 ring carbon atoms include a phenyl group, a naphthylphenyl group, a biphenylyl group, a terphenylyl group, a biphenylenyl group, a naphthyl group, a phenylnaphthyl group, an acenaphthylenyl, an anthryl group, a benzanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group.

Of the above, preferred are a phenyl group, a naphthylphenyl group, a biphenylyl group, a terphenylyl group, a naphthyl group, and a 9,9-dimethylfluorenyl group, with a phenyl group, a biphenylyl group, a naphthyl group, and a 9,9-dimethylfluorenyl group being more preferred, and a phenyl group being still more preferred.

The heteroaryl group having 5 to 50 ring atoms comprises at least one, preferably 1 to 3 heteroatoms which may be the same or different, such as a nitrogen atom, a sulfur atom and an oxygen atom.

Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group.

Of the above, preferred are a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, and a dibenzothiophenyl group, with a benzofuranyl group, a benzothiophenyl group, a dibenzofuranyl group, and a dibenzothiophenyl group being more preferred.

Examples of the halogen atom include a fluorine atom, a chlorine atom, a bromine atom, and a iodine atom, with a fluorine atom being preferred.

Examples of the fluoroalkyl group having 1 to 20 carbon atoms include, for example, those derived from the above alkyl group having 1 to 20 carbon atoms by replacing at least one hydrogen atom, preferably 1 to 7 hydrogen atoms or all hydrogen atoms with a fluorine atom or fluorine atoms.

Preferred examples thereof are a heptafluoropropyl group, a pentafluoroethyl group, a 2,2,2-trifluoroethyl group, and a trifluoromethyl group, with a pentafluoroethyl group, a 2,2,2-trifluoroethyl group, and a trifluoromethyl group being more preferred, and a trifluoromethyl group being still more preferred.

The alkoxy group having 1 to 20 carbon atoms is represented by $-OR^X$, wherein $R^X$ is the above alkyl group having 1 to 20 carbon atoms.

Preferred examples thereof include a t-butoxy group, a propoxy group, an ethoxy group, and a methoxy group, with an ethoxy group and a methoxy group being more preferred, and a methoxy group being still more preferred.

The fluoroalkoxy group having 1 to 20 carbon atoms is represented by $-OR^Y$, wherein $R^Y$ is the above fluoroalkyl group having 1 to 20 carbon atoms.

Preferred examples thereof include a heptafluoropropoxy group, a pentafluoroethoxy group, a 2,2,2-trifluoroethoxy group, and a trifluoromethoxy group, with a pentafluoroethoxy group, a 2,2,2-trifluoroethoxy group, and a trifluoromethoxy group being more preferred, and a trifluoromethoxy group being still more preferred.

The aryloxy group having 6 to 50 ring carbon atoms is represented by $-OR^Z$, wherein $R^Z$ is the above aryl group having 6 to 50 ring carbon atoms.

Preferred examples thereof include a phenyloxy group, 1-naphthyloxy group, 2-naphthyloxy group, a 4-biphenylyloxy group, a p-terphenyl-4-yloxy group, and a p-tolyloxy group, with a phenyloxy group and a 2-naphthyloxy group being more preferred and a phenyloxy group being still more preferred.

$L^0$ to $L^2$ in formula (1)

In formula (1), $L^0$ to $L^2$ each independently represent a single bond, a substituted or unsubstituted arylene group having 6 to 50, preferably 6 to 24, and more preferably 6 to 12 ring carbon atoms, or a substituted or unsubstituted heteroarylene group having 5 to 50, preferably 5 to 10, more preferably 5 to 8, and still more preferably 5 or 6 ring atoms.

Examples of the arylene group having 6 to 50 ring carbon atoms include divalent groups derived from the aryl group having 6 to 50 ring carbon atoms mentioned above with respect to $R^1$ to $R^4$ of formula (1) by removing one hydrogen atom.

Preferred examples thereof include a terphenyldiyl group (inclusive of isomeric groups), a biphenyldiyl group (inclusive of isomeric groups), and a phenylene group (inclusive of isomeric groups), with a biphenyldiyl group (inclusive of isomeric groups) and a phenylene group (inclusive of isomeric groups) being more preferred and an o-phenylene group, a m-phenylene group, and a p-phenylene group being still more preferred.

The substituted or unsubstituted heteroarylene group having 5 to 50 ring atoms comprises at least one, preferably 1 to 3 hetero atoms which may be the same or different, such as a nitrogen atom, a sulfur atom and an oxygen atom.

Examples thereof include divalent groups derived from the heteroaryl group having 5 to 50 ring atoms mentioned above with respect to $R^1$ to $R^4$ of formula (1) by removing one hydrogen atom.

Preferred examples thereof include a furylene group, a thienylene group, a pyridylene group, a pyridazinylene group, a pyrimidinylene group, a pyrazinylene group, a triazinylene group, a benzofuranylene group, a benzothiophenylene group, a dibenzofuranylene group, and a dibenzothiophenylene group, with a benzofuranylene group, a benzothiophenylene group, a dibenzofuranylene group, and a dibenzothiophenylene group being more preferred.

$L^0$ is bonded to one of the carbon atoms *A, *B, *C, *D, and *E of the following 9,9-diphenyl-9H-fluorene skeleton in formula (1) and preferably bonded to the carbon atom *C.

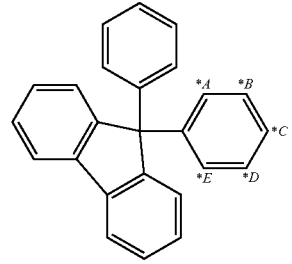 [SMILES: c1ccc(C2(c3ccccc3)c3ccccc3-c3ccccc32)cc1]

$L^0$ preferably represents a single bond or a substituted or unsubstituted arylene group having 6 to 50 ring carbon atoms, more preferably a single bond or a group represented by formula (i) or (ii), still more preferably a single bond or a group represented by formula (i), and further preferably a single bond.

$L^1$ and $L^2$ each preferably represent a single bond or a substituted or unsubstituted arylene group having 6 to 50 ring carbon atoms and more preferably a single bond or a group represented by formula (i) or (ii).

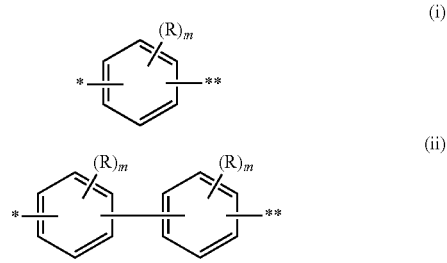

In formula (i) and (ii), * and ** each represent a bonding site.

One of * and ** is the bonding site to the nitrogen atom in formula (1) and the other is the bonding site to $Ar^1$, $Ar^2$, or the carbon atom of the phenyl group in the 9,9-diphenyl-9H-fluorene skeleton in formula (1).

In formula (i) and (ii), each R and preferred examples thereof are independently the same as those described with respect to $R^1$ in formula (1). Each R is a substituent which is bonded to the carbon atom of each benzene ring in formula (i) and (ii).

In an embodiment of the invention, when more than one R occurs, groups R may be the same or different. In another embodiment of the invention, when more than one R occurs, two selected from groups R may be bonded to each other to form a ring structure.

Examples of formula (i) wherein a ring structure is formed are shown below:

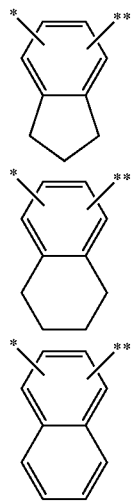

wherein * and ** are as defined in formula (i).

Examples of formula (ii) wherein a ring structure is formed are shown below:

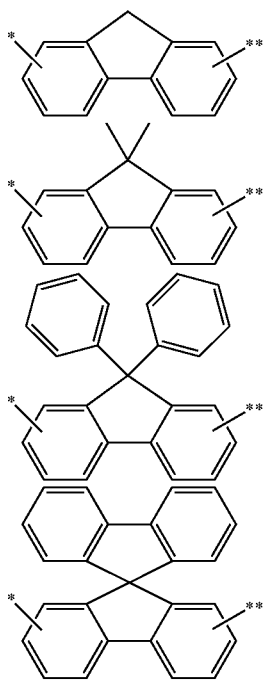

wherein * and ** are as defined in formula (ii).

In formula (1) and (ii), each m independently represents an integer of 0 to 4, preferably an integer of 0 to 2, more preferably 0 or 1, and still more preferably 0.

When m is 0, each benzene ring has no substituent.

The group represented by formula (i) is preferably represented by formula (i-a), and the group represented by formula (ii) is preferably represented by formula (ii-a):

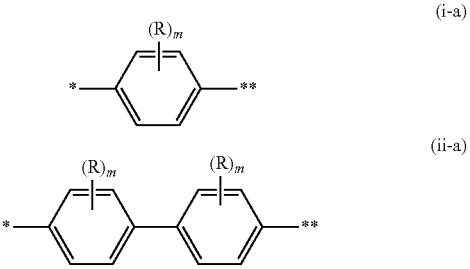

wherein R, m, *, and ** are as defined in formulae (i) and (ii).

$Ar^1$ in formula (1)

In formula (1), $Ar^1$ represents a monovalent residue of a compound represented by formula (2):

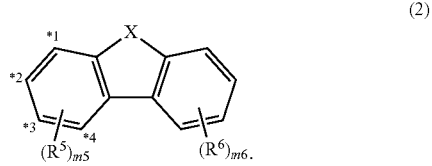

In formula (2), X represents $-C(R^A)(R^B)-$, $-O-$, $-S-$, or $-NH-$.

$R^5$ and $R^6$ and preferred examples thereof are independently the same as those described with respect to $R^1$ in formula (1). $R^5$ and $R^6$ are each a substituent which is bonded to a carbon atom of each benzene ring in formula (2).

The subscripts m5 and m6 each independently represent an integer of 0 to 4, preferably 0 to 2, more preferably 0 or 1, and still more preferably 0. When m5 and m6 are 0, each benzene ring has no substituent.

In an embodiment of the invention, when $R^5$ and $R^6$ are each plurality in number, groups $R^5$ and groups $R^6$ may be the same or different, respectively. In another embodiment, two selected from $R^5$ and $R^6$ may be bonded to each other to form a ring structure.

$R^A$ and $R^B$ may be the same or different and each independently represent a substituted or unsubstituted aryl group having 6 to 50, preferably 6 to 25, more preferably 6 to 18, and still more preferably 6 to 12 ring carbon atoms or a substituted or unsubstituted heteroaryl group having 5 to 50, preferably 5 to 10, more preferably 5 to 8, and still more preferably 5 or 6 ring atoms.

Examples of the aryl group having 6 to 50 ring carbon atoms and the heteroaryl group having 5 to 50 ring atoms include those described with respect to $R^1$ to $R^4$ in formula (1).

$R^A$ and $R^B$ each preferably represent a substituted or unsubstituted aryl group having 6 to 50 ring carbon atoms and more preferably a substituted or unsubstituted phenyl group.

$R^A$ and $R^B$ are not bonded to each other, thereby failing to form a ring structure.

In the compound (1) in an aspect of the invention, $Ar^1$ should meet the following requirements (I) and (II)

(I) when X in formula (2) is —C(R$^A$)(R$^B$)—, —O—, or —S—, the hydrogen atom or R$^5$ attached to one of carbon atoms *1 to *4 is eliminated and a remaining carbon atom is bonded to L$^1$ or the nitrogen atom in formula (1); and (II) when X in formula (2) is —NH—, the hydrogen atom of —NH— is eliminated and a remaining nitrogen atom is bonded to L$^1$ or the nitrogen atom in formula (1).

Namely, Ar$^1$ is a group represented by any of formulae (2-1) to (2-13):

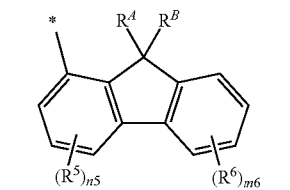
(2-1)

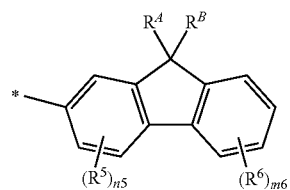
(2-2)

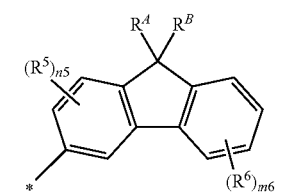
(2-3)

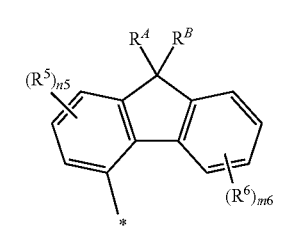
(2-4)

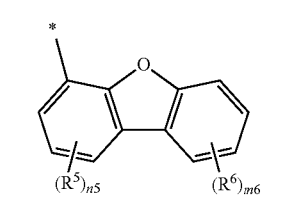
(2-5)

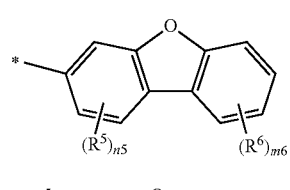
(2-6)

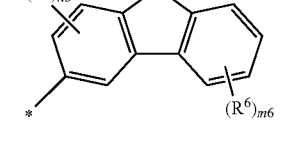
(2-7)

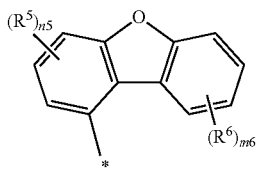
(2-8)

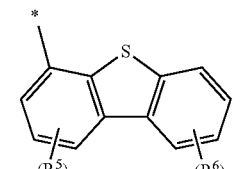
(2-9)

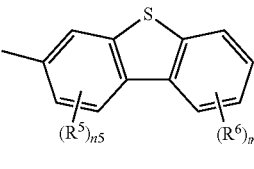
(2-10)

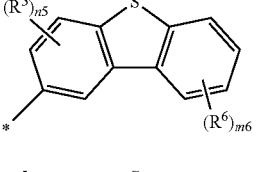
(2-11)

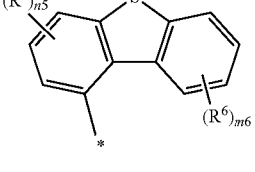
(2-12)

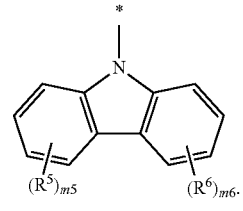
(2-13)

wherein R$^5$, R$^6$, m5, and m6 are as defined in formula (2); each n5 independently represents an integer of 0 to 3, preferably an integer of 0 to 2, more preferably 0 or 1, and still more preferably 0; and

* represents a bonding site to L$^1$ or the nitrogen atom in formula (1).

Of the above, Ar$^1$ is preferably a group represented by any of formulae (2-2), (2-5), (2-7), (2-9), (2-11), and (2-13).

Ar$^2$ in formula (1)

In formula (1), Ar$^2$ represents a substituted or unsubstituted aryl group having 6 to 50, preferably 6 to 25, more preferably 6 to 18, and still more preferably 6 to 12 ring carbon atoms or a substituted or unsubstituted heteroaryl group having 5 to 50, preferably 5 to 10, more preferably 5 to 8, and still more preferably 5 or 6 ring atoms.

The examples of the aryl group having 6 to 50 ring carbon atoms and the heteroaryl group having 5 to 50 ring atoms include those described with respect to R$^1$ to R$^4$ in formula (1).

In an embodiment of the invention, Ar$^2$ is preferably a substituted or unsubstituted aryl group having 6 to 50 ring carbon atoms, a substituted or unsubstituted dibenzofuranyl group, a substituted or unsubstituted dibenzothiophenyl group, or a substituted or unsubstituted 9-carbazolyl group, and more preferably a group represented by any of formulae (a) to (j);

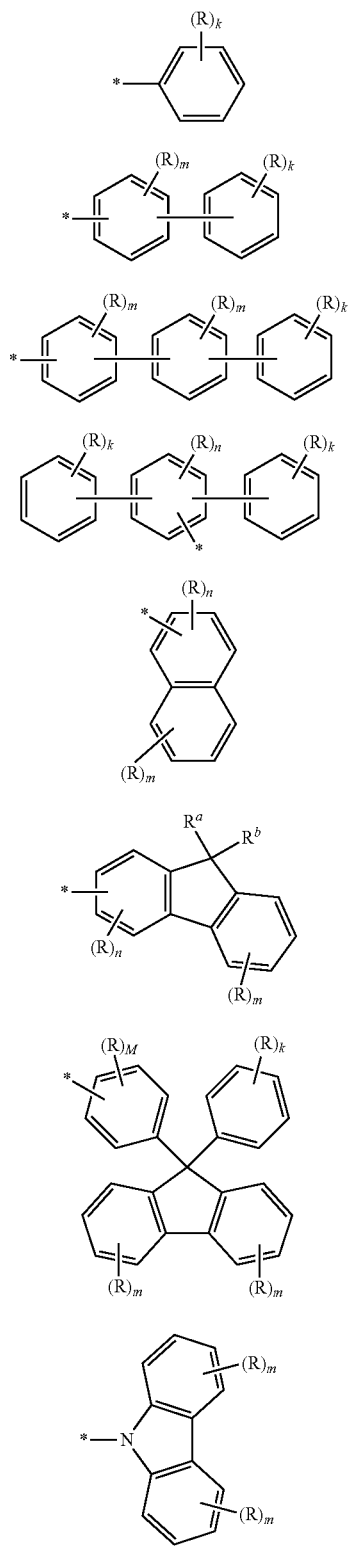

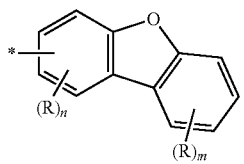

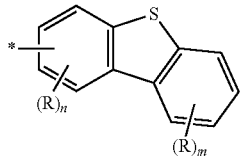

In formulae (a) to (j), examples of R, $R^a$, and $R^b$ and preferred examples thereof are each independently the same as those described with respect to $R^1$ in formula (1). R is a substituent which is bonded to a carbon atom of each benzene ring in formulae (a) to (j).

$R^a$ and $R^b$ in formula (f) are each preferably selected from a hydrogen atom, a substituted or unsubstituted alkyl group having 1 to 20, preferably 1 to 8, and more preferably 1 to 3 carbon atoms, a substituted or unsubstituted aryl group having 6 to 50, preferably 6 to 25, more preferably 6 to 18, and still more preferably 6 to 12 ring carbon atoms.

When more than one R occurs, groups R may be the same or different, and two selected from groups R may be bonded to each other to form a ring structure.

In formula (f), two selected from groups R, $R^a$, or $R^b$ may be bonded to each other to form a ring structure.

In formulae (a) to (j), each k independently represents an integer of 0 to 5, preferably an integer of 0 to 2, more preferably 0 or 1, and still more preferably 0.

Each m independently represents an integer of 0 to 4, preferably an integer of 0 to 2, more preferably 0 or 1, and still more preferably 0.

Each n independently represents an integer of 0 to 3, preferably an integer of 0 to 2, more preferably 0 or 1, and still more preferably 0.

When k, m, and n are each 0, each benzene ring has no substituent.

\* represents a bonding site to $L^2$ or the nitrogen atom in formula (1).

In view of emission efficiency, the group represented by formula (i) is preferably represented by formula (i') or (i'') and more preferably represented by formula (i''):

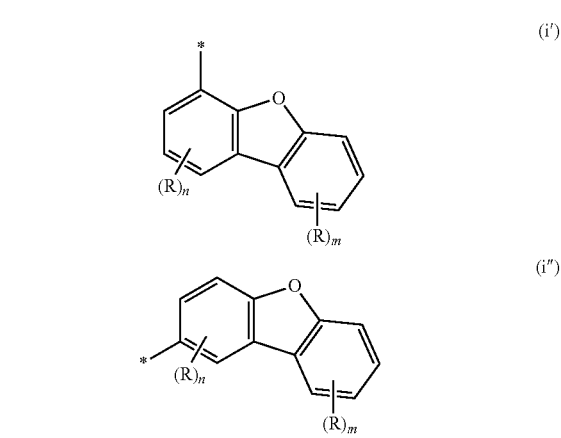

wherein R, n, and m are as defined in formula (i).

In view of emission efficiency, the group represented by formula (j) is preferably represented by formula (j') or (j") and more preferably represented by formula (j"):

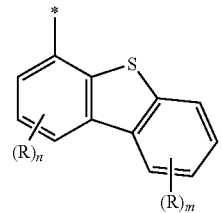
(j')

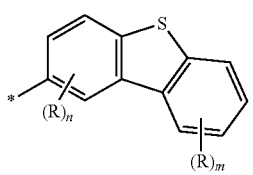
(j")

wherein R, n, and m are as defined in formula (j).

In an embodiment of the invention, of the groups for Ar², the group represented by formula (b) is preferably represented by formula (b-1) or (b-2), the group represented by formula (c) is preferably represented by formula (c-1) or (c-2), and the group represented by formula (d) is preferably represented by formula (d-1)

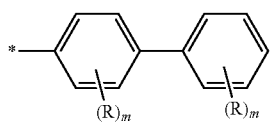
(b-1)

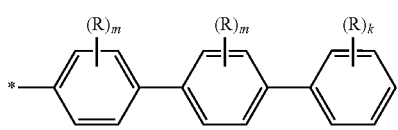
(c-1)

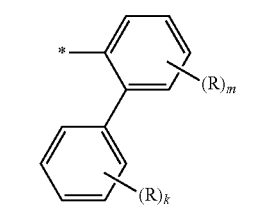
(b-2)

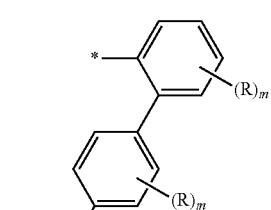
(c-2)

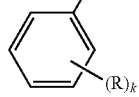

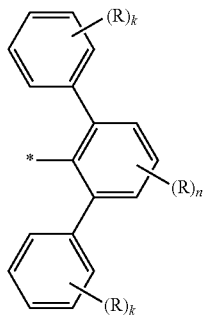
(d-1)

wherein R, k, m, n, and * are as defined in formulae (a) to (j).

In an embodiment of the invention, the group represented by formula (f) for Ar² is preferably represented by formula (f-1):

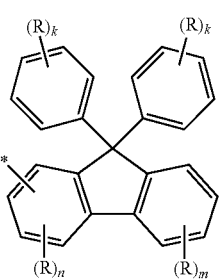
(f-1)

wherein, R, k, m, n, and * are as defined in formulae (a) to (j).

In formula (f-1), when more than one R occurs, groups R may be the same or different, and two selected from groups R may be bonded to each other to form a ring structure. The group represented by formula (f-1) wherein a ring structure is formed may include the following group represented by formula (f-2):

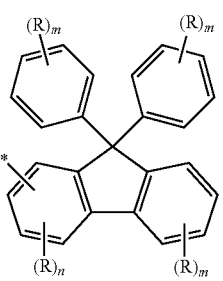
(f-2)

wherein R, m, n, and * are as defined in formulae (a) to (j).

The group -L²-Ar² is preferably a group represented by any of the following formulae:

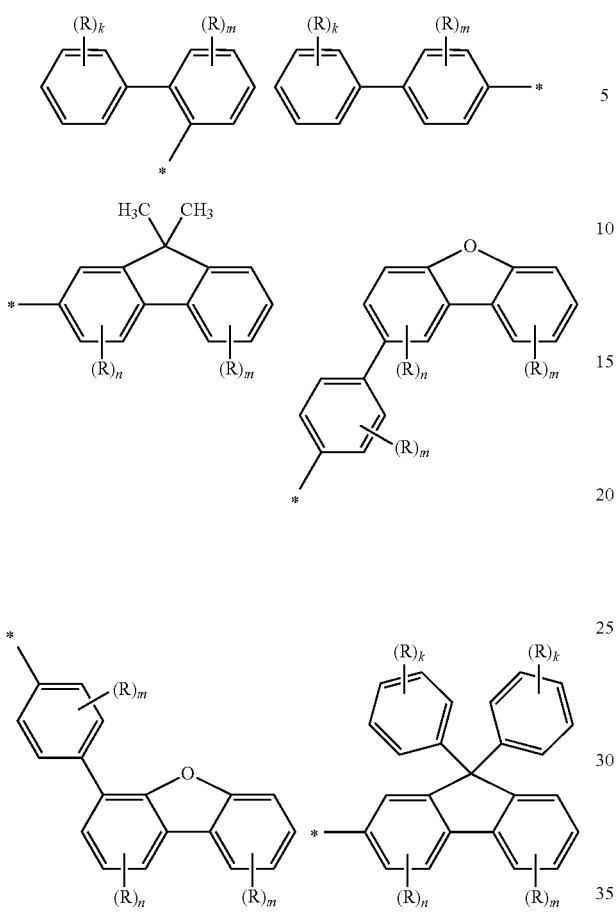
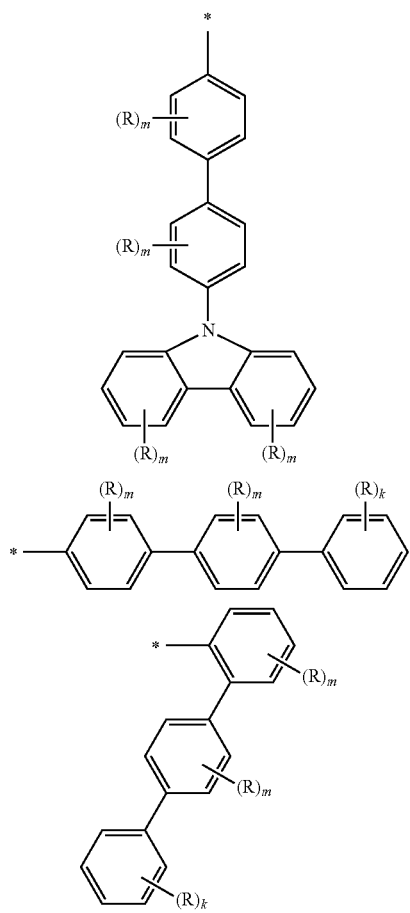
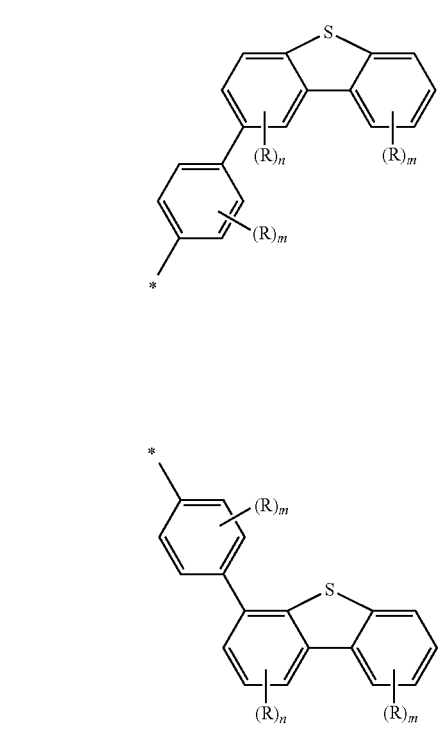

wherein R, k, m, and n are as defined in formula (a) to (j), and * represents a bonding site to the nitrogen atom in formula (1).

Compound in an Aspect of the Invention

The compound (1) in an aspect of the invention is preferably a compound represented by formula (1-1) (also referred to as "compound (1-1)"):

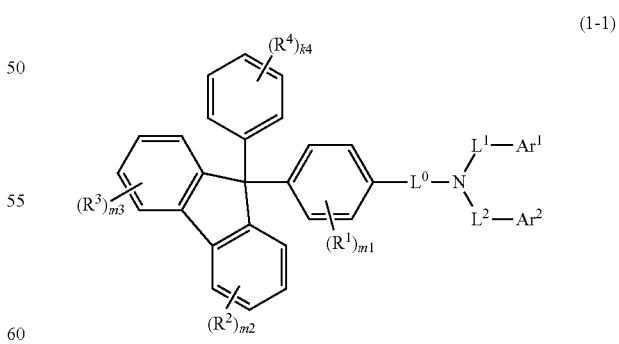

wherein $R^1$ to $R^4$, m1 to m3, k4, $L^0$ to $L^2$, $Ar^1$, and $Ar^2$ are as defined in formula (1).

The compound (1-1) in an aspect of the invention is more preferably a compound represented by formula (1-2) (also referred to as "compound (1-2)"):

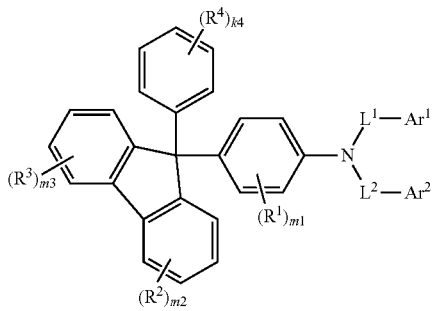

(1-2)

wherein $R^1$ to $R^4$, m1 to m3, k4, $L^1$ to $L^2$, $Ar^1$, and $Ar^2$ are as defined in formula (1).

The compound (1) in an aspect of the invention is also preferably a compound represented by formula (1-3) (also referred to as "compound (1-3)"):

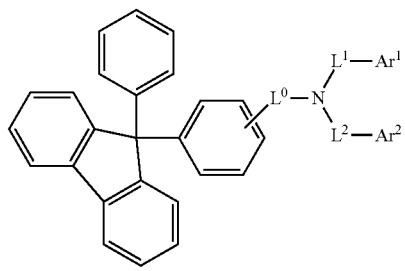

(1-3)

wherein $L^0$ to $L^2$, $Ar^1$, and $Ar^2$ are defined in formula (1).

The compound (1) in an aspect of the invention is also preferably a compound represented by formula (1-4) (also referred to as "compound (1-4)"):

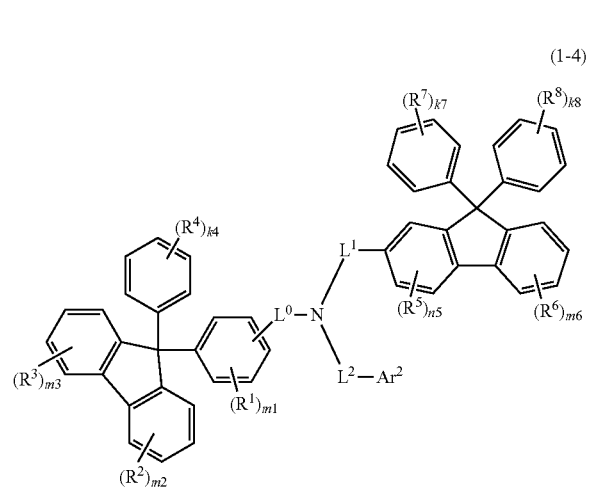

(1-4)

wherein $R^1$ to $R^6$, m1 to m3, k4, m6, $L^0$ to $L^2$, and $Ar^2$ are as defined in formulae (1) and (2);

examples of $R^7$ and $R^8$ and preferred examples thereof are each independently the same as those described with respect to $R^1$ in formula (1);

n5 represents an integer of 0 to 3, preferably an integer of 0 to 2, more preferably 0 or 1, and still more preferably 0; and k7 and k8 each independently represent an integer of 0 to 5, preferably an integer of 0 to 2, more preferably 0 or 1, and still more preferably 0.

In an embodiment of the invention, $R^7$ and $R^8$ may be bonded to each other to form a ring structure, and preferably do not form a ring structure. Example of a compound wherein a ring structure is formed include a compound represented by formula (1-4a):

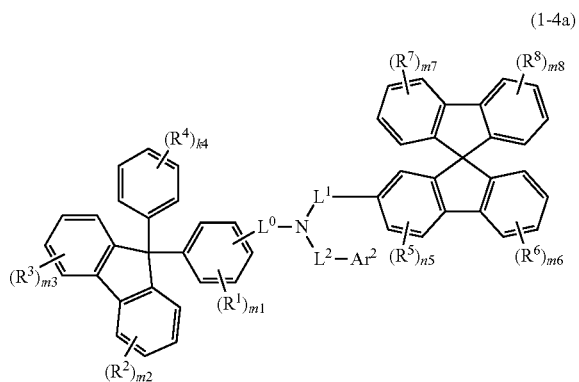

(1-4a)

wherein $R^1$ to $R^8$, m1 to m3, k4, n5, m6, $L^0$ to $L^2$, and $Ar^2$ are as defined in formulae (1), (2), and (1-4); and m7 and m8 each independently represent an integer of 0 to 4, preferably an integer of 0 to 2, more preferably 0 or 1, and still more preferably 0.

Of the compound (1-4) in an aspect of the invention, more preferred is a compound represented by formula (1-4-1) (also referred to as "compound (1-4-1)"):

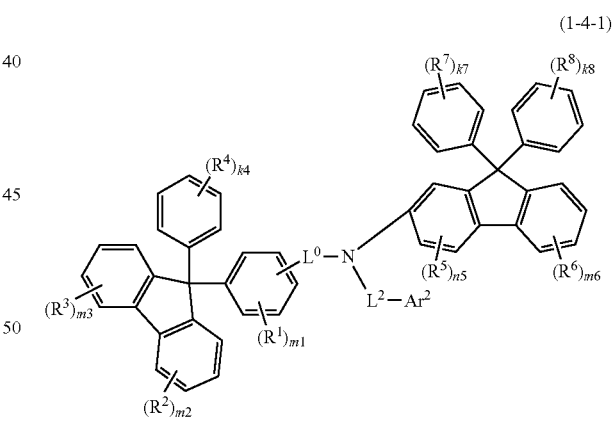

(1-4-1)

wherein $R^1$ to $R^8$, m1 to m3, k4, n5, m6, k7, k8, $L^0$, $L^2$, and $Ar^2$ are as defined in formulae (1), (2), and (1-4).

$Ar^2$ in formulae (1-4) and (1-4-1) is preferably a group represented by any of the above formulae (a) to (g) and more preferably a group represented by any of the above formulae (b) to (g).

The compound (1) in an aspect of the invention is also preferably a compound represented by formula (1-5) or (1-6) (also referred to as "compound (1-5)" and "compound (1-6)"):

(1-5)

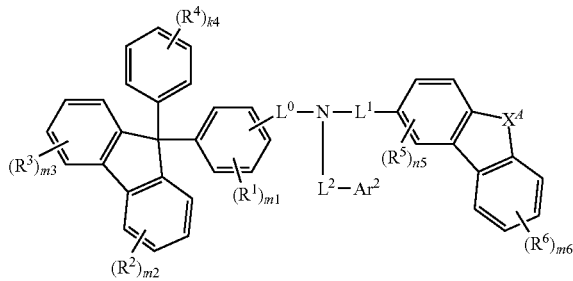

(1-6)

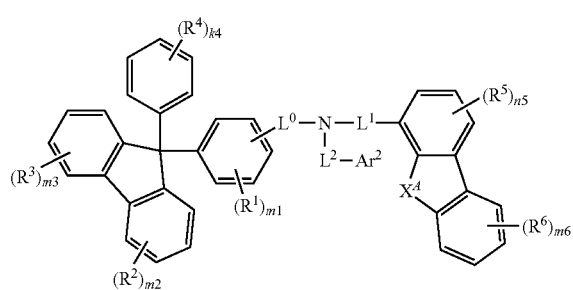

wherein $R^1$ to $R^6$, m1 to m3, k4, m6, $L^0$ to $L^2$, and $Ar^2$ are as defined in formulae (1) and (2);

$X^A$ represents —O— or —S—; and n5 represents an integer of 0 to 3, preferably an integer of 0 to 2, more preferably 0 or 1, and still more preferably 0.

Of the compound (1-5) in an aspect of the invention, more preferred is a compound represented by formula (1-5-1) (also referred to as "compound (1-5-1)"), and of the compound (1-6) in an aspect of the invention, more preferred is a compound represented by formula (1-6-1) (also referred to as "compound (1-6-1)");

(1-5-1)

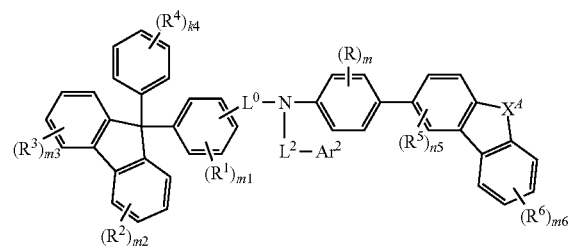

(1-6-1)

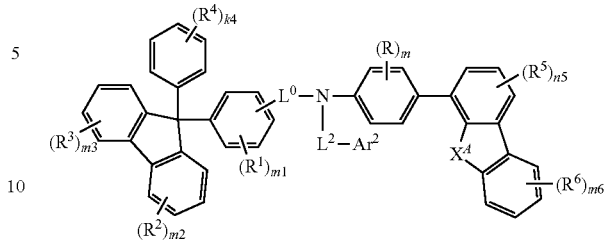

wherein $R^1$ to $R^6$, m1 to m3, k4, n5, m6, $L^0$, $L^2$, $Ar^2$, and $X^A$ are as defined in formulae (1), (2), (1-5), and (1-6);

examples of R and preferred examples thereof are the same as those described with respect to $R^1$ in formula (1); and m represents an integer of 0 to 4, preferably an integer of 0 to 2, more preferably 0 or 1, and still more preferably 0.

$Ar^2$ in formulae (1-5), (1-6), (1-5-1), and (1-6-1) is preferably a group represented by any of the above formulae (a) to (j) and more preferably a group represented by any of the above formulae (b) to (j).

The compound (1) in an aspect of the invention is also preferably a compound represented by formula (1-7) (also referred to as "compound (1-7)"):

(1-7)

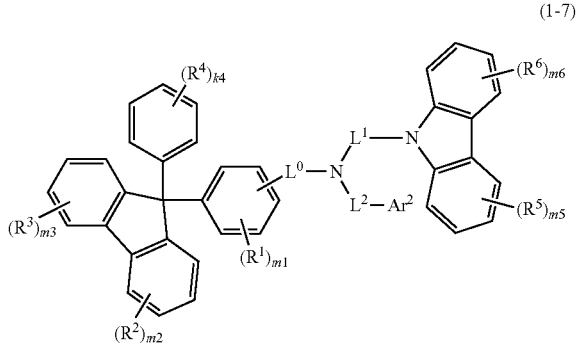

wherein $R^1$ to $R^6$, m1 to m3, k4, m5, m6, $L^0$ to $L^2$, and $Ar^2$ are as defined in formulae (1) and (2).

Of the compound (1-7) in an aspect of the invention, more preferred are a compound represented by formula (1-7-1) (also referred to as "compound (1-7-1)") and a compound represented by formula (1-7-2) (also referred to as "compound (1-7-2)"):

(1-7-1)

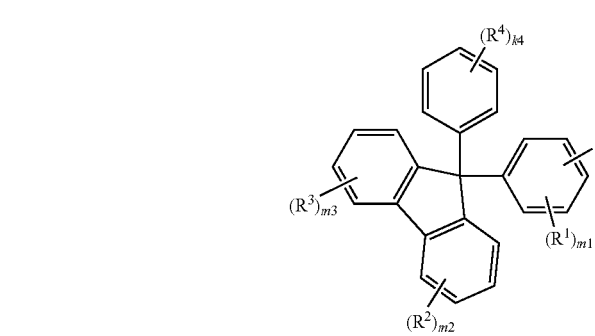

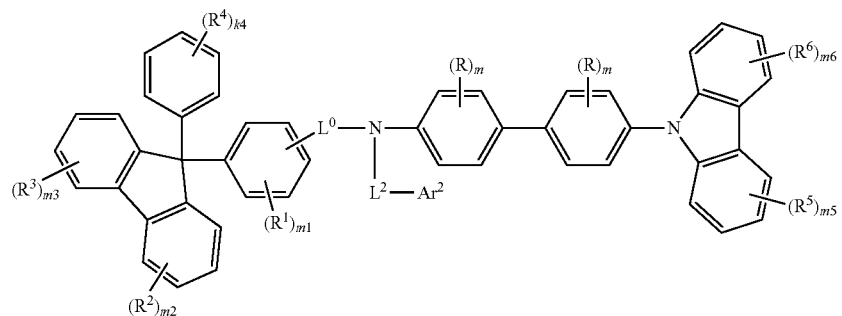

(1-7-2)

wherein $R^1$ to $R^6$, m1 to m3, k4, m5, m6, $L^0$, $L^2$, and $Ar^2$ are as defined in formula (1-7);

examples of R and preferred examples thereof are the same as those described with respect to $R^1$ in formula (1); and each m independently represents an integer of 0 to 4, preferably an integer of 0 to 2, more preferably 0 or 1, and still more preferably 0.

$Ar^2$ in formulae (1-7), (1-7-1), and (1-7-2) is preferably a group represented by any of the above formulae (a) to (h) and more preferably a group represented by any of the above formulae (b) to (h).

Examples of the compound (1) in an aspect of the invention are shown below, although not limited thereto.

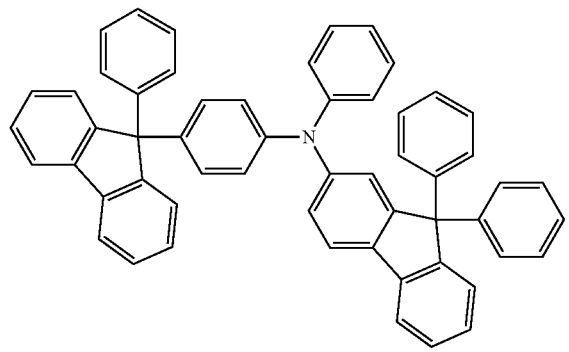

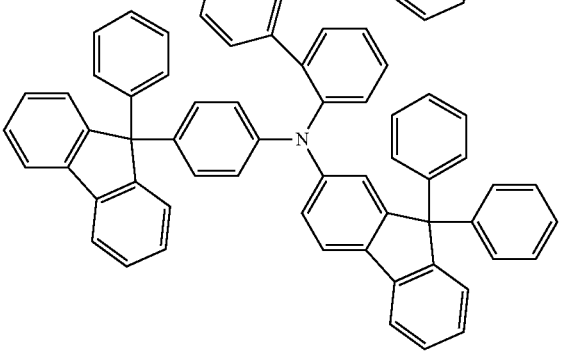

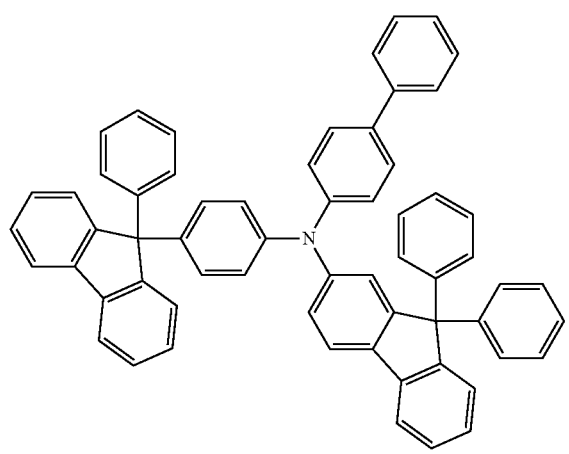

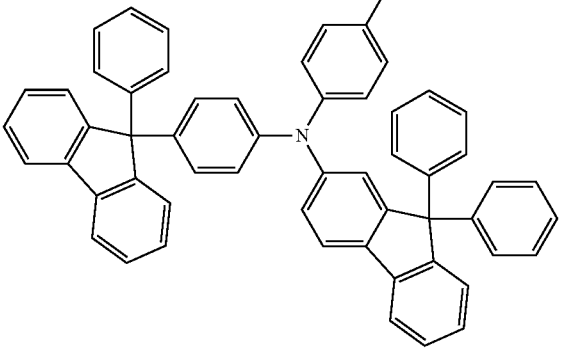

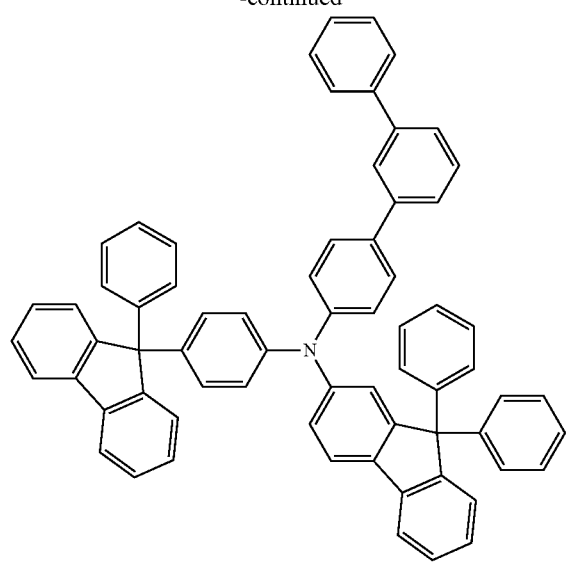
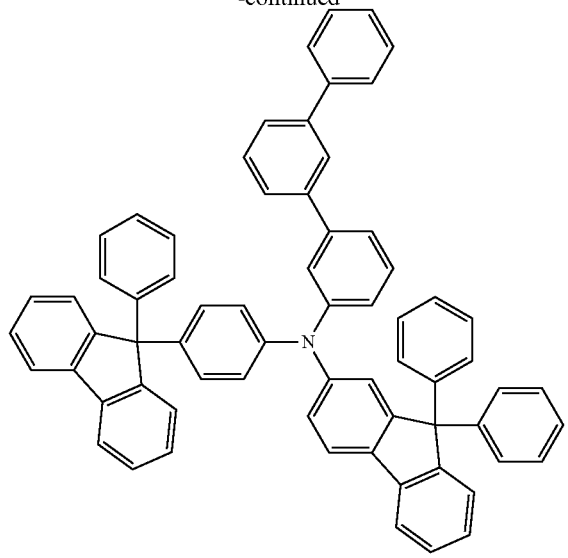
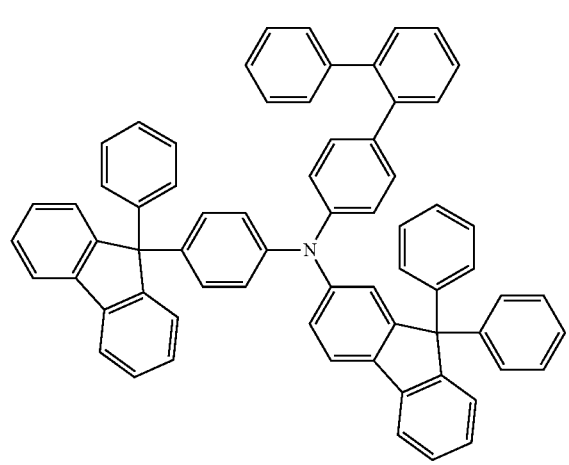
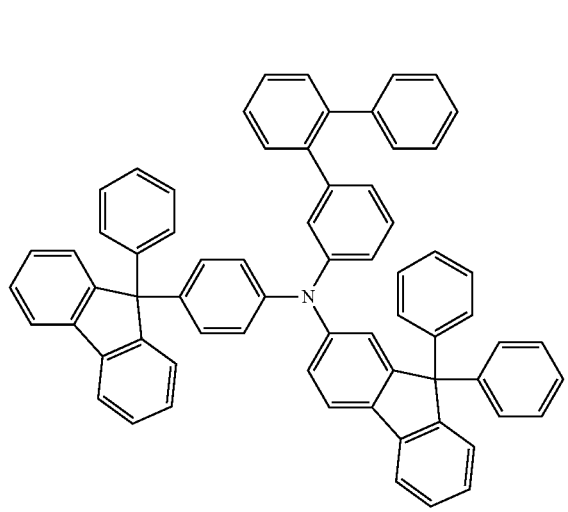
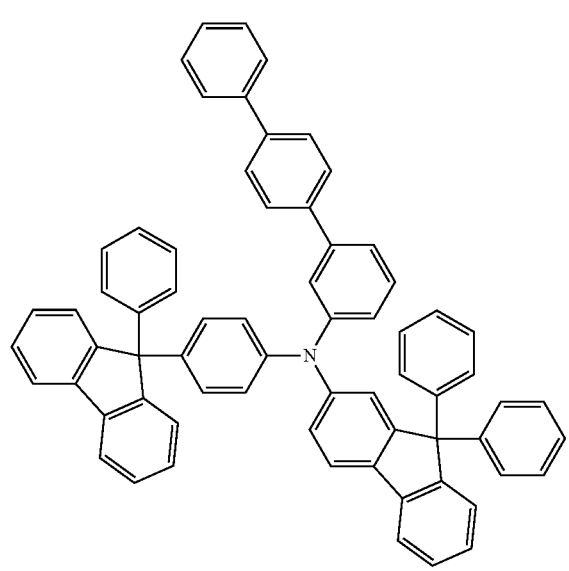
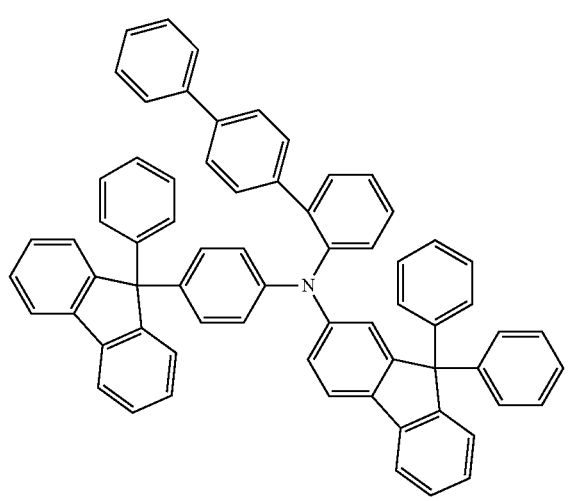

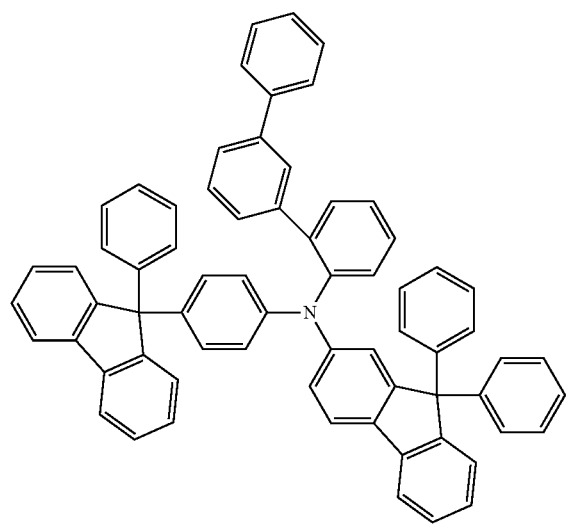
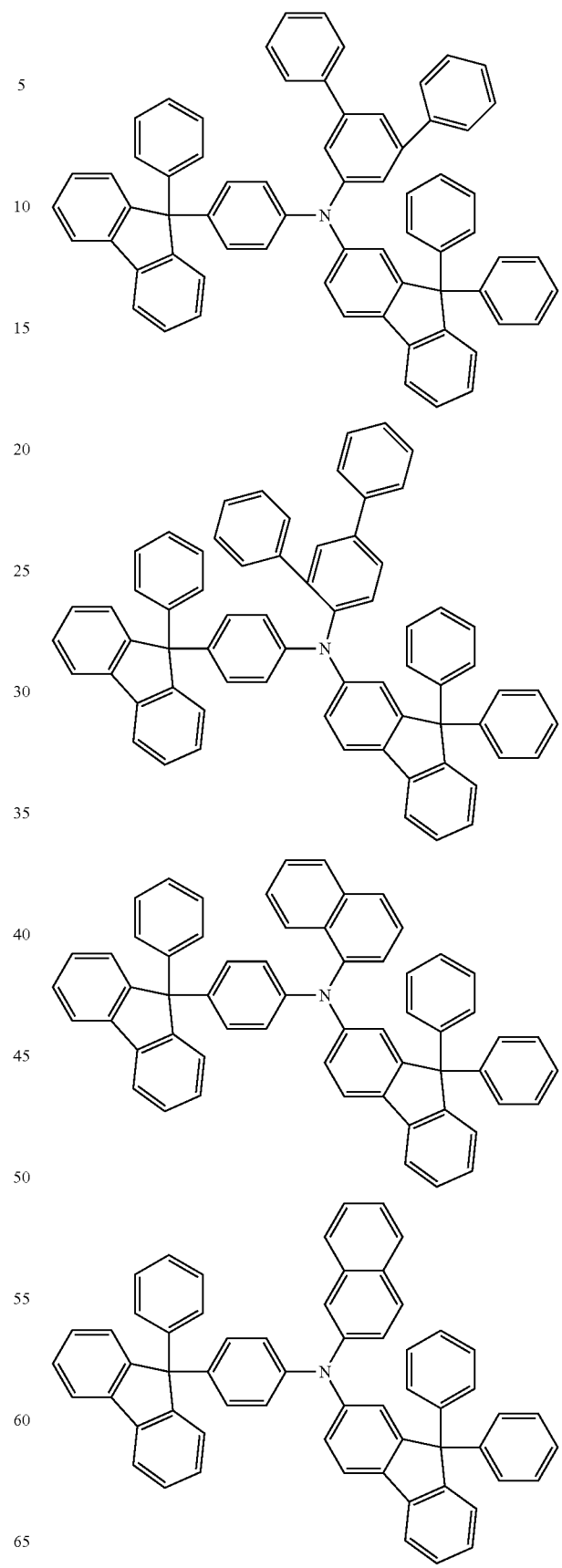

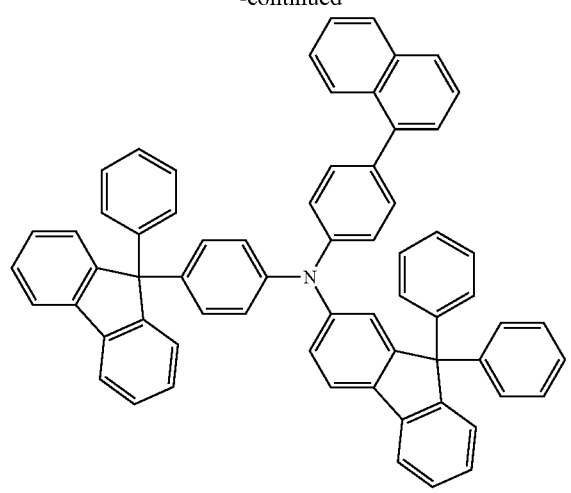
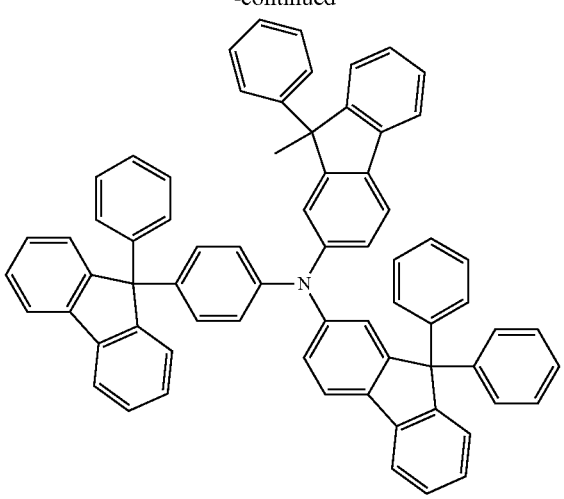
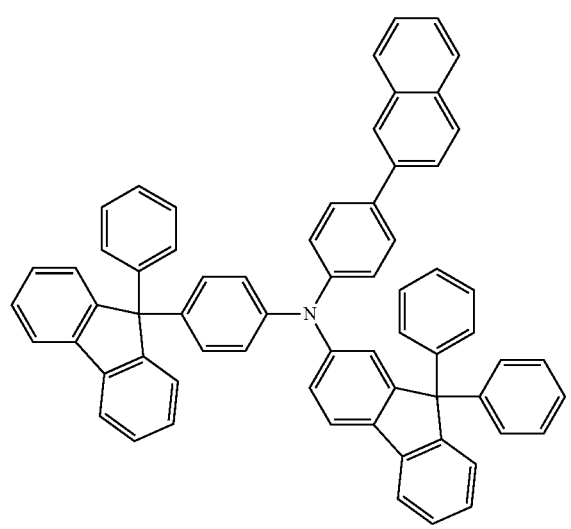
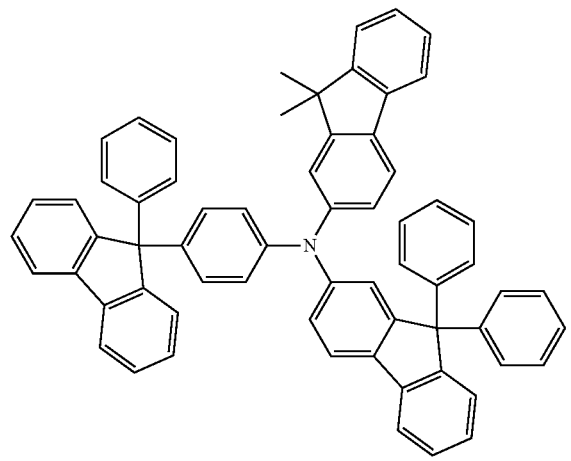
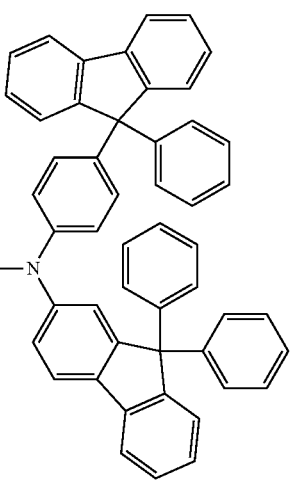

31
-continued
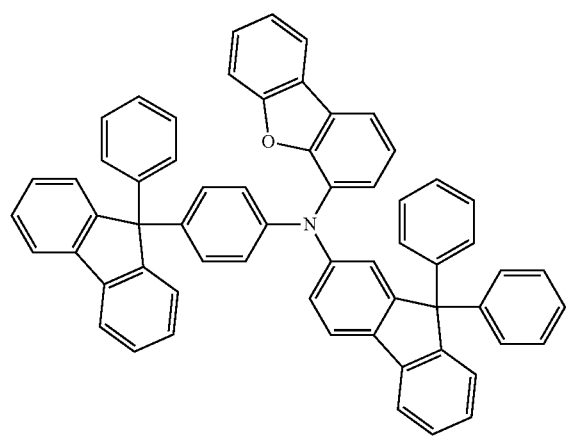
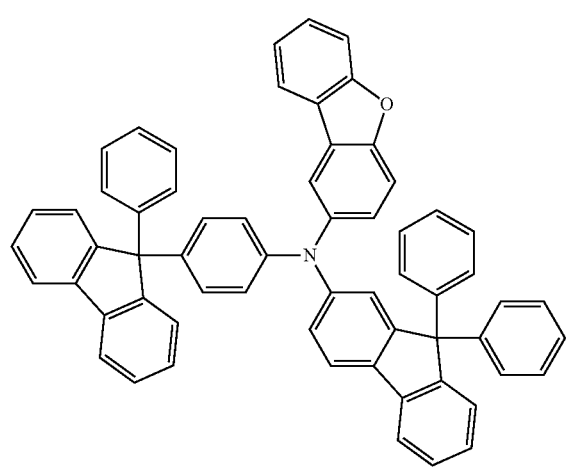
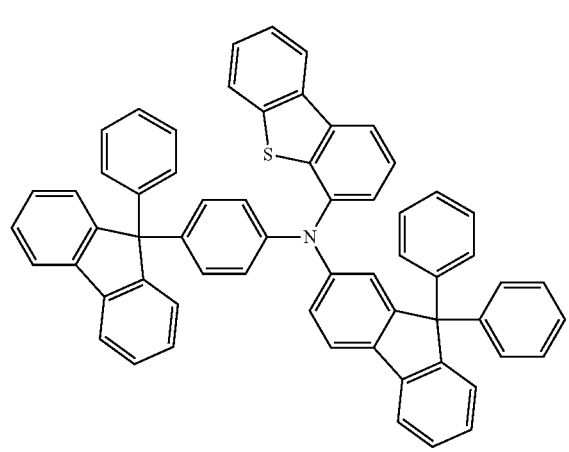
32
-continued
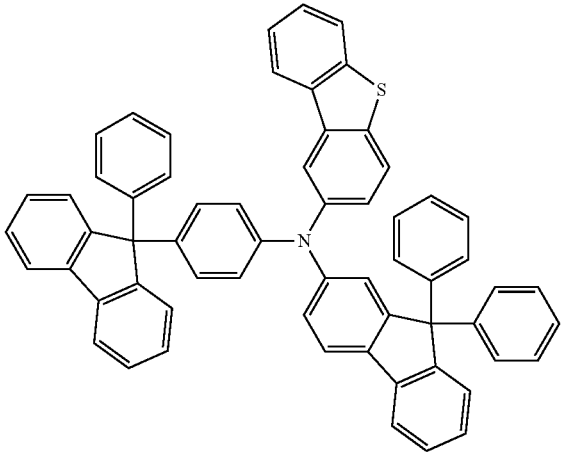
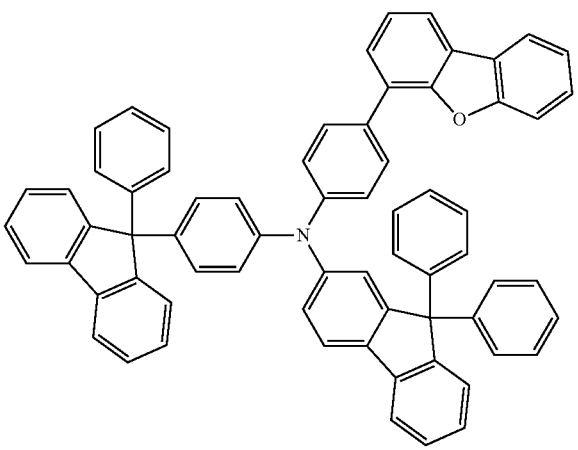
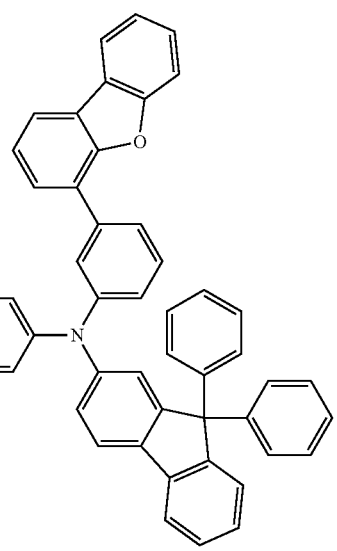

33
-continued
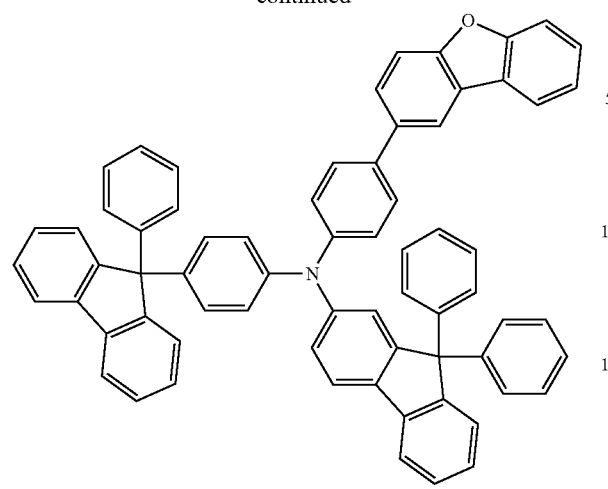
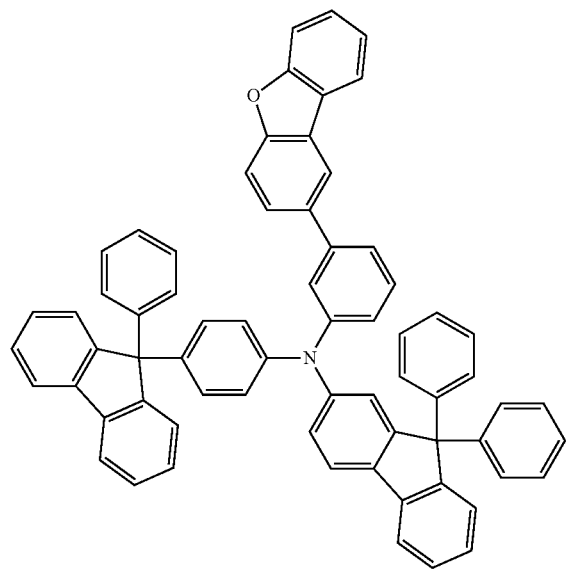
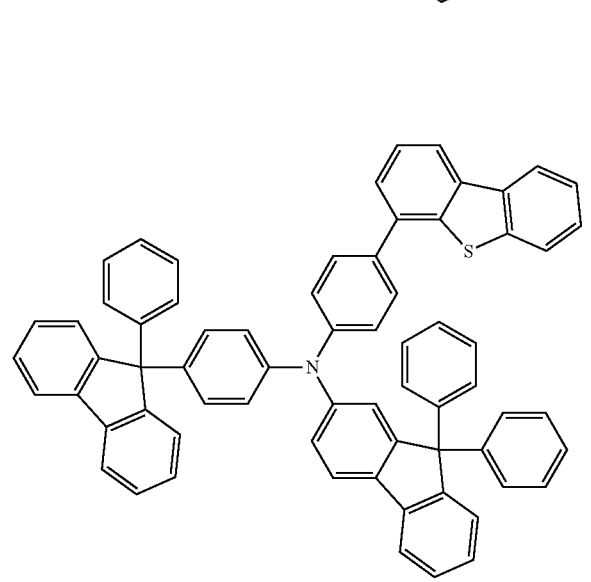
34
-continued
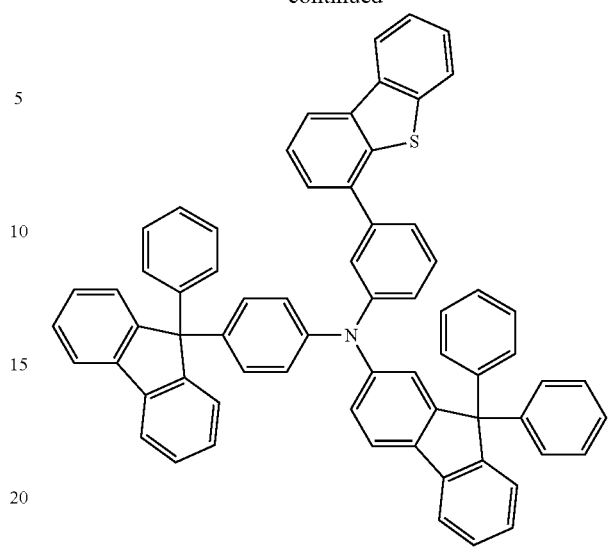
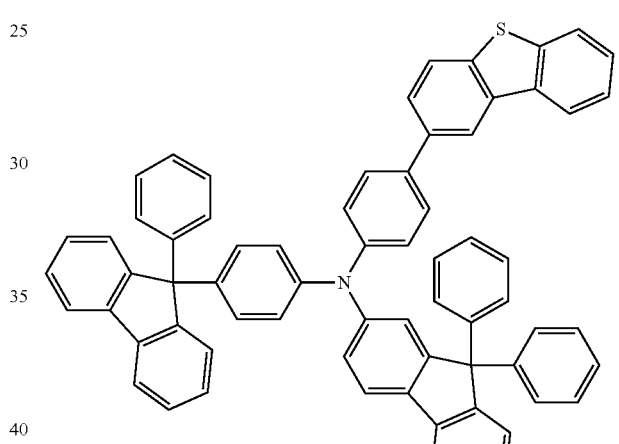
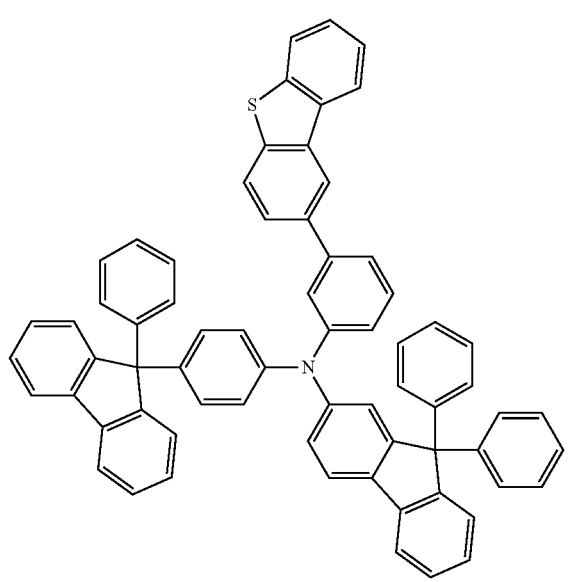

-continued
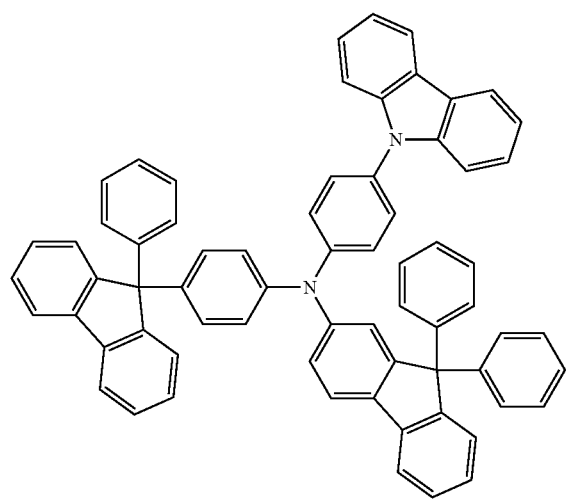
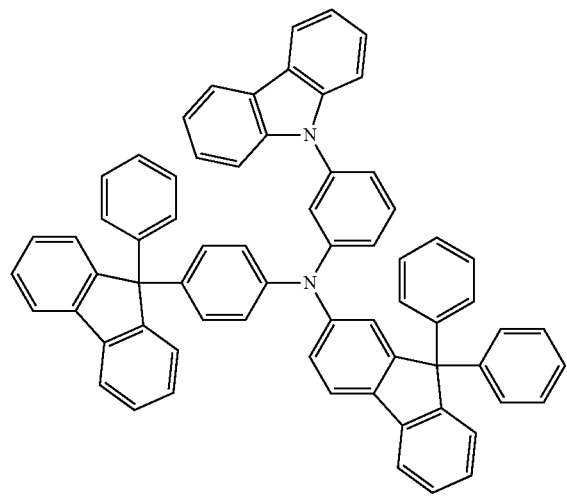
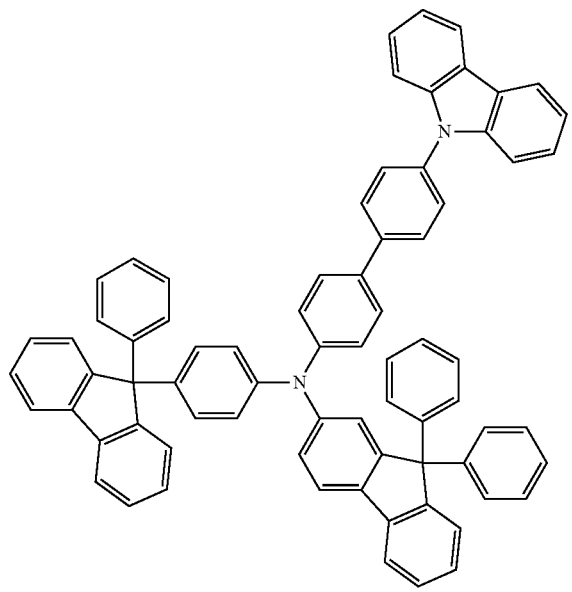
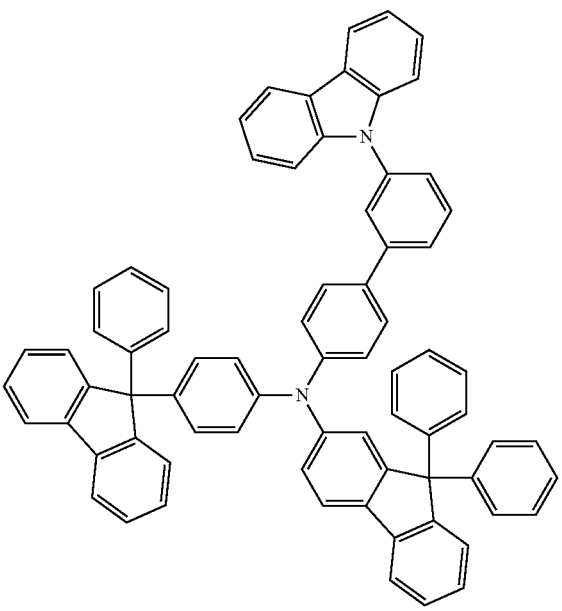 [SMILES: c1ccc(C2(c3ccc(N(c4ccc(-c5cccc(-n6c7ccccc7c7ccccc76)c5)cc4)c4ccc5c(c4)C(c4ccccc4)(c4ccccc4)c4ccccc4-5)cc3)c3ccccc3-c3ccccc32)cc1]
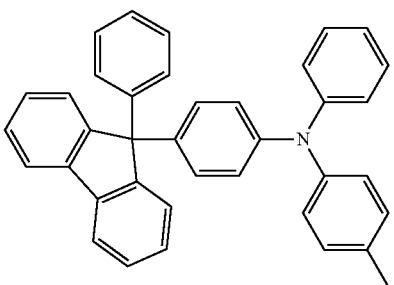
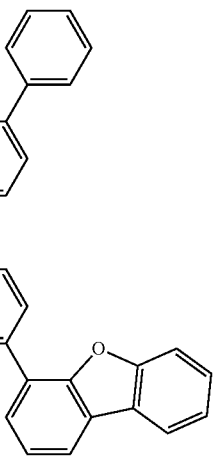

37
-continued
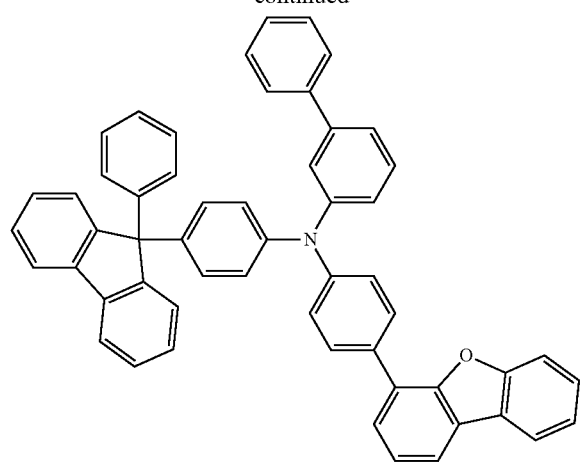
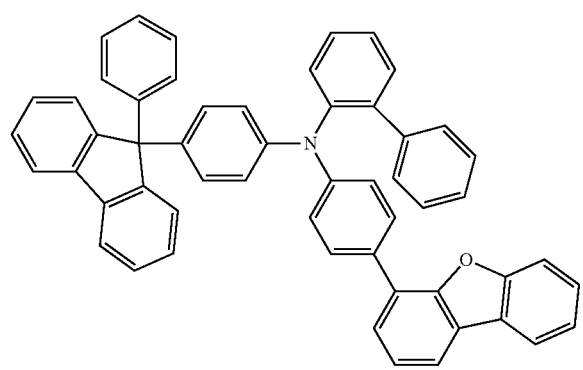
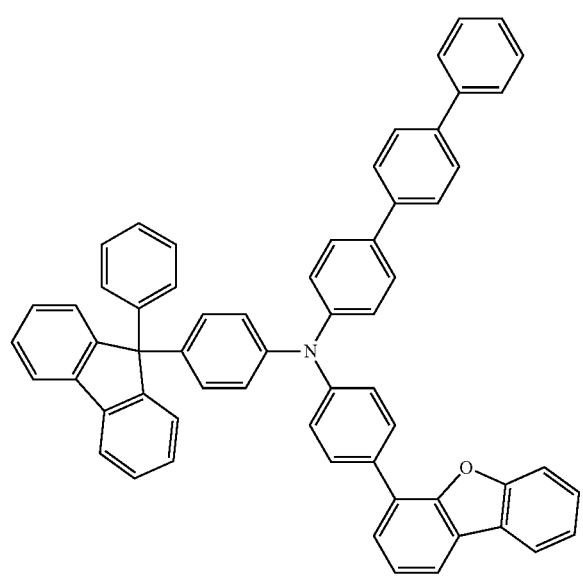
38
-continued
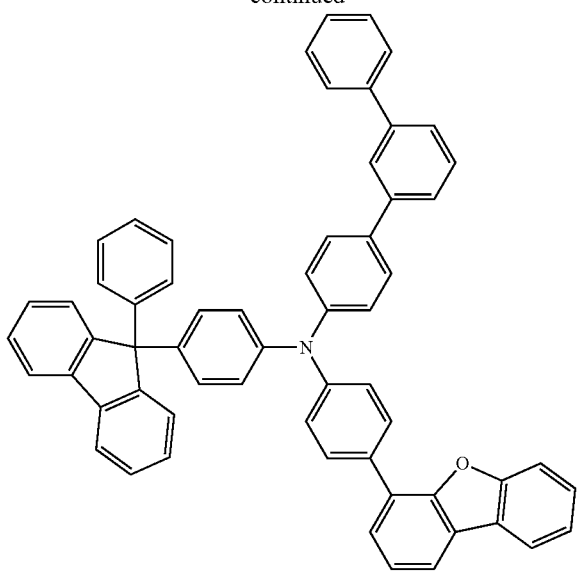
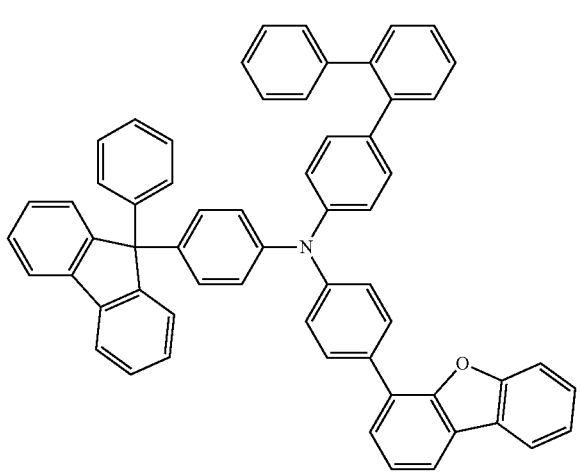
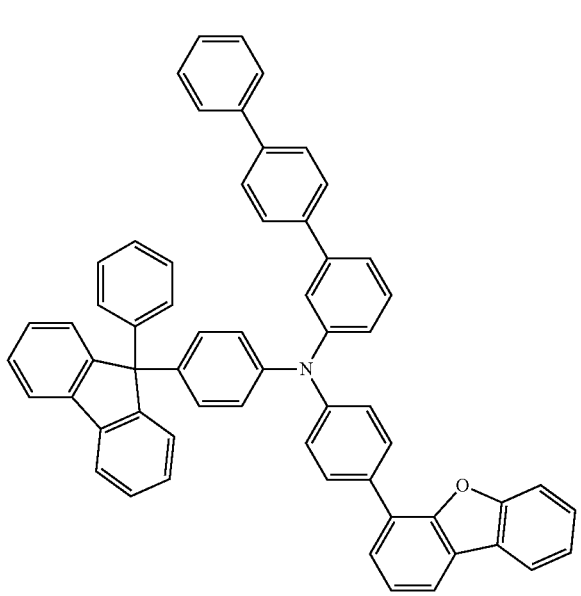

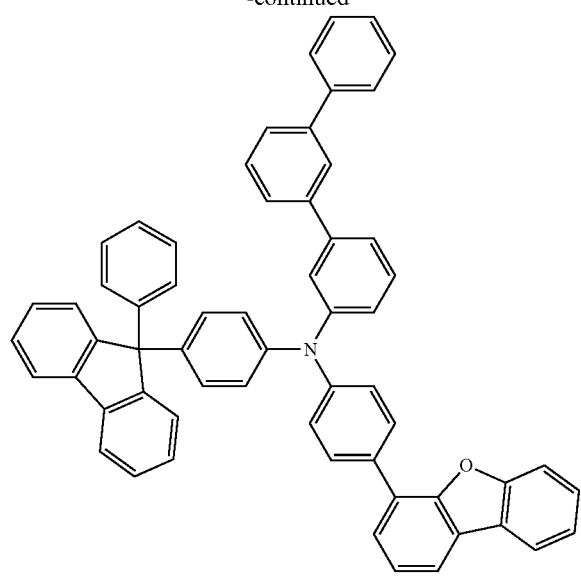
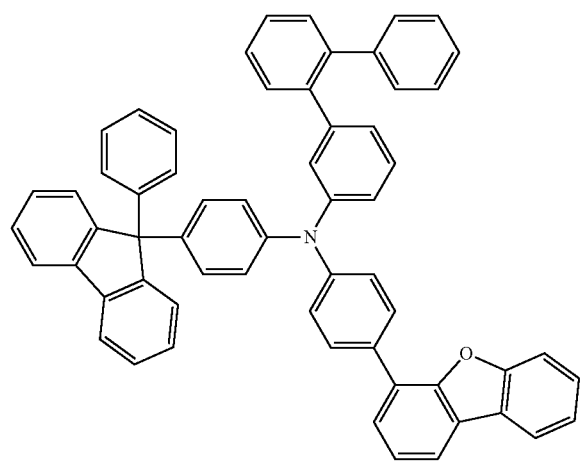
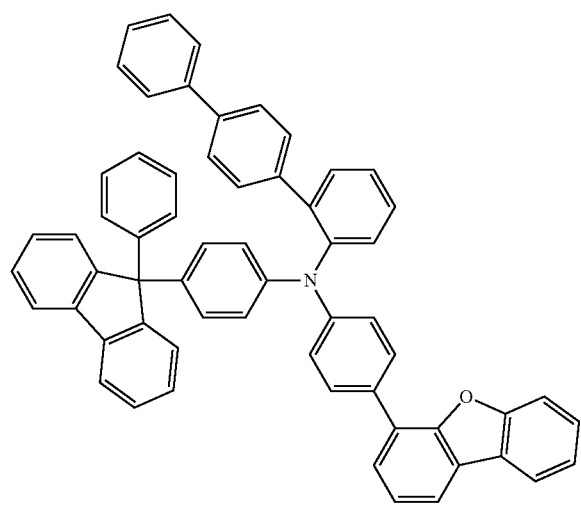
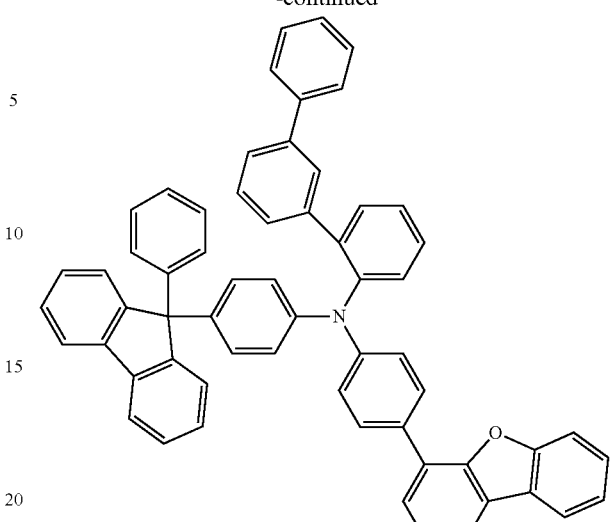
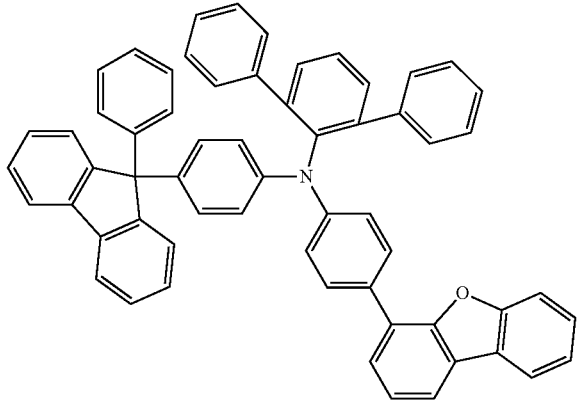

-continued
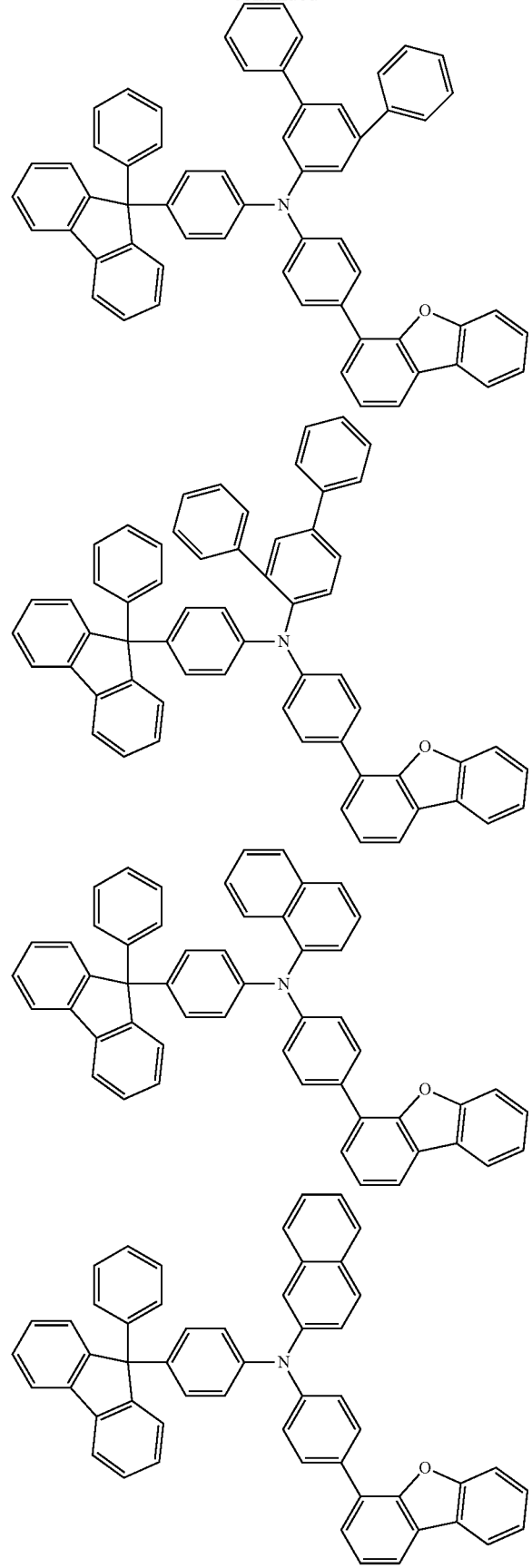
-continued
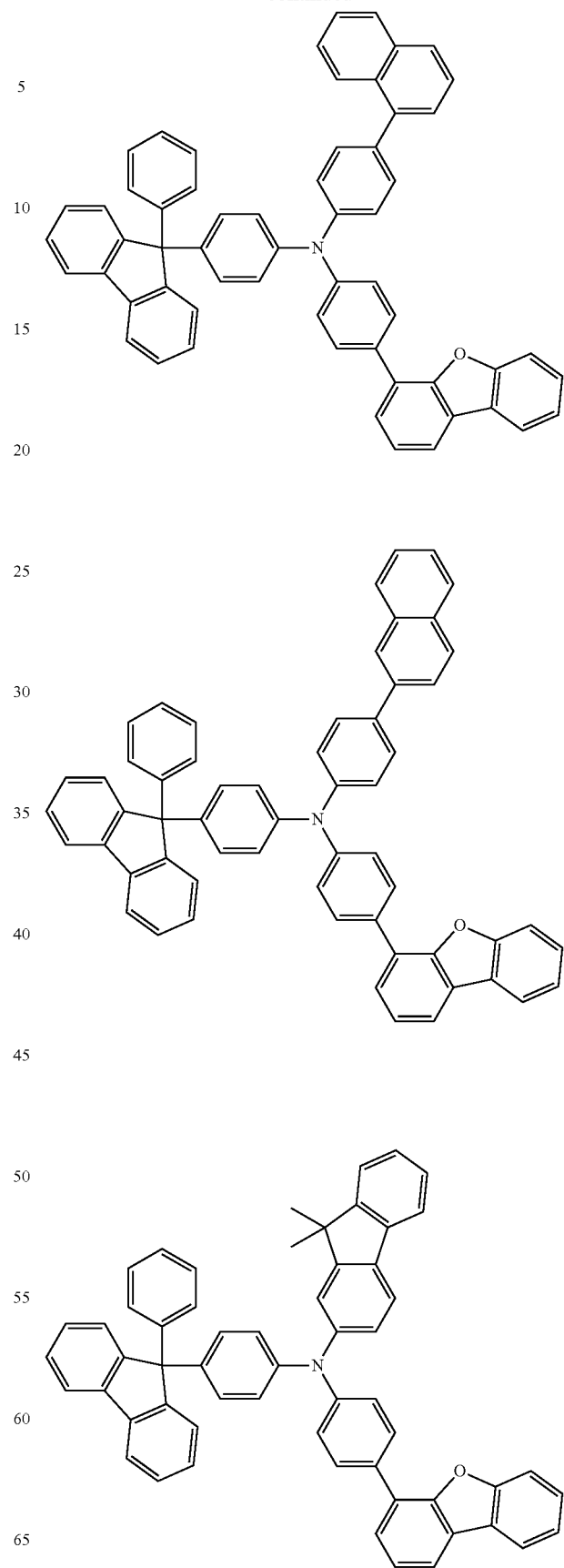

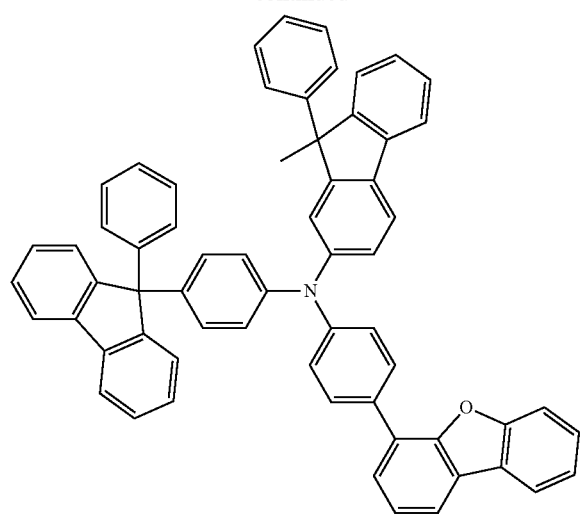
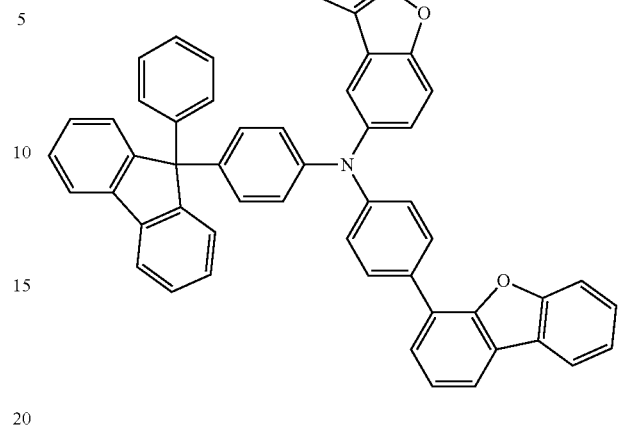
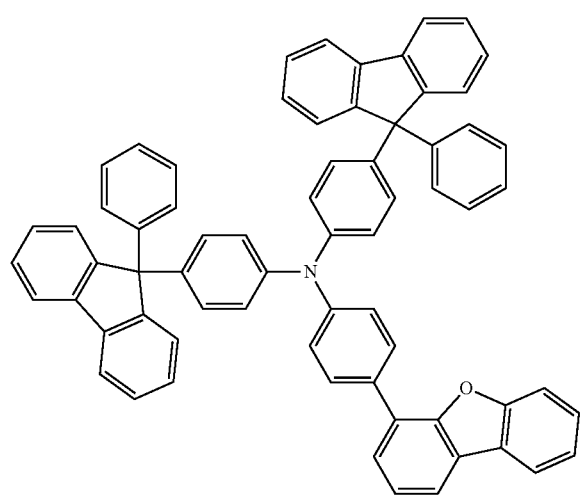
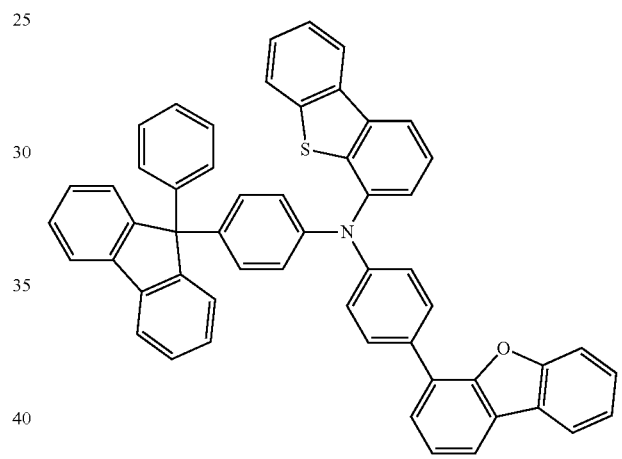
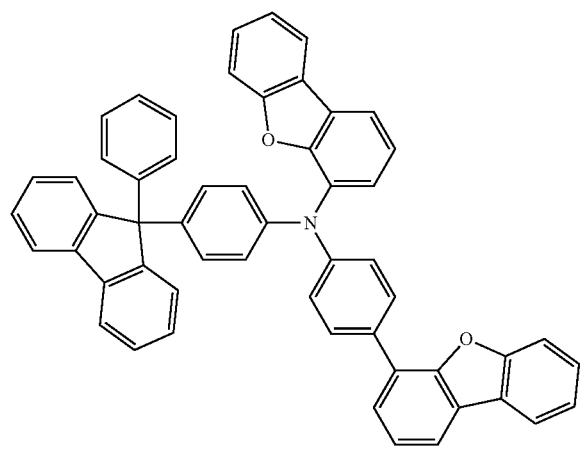
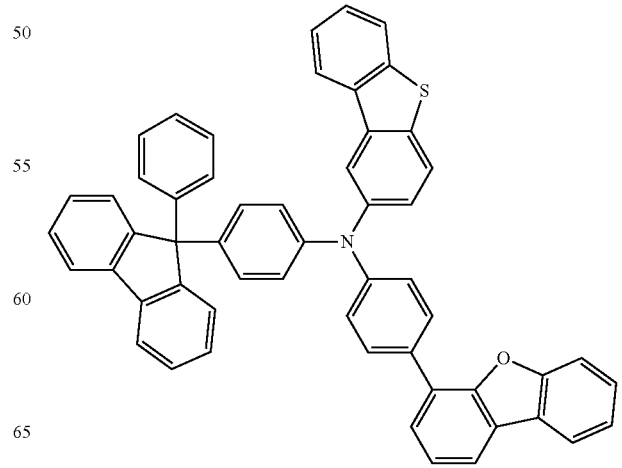

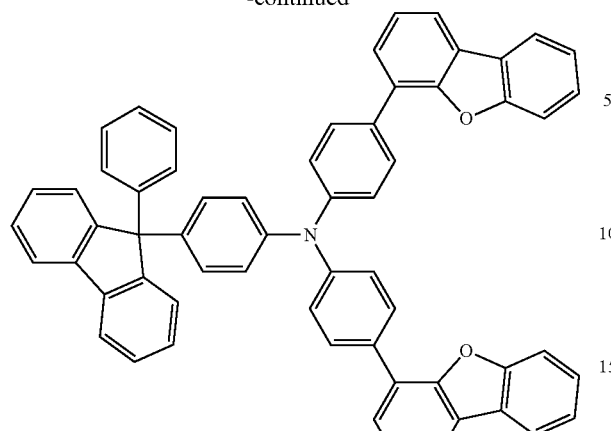
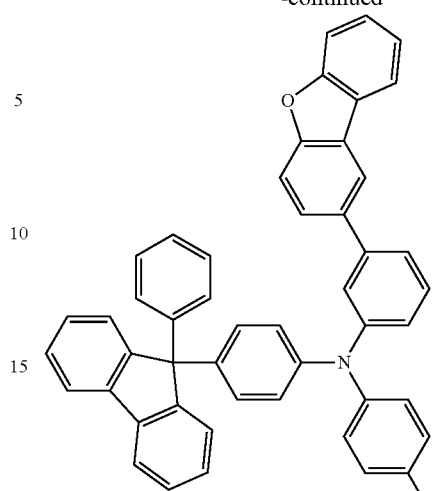
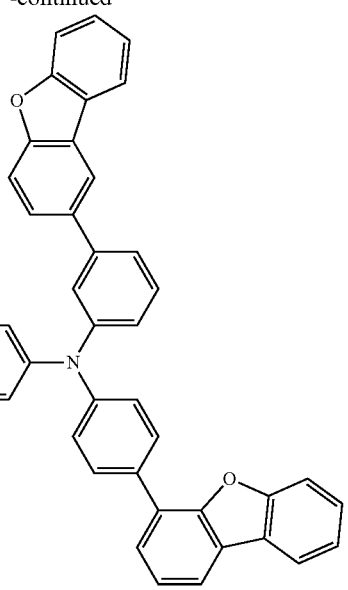
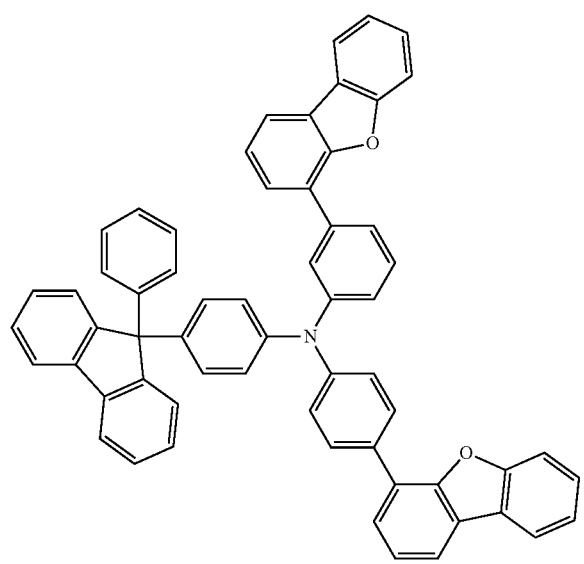
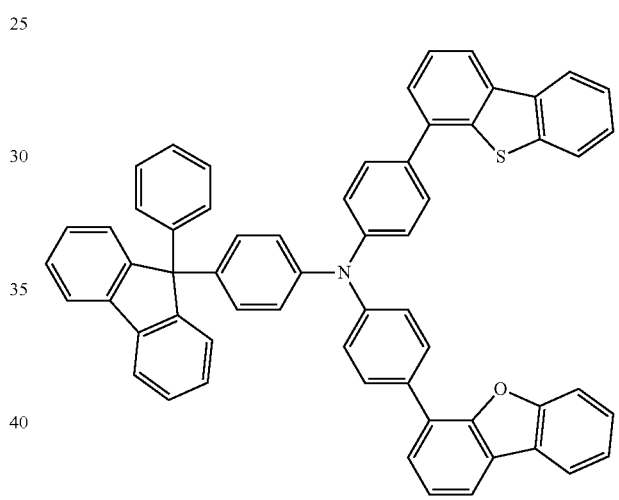
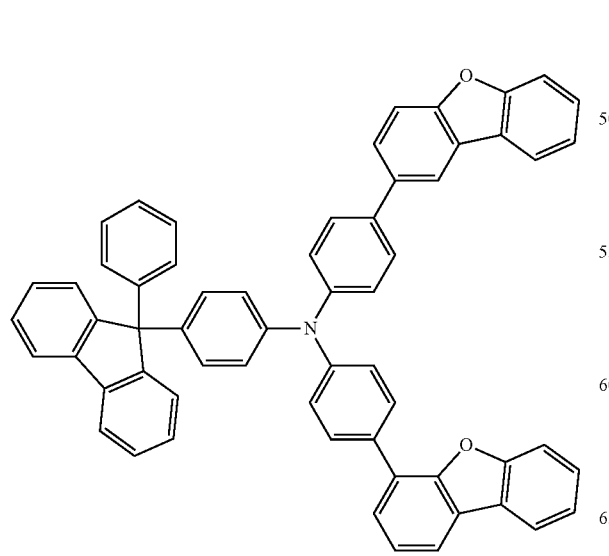
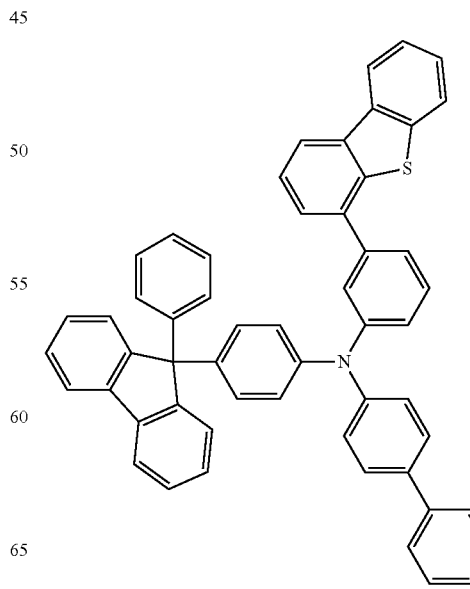

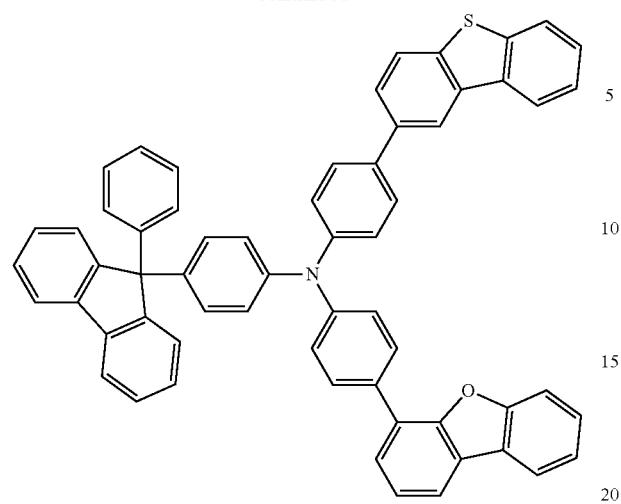
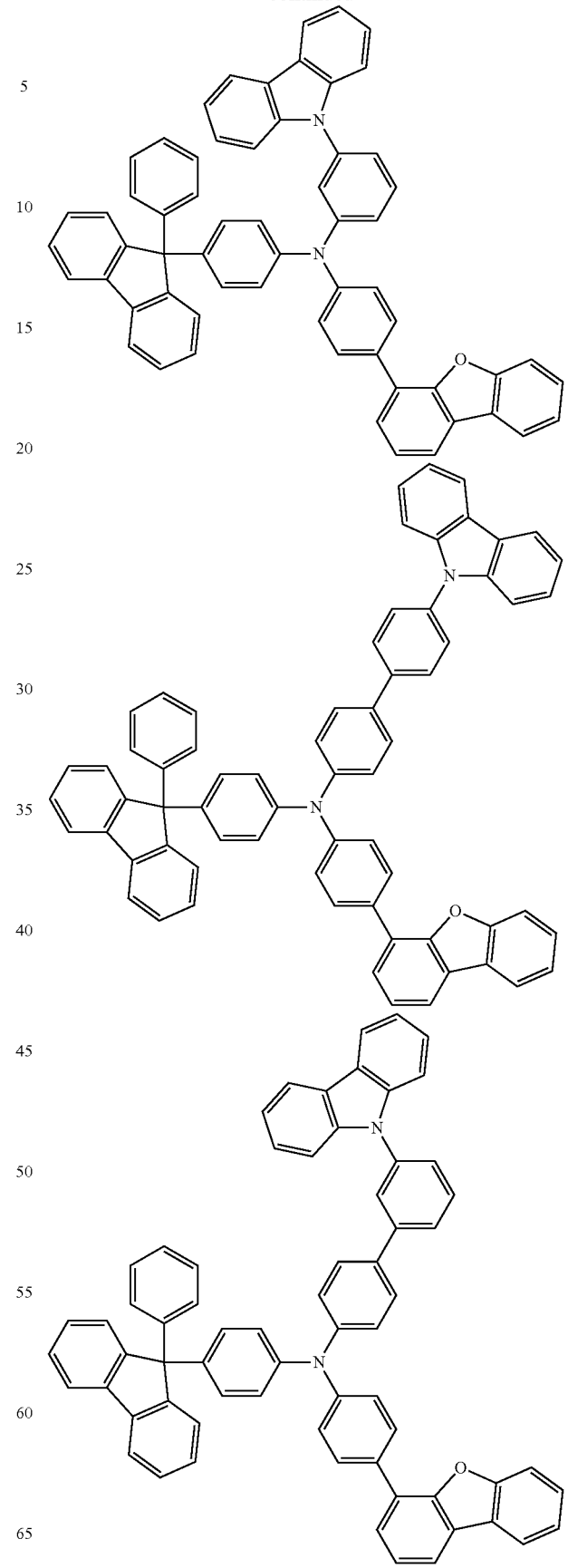

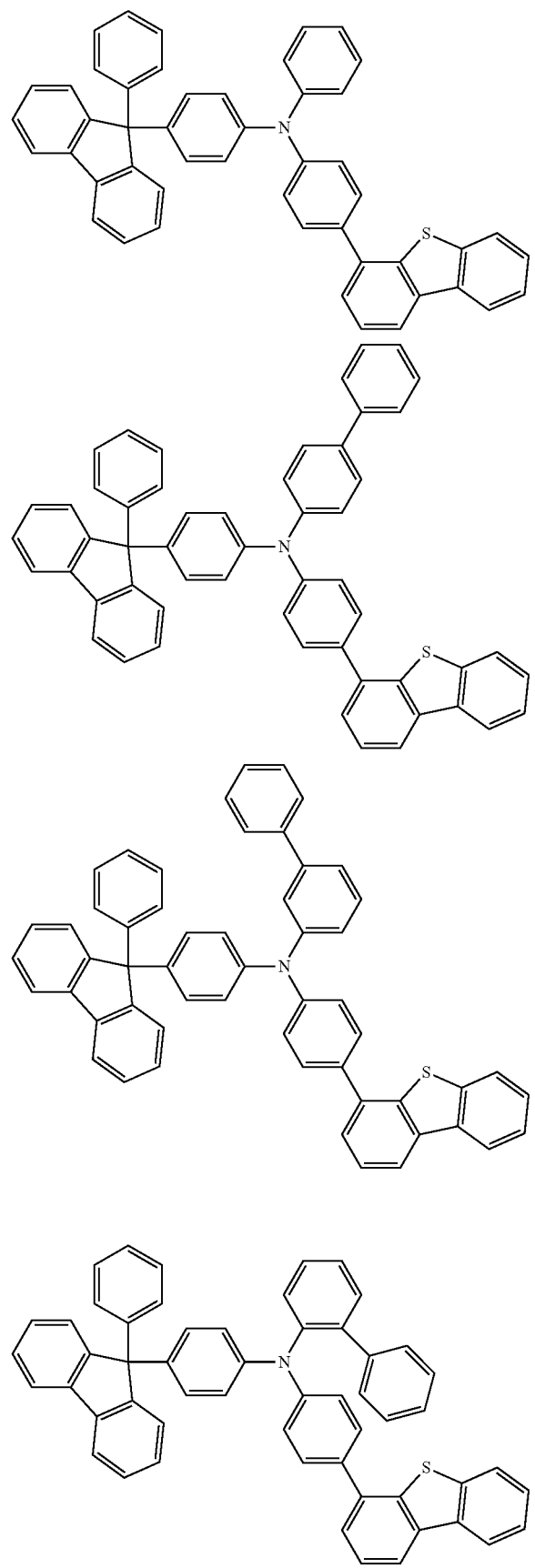
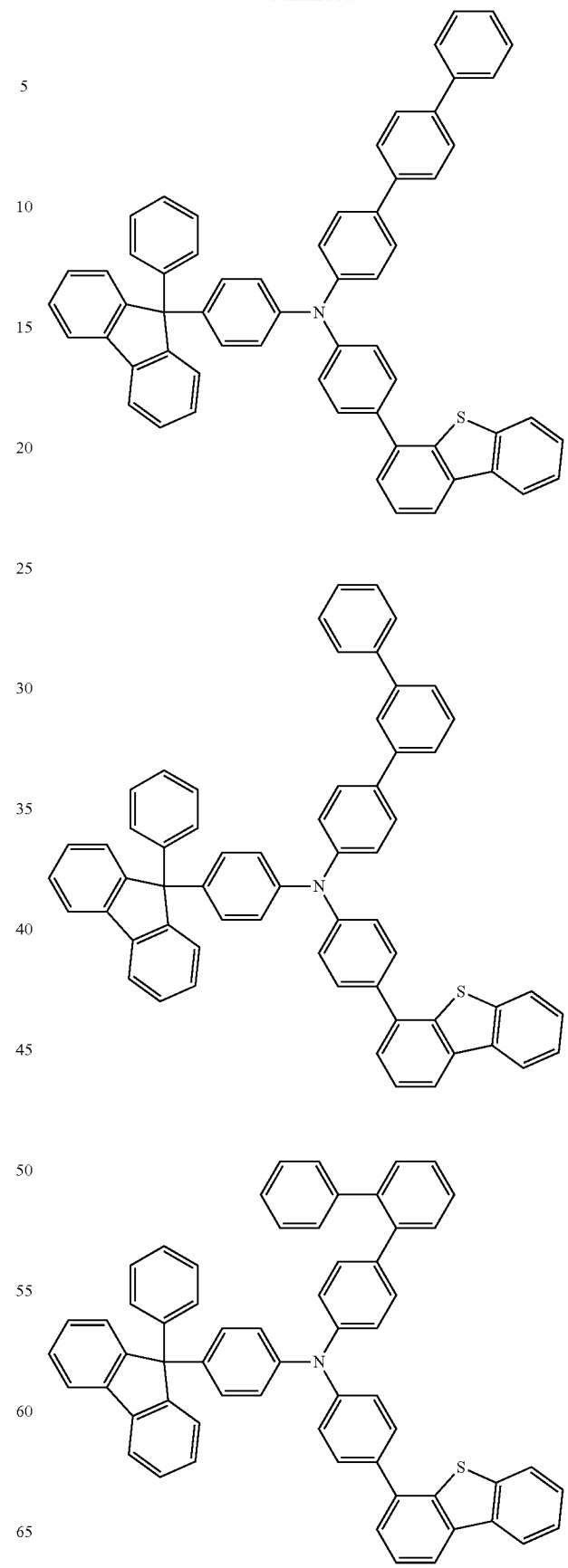

51
-continued
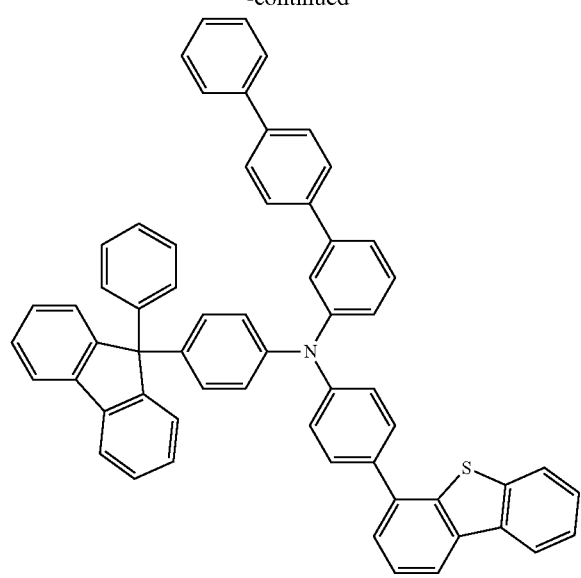
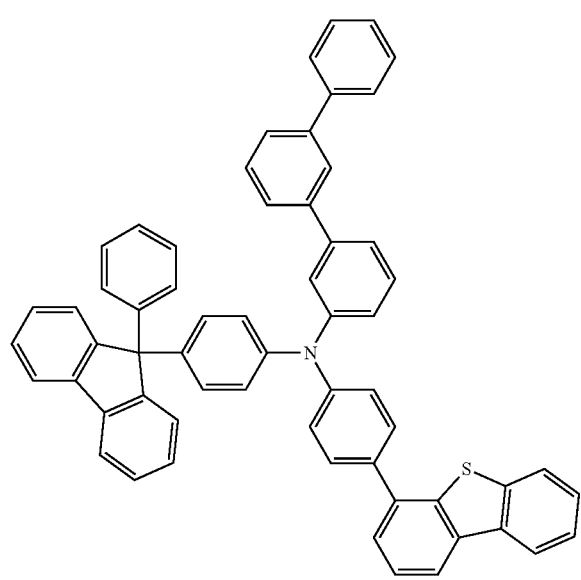
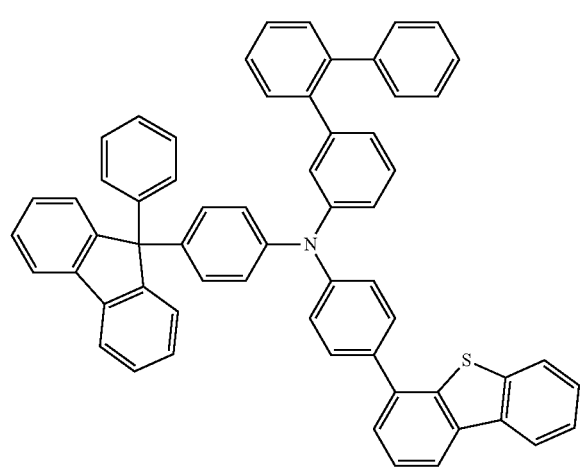
52
-continued
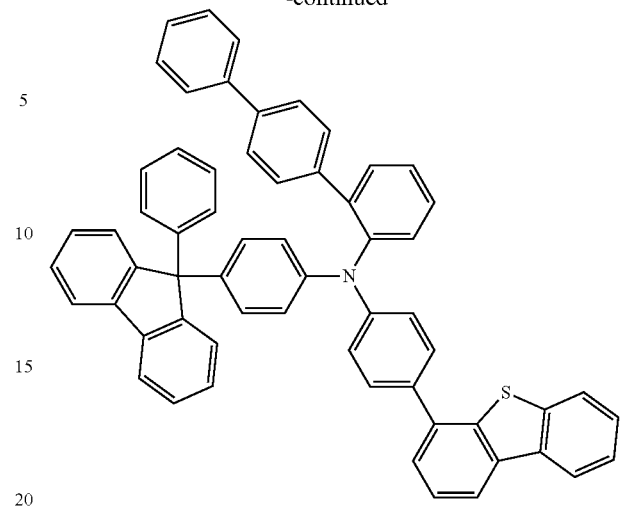
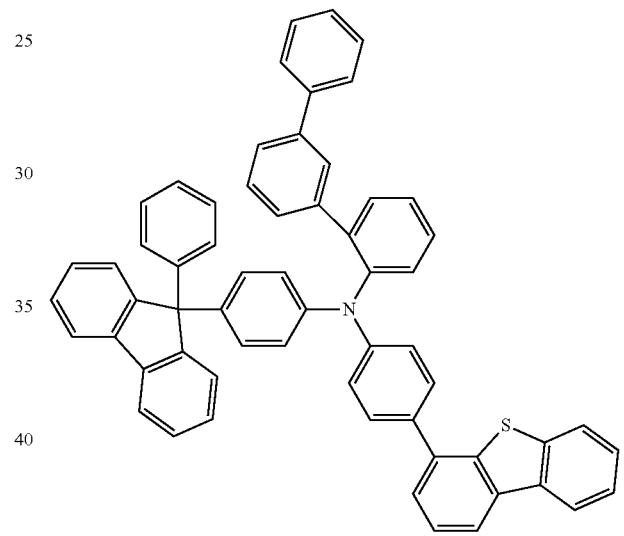
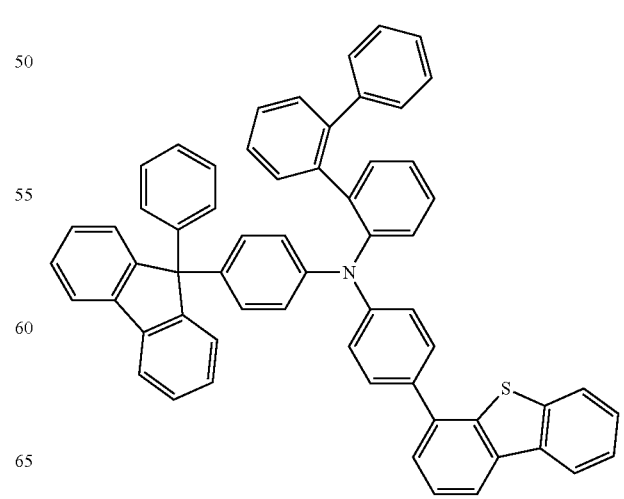

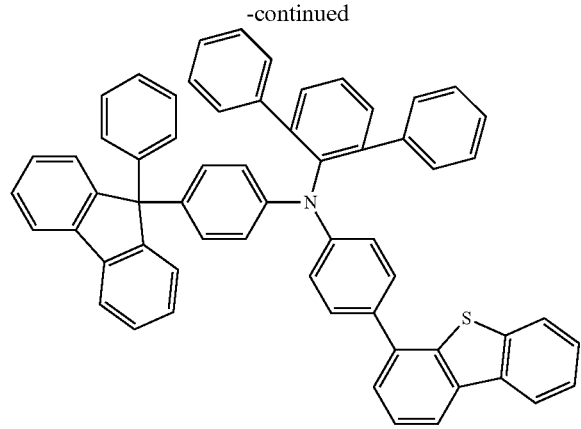
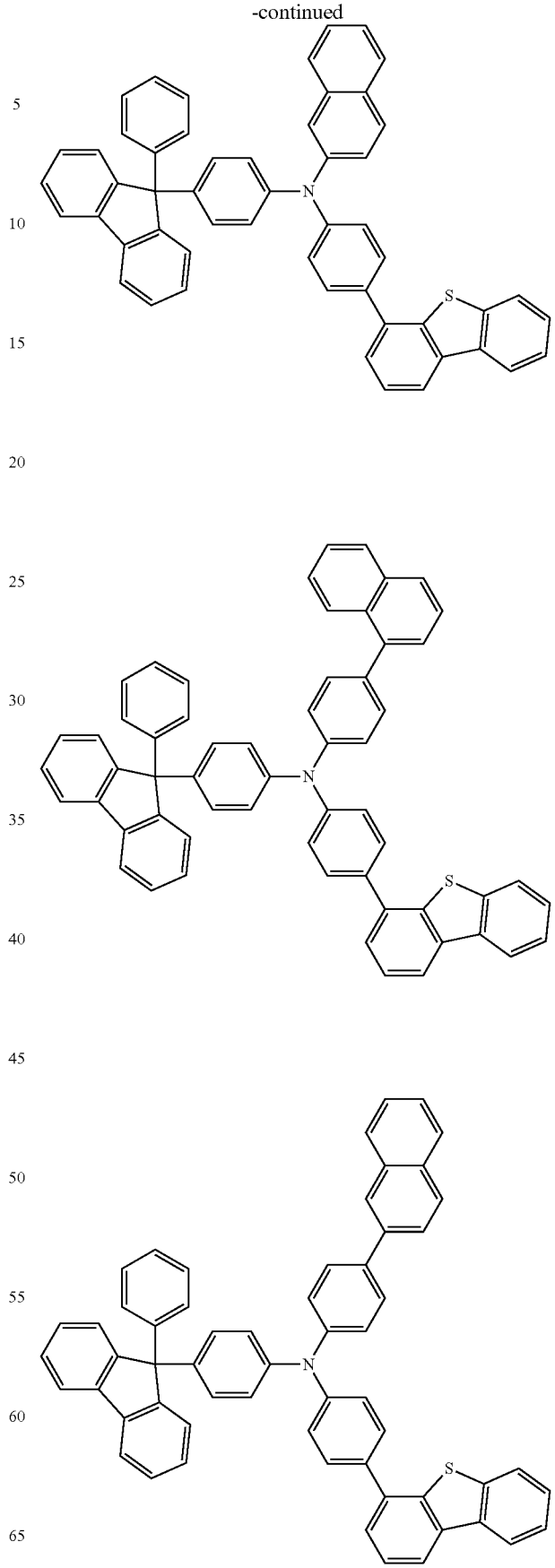

55
-continued
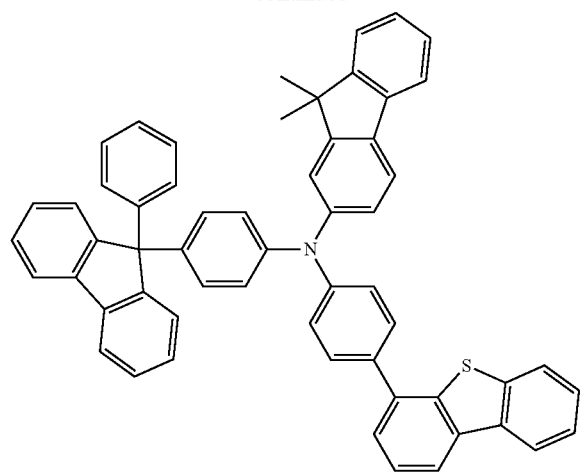
56
-continued
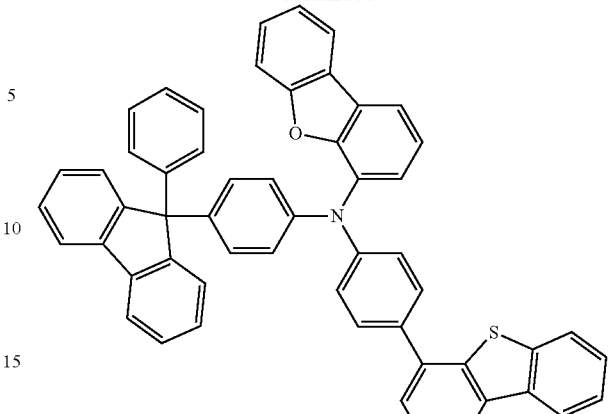
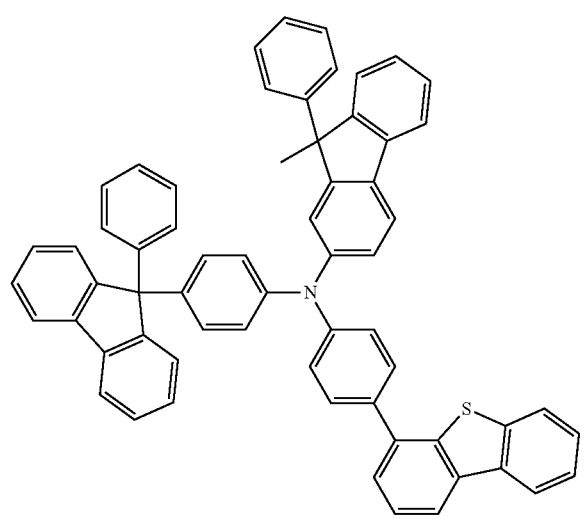
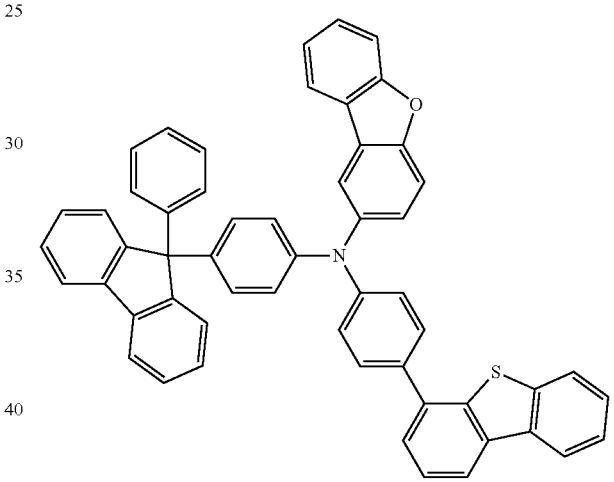
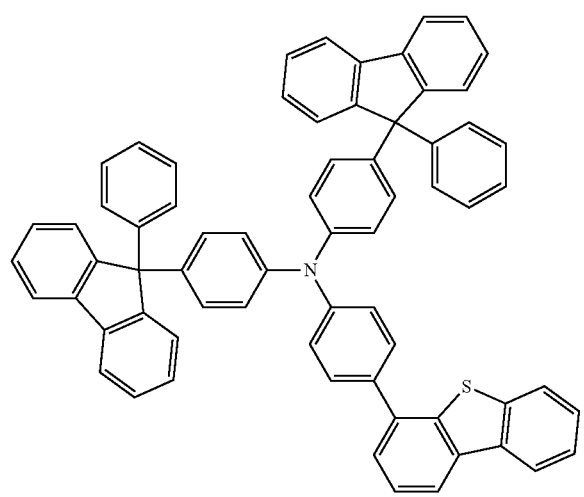
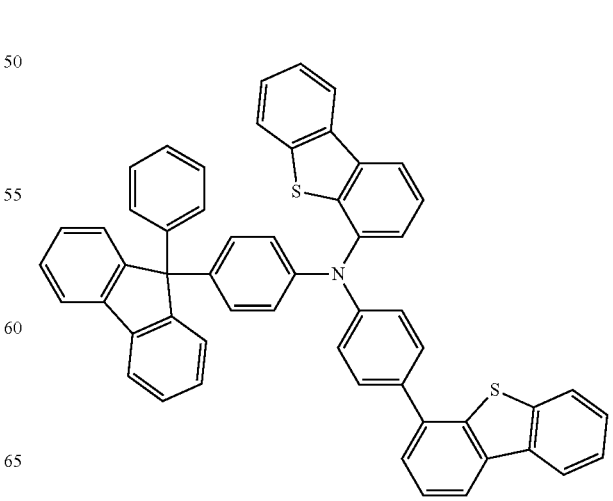

57
-continued
58
-continued
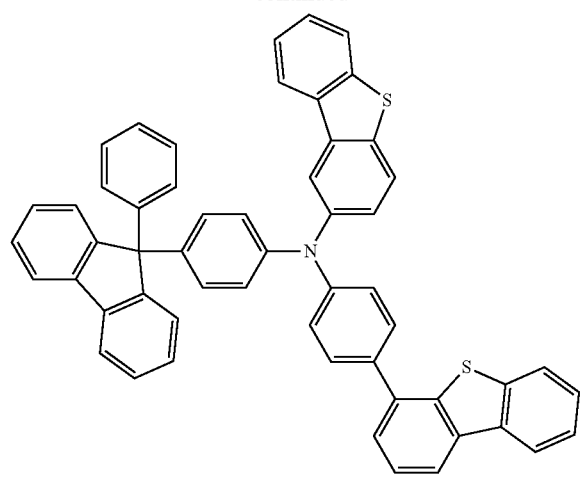
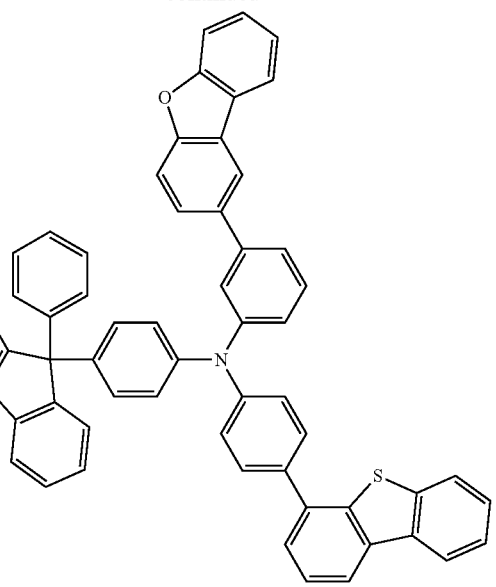
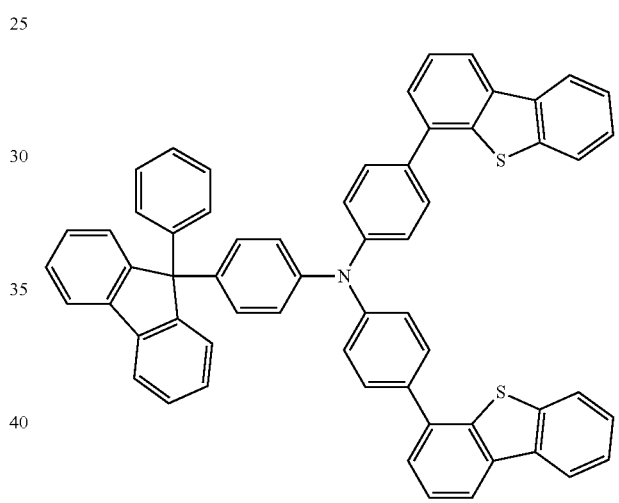
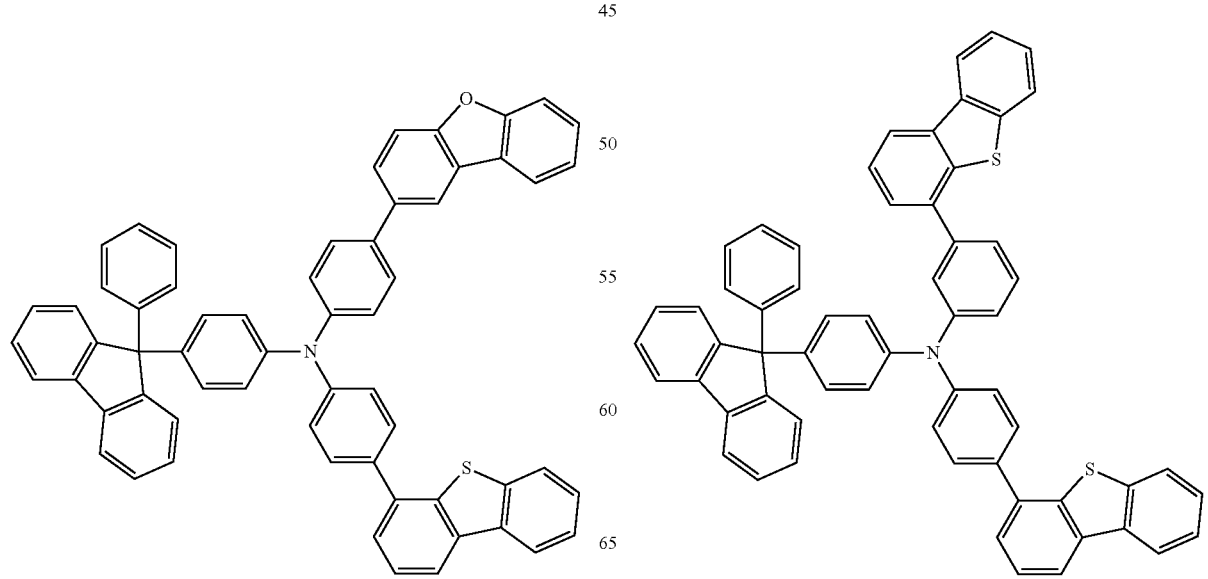

59
-continued
60
-continued
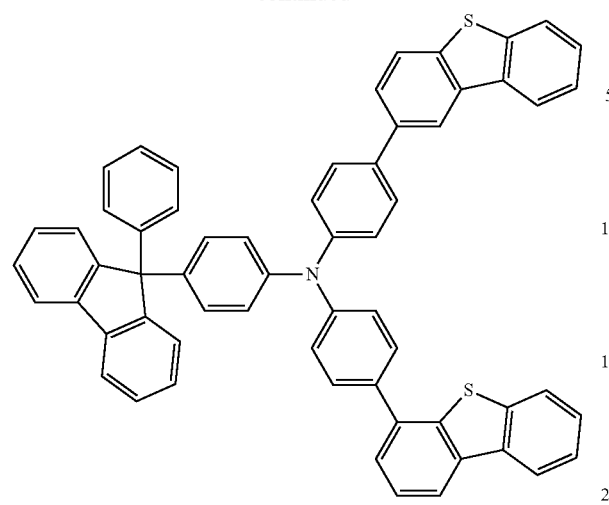
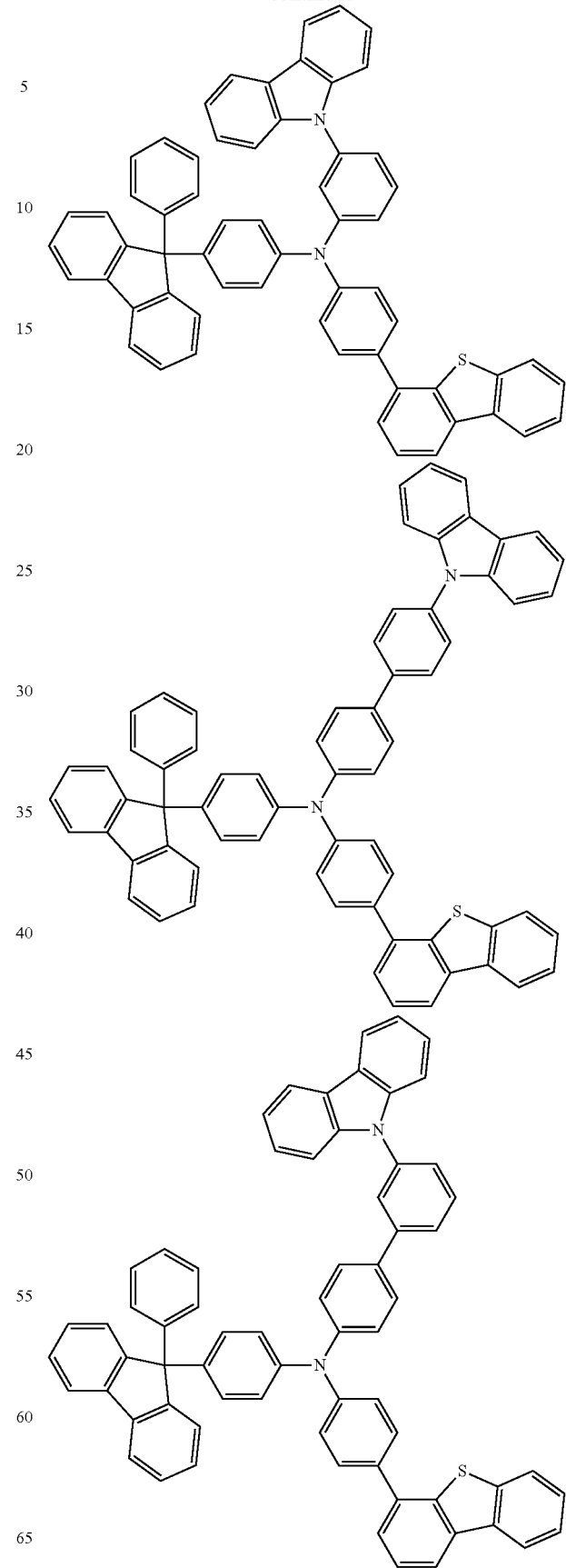

61
-continued
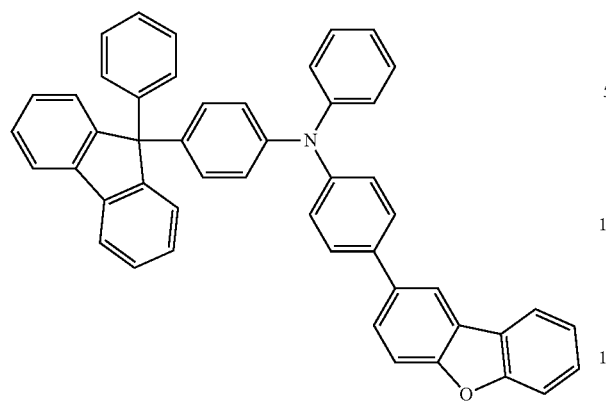
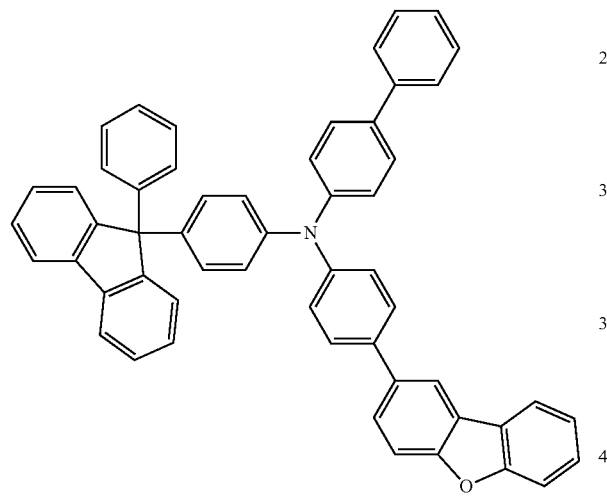
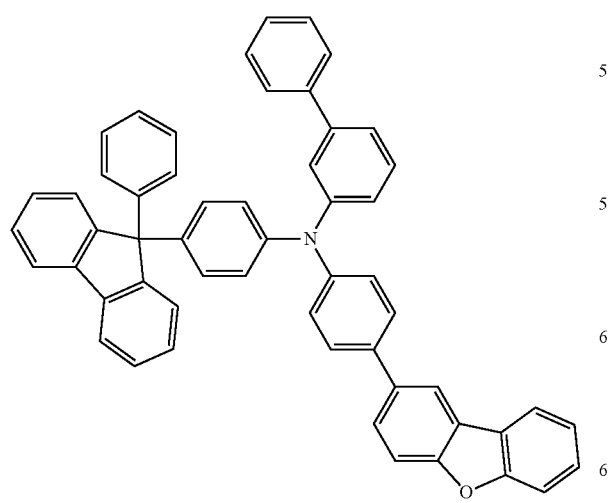
62
-continued
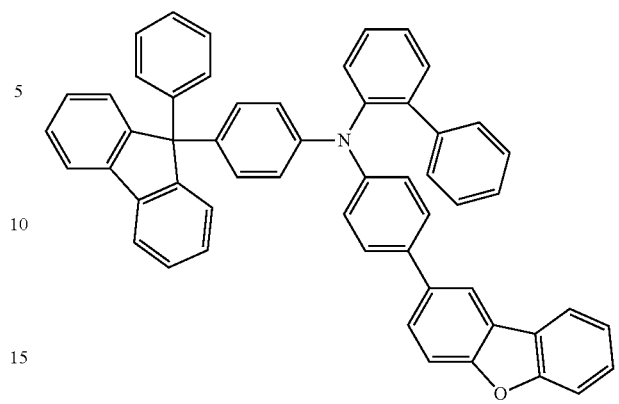
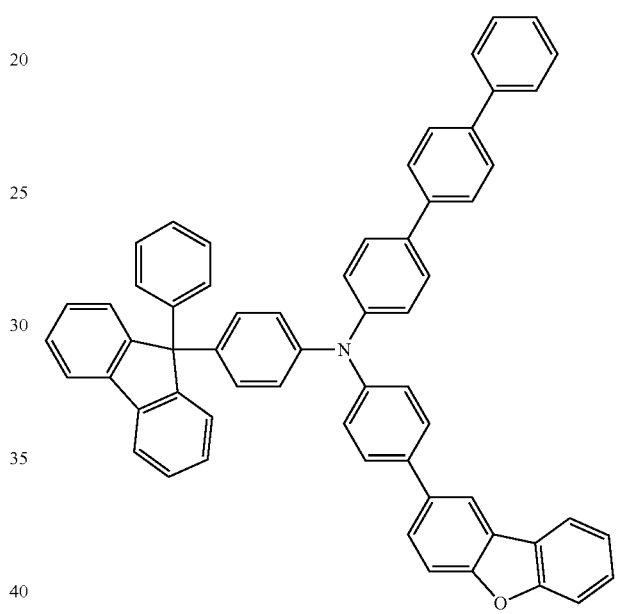

63
-continued
64
-continued
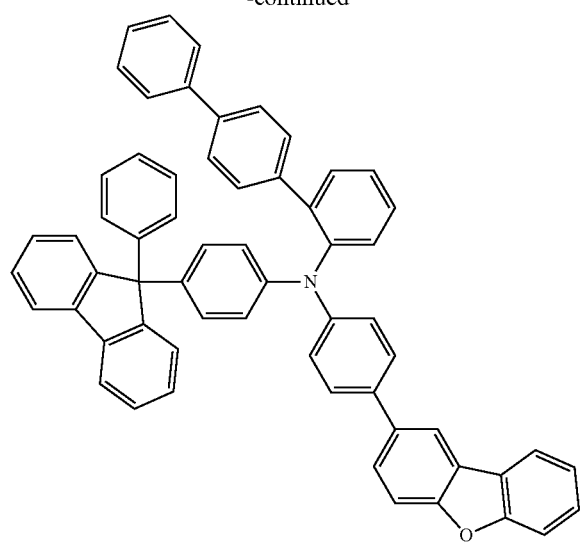
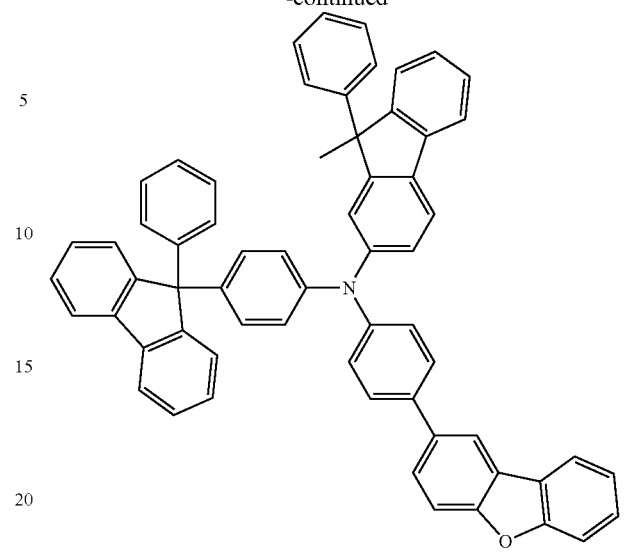
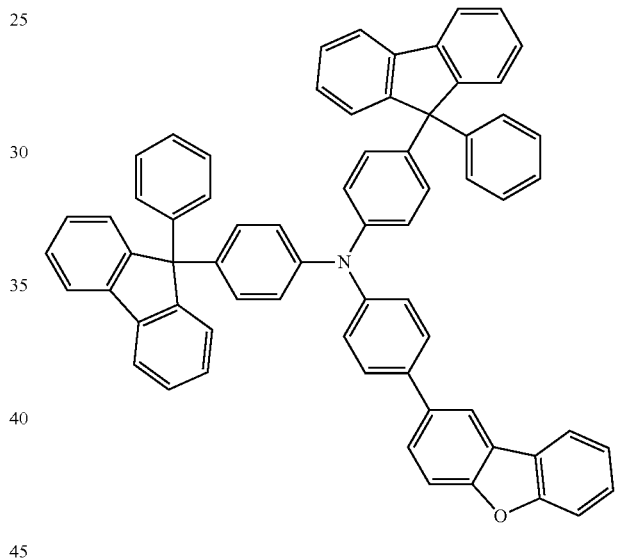
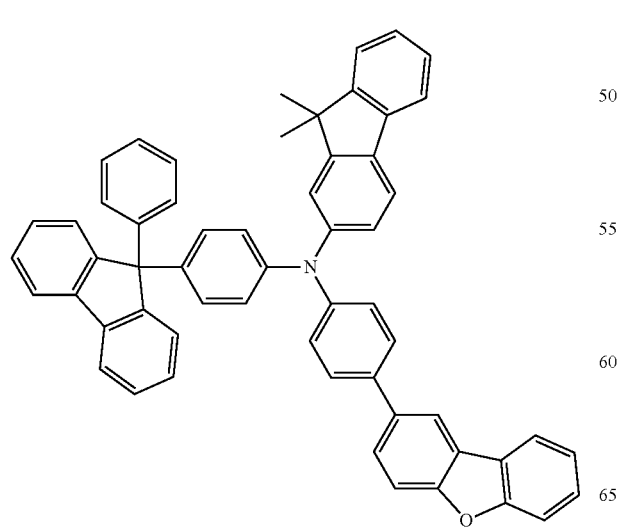

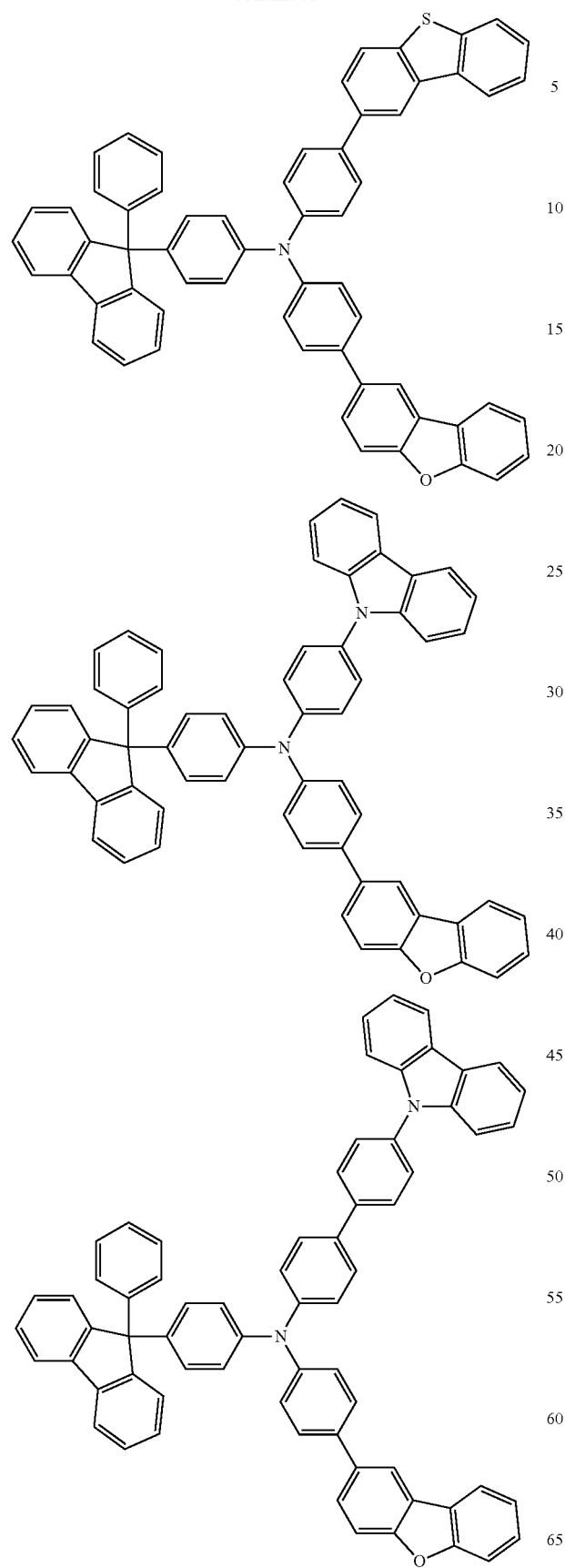
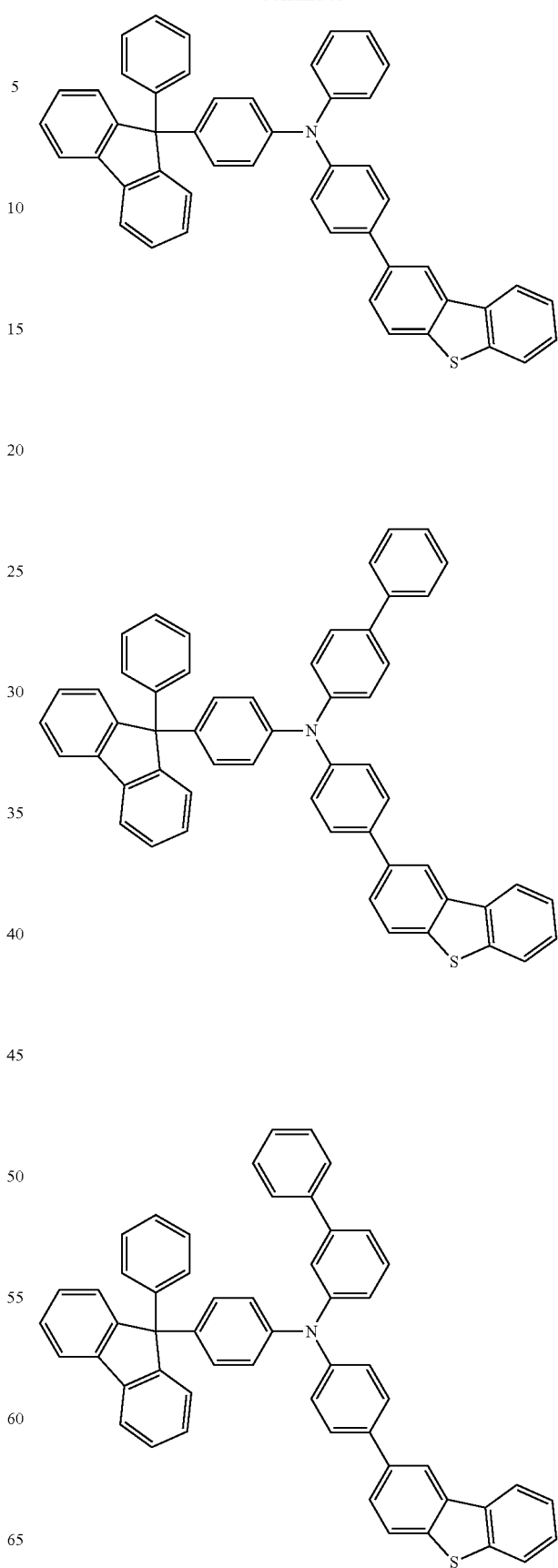

67
-continued
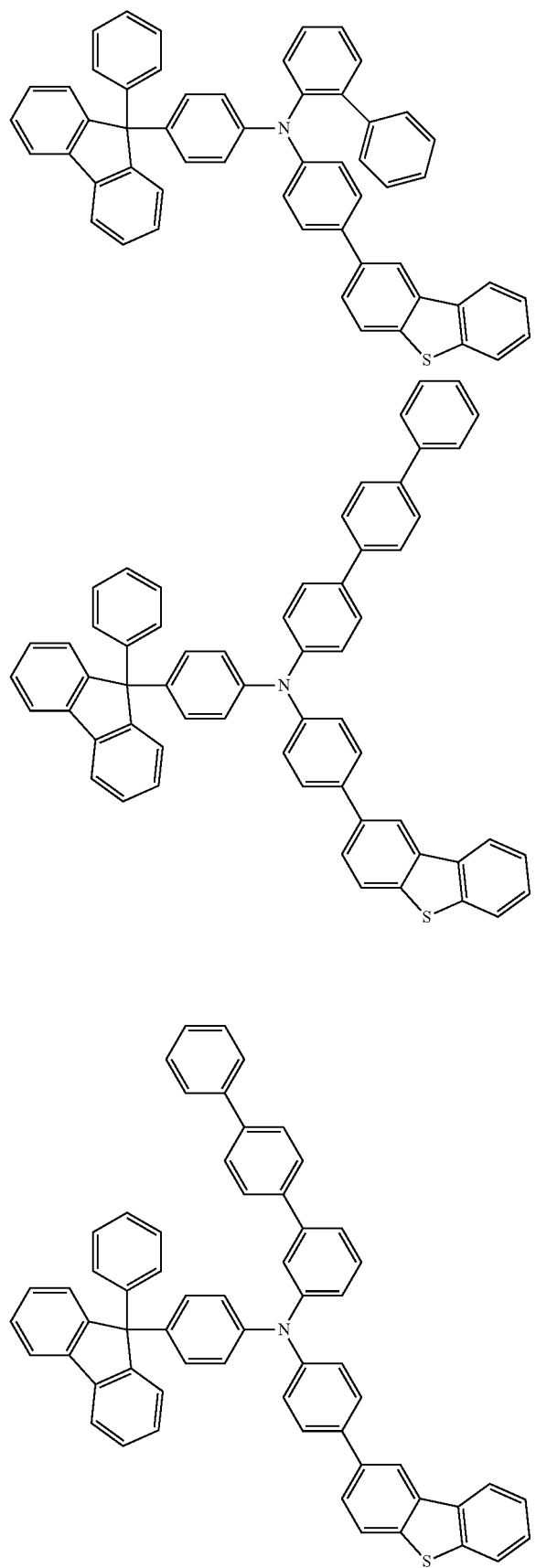
68
-continued
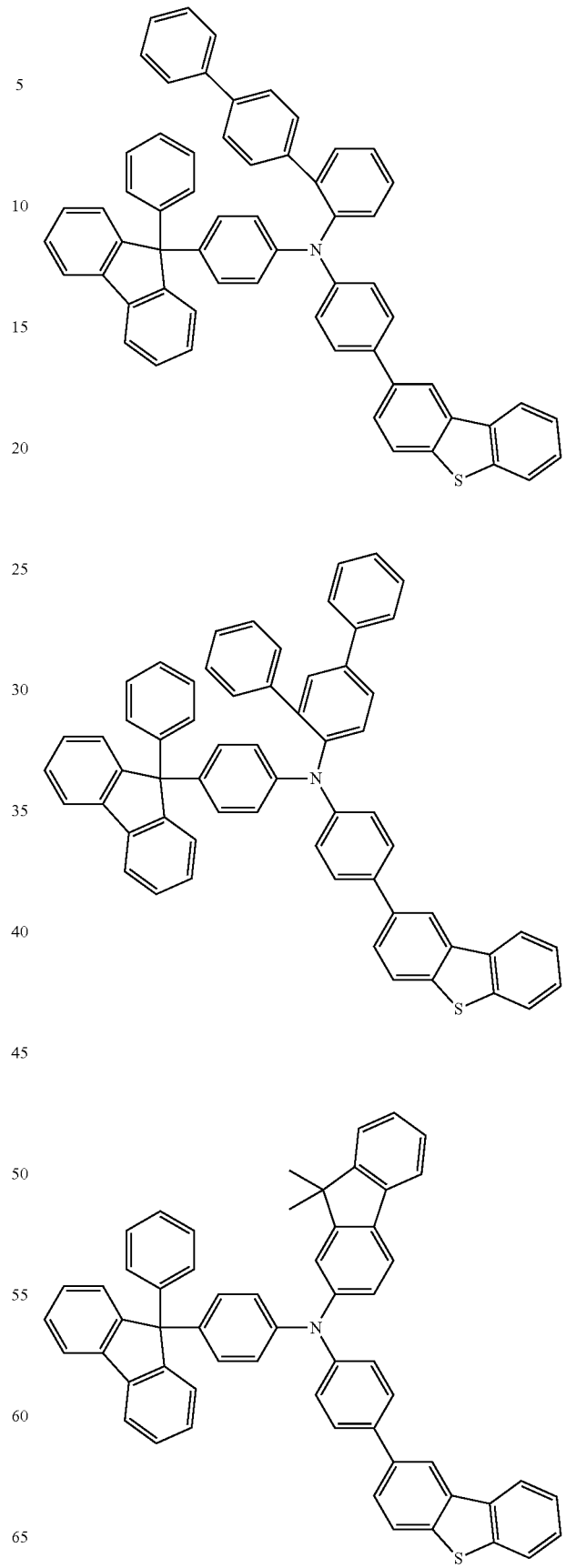

69
-continued
70
-continued
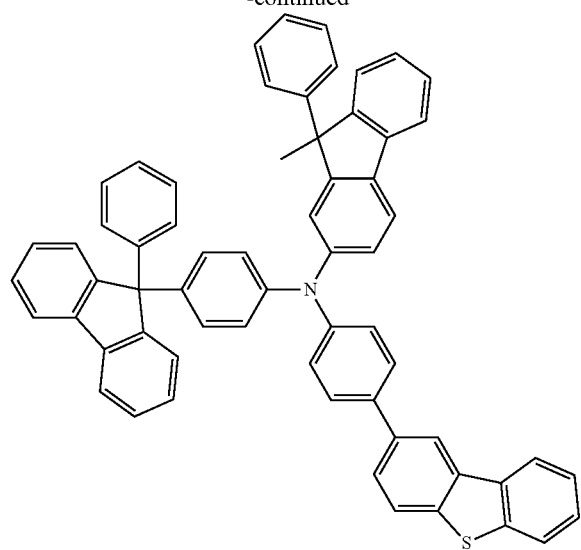
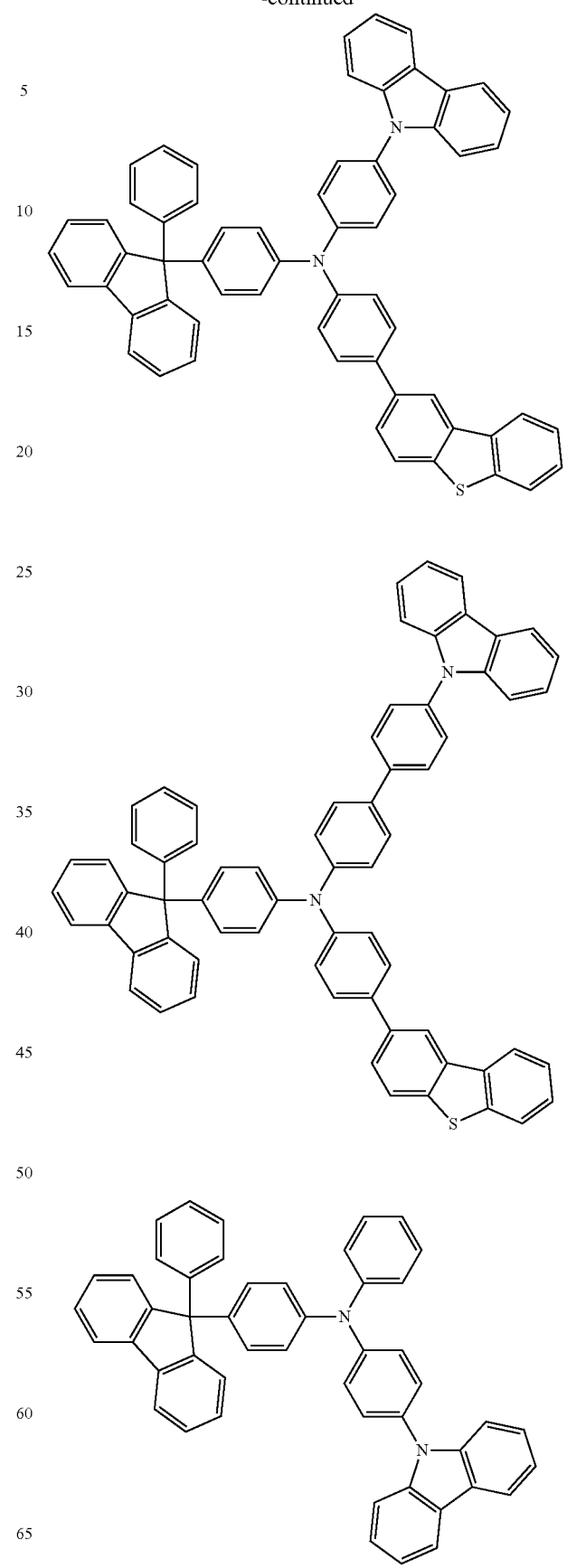

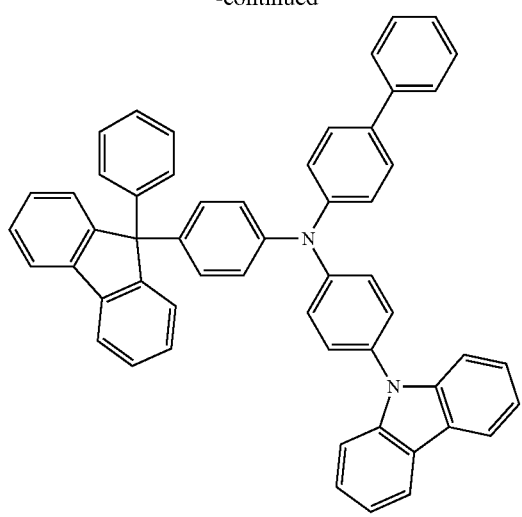
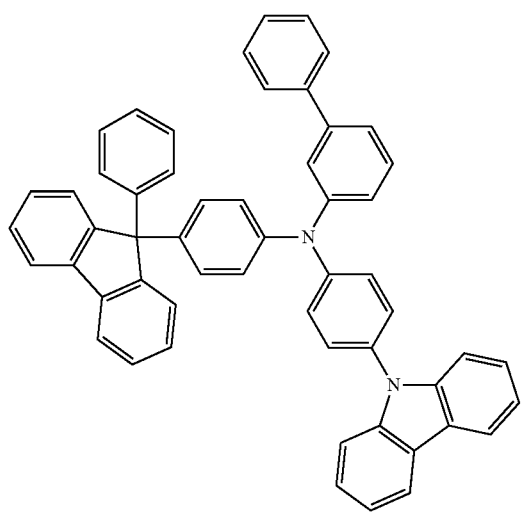
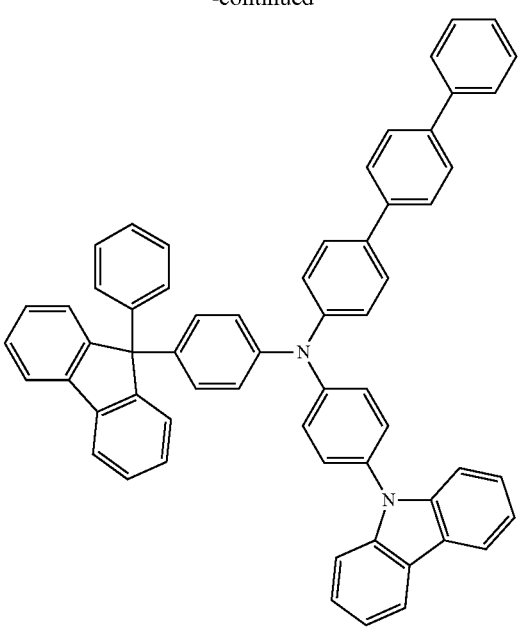
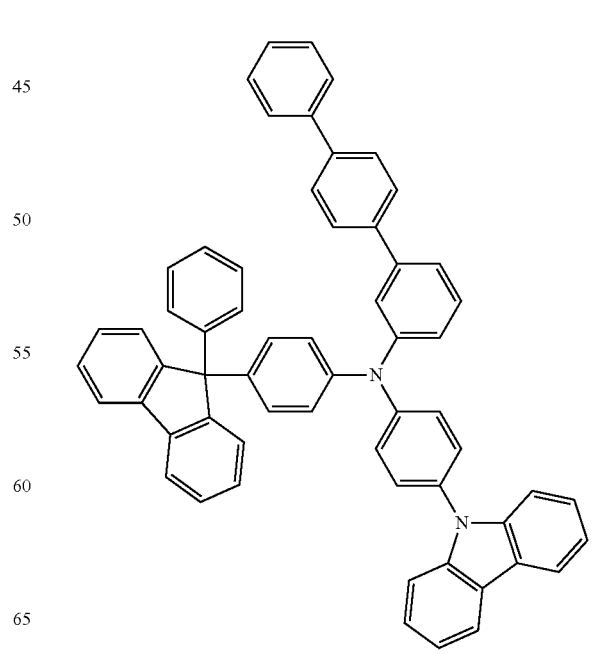

73
-continued
74
-continued
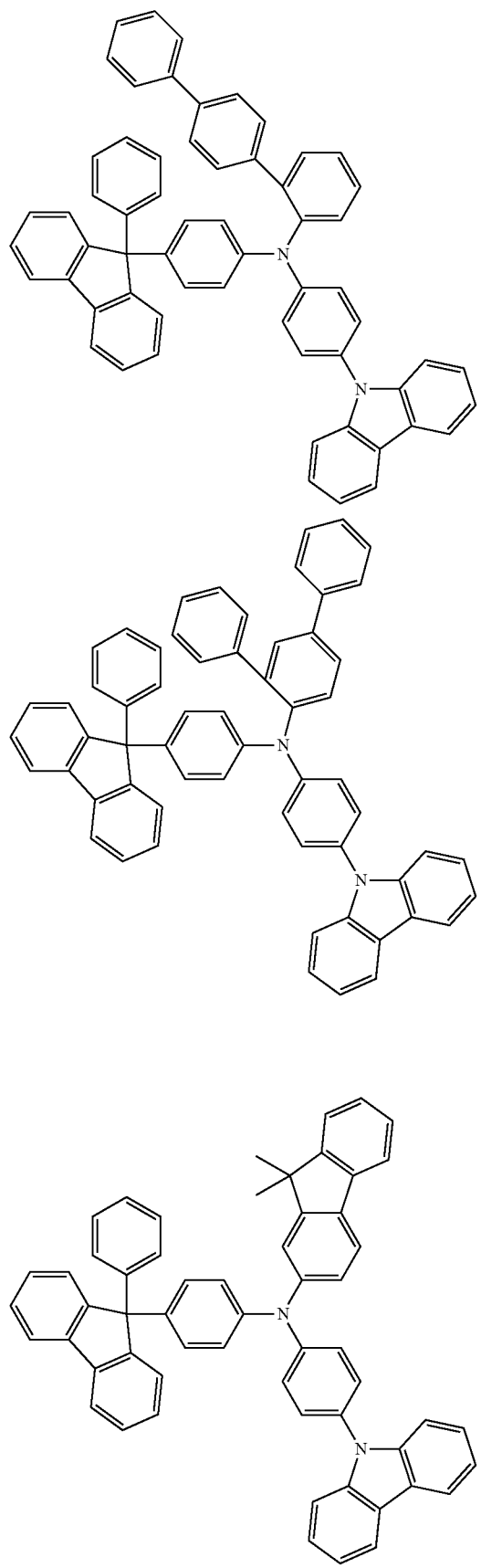
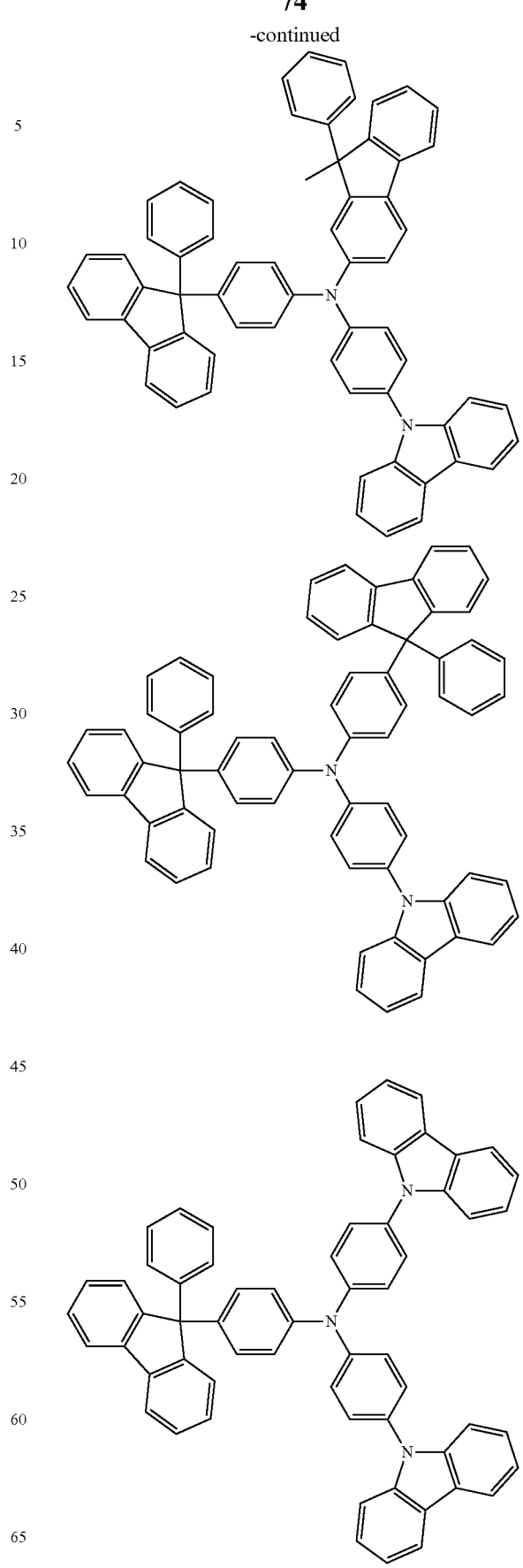

75
-continued
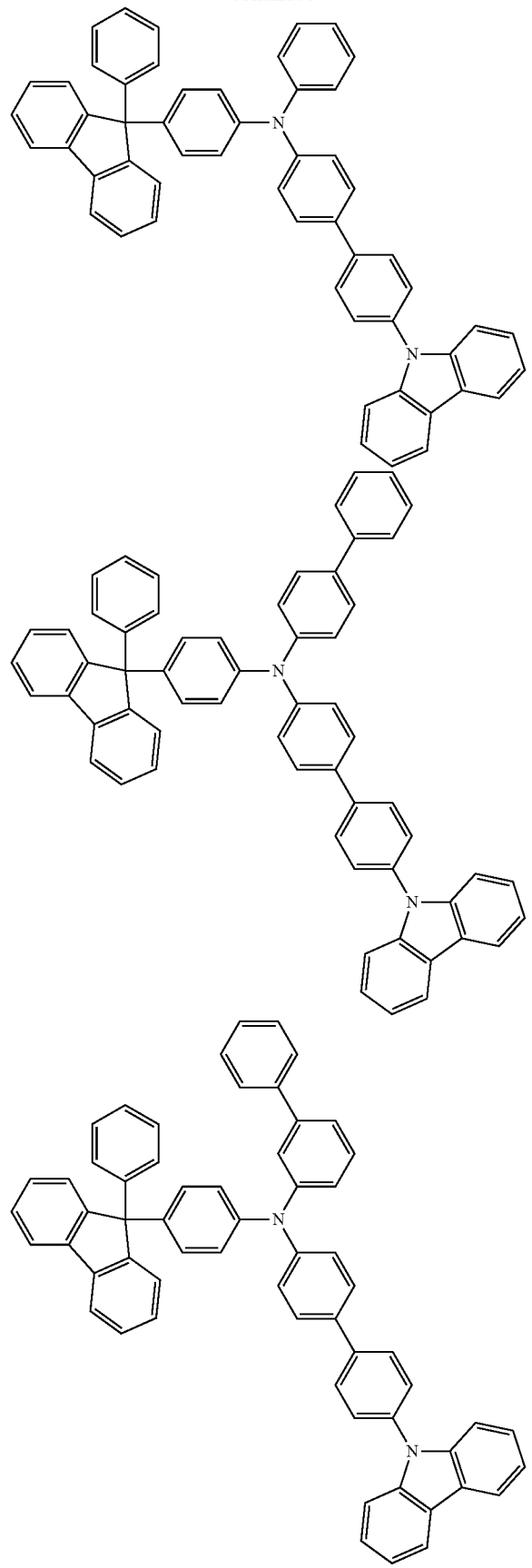
76
-continued

77
-continued
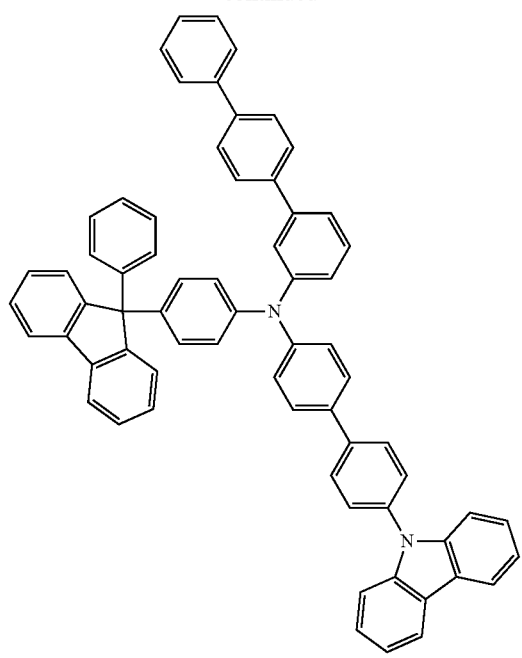
78
-continued
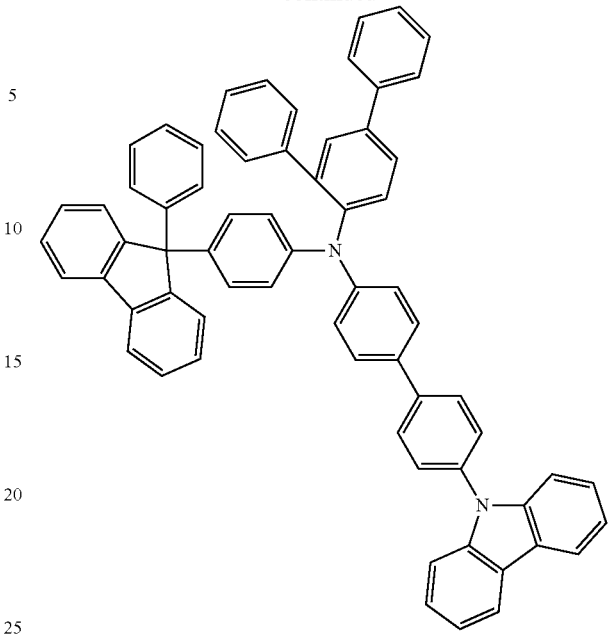
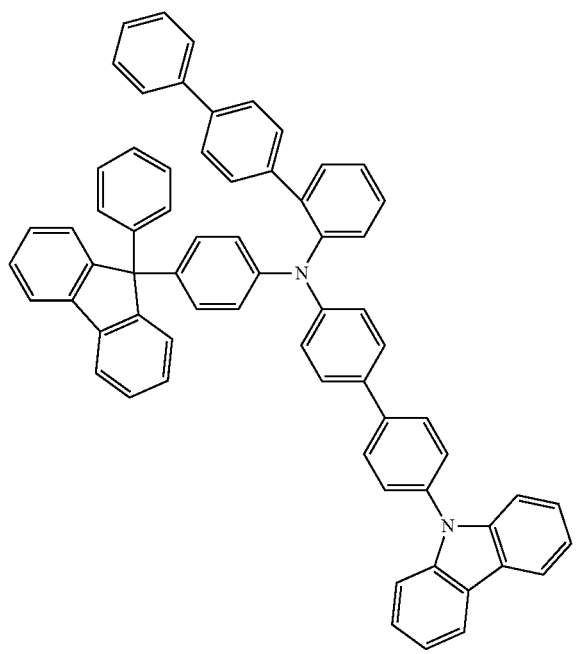
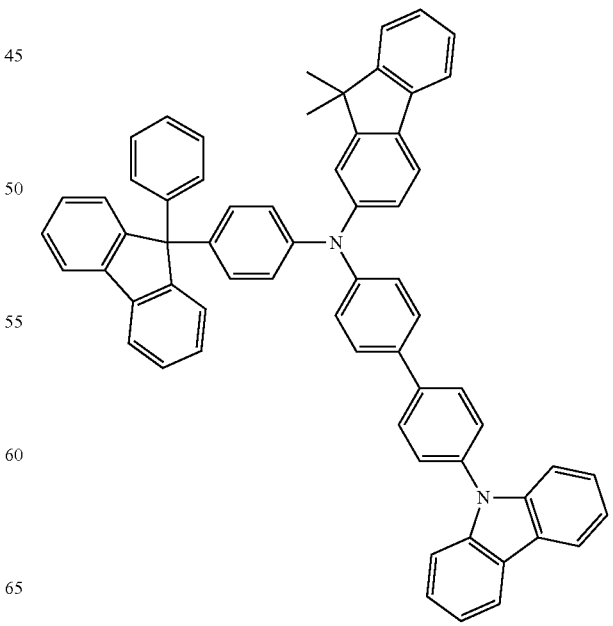

79
-continued
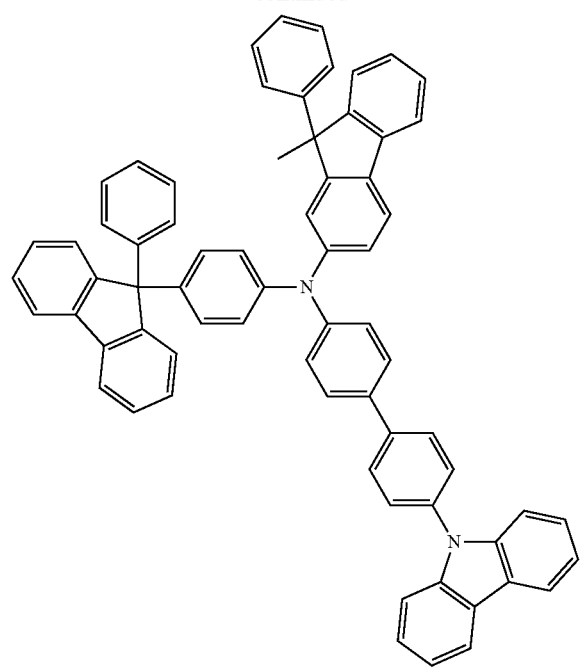
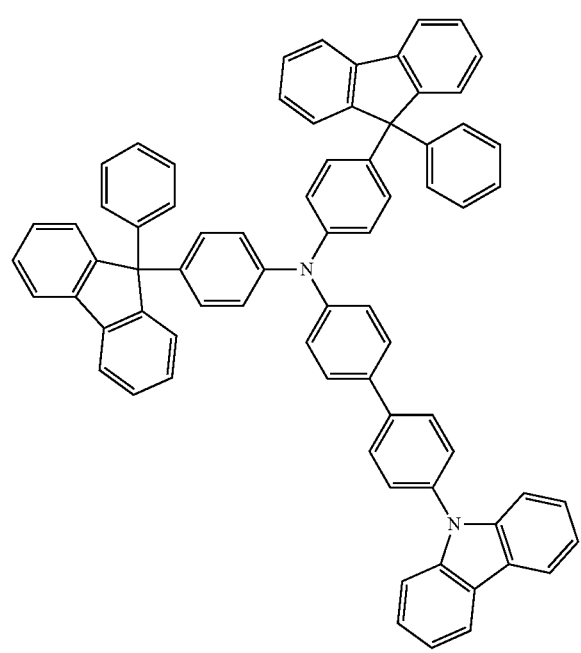
80
-continued
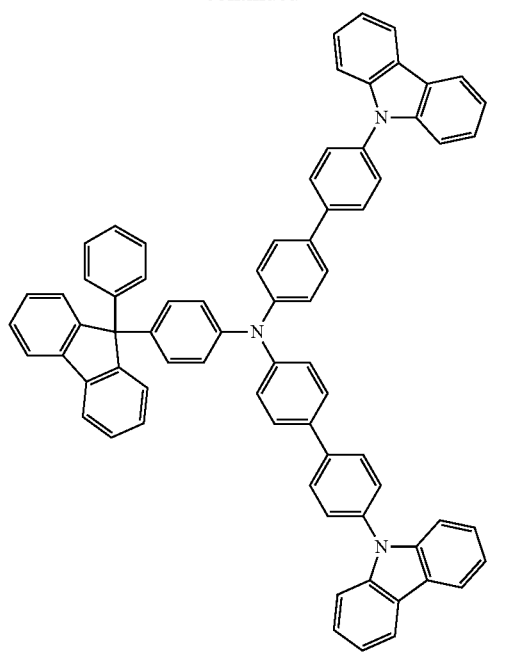 [SMILES: c1ccc(C2(c3ccc(N(c4ccc(-c5ccc(-n6c7ccccc7c7ccccc76)cc5)cc4)c4ccc(-c5ccc(-n6c7ccccc7c7ccccc76)cc5)cc4)cc3)c3ccccc3-c3ccccc32)cc1]
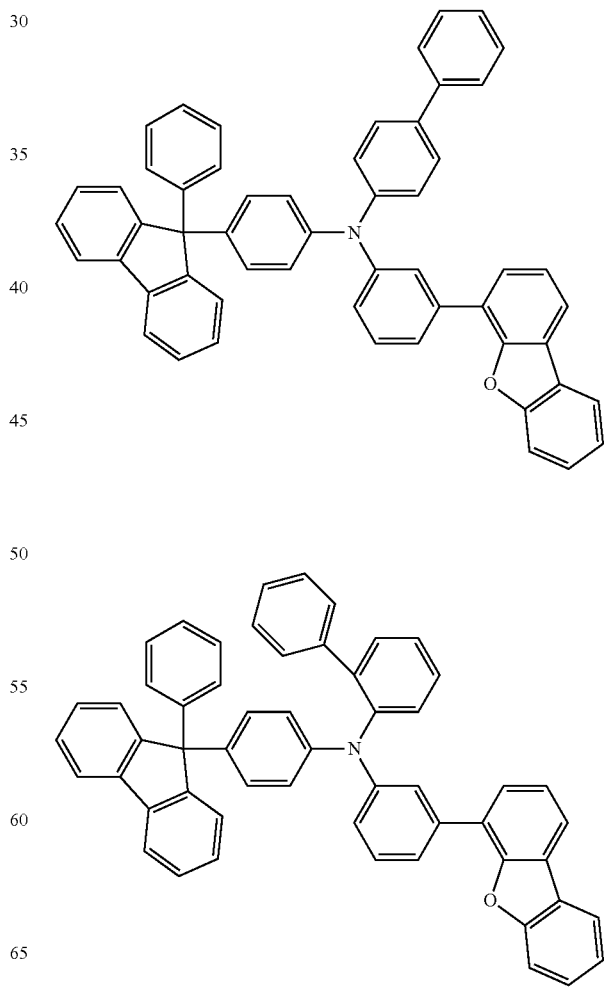

81
-continued
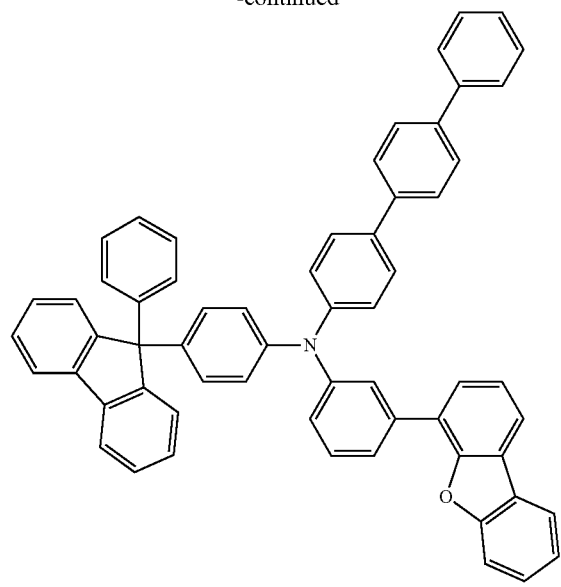
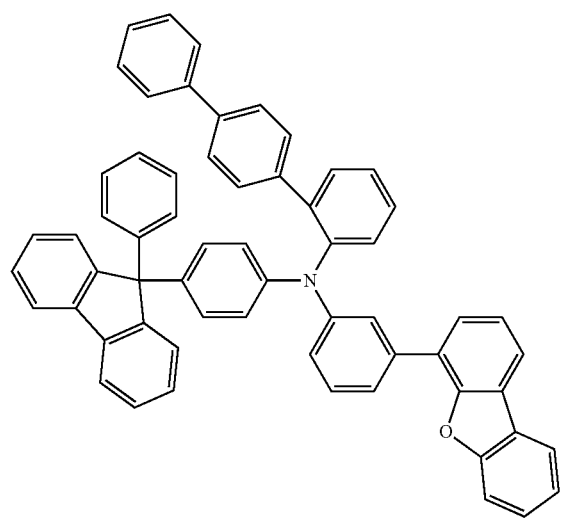
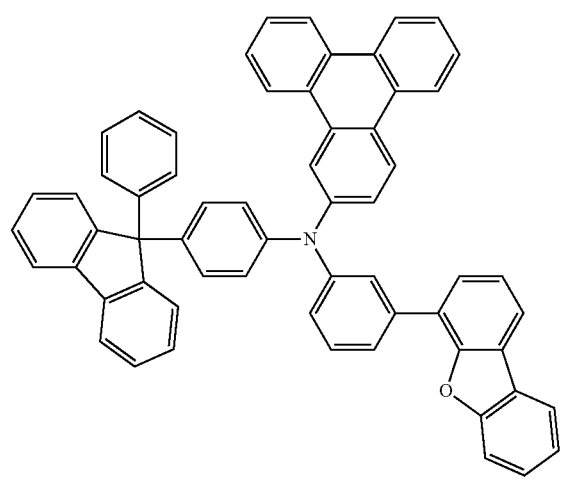
82
-continued
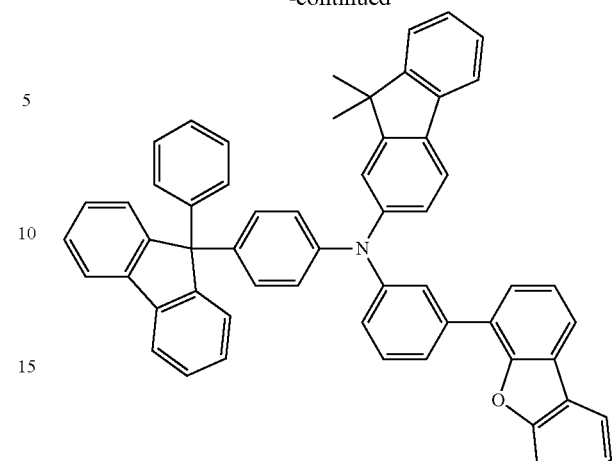
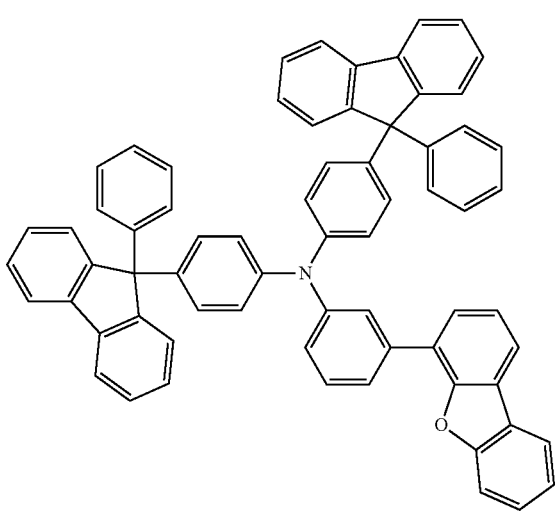
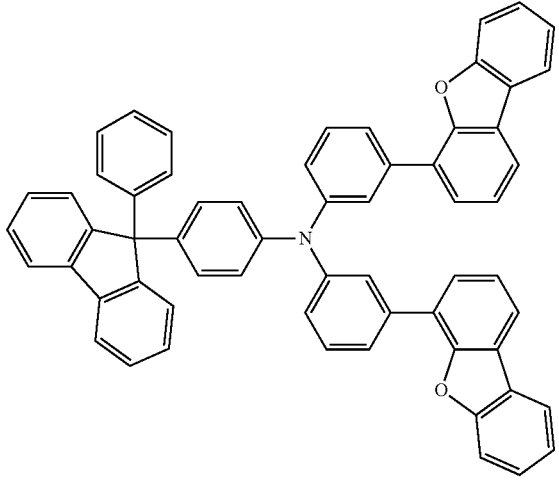

83
-continued
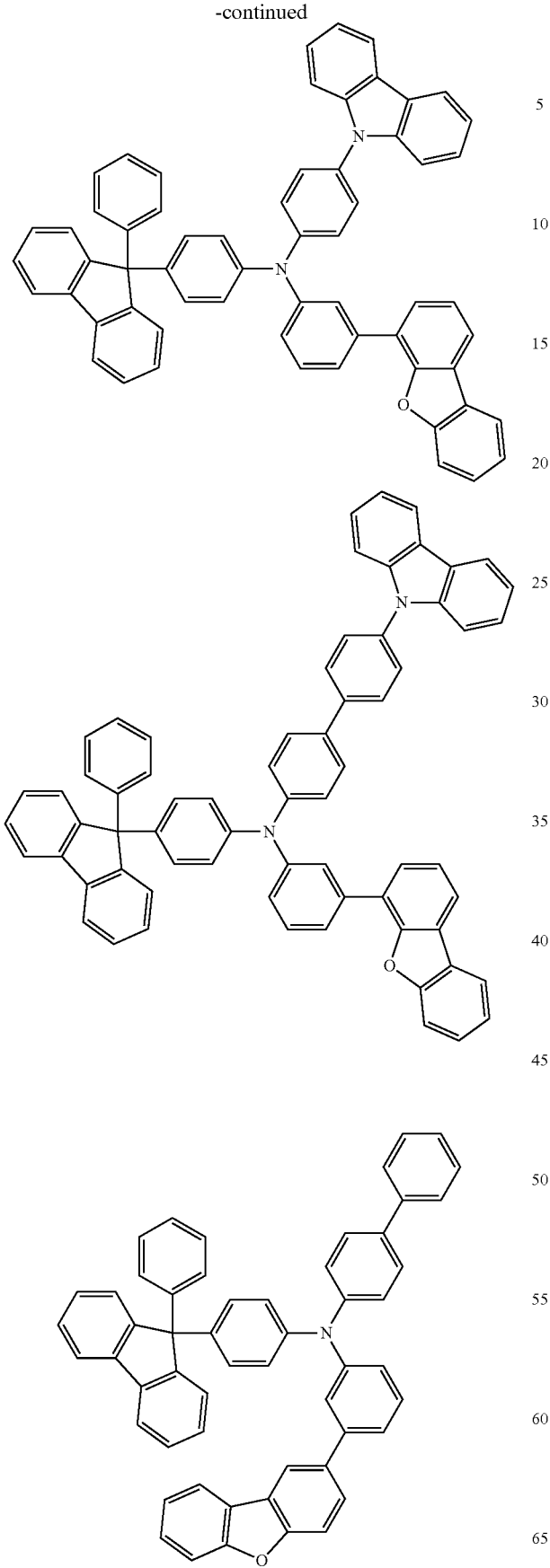
84
-continued
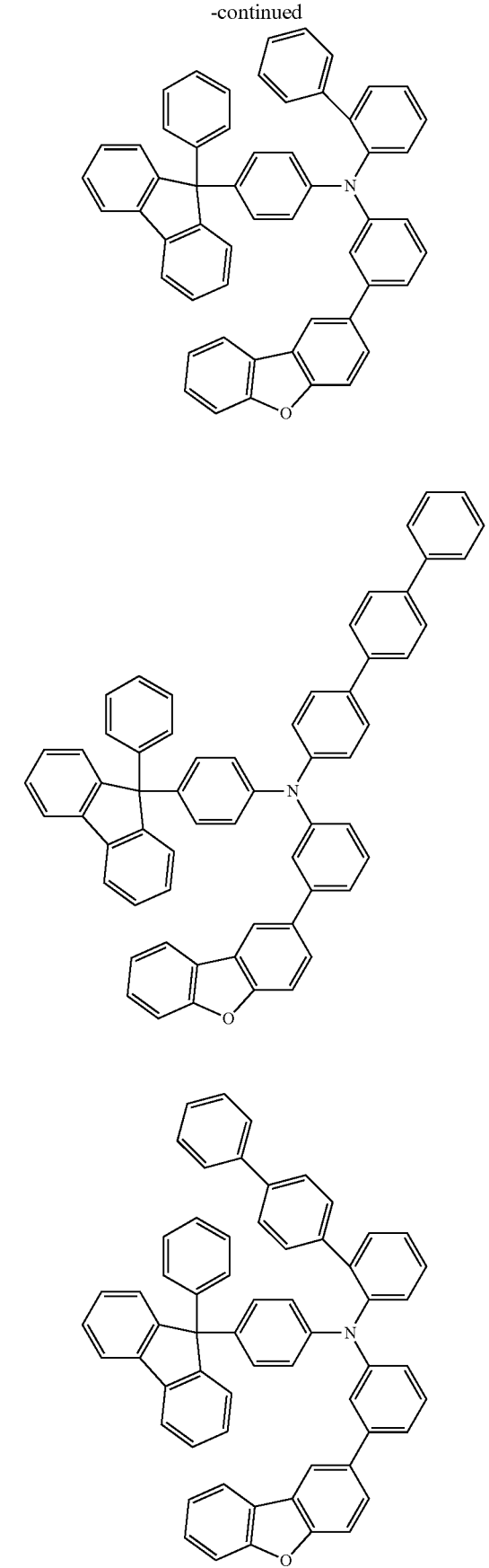

85
-continued
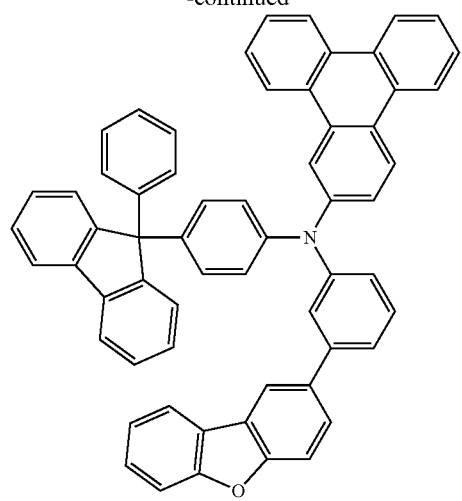
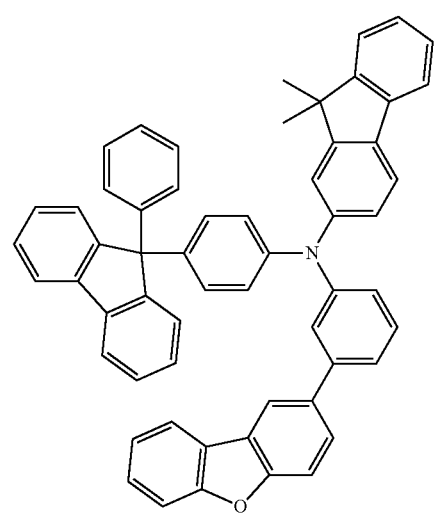
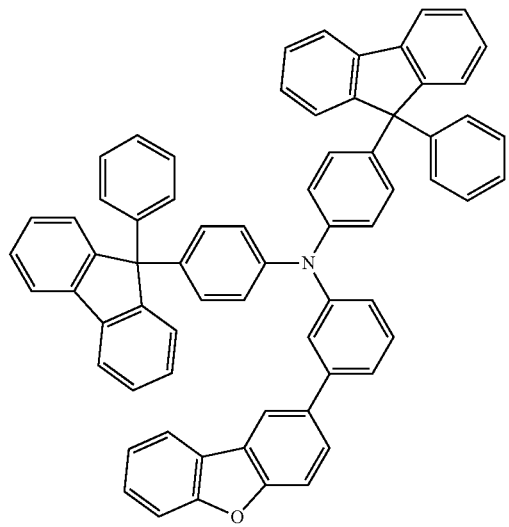
86
-continued
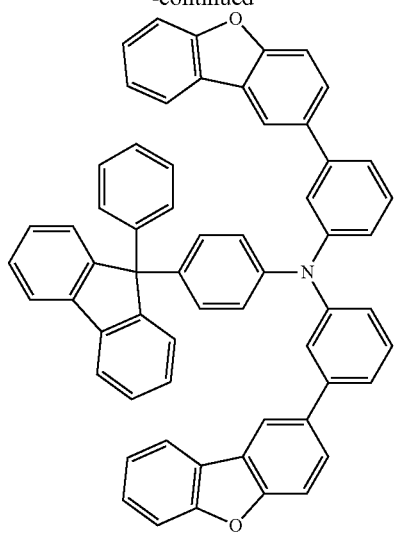
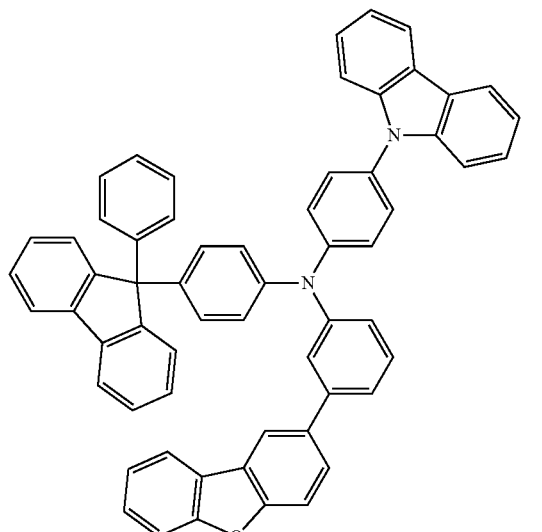
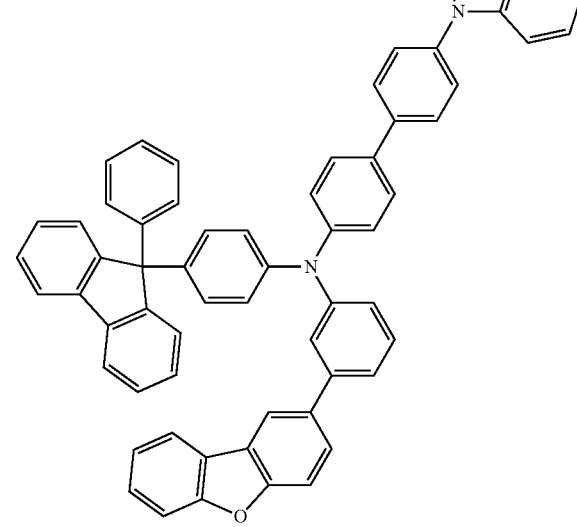

87
-continued
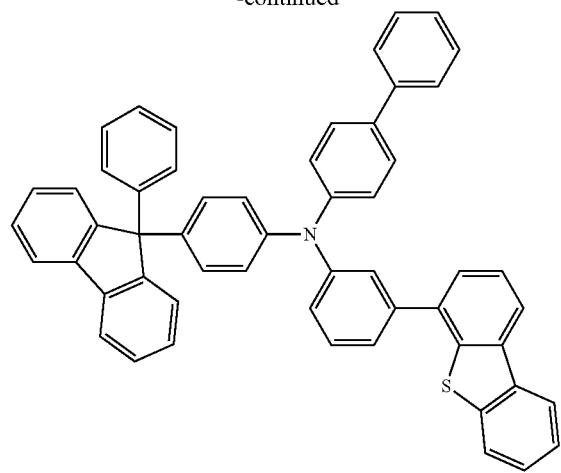
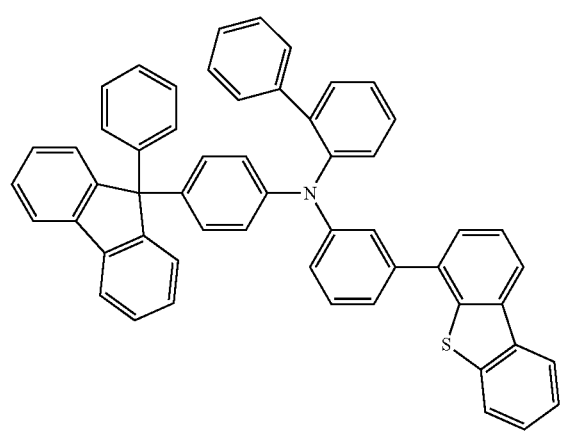
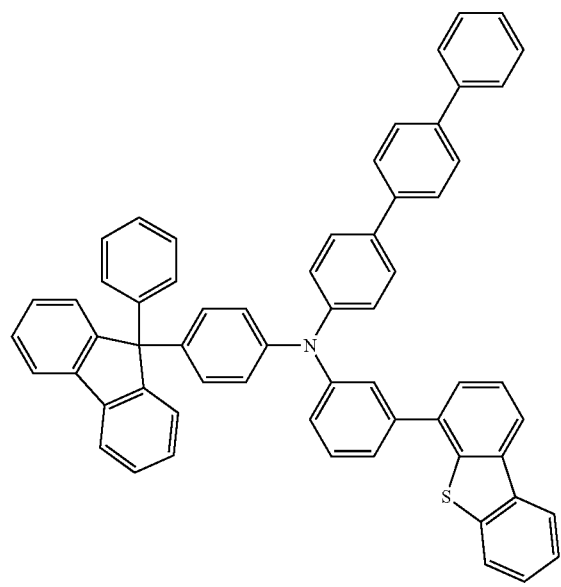
88
-continued
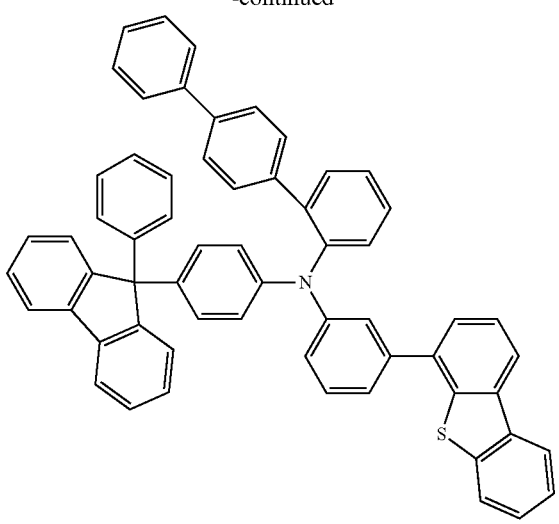
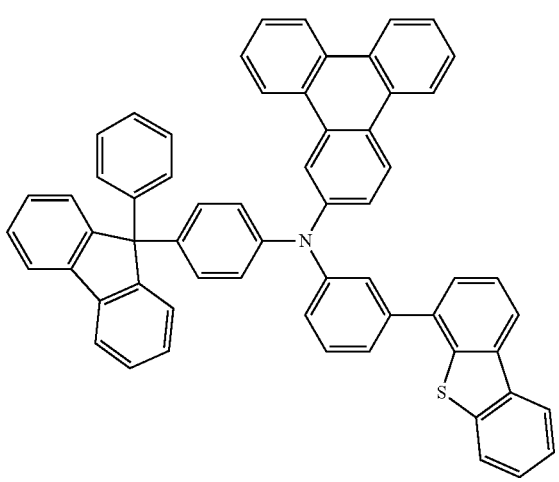
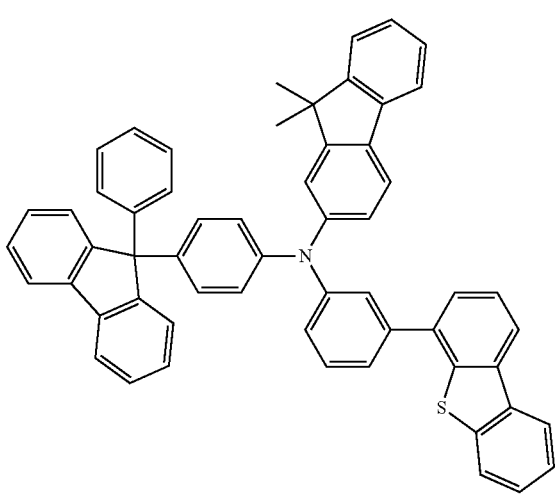

89
-continued
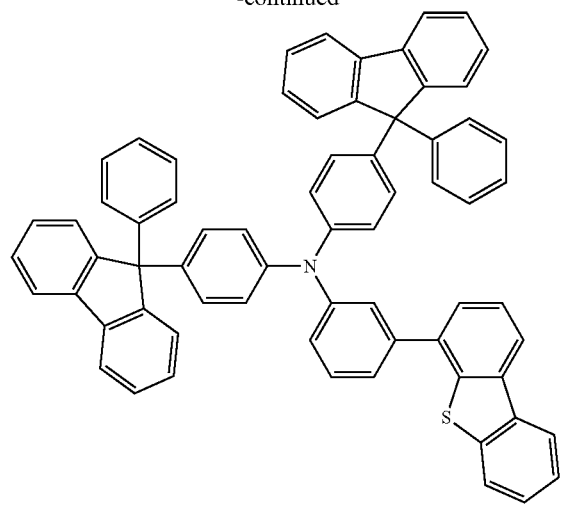
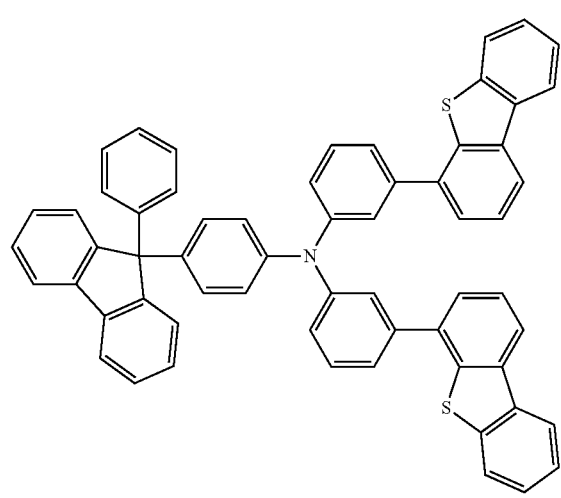
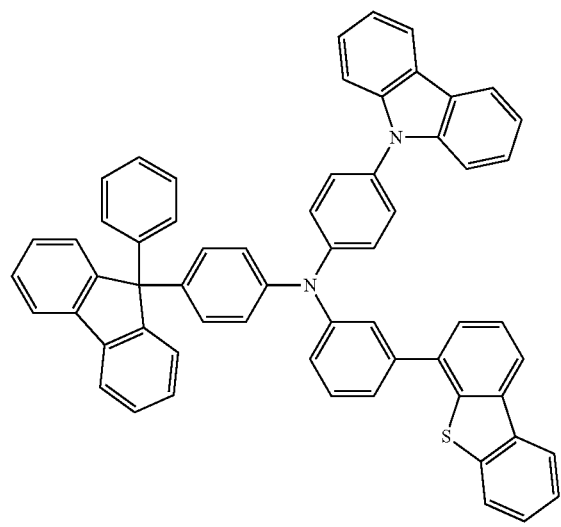
90
-continued
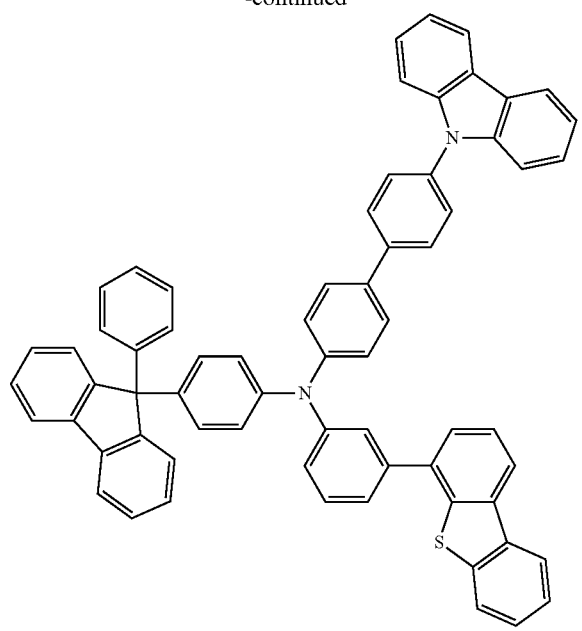
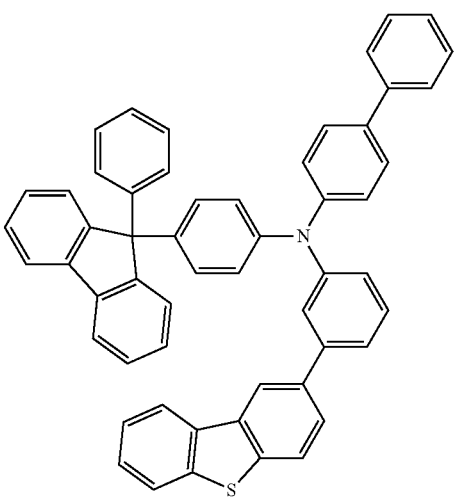
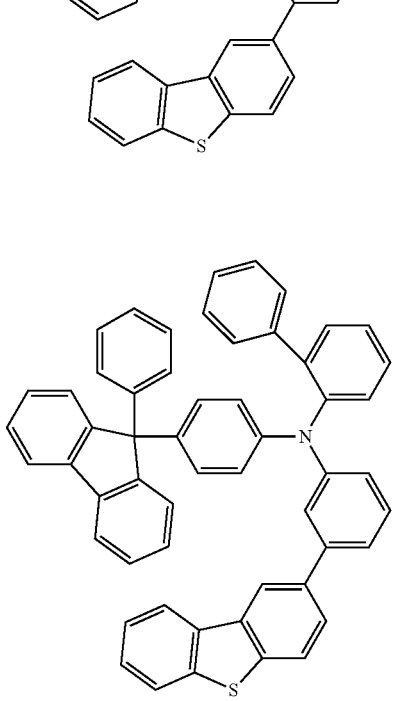

91
-continued
92
-continued
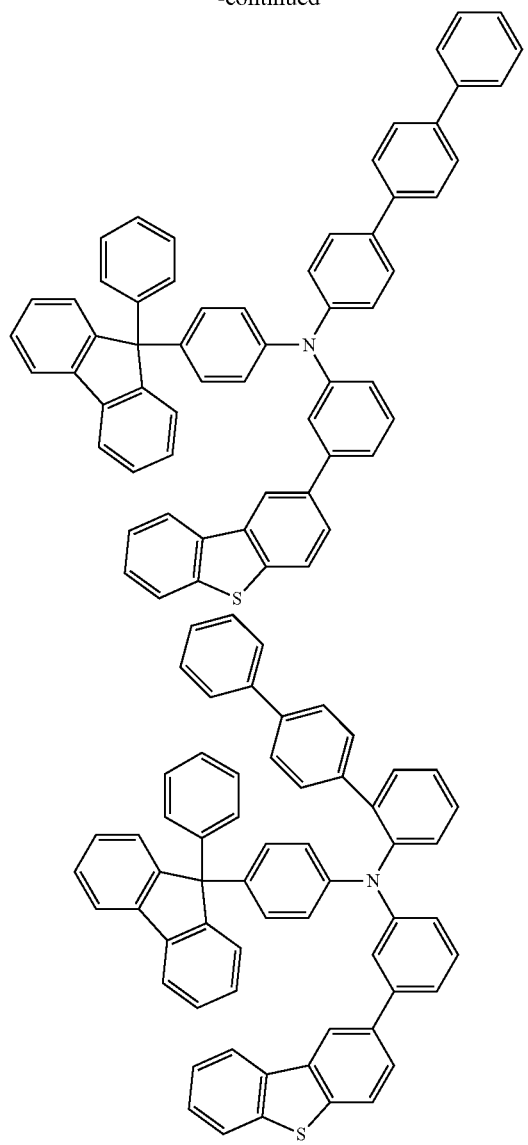
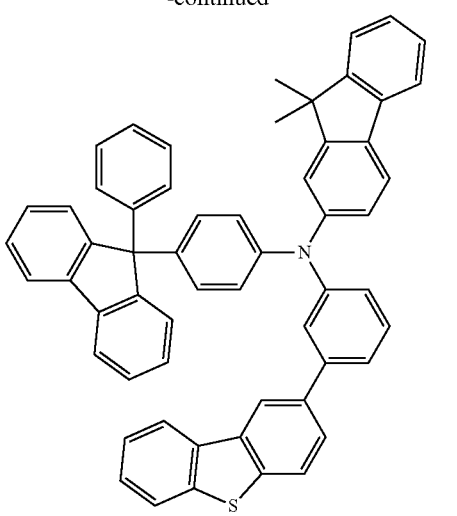
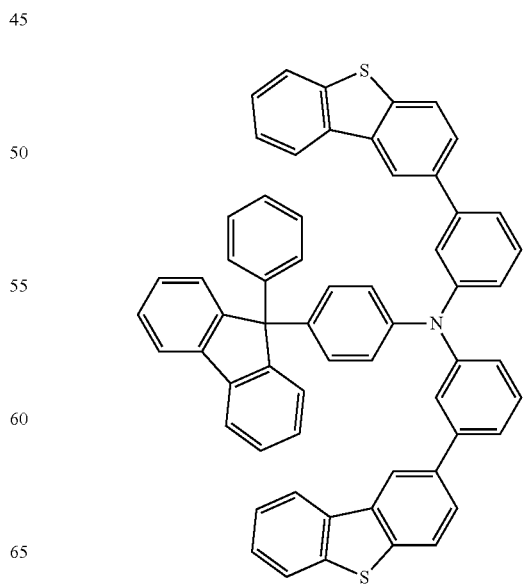

93
-continued
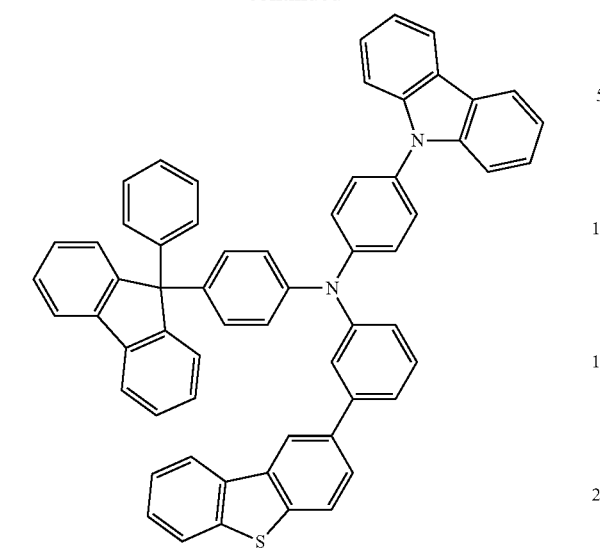
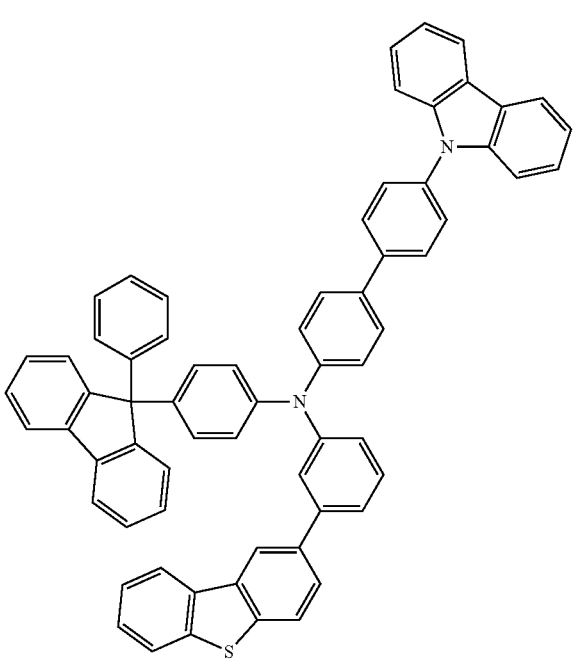
94
-continued
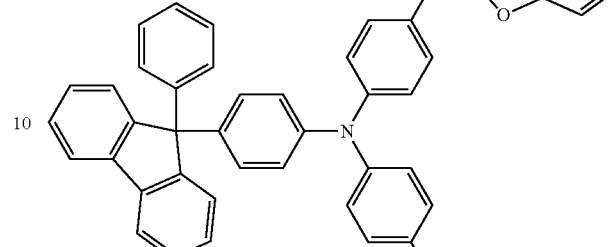
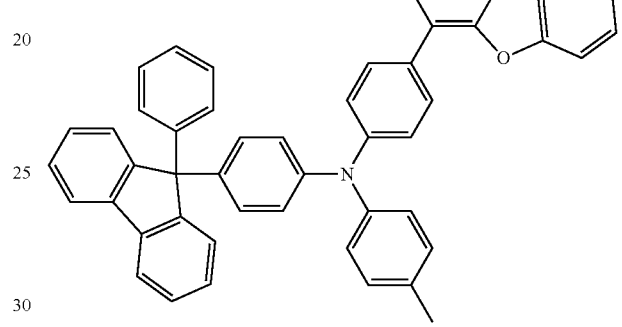
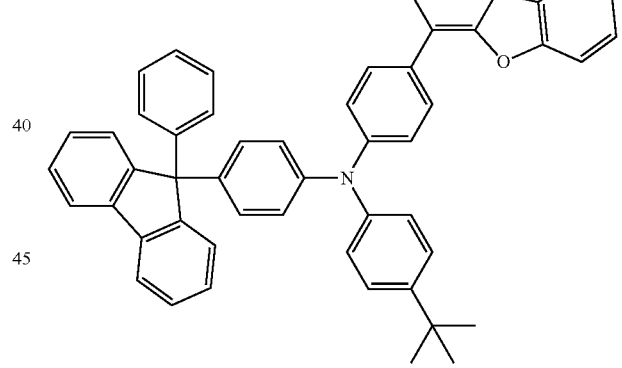
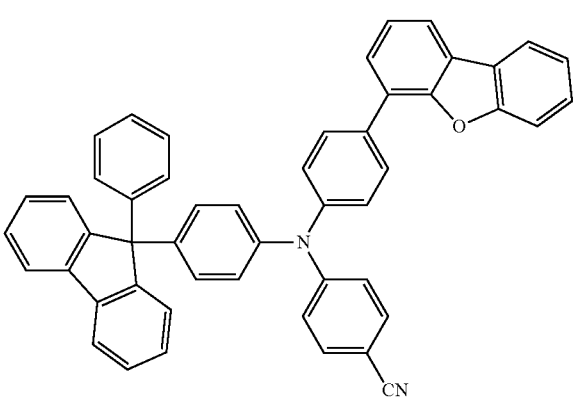
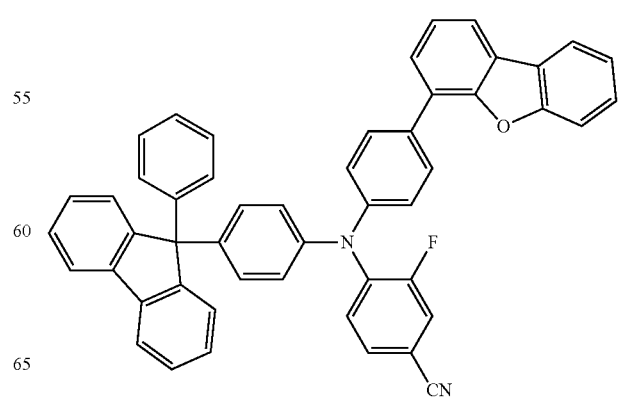

95
-continued
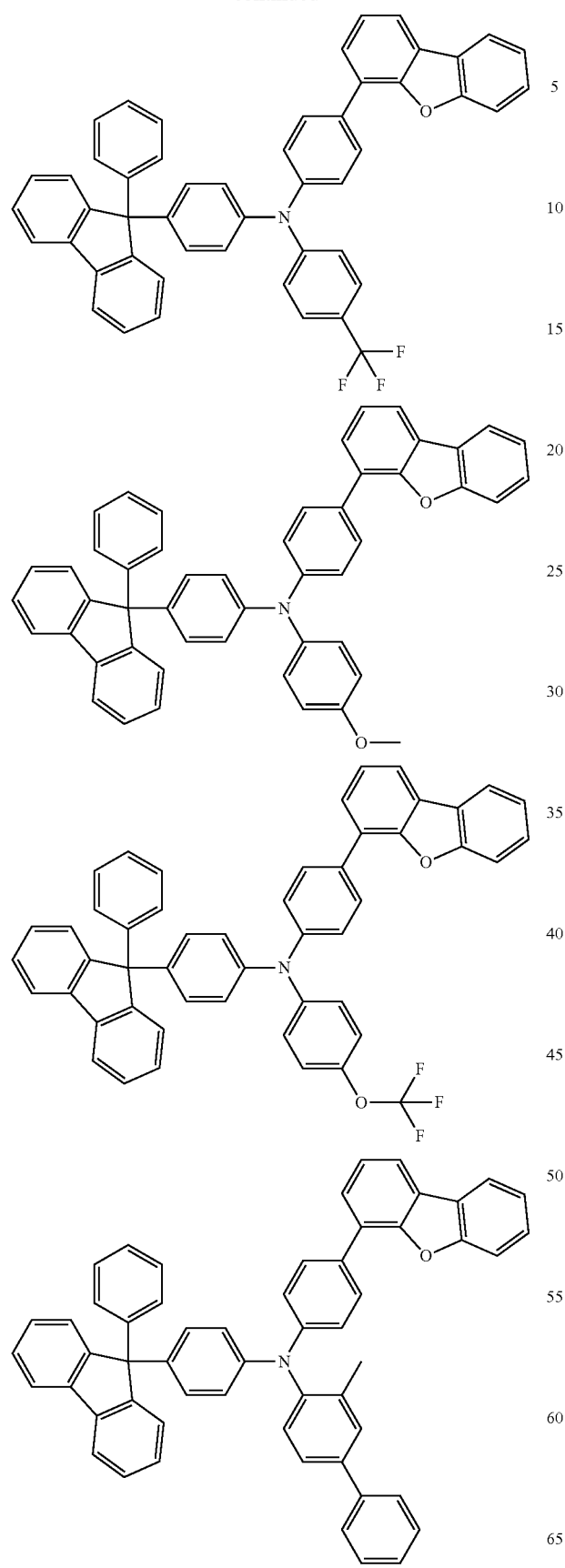
96
-continued
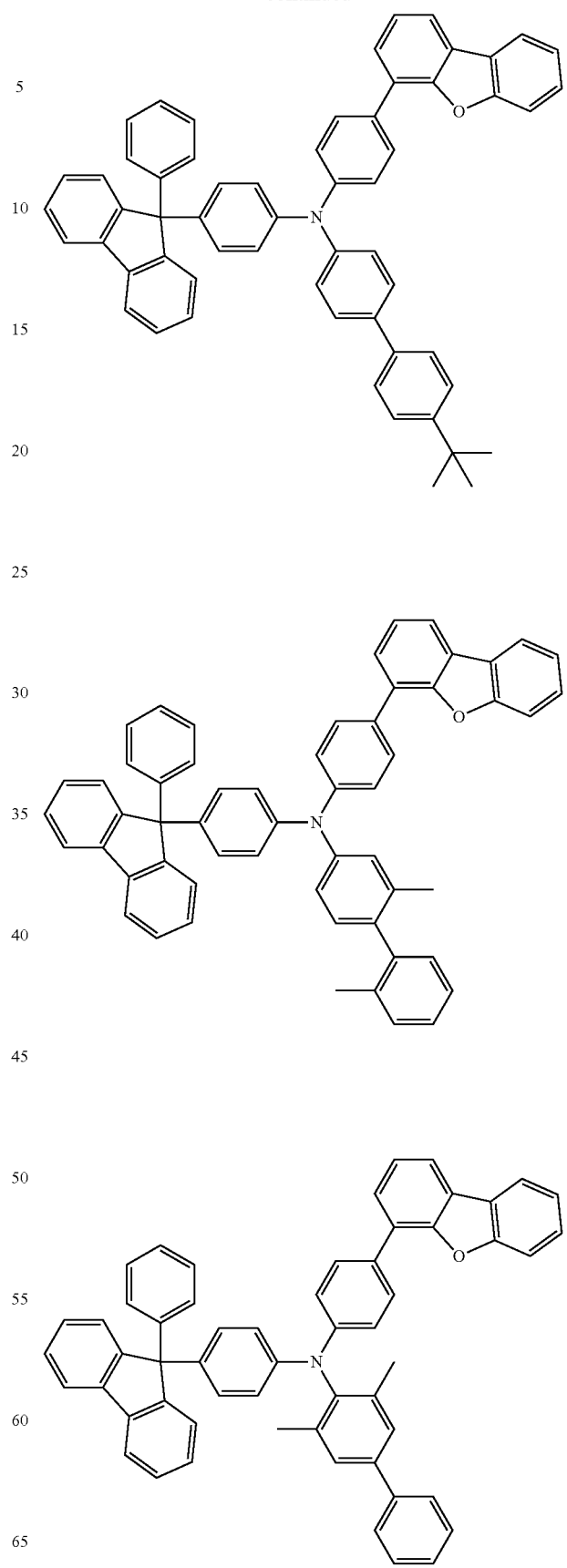

97
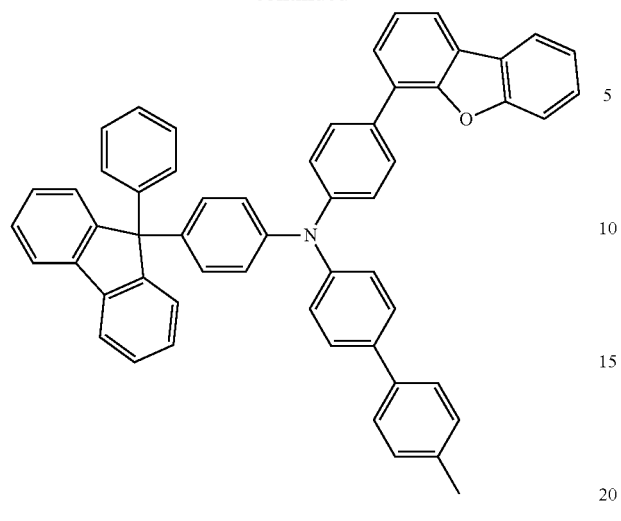
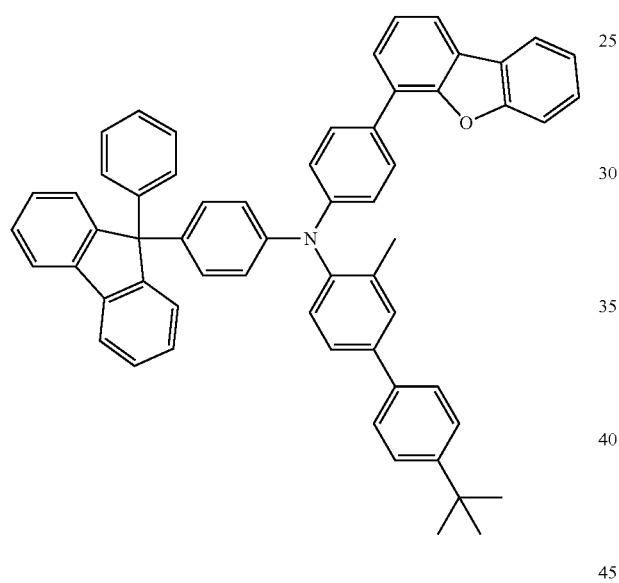
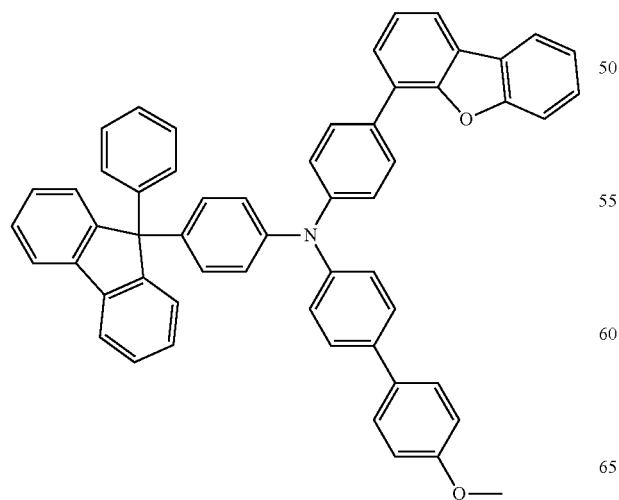
98
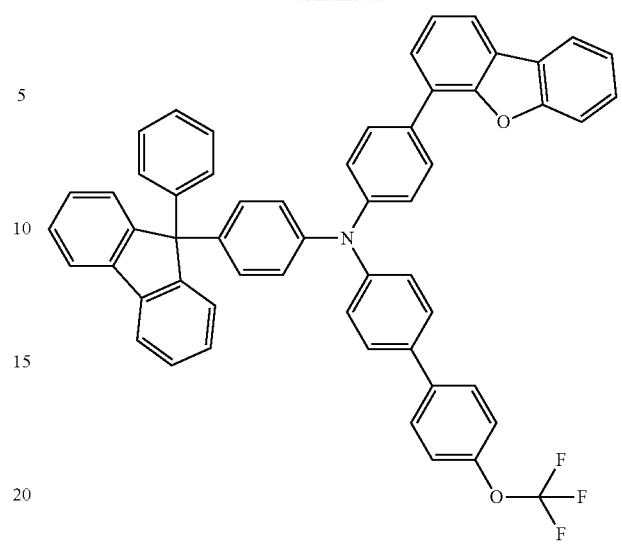
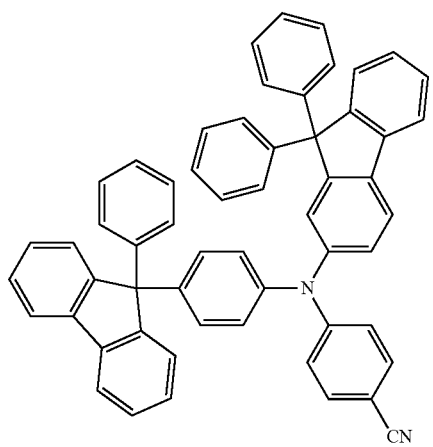
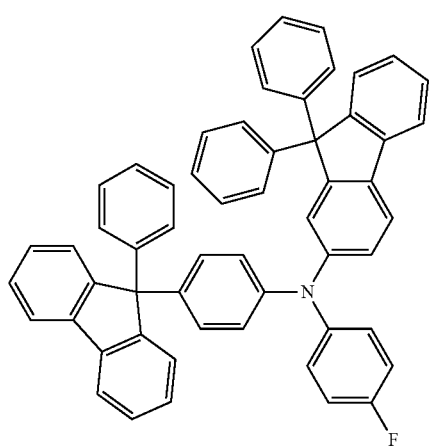

99
-continued
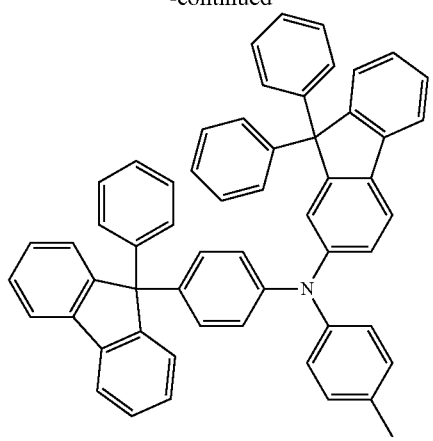
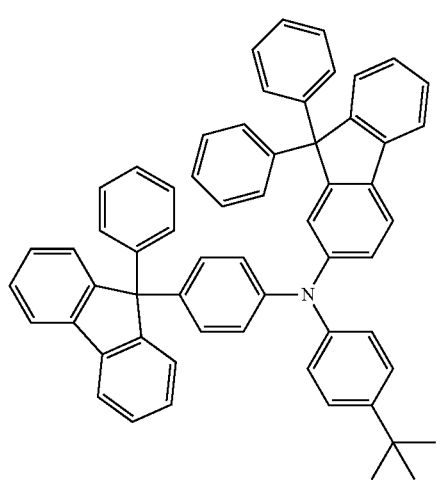
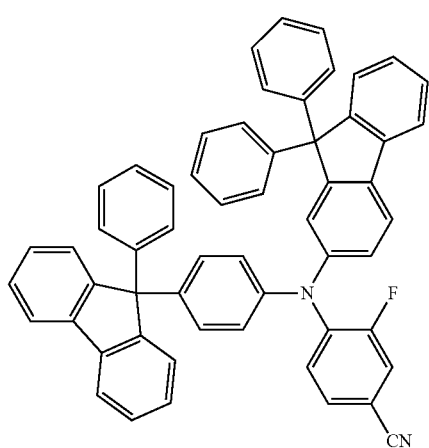 [SMILES: N#Cc1ccc(N(c2ccc(C3(c4ccccc4)c4ccccc4-c4ccccc43)cc2)c2ccc3c(c2)C(c2ccccc2)(c2ccccc2)c2ccccc2-3)c(F)c1]
100
-continued
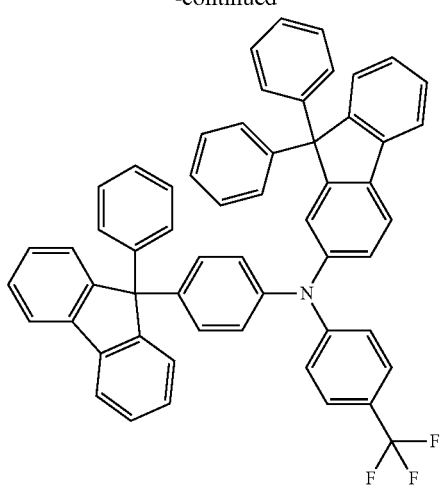
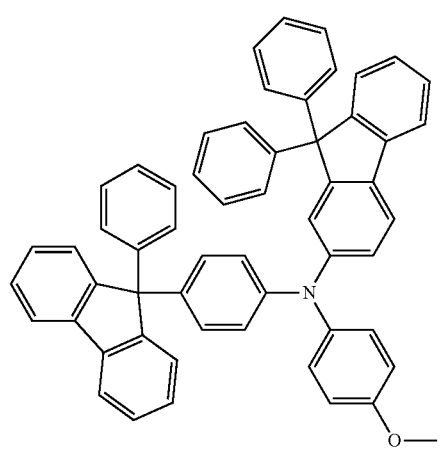
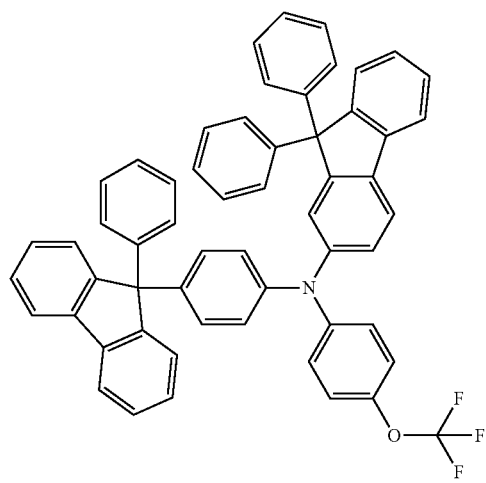

101
-continued
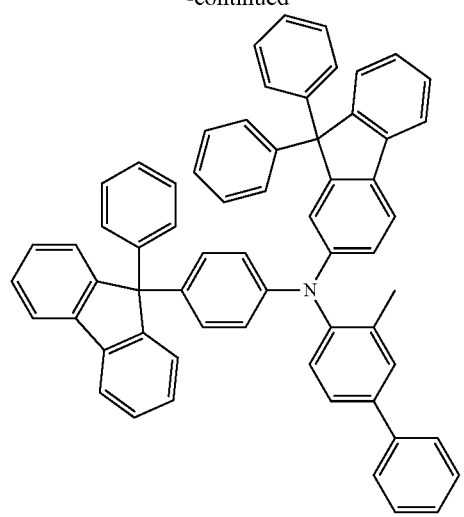
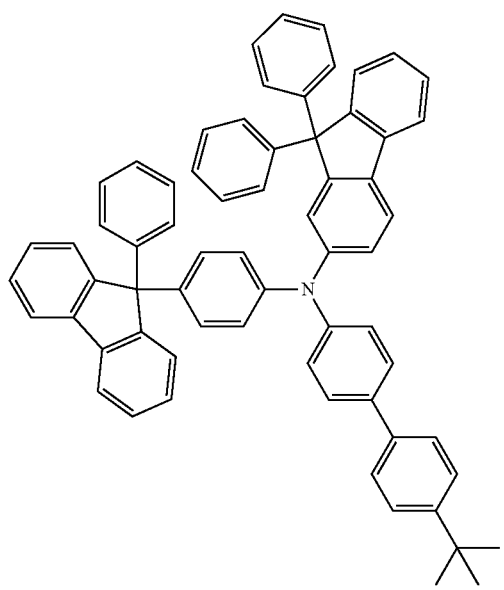
102
-continued
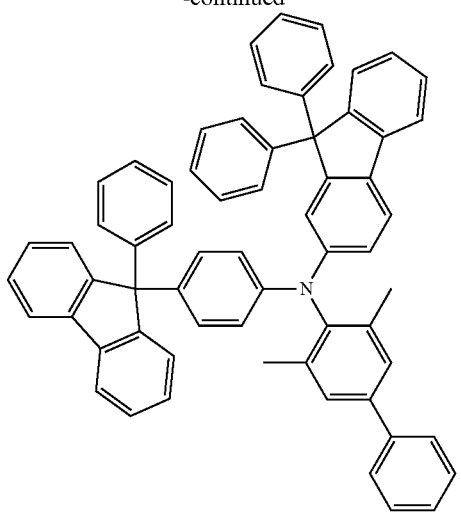
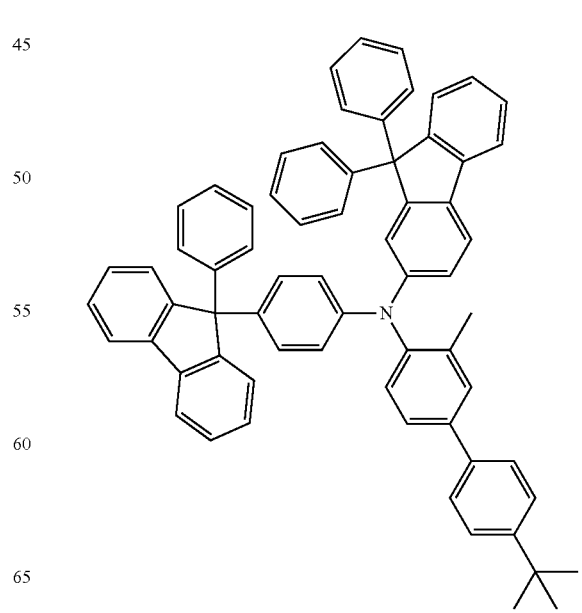

103
-continued
104
-continued
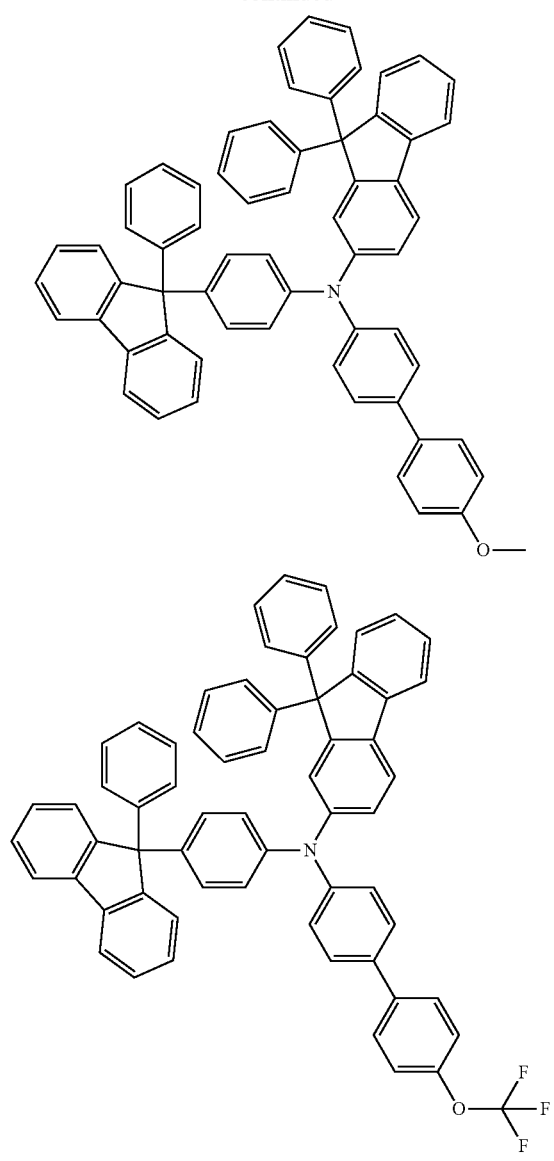

105
-continued
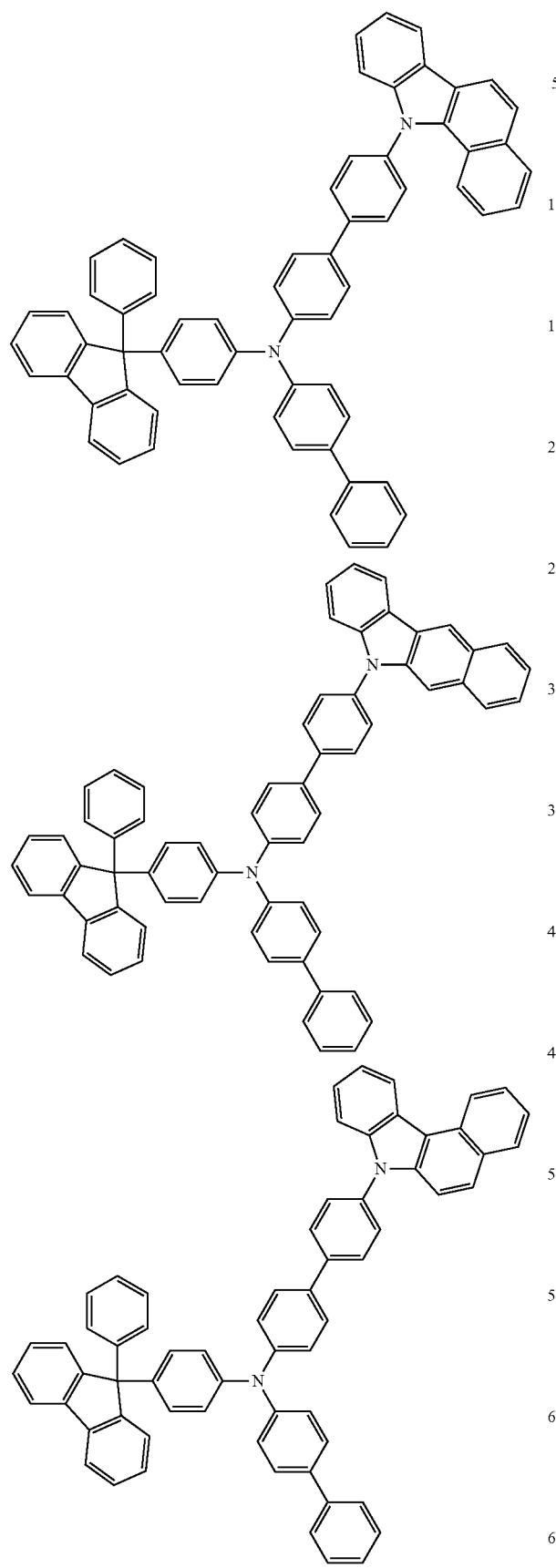
106
-continued
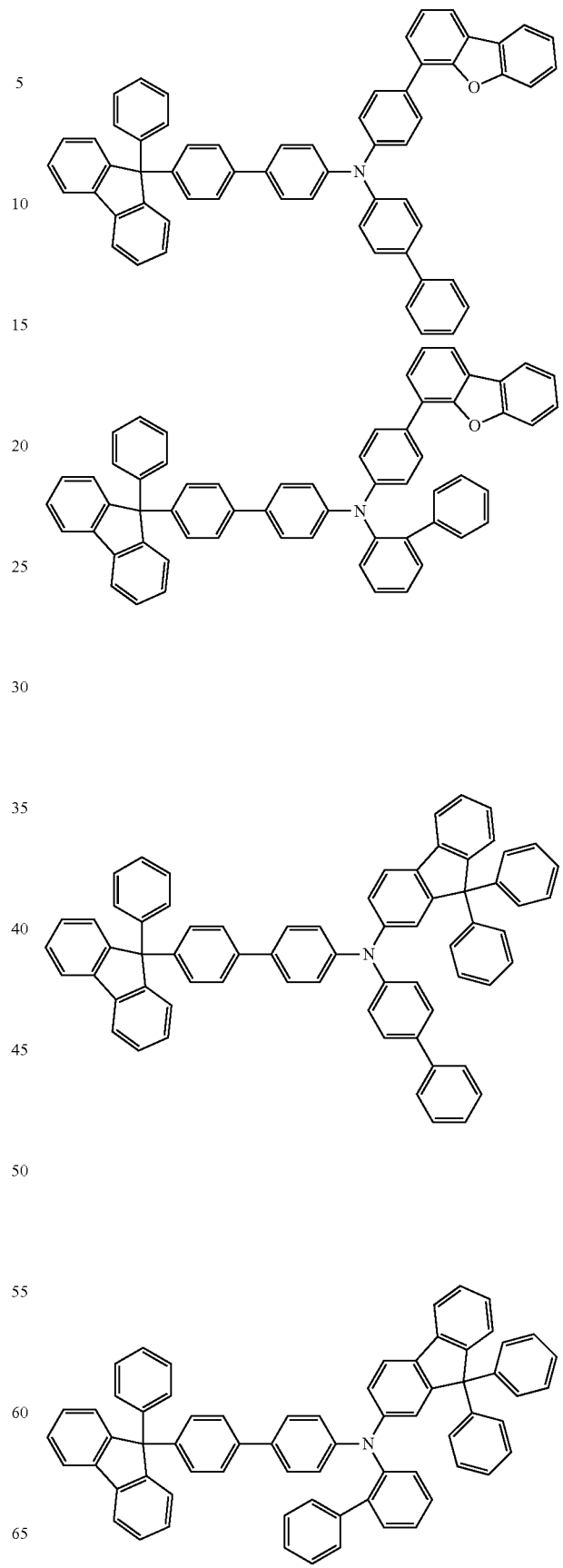

107
-continued
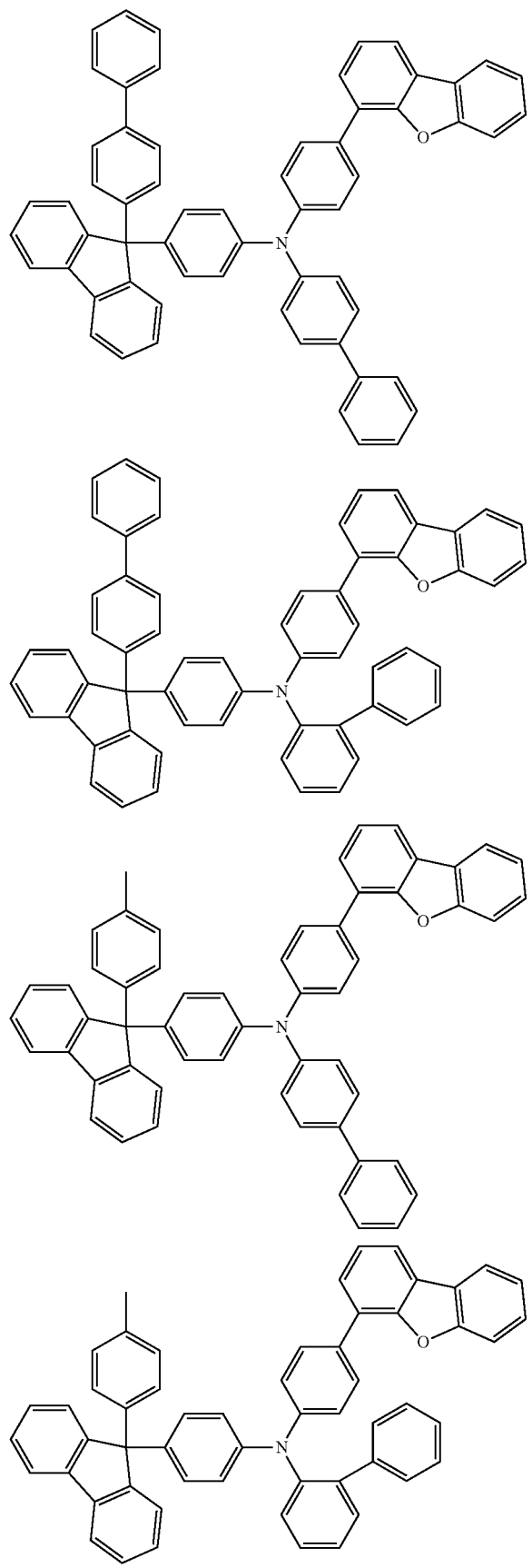
108
-continued
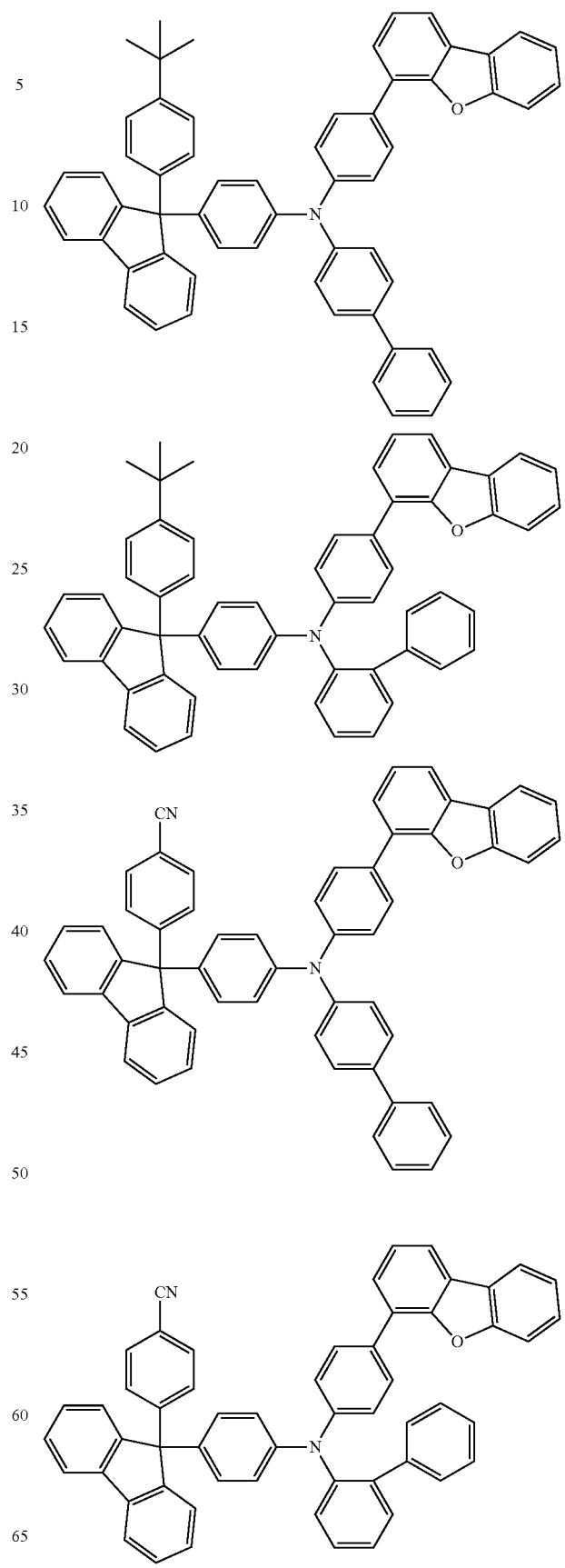

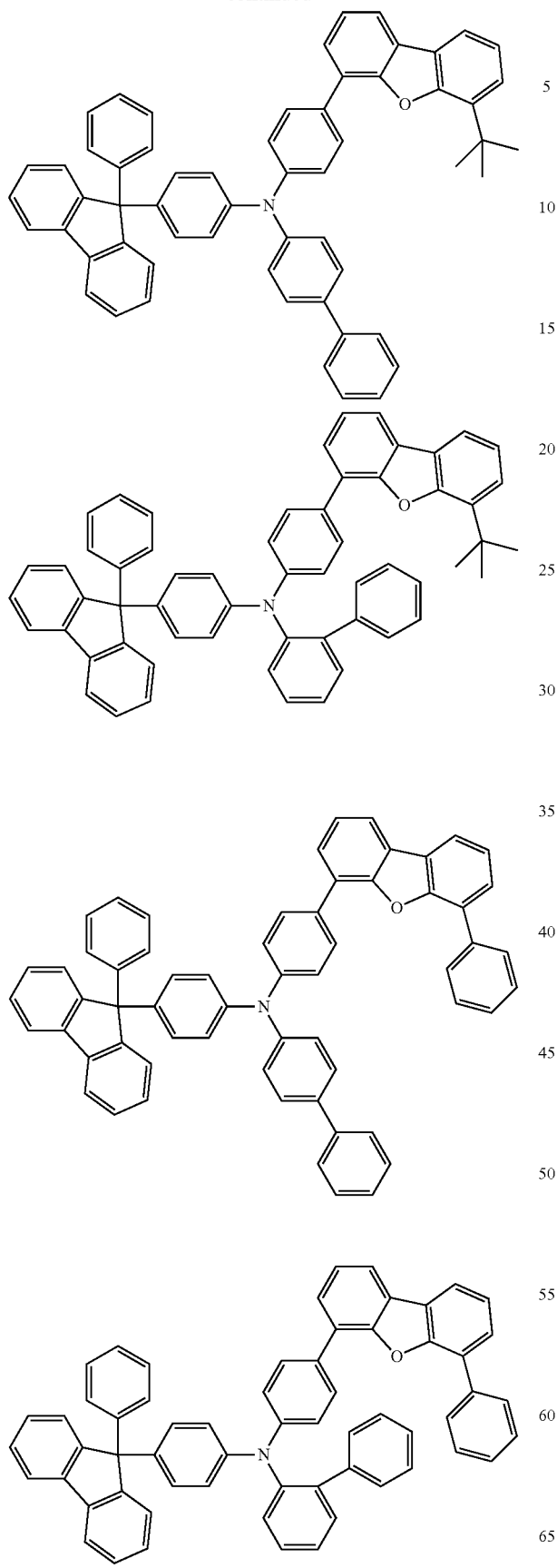
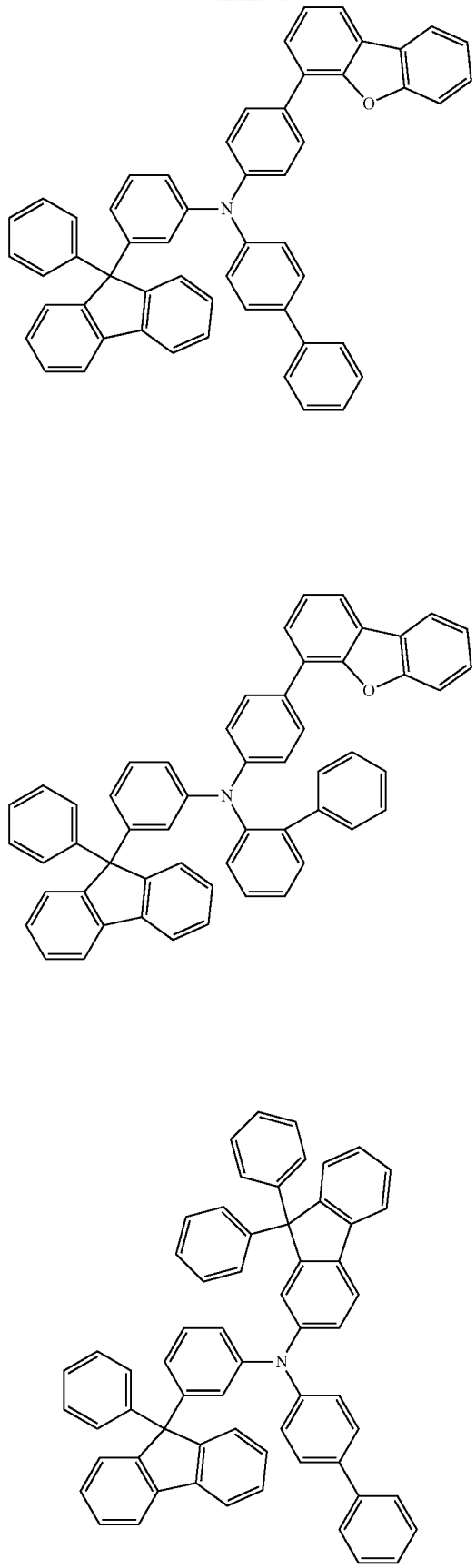

111
-continued
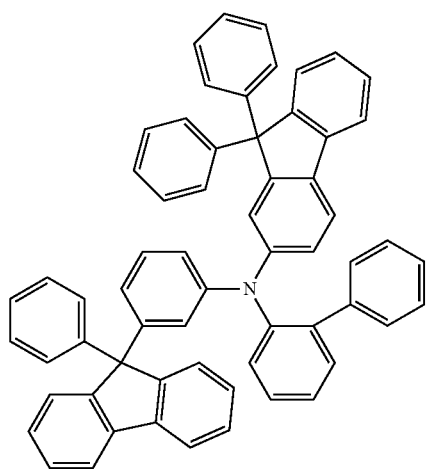 [SMILES: c1ccc(-c2ccccc2N(c2cccc(C3(c4ccccc4)c4ccccc4-c4ccccc43)c2)c2ccc3c(c2)C(c2ccccc2)(c2ccccc2)c2ccccc2-3)cc1]
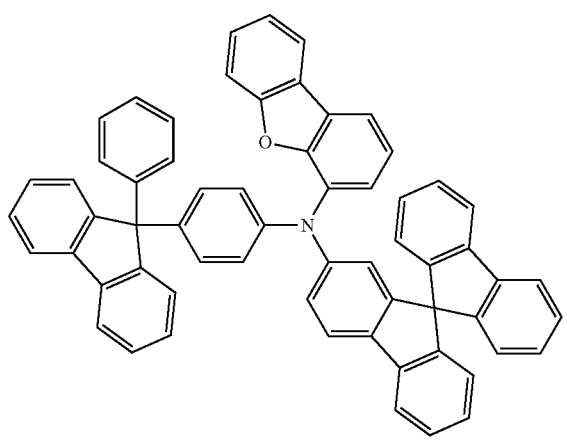
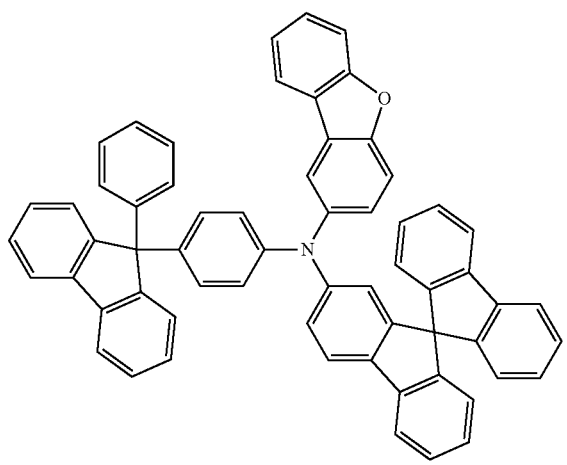
112
-continued
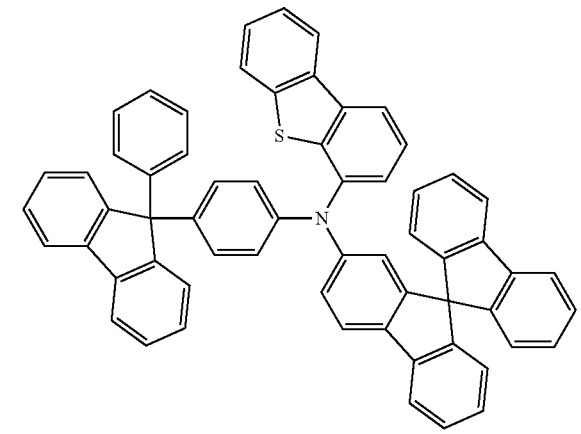
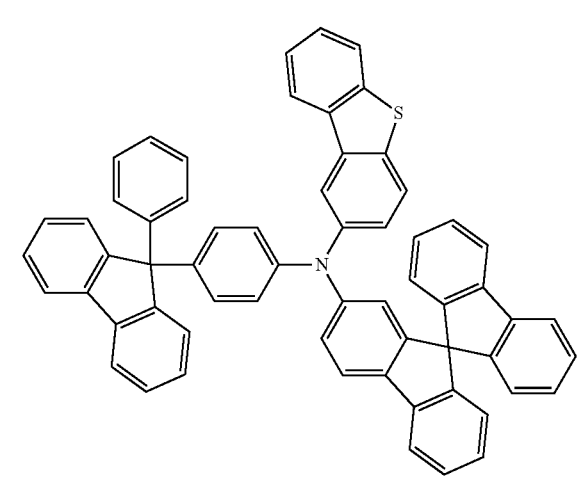
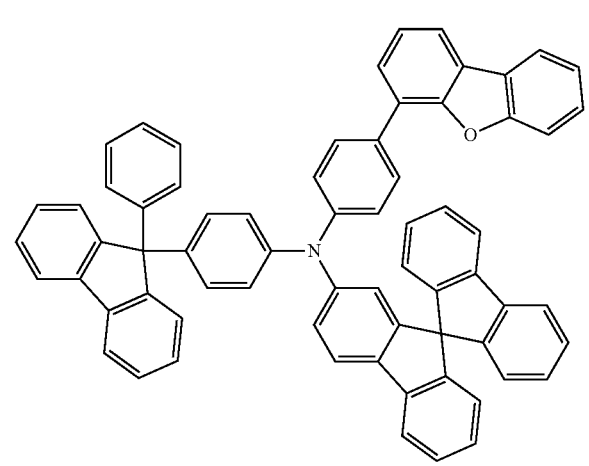

113
-continued
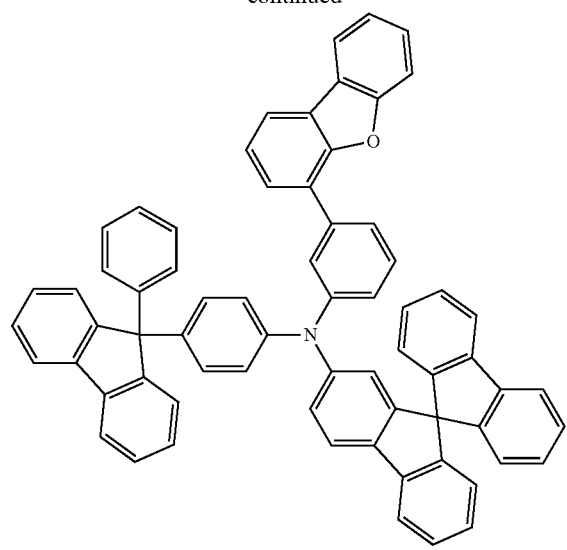
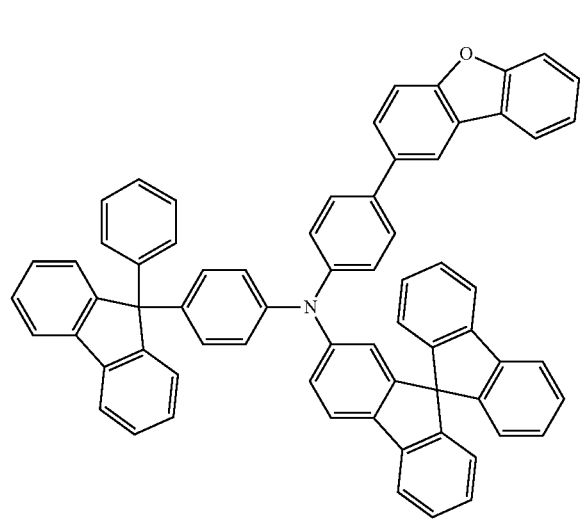
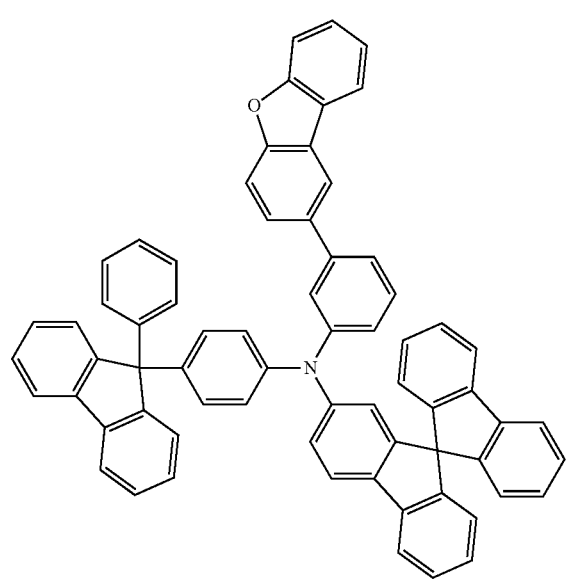
114
-continued
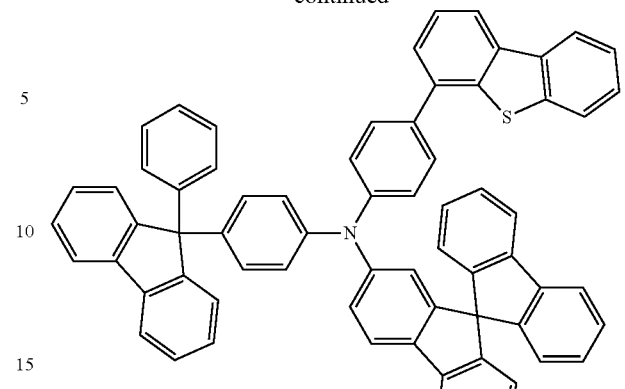
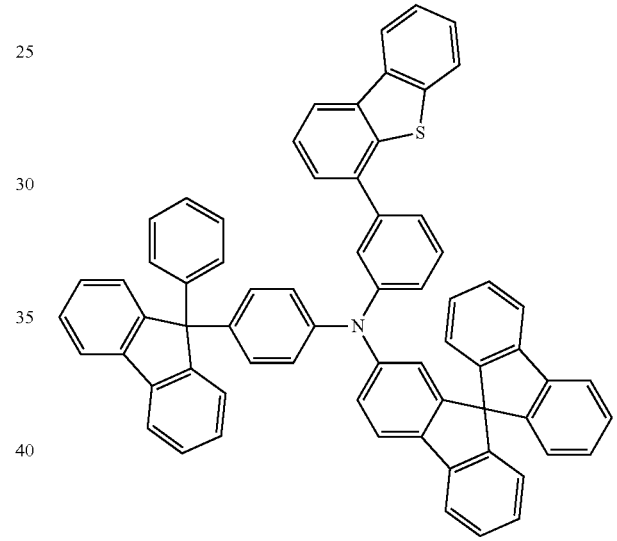
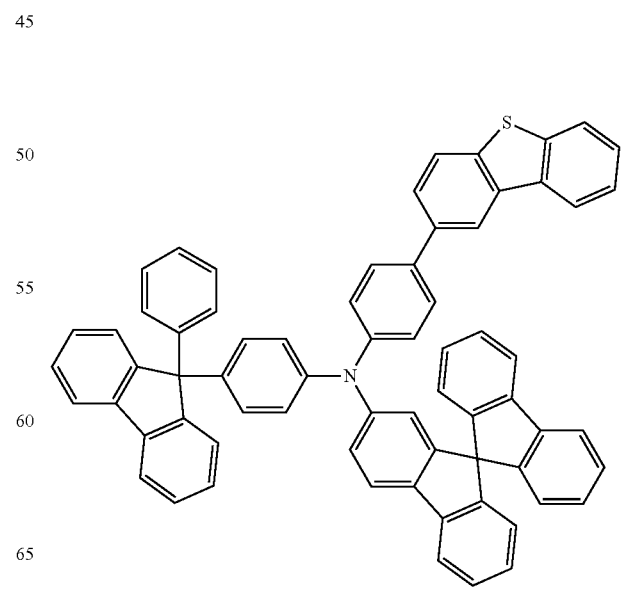

-continued
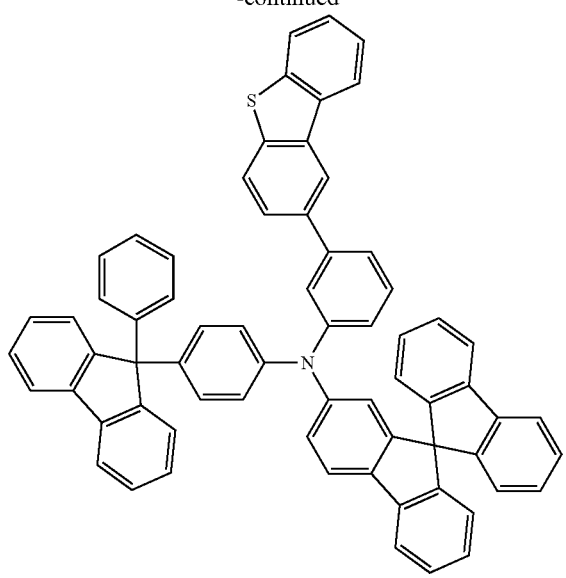
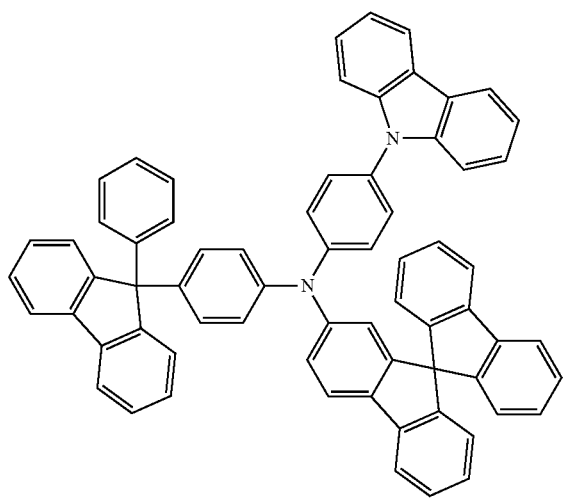
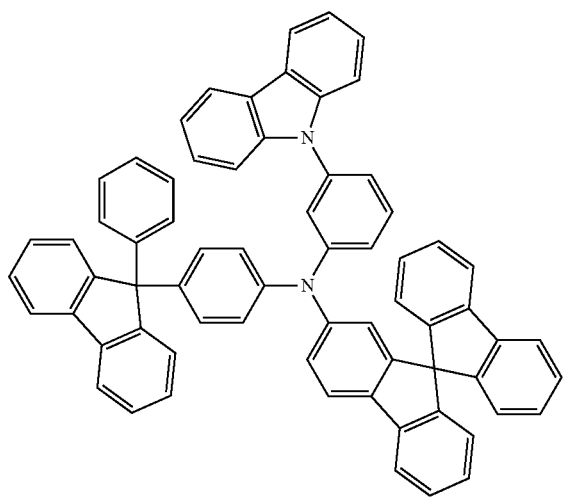
-continued
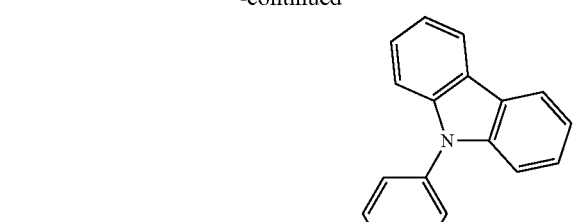
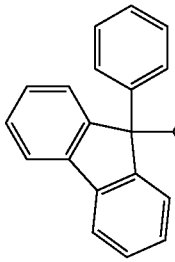
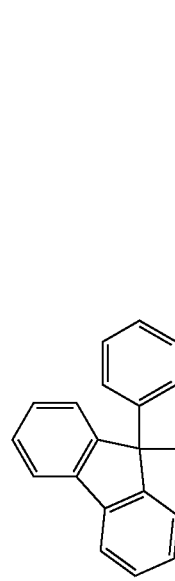
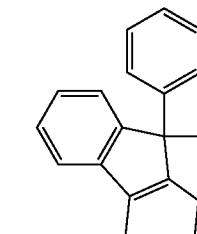
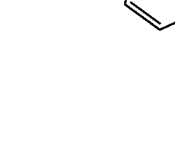

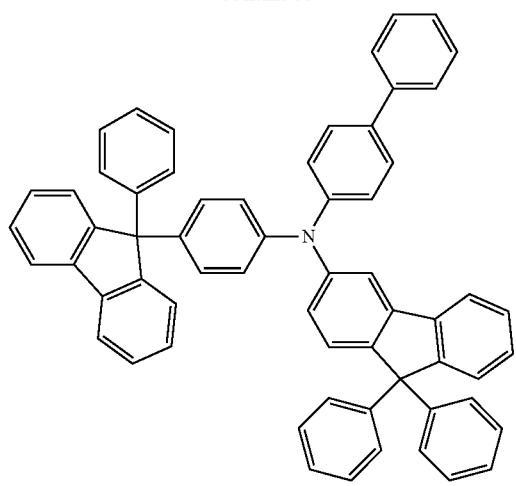
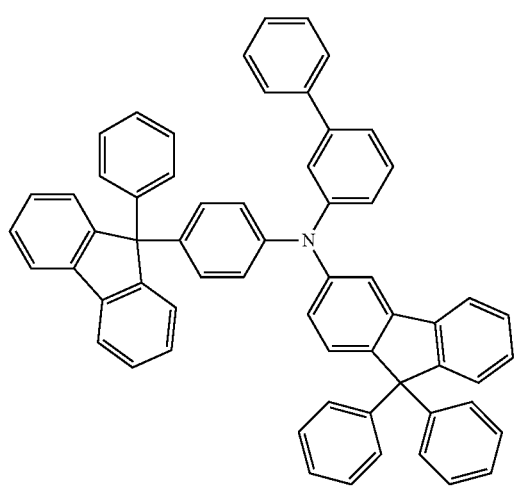
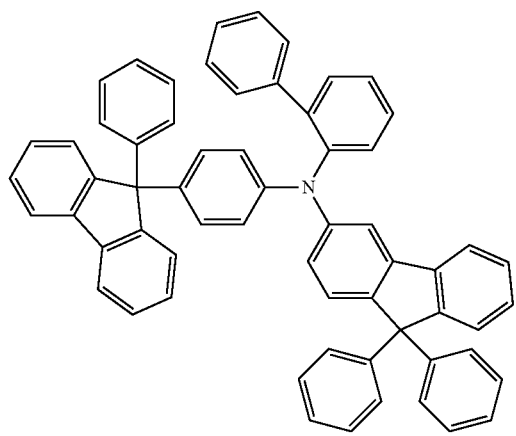
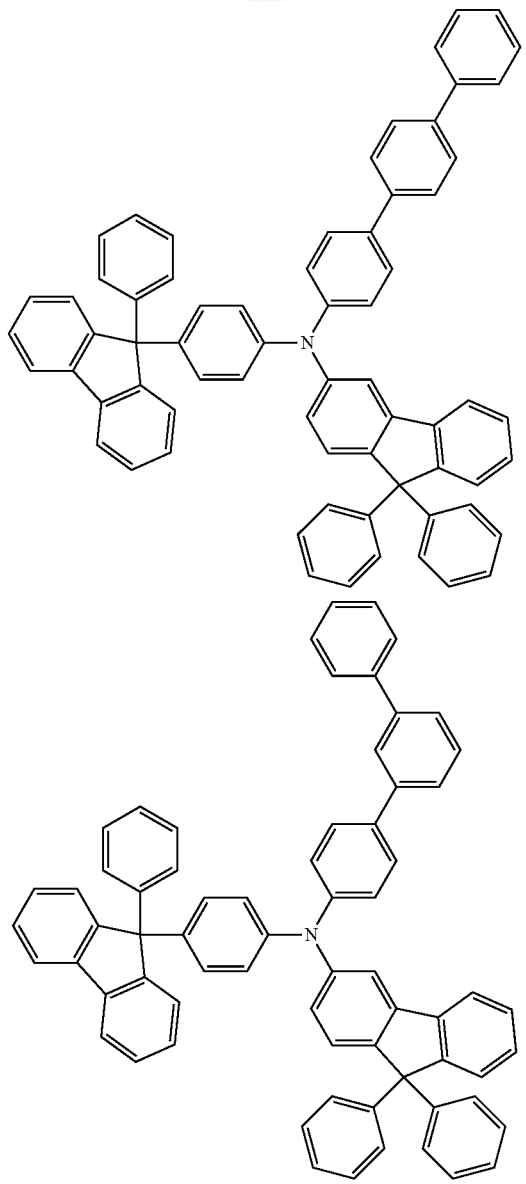
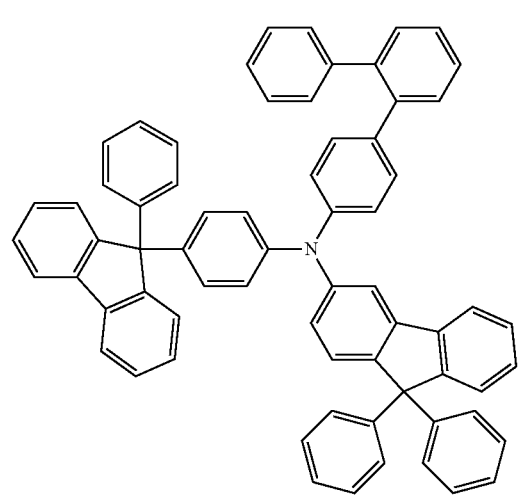

119
-continued
120
-continued
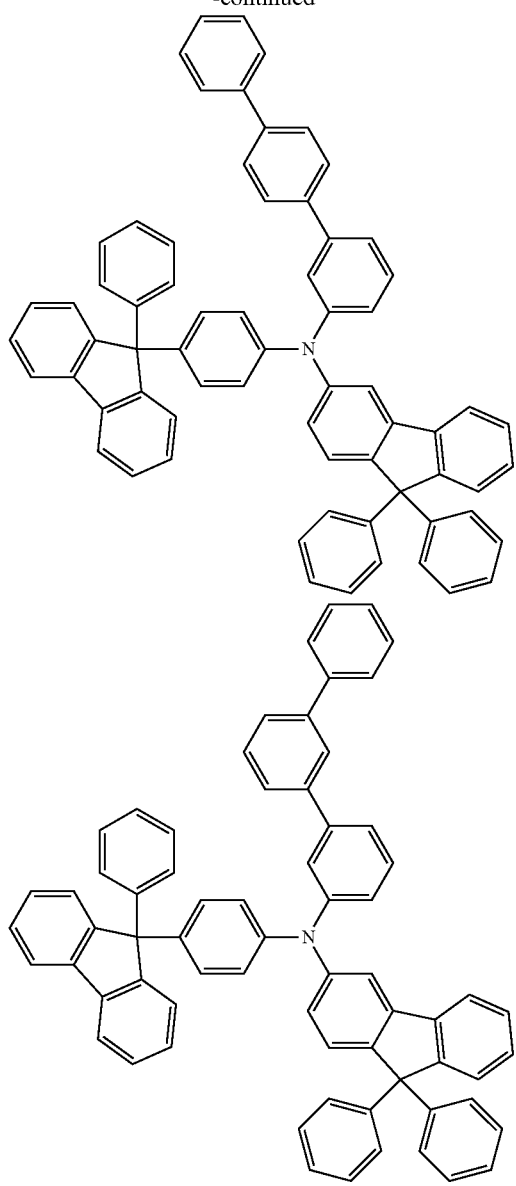
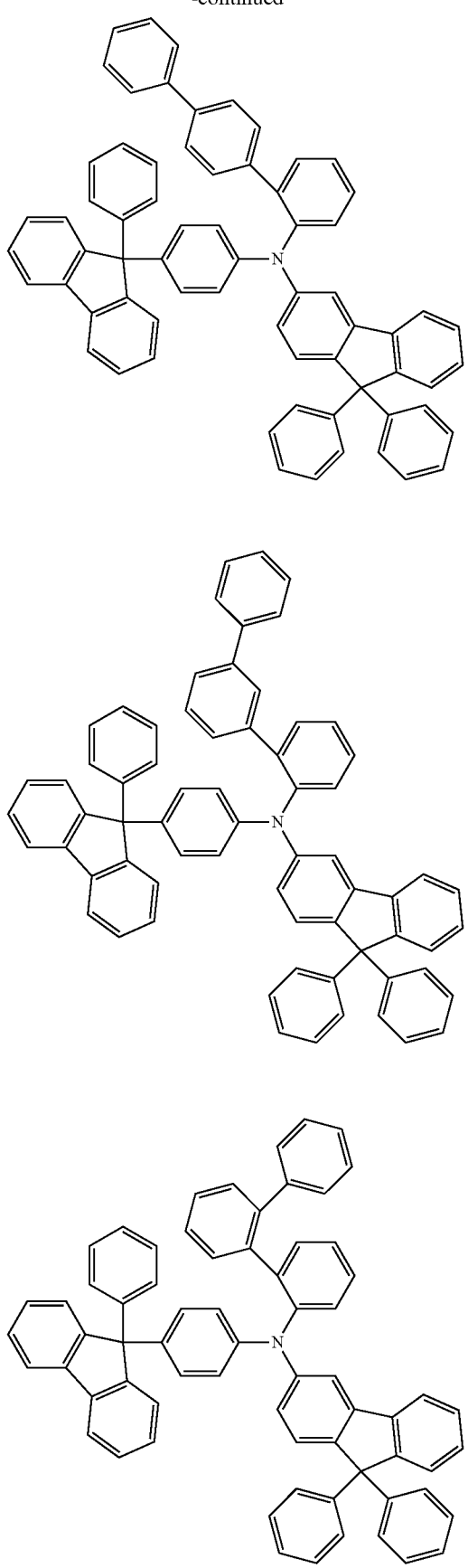

121
-continued
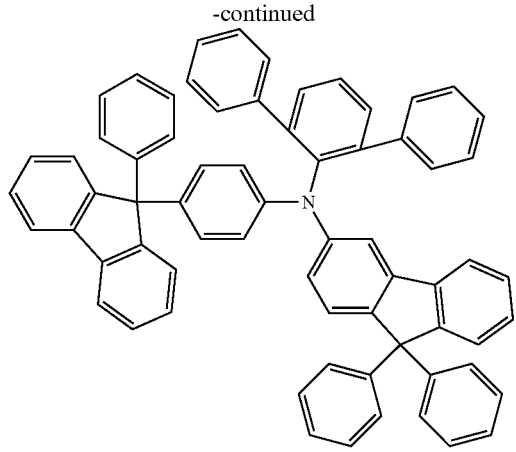
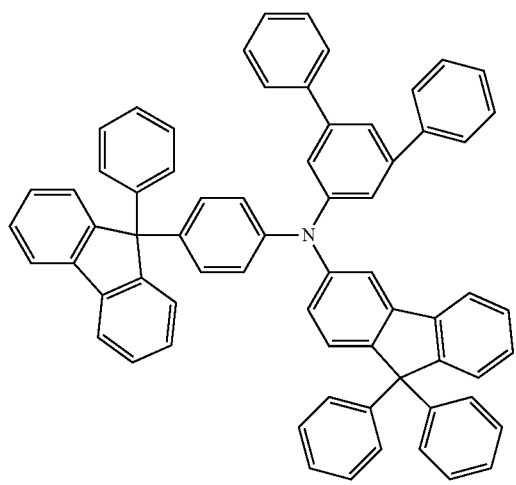
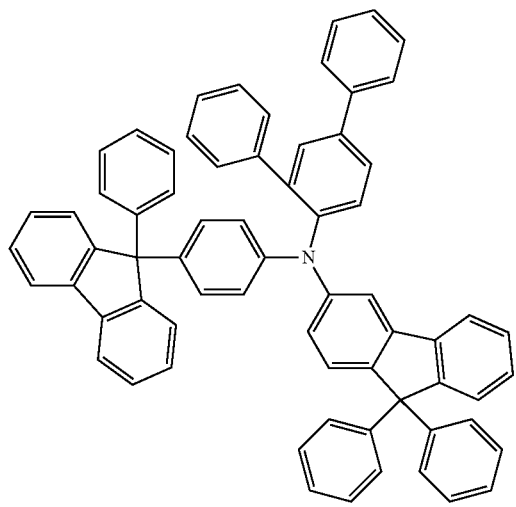
122
-continued
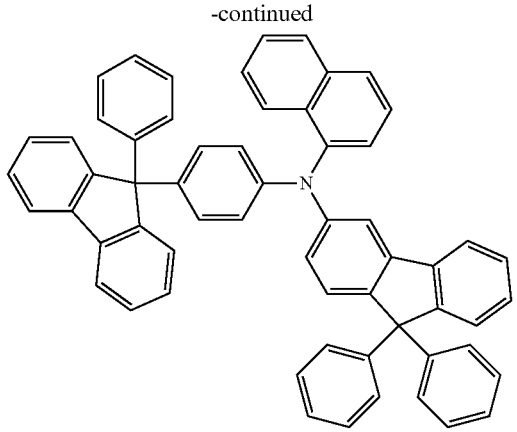
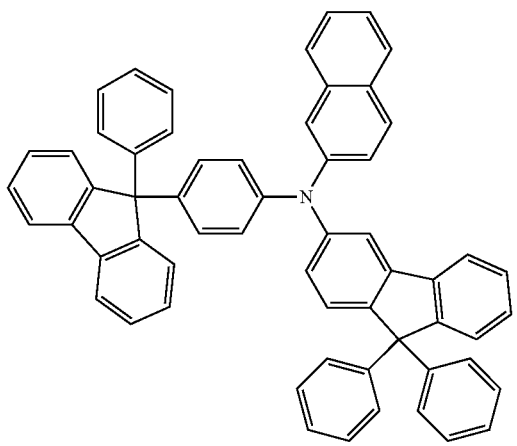
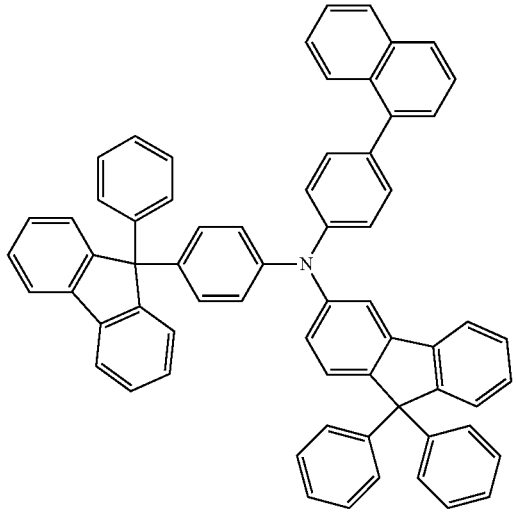

123
-continued
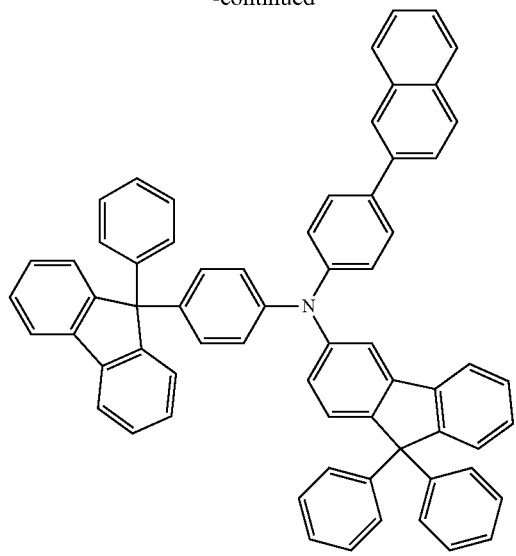
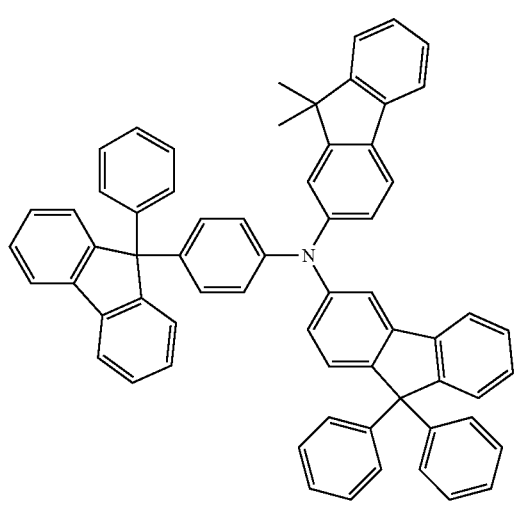
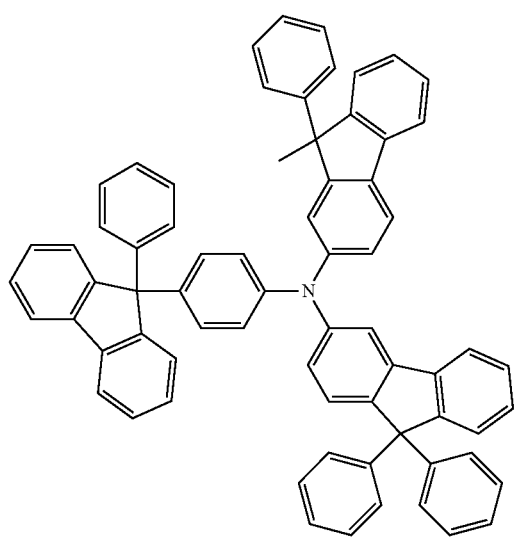
124
-continued
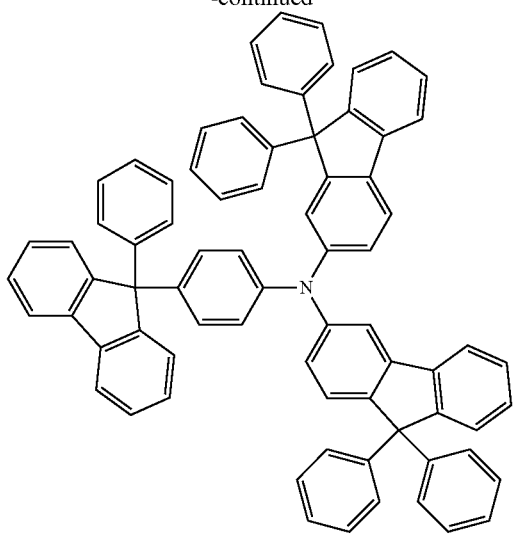
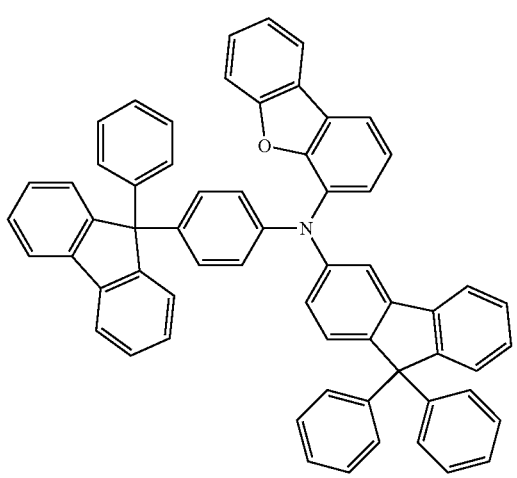

125
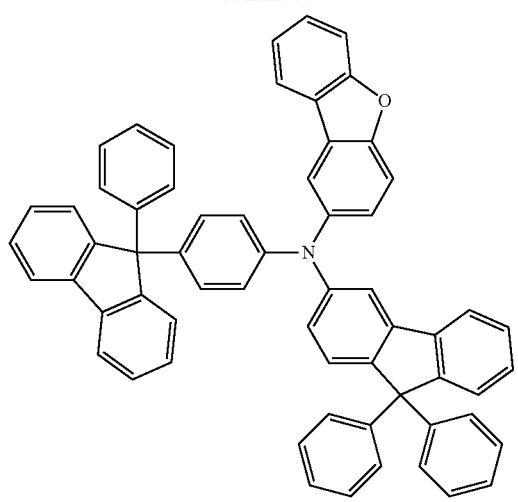
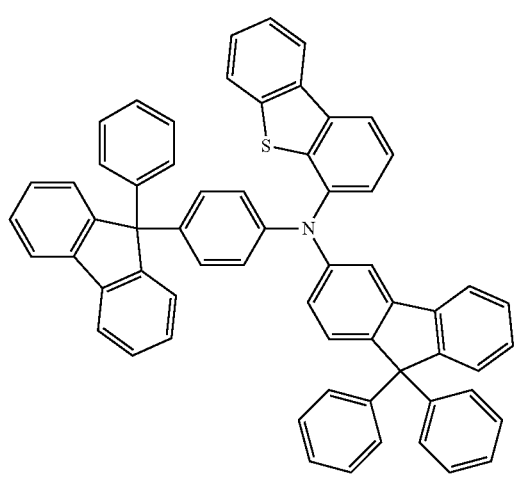
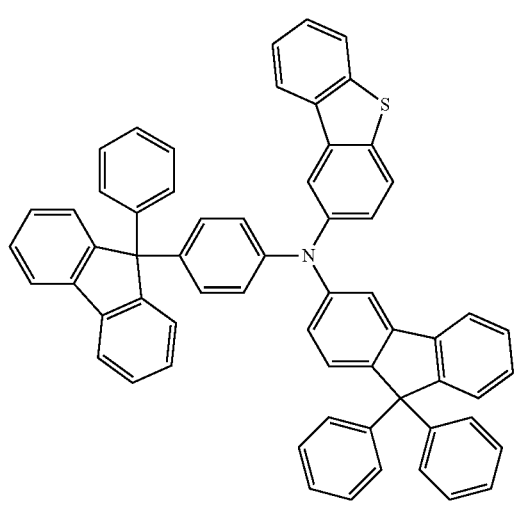
126
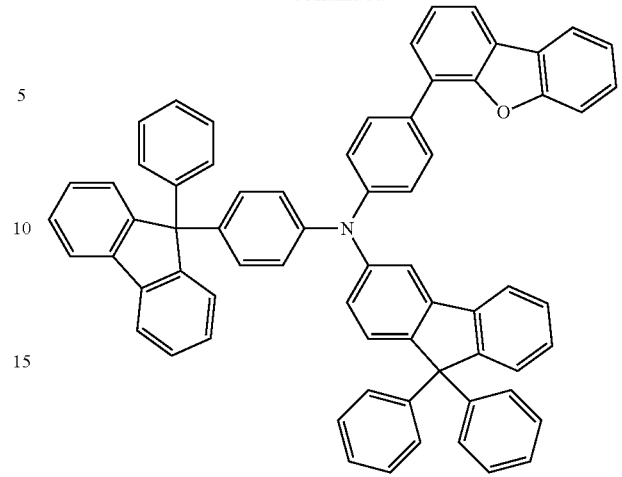
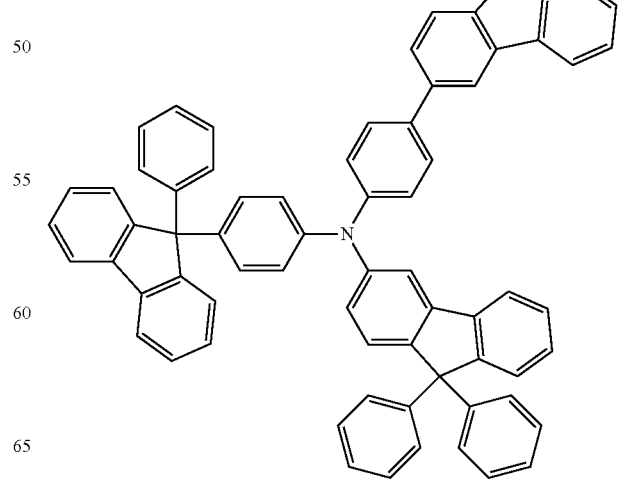

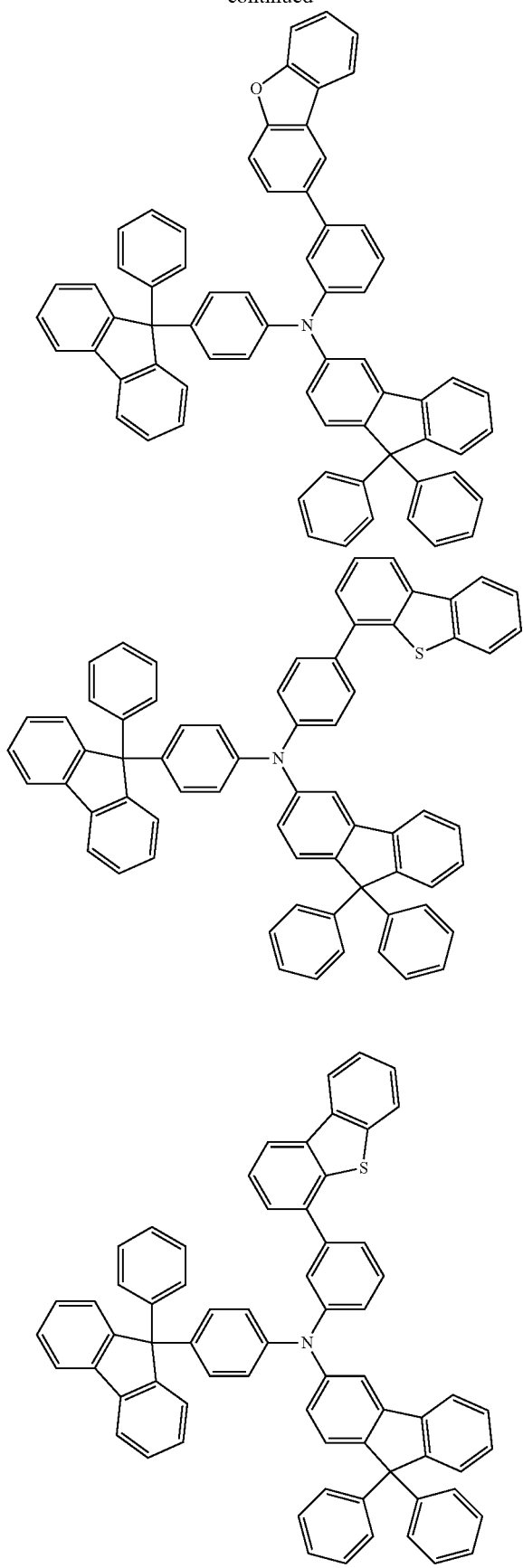

129
-continued
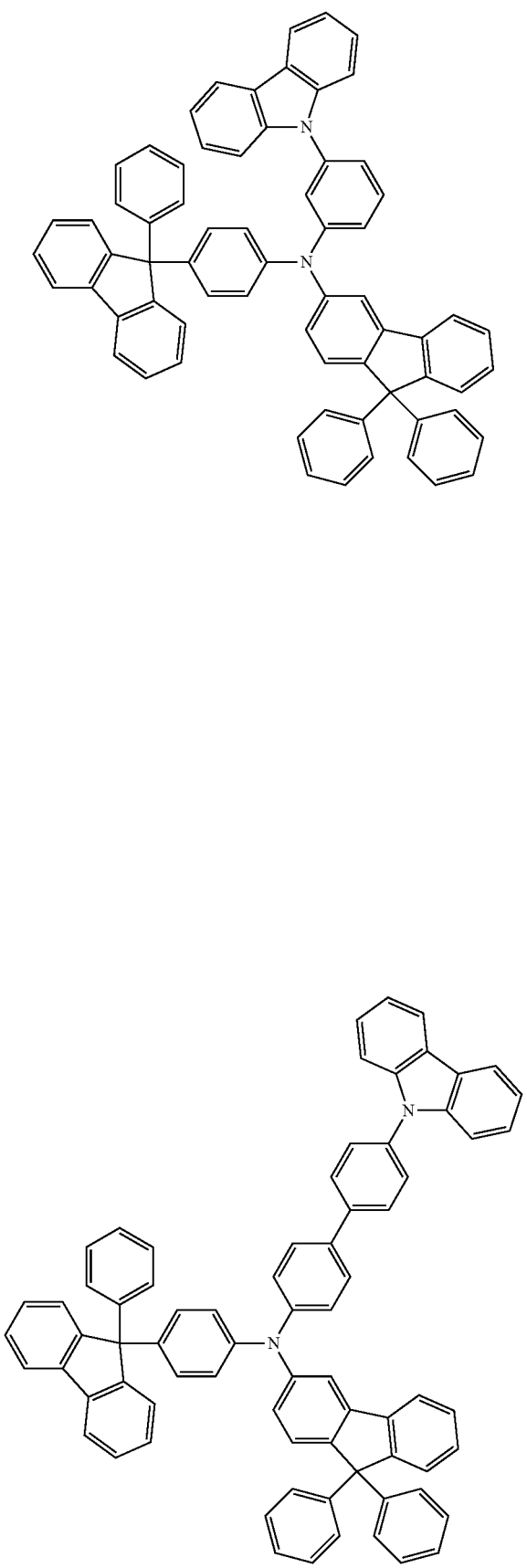
130
-continued
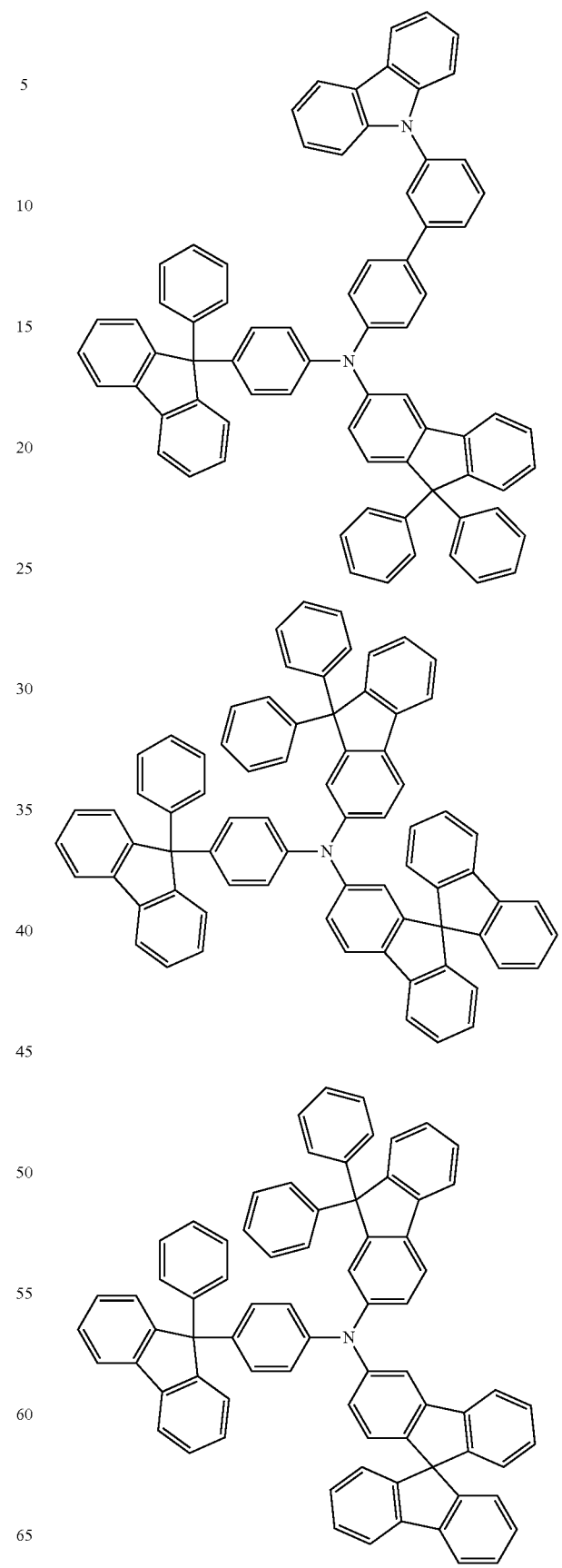

131
-continued
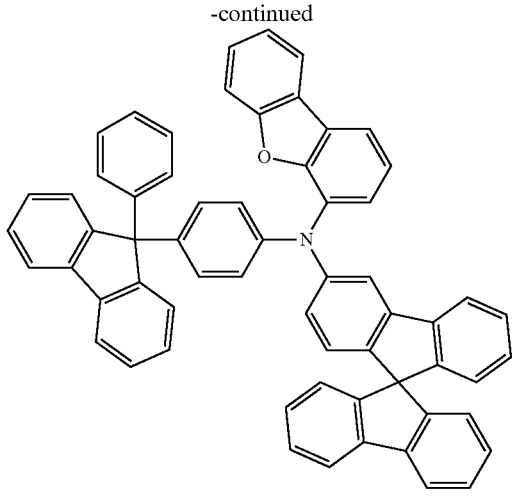
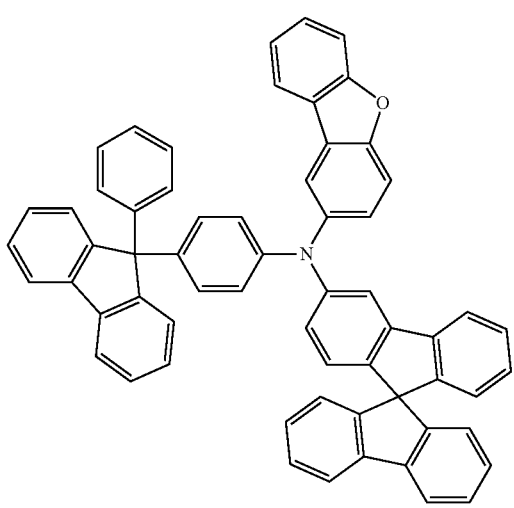
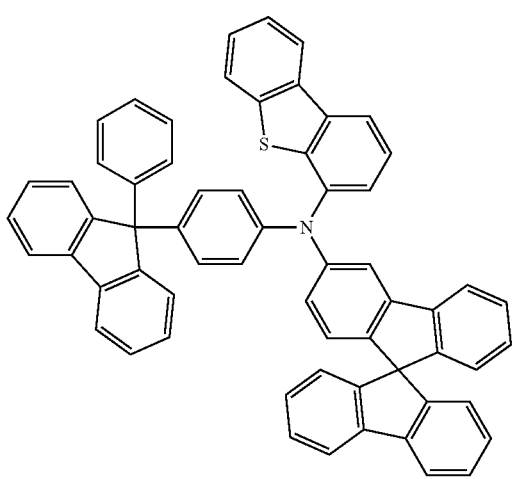
132
-continued
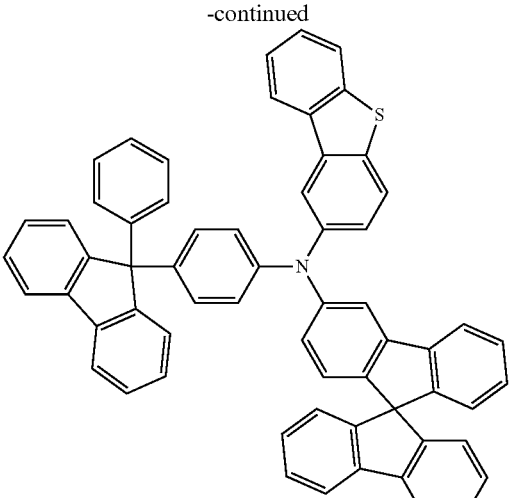
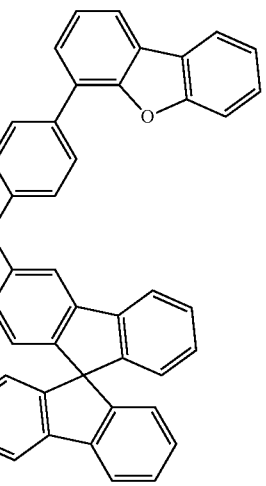
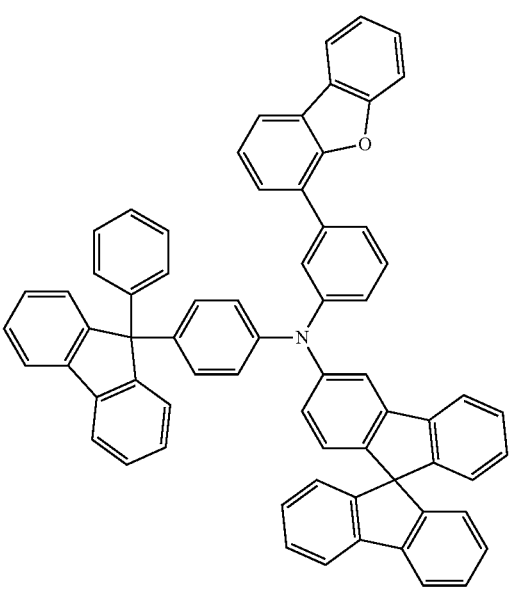

133
-continued
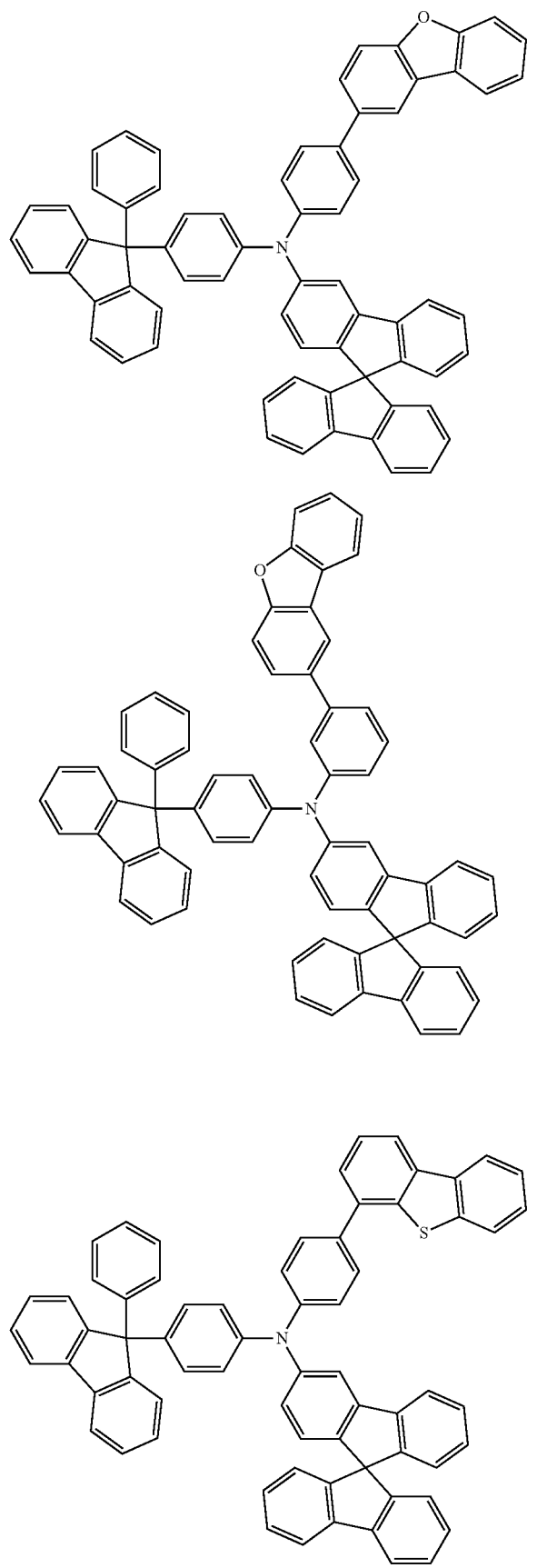
134
-continued
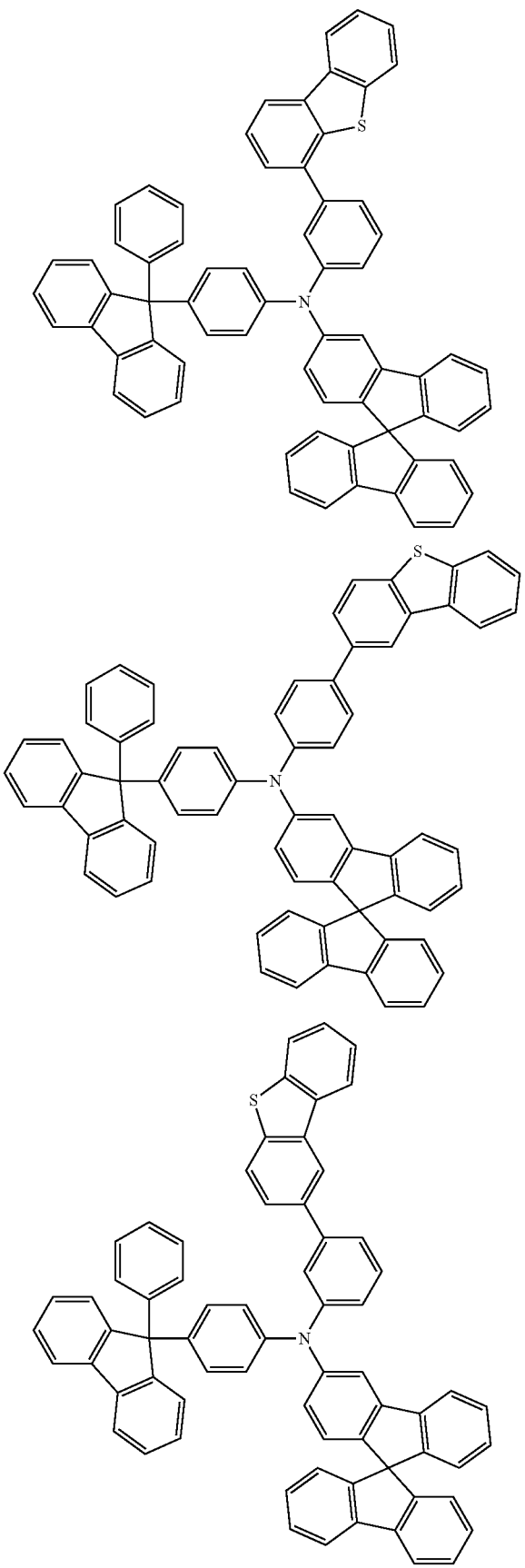

135
-continued
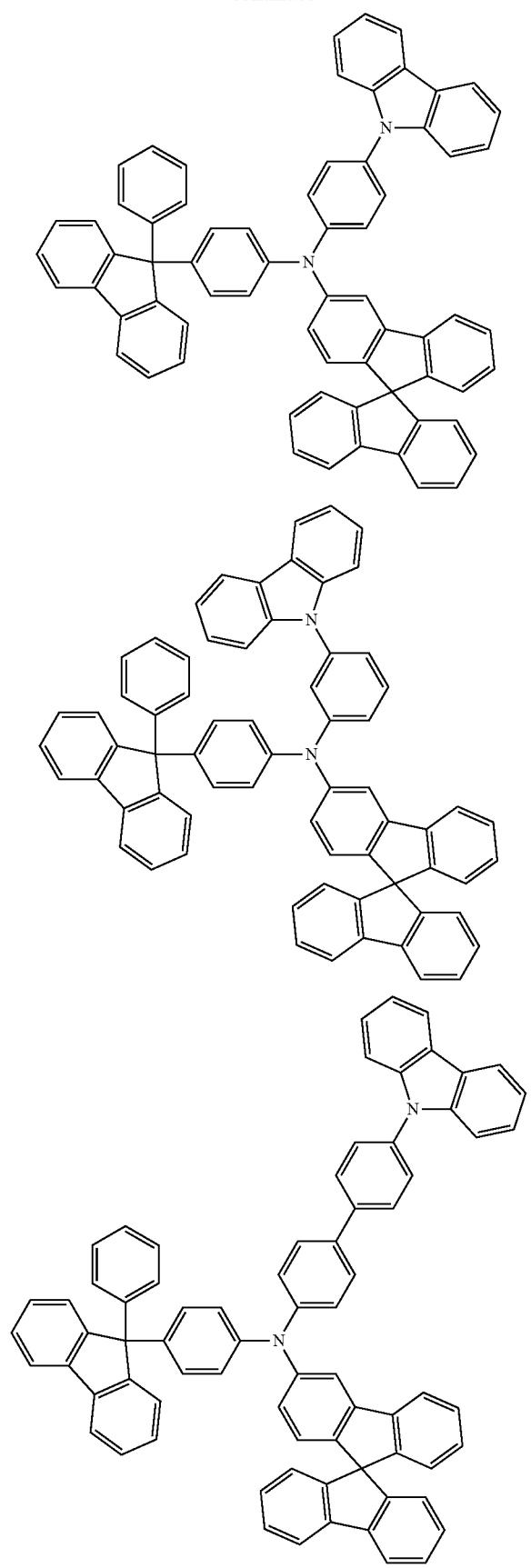
136
-continued
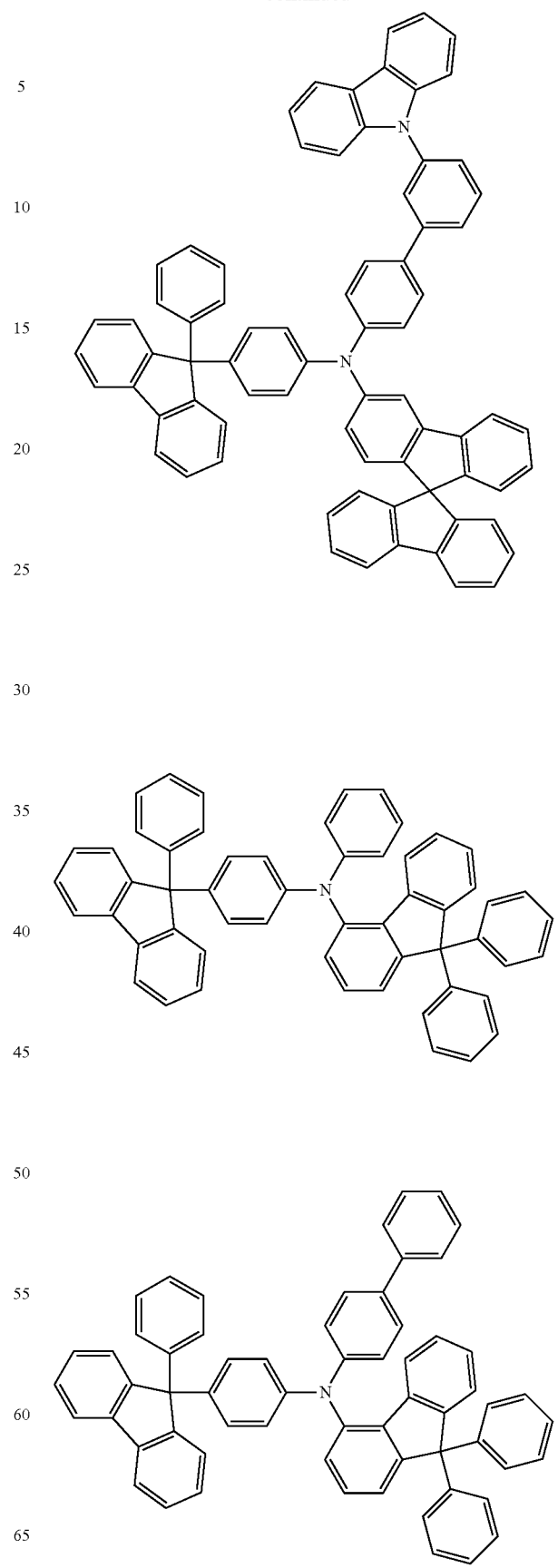

137
-continued
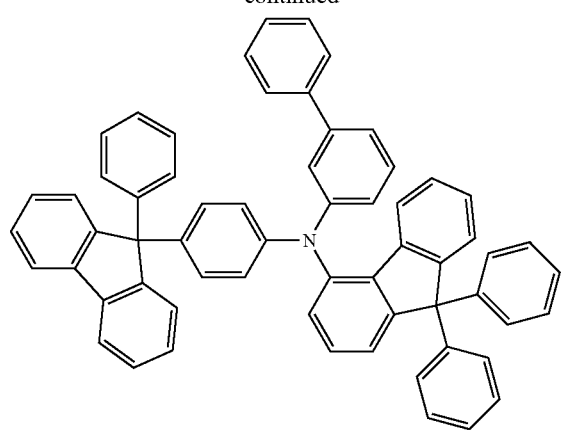
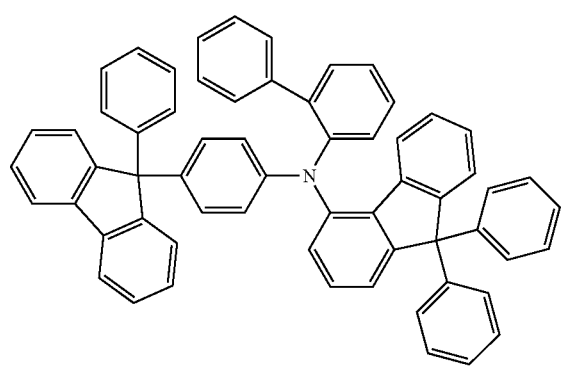
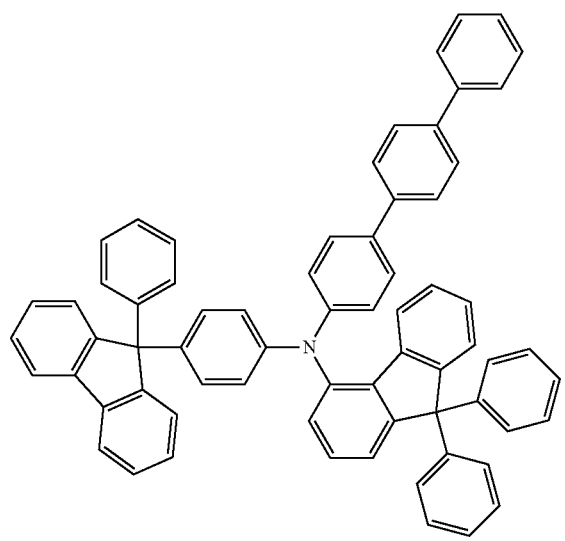
138
-continued
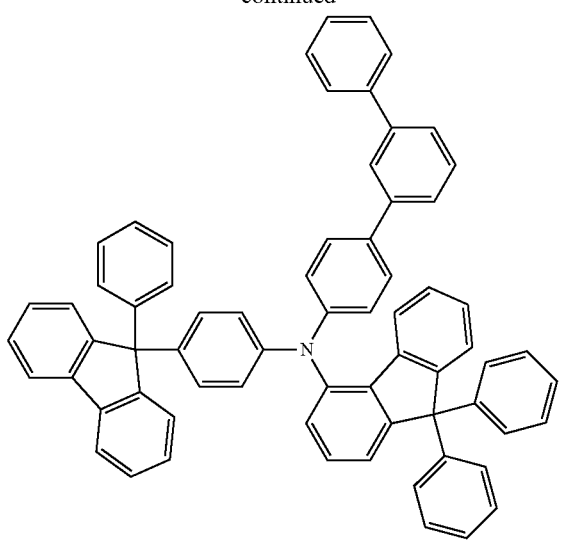
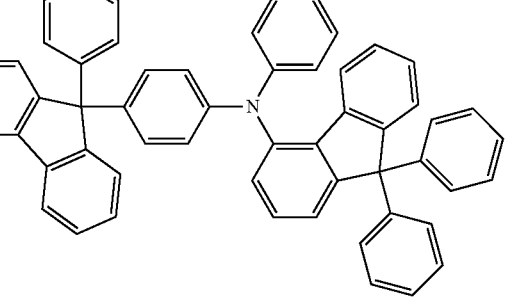
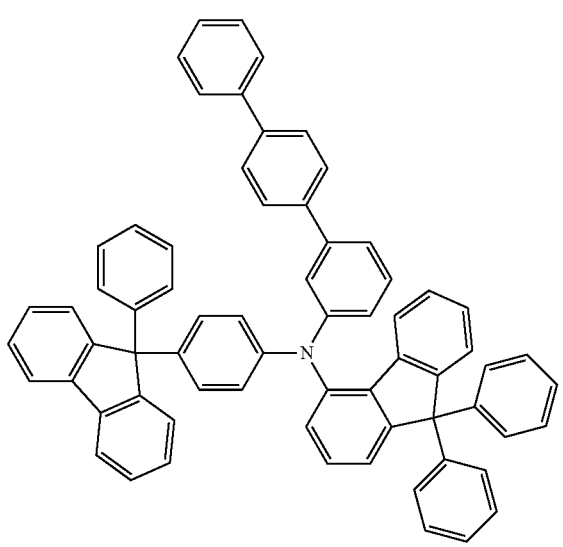

139
-continued
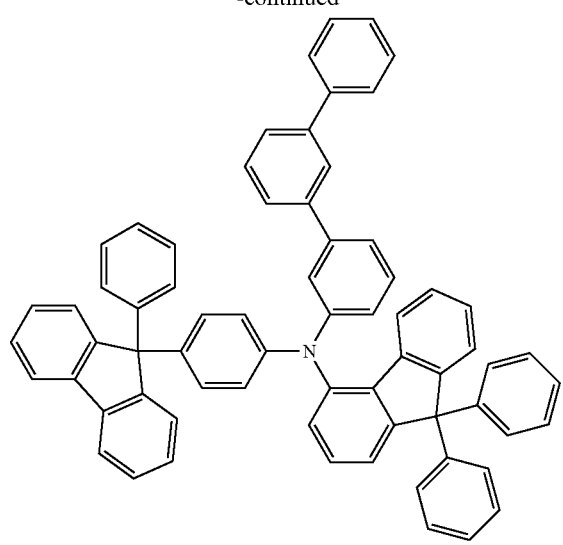
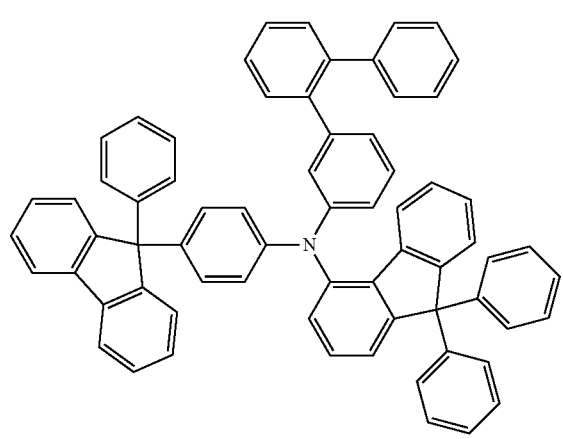
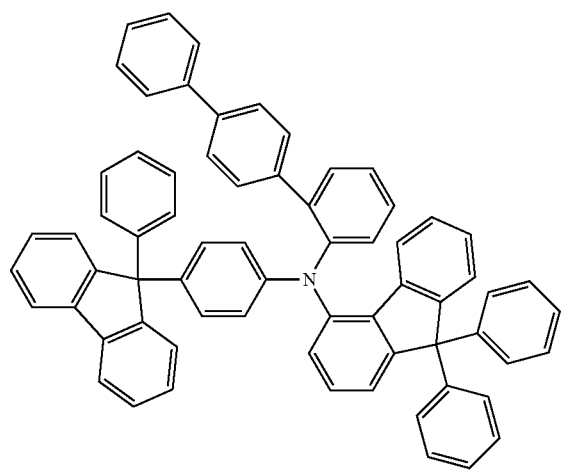
140
-continued
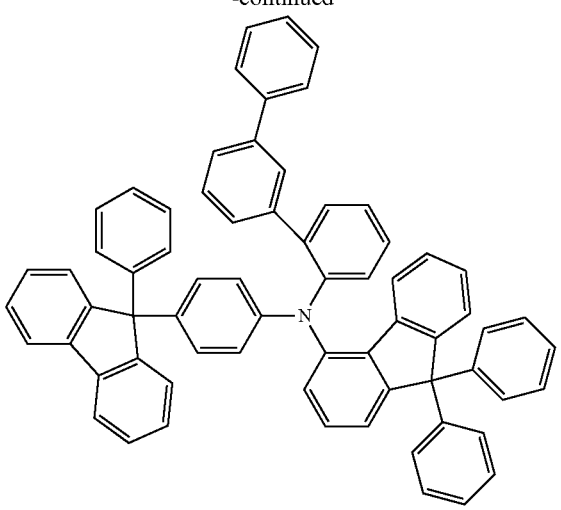
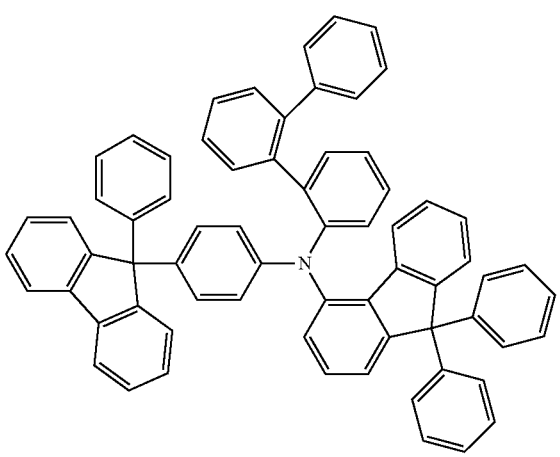
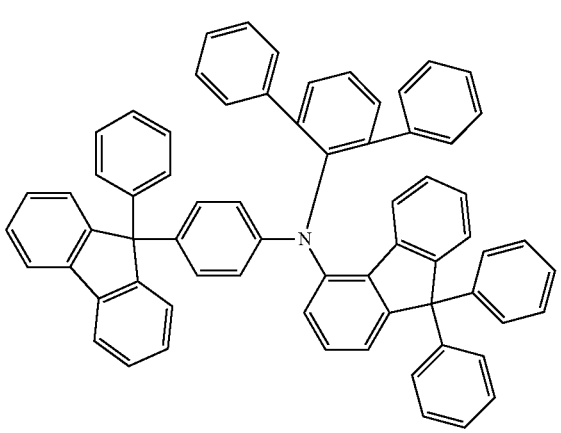

141
-continued
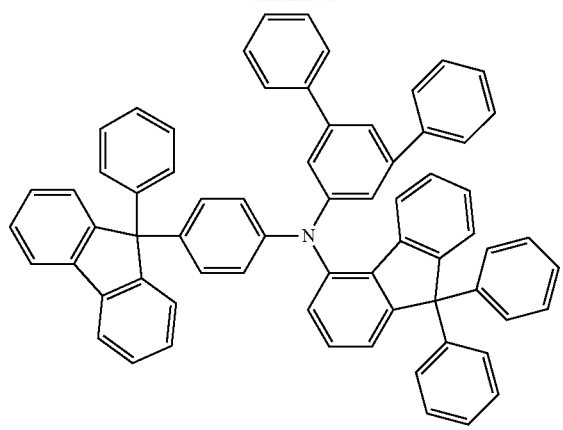
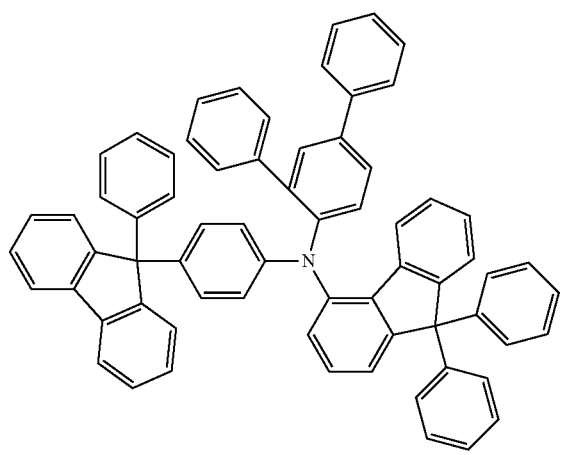
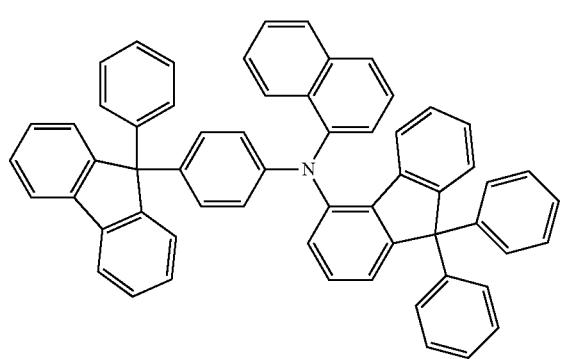
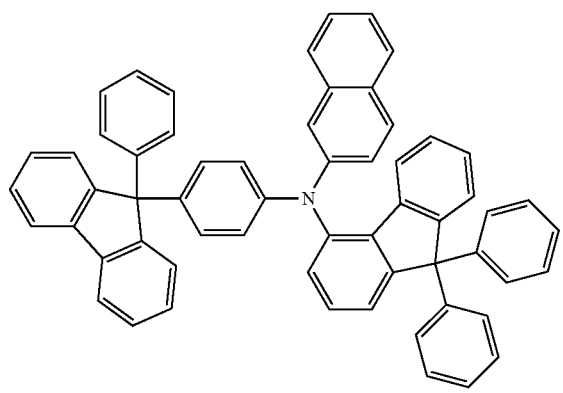
142
-continued
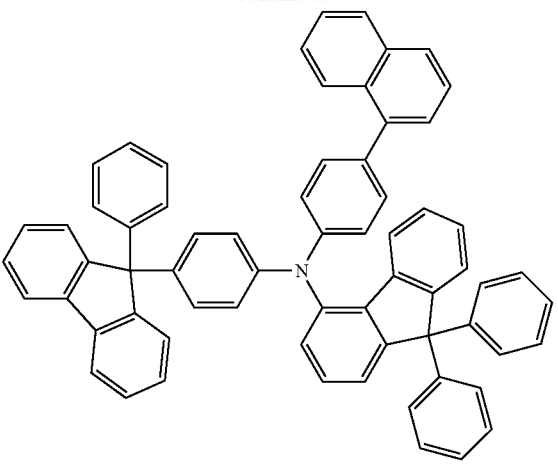
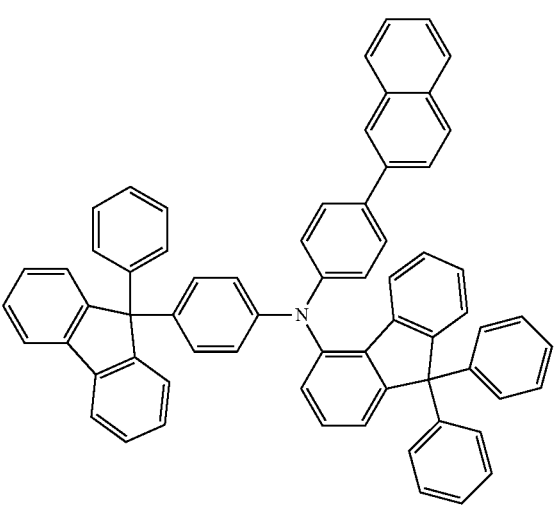
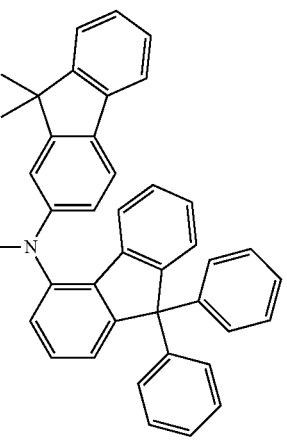

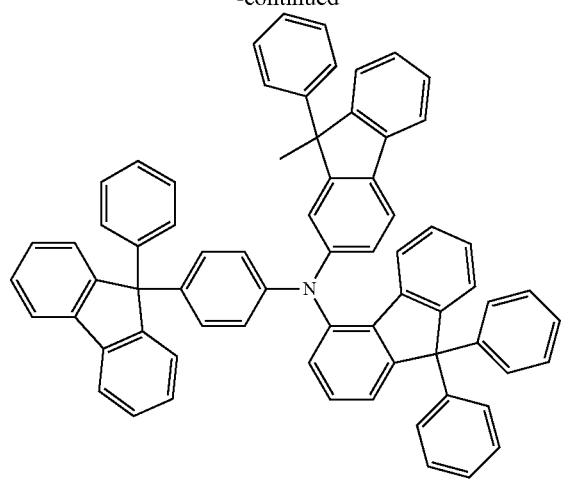
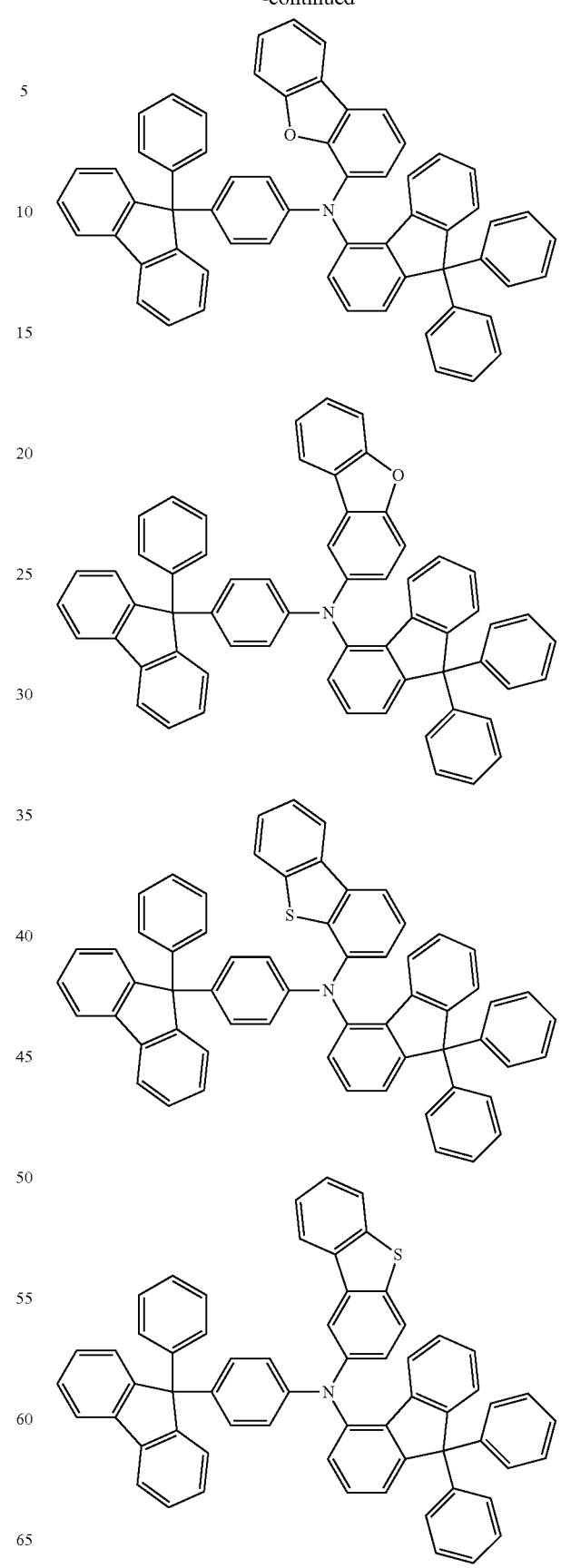

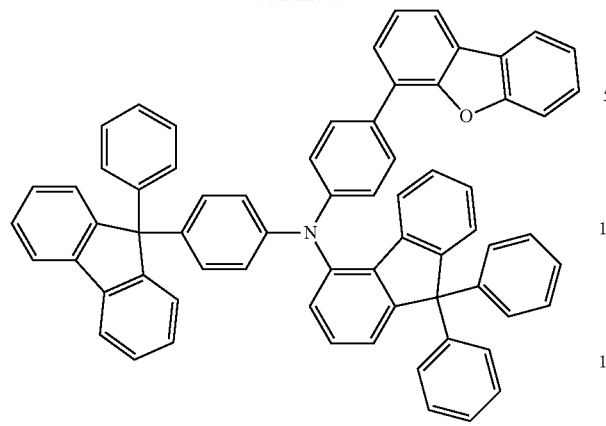
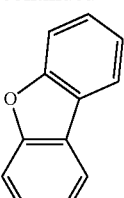
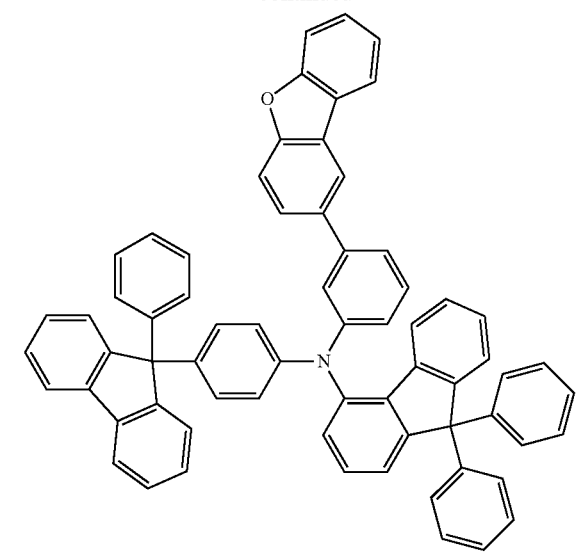
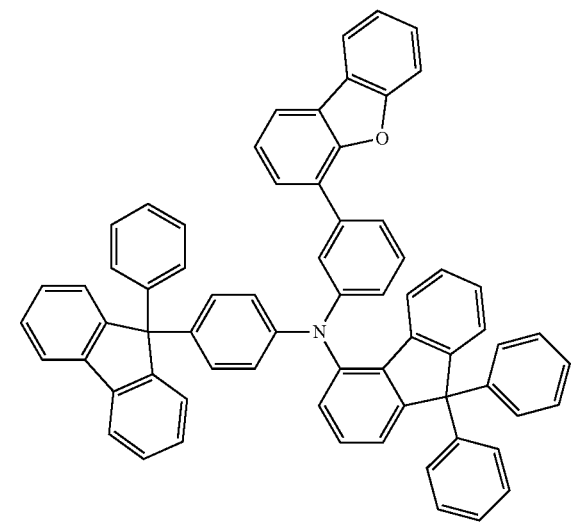
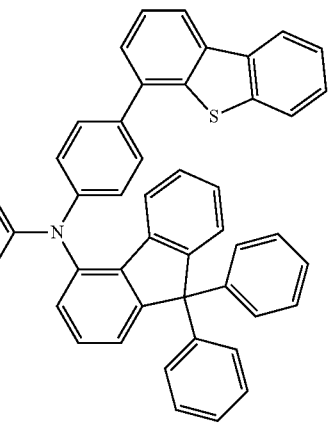
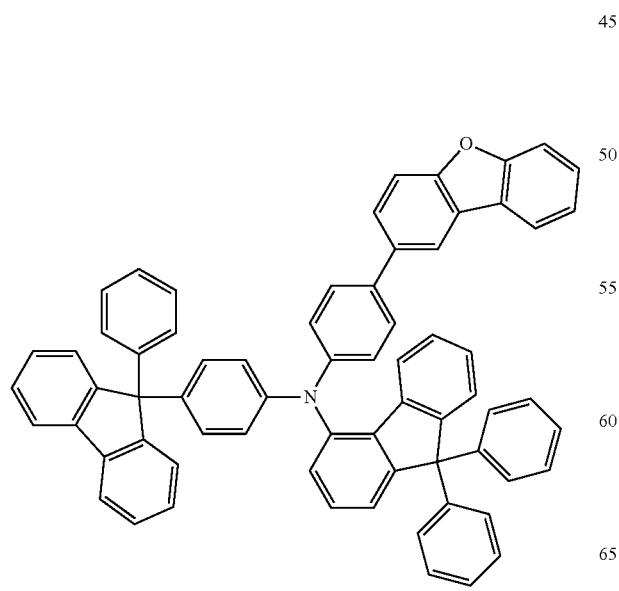
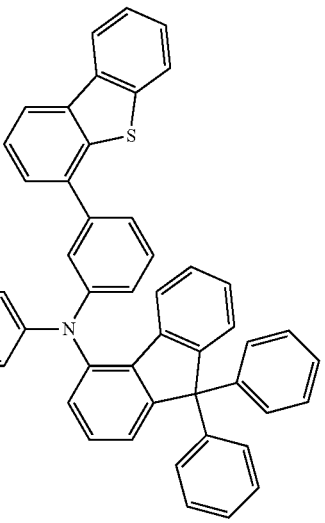

147
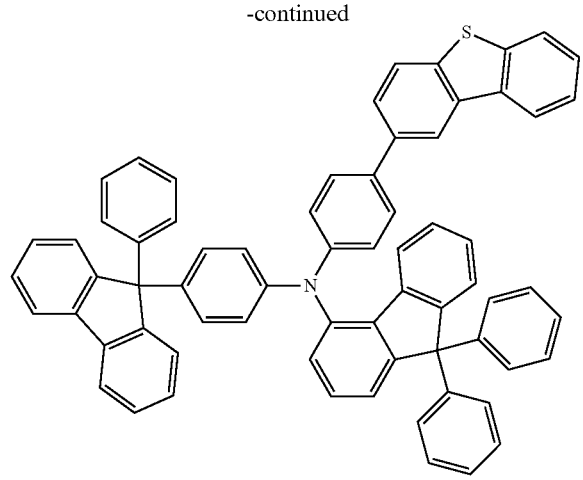
148
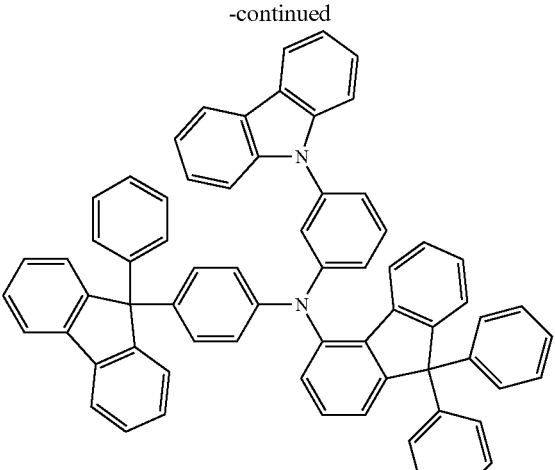

149
-continued
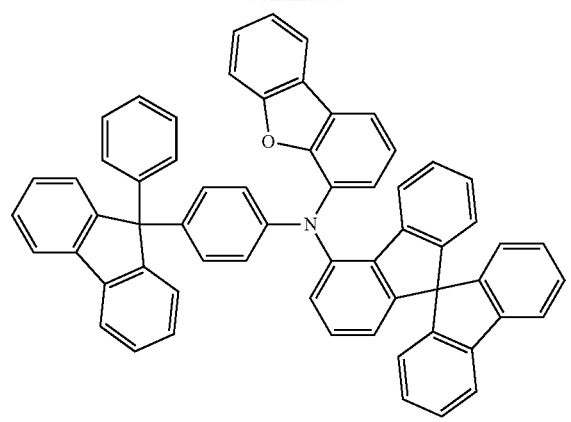
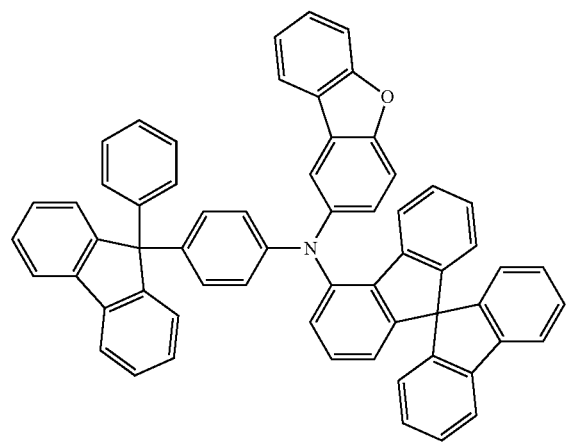
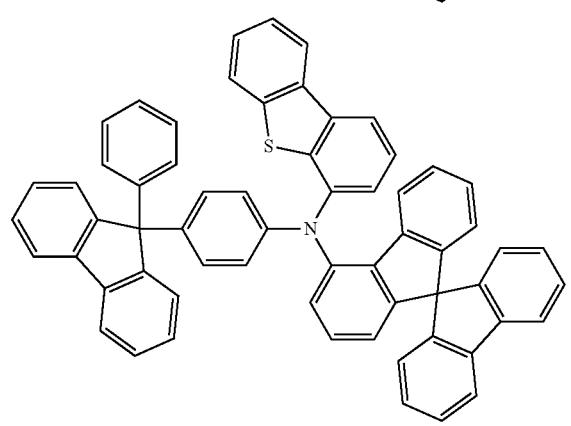
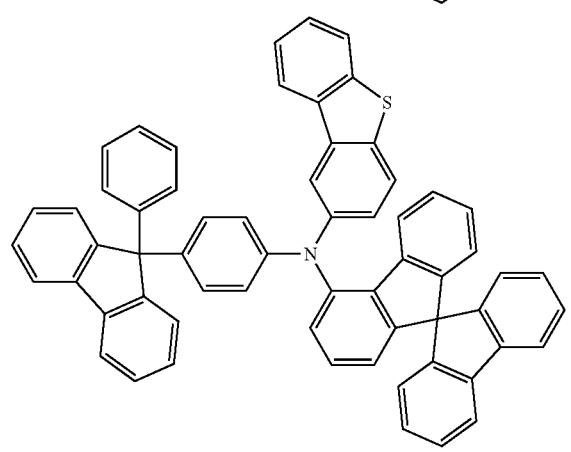
150
-continued
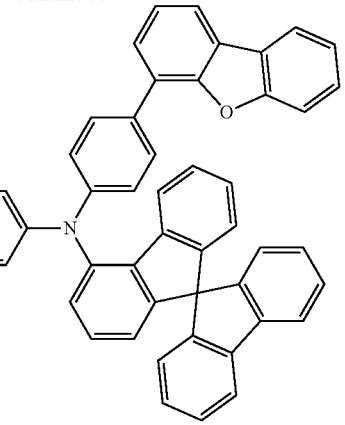
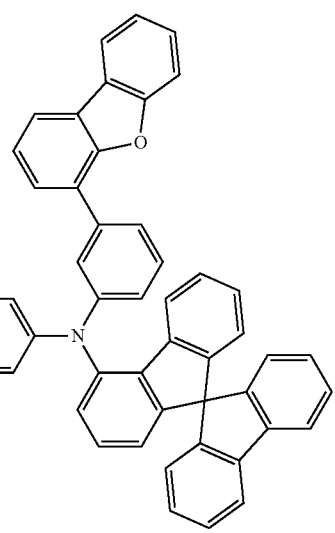
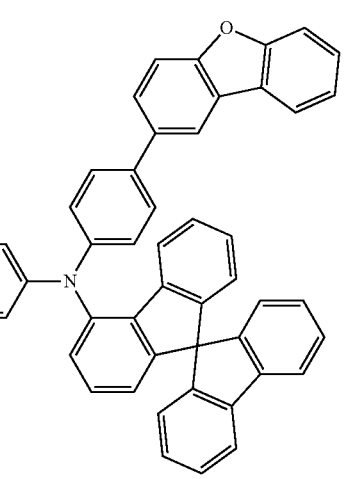

151
-continued
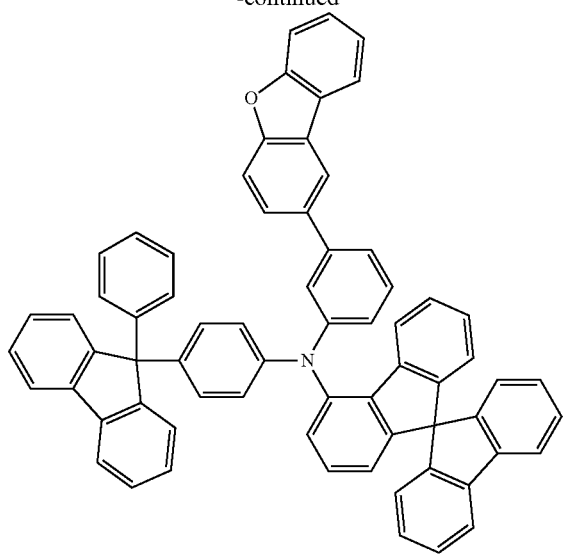
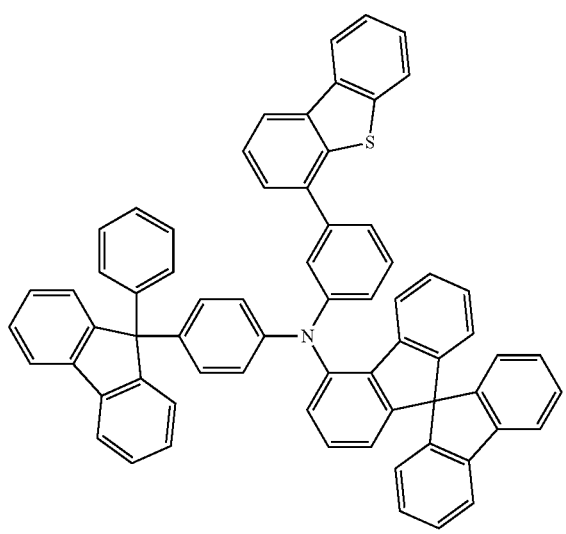
152
-continued
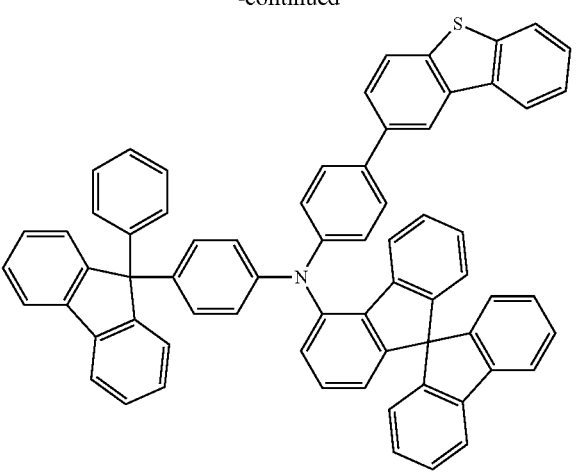
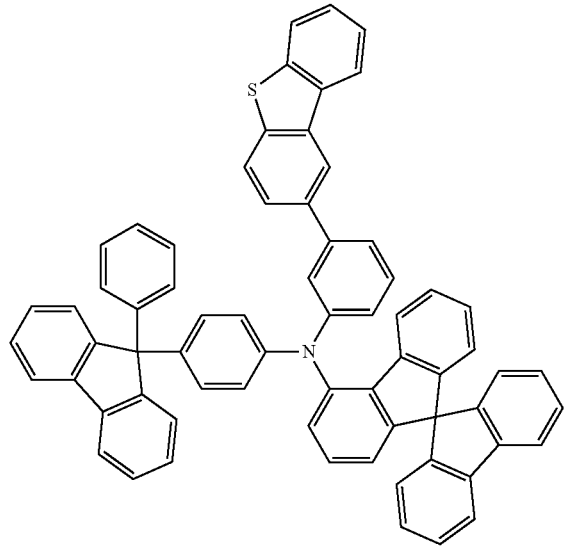
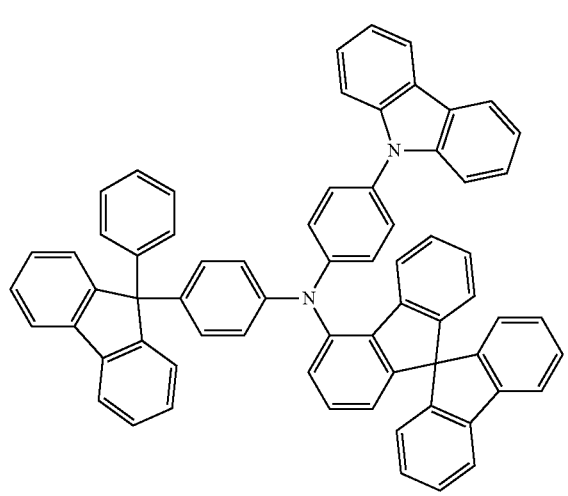

153
-continued
154
-continued
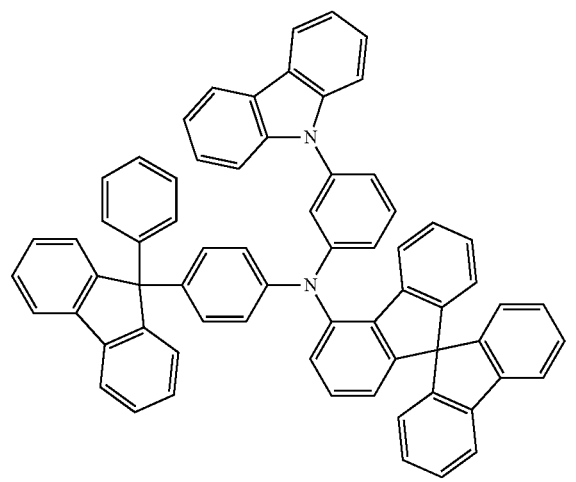
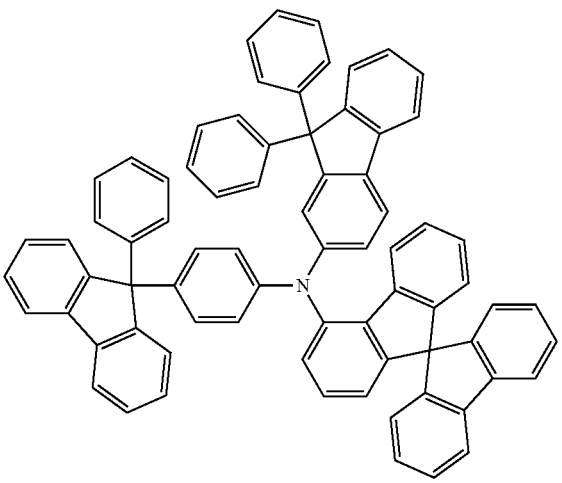 [SMILES: c1ccc(C2(c3ccc(N(c4ccc5c(c4)C(c4ccccc4)(c4ccccc4)c4ccccc4-5)c4cccc5c4-c4ccccc4C54c5ccccc5-c5ccccc54)cc3)c3ccccc3-c3ccccc32)cc1]
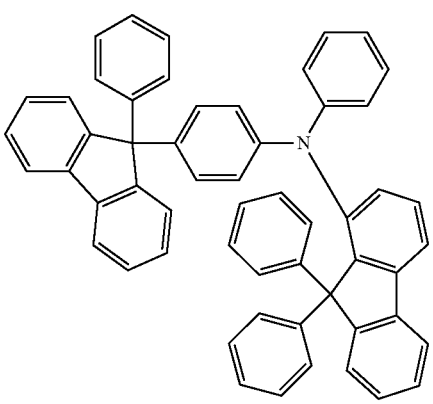
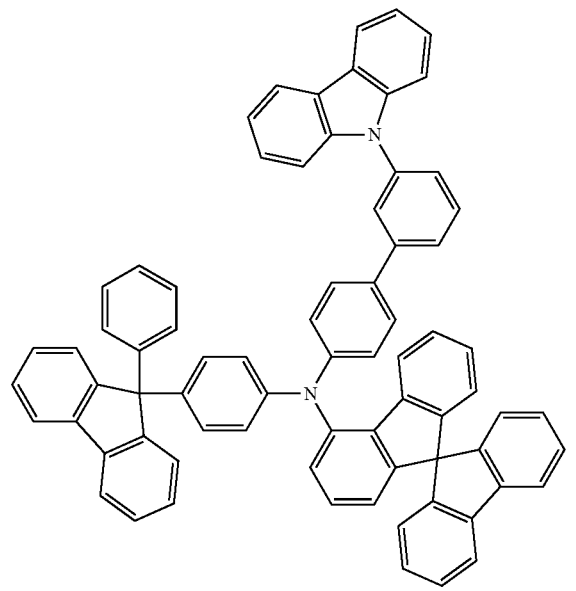

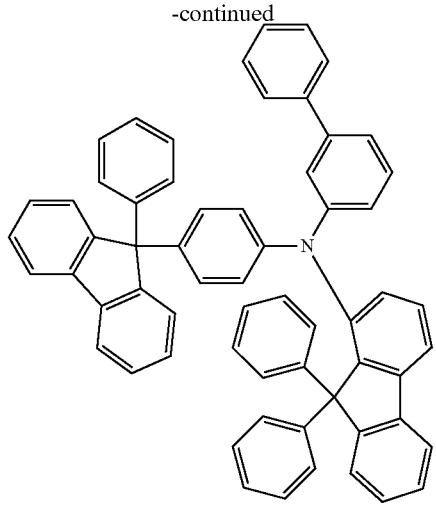
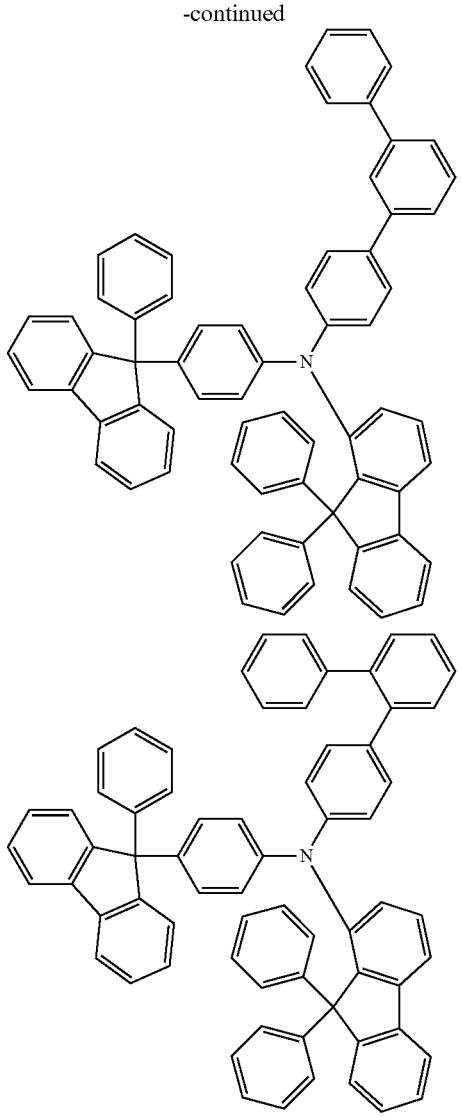
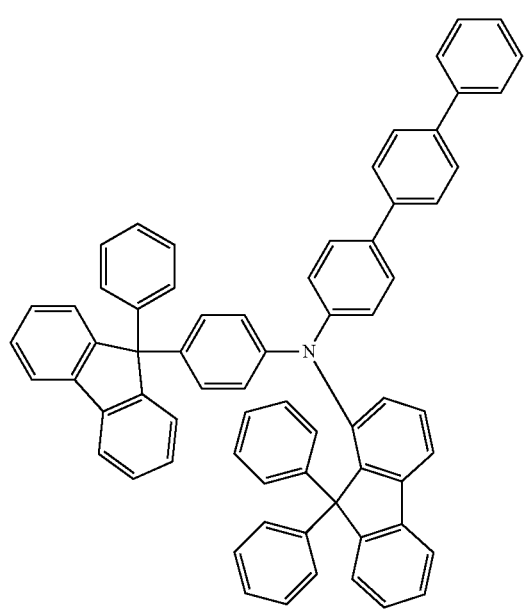

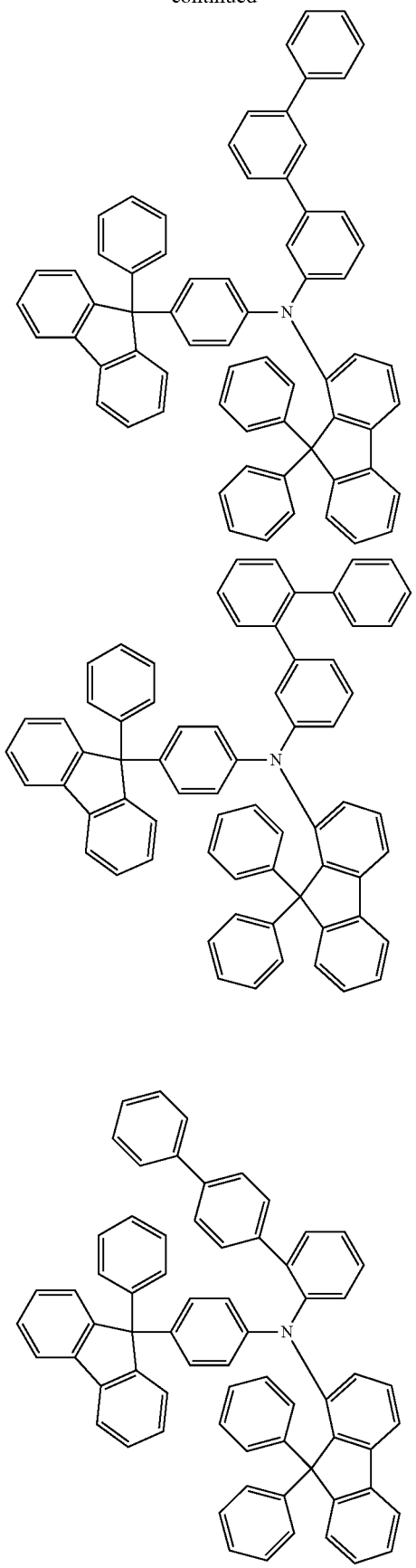
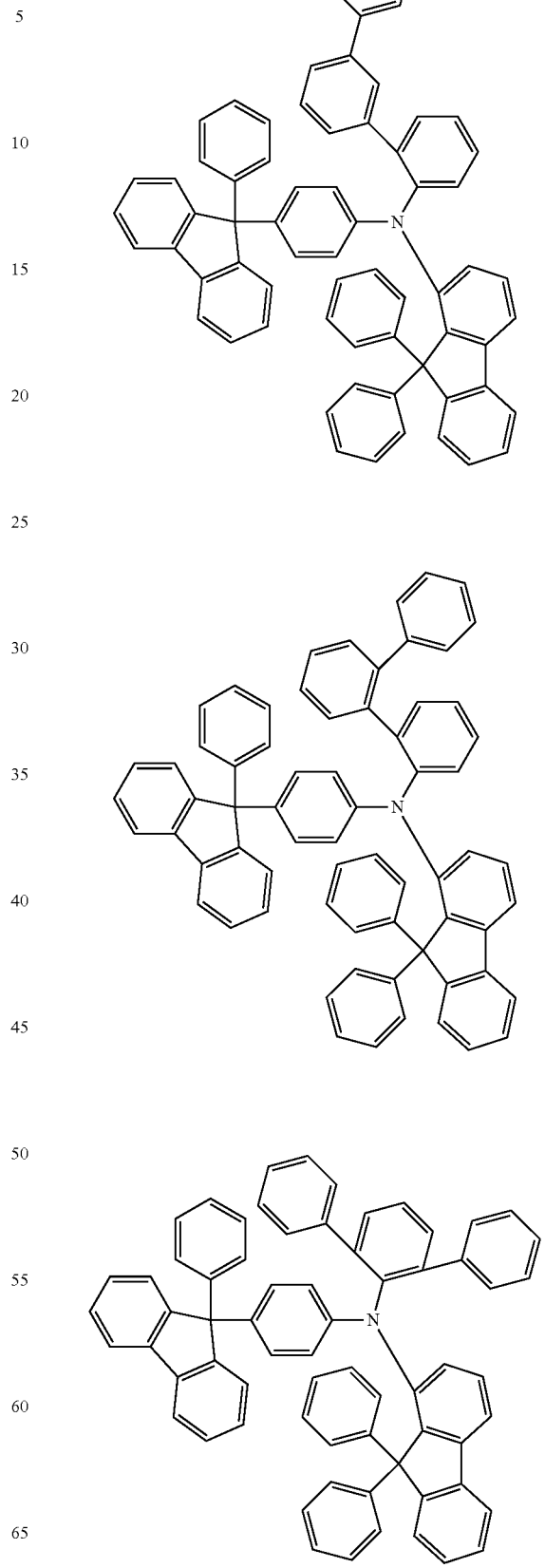

-continued
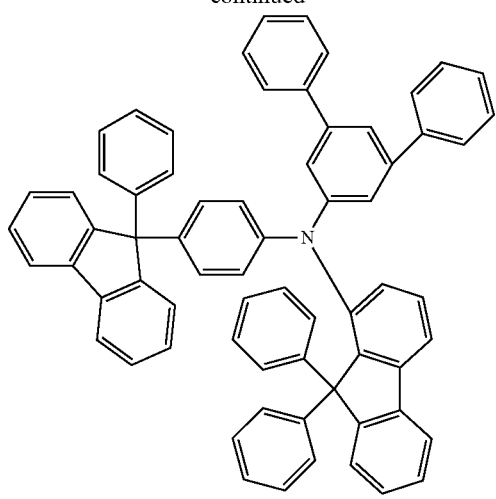
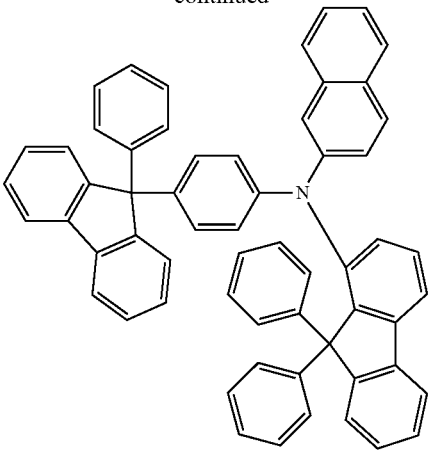
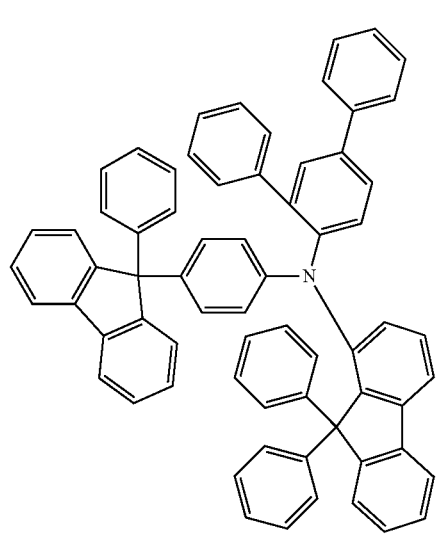
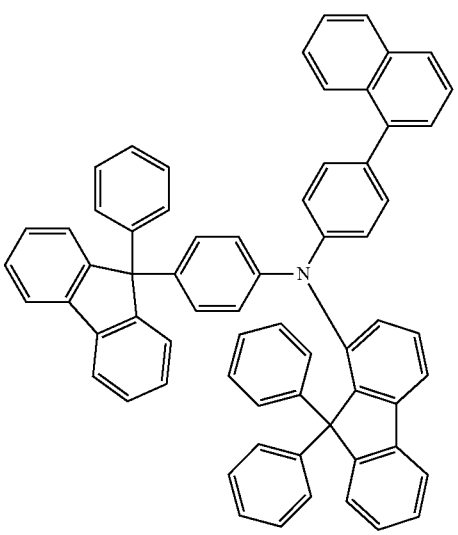
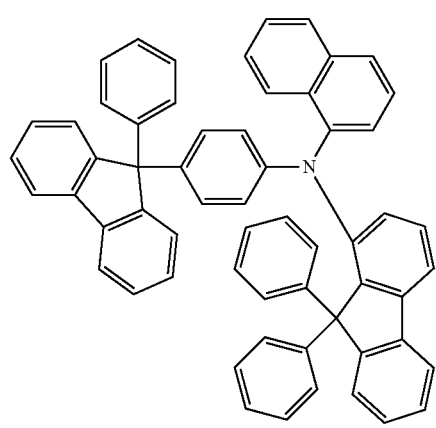
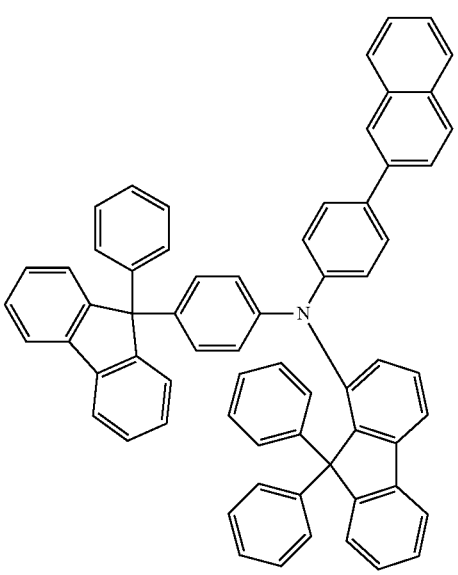

-continued
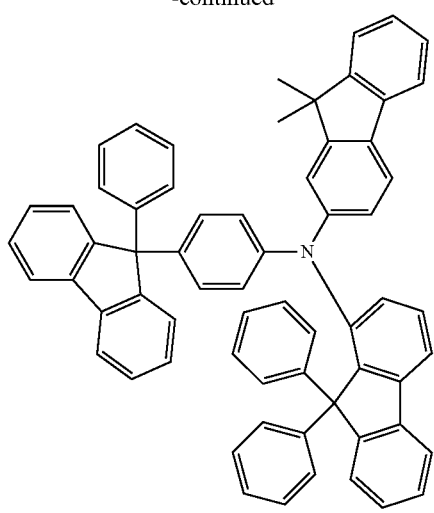
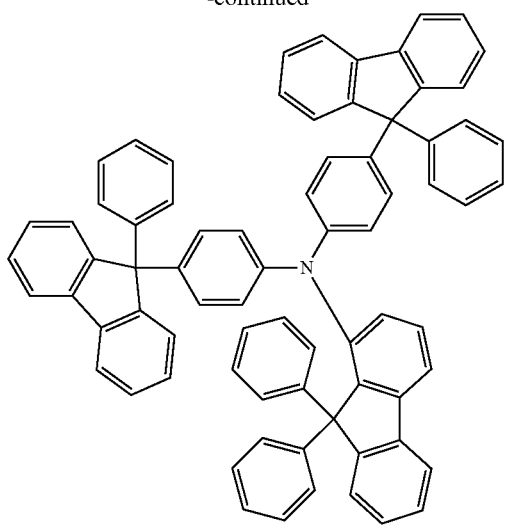
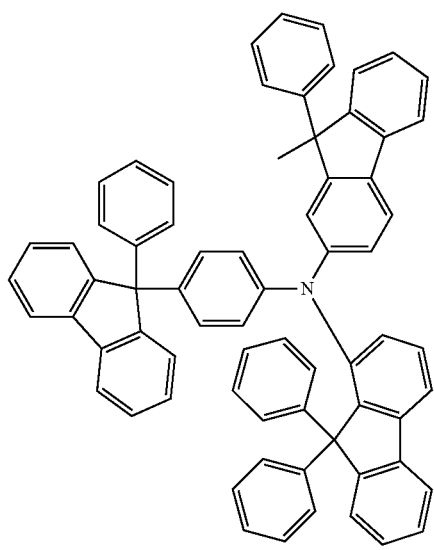
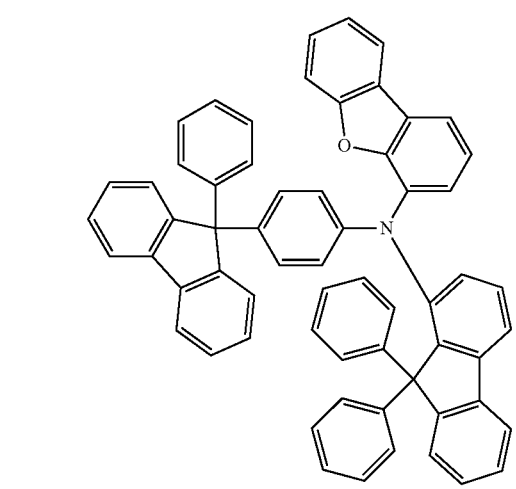
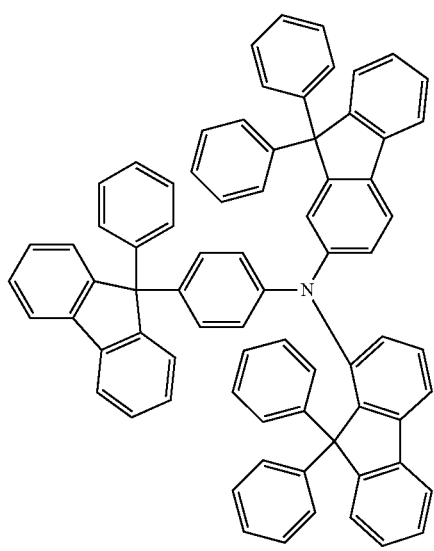
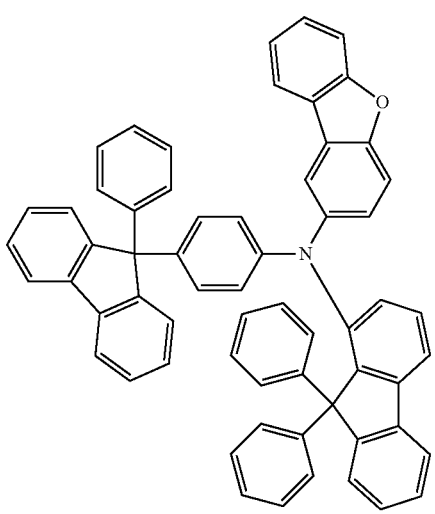

163
-continued
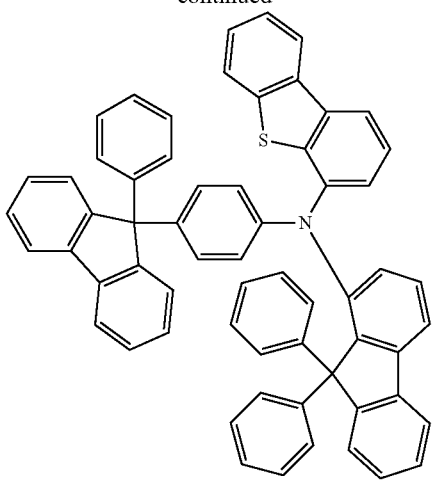
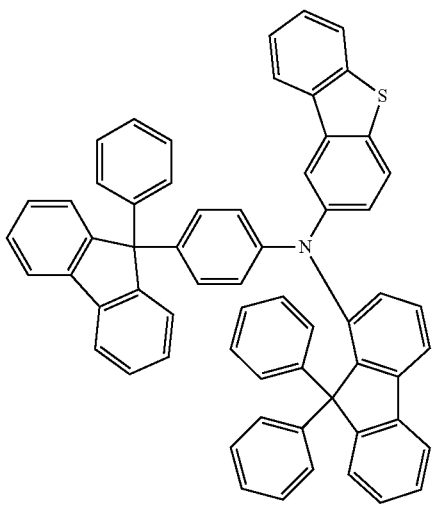
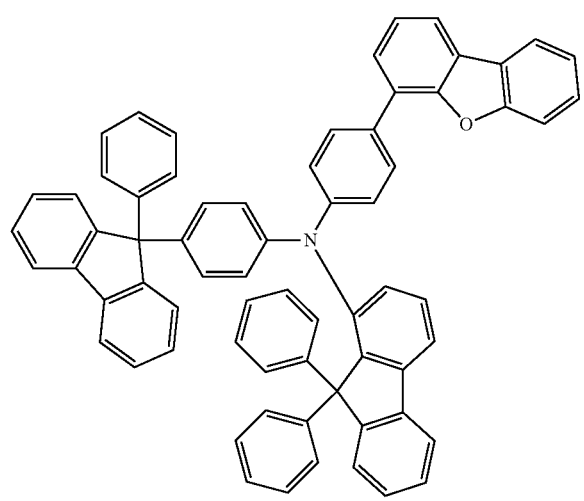
164
-continued
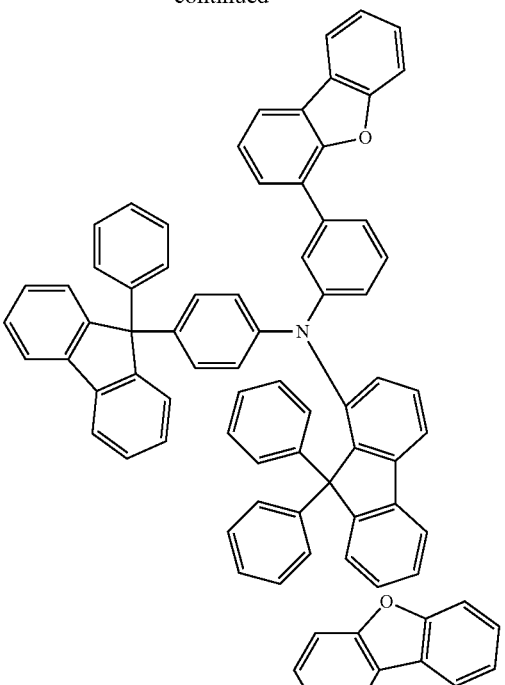
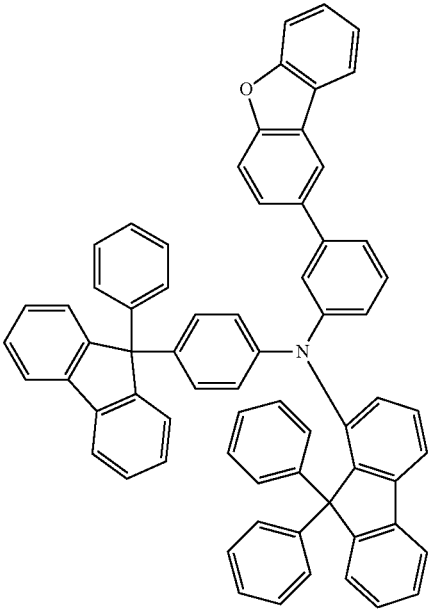

165
-continued
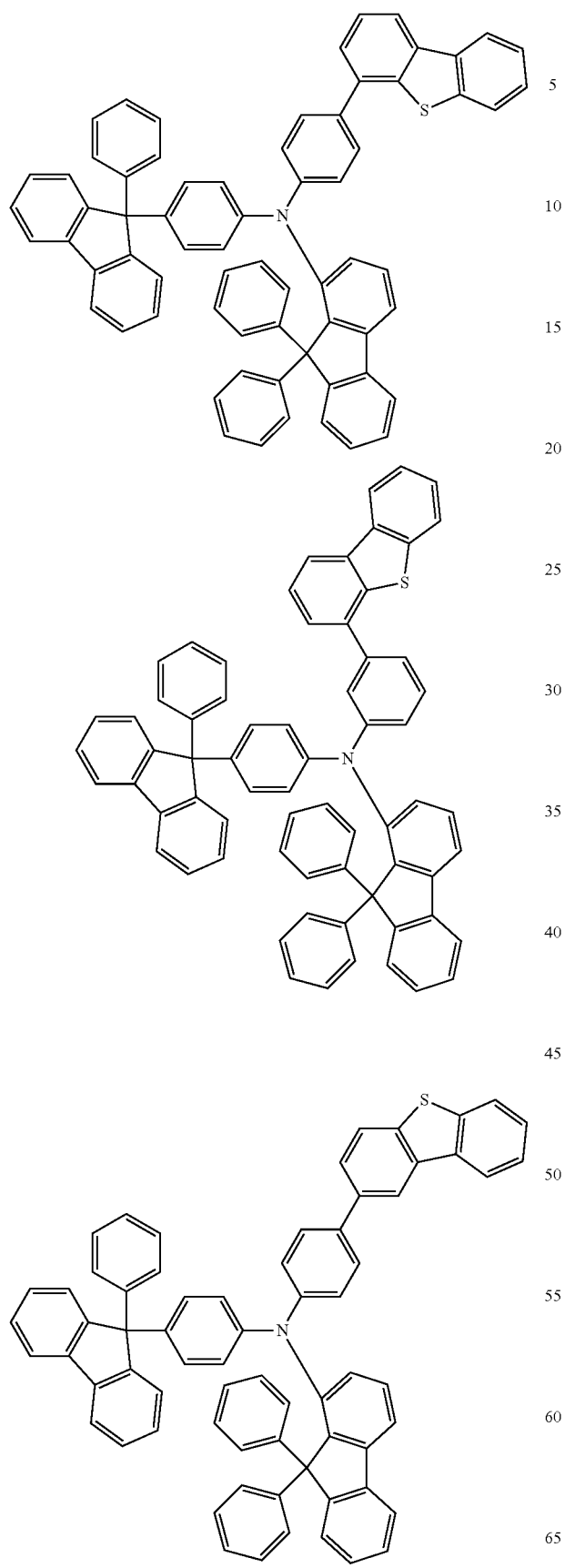
166
-continued
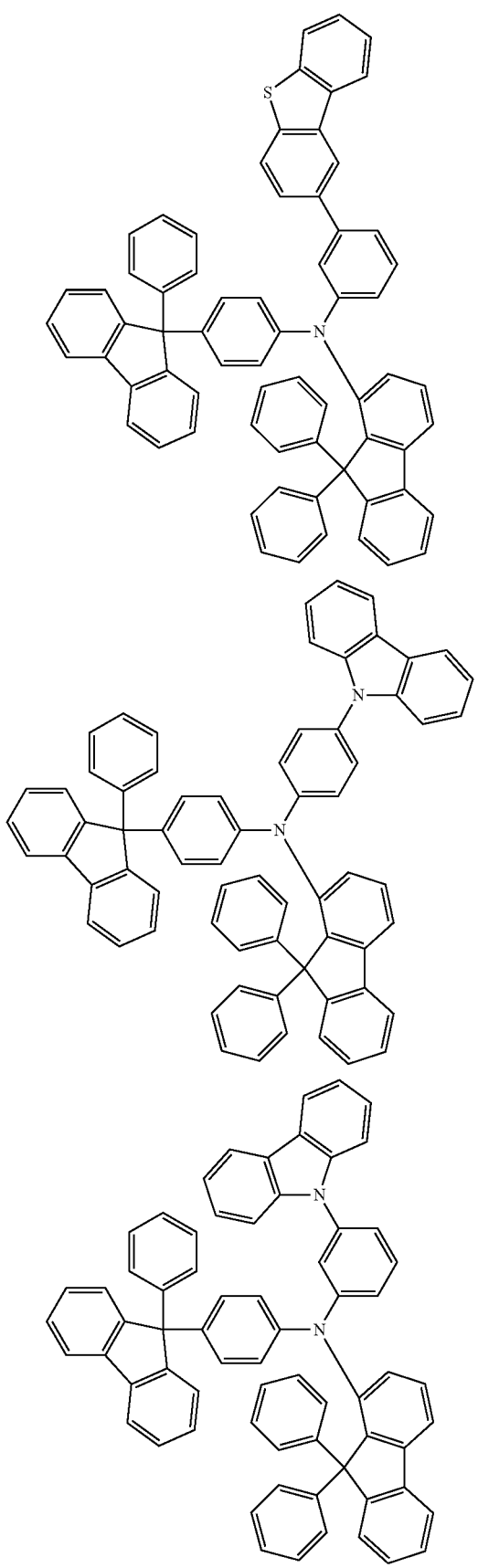

167
-continued
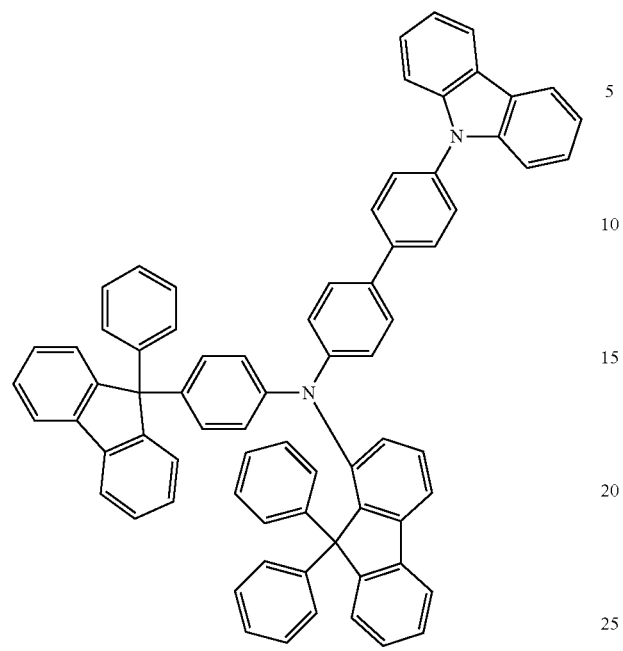
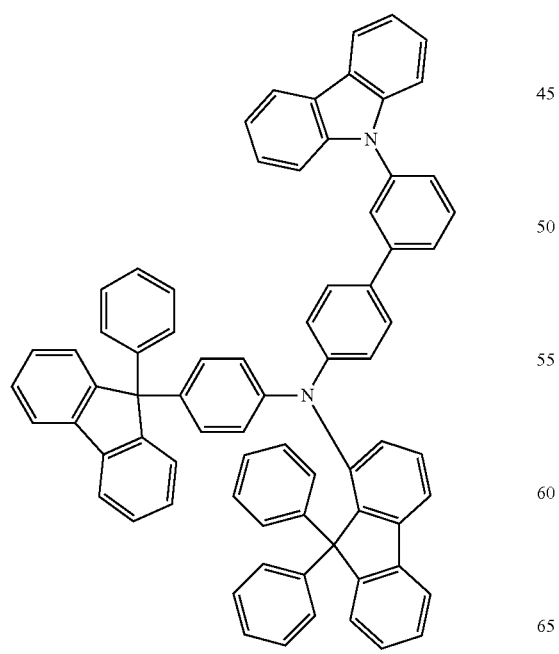
168
-continued
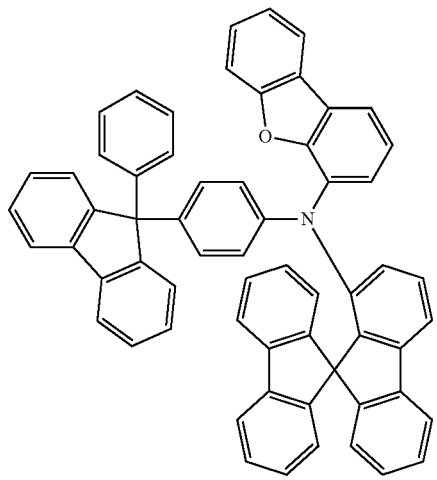
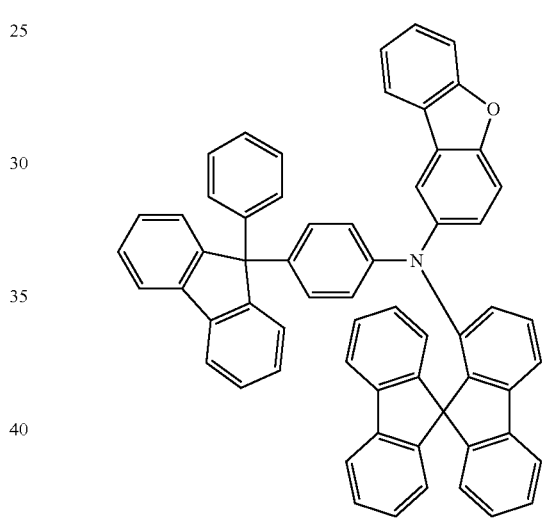
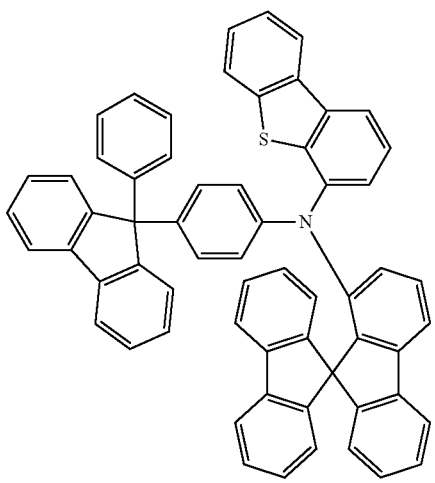

169
-continued
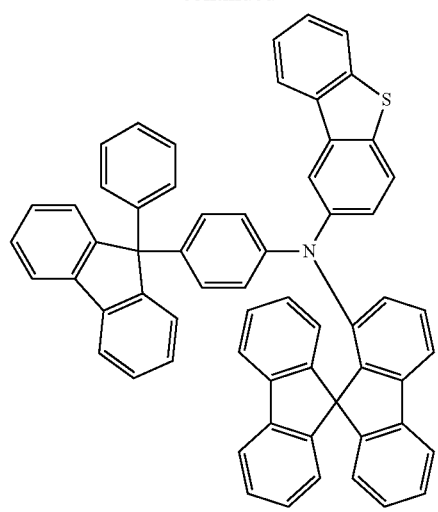
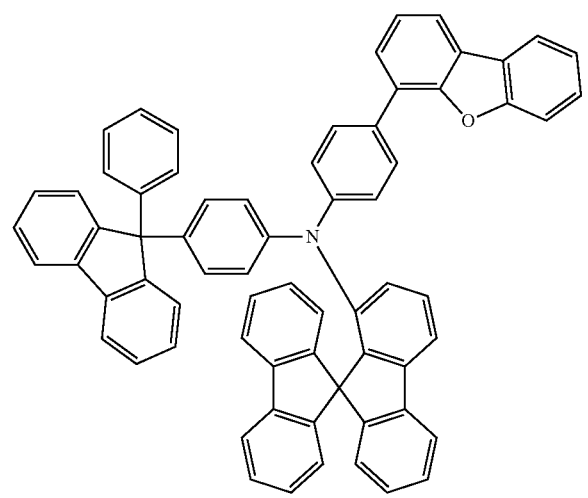
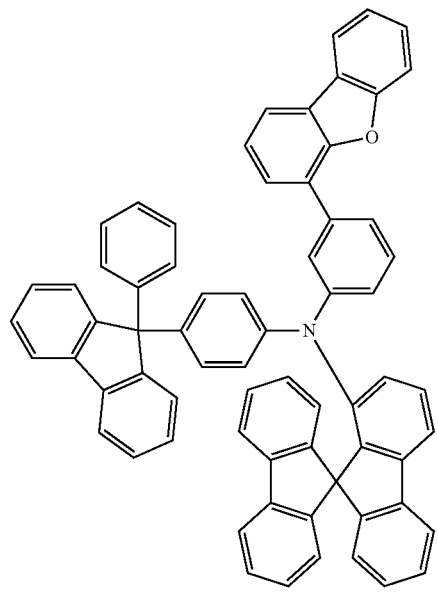
170
-continued
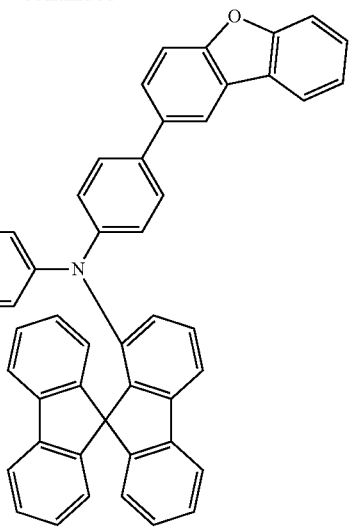
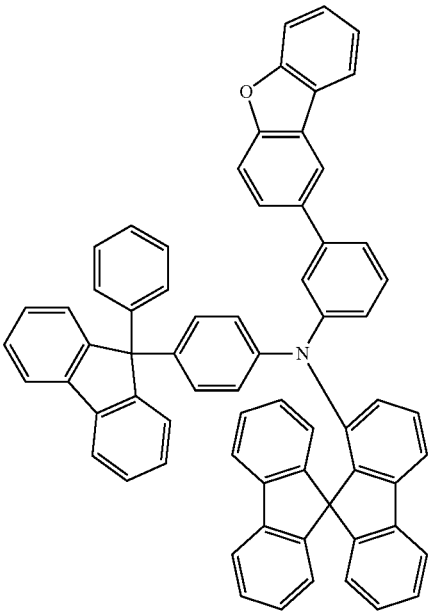
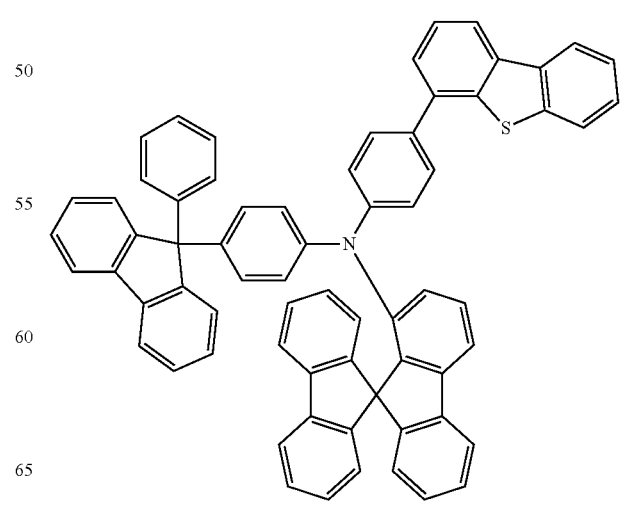

171
-continued
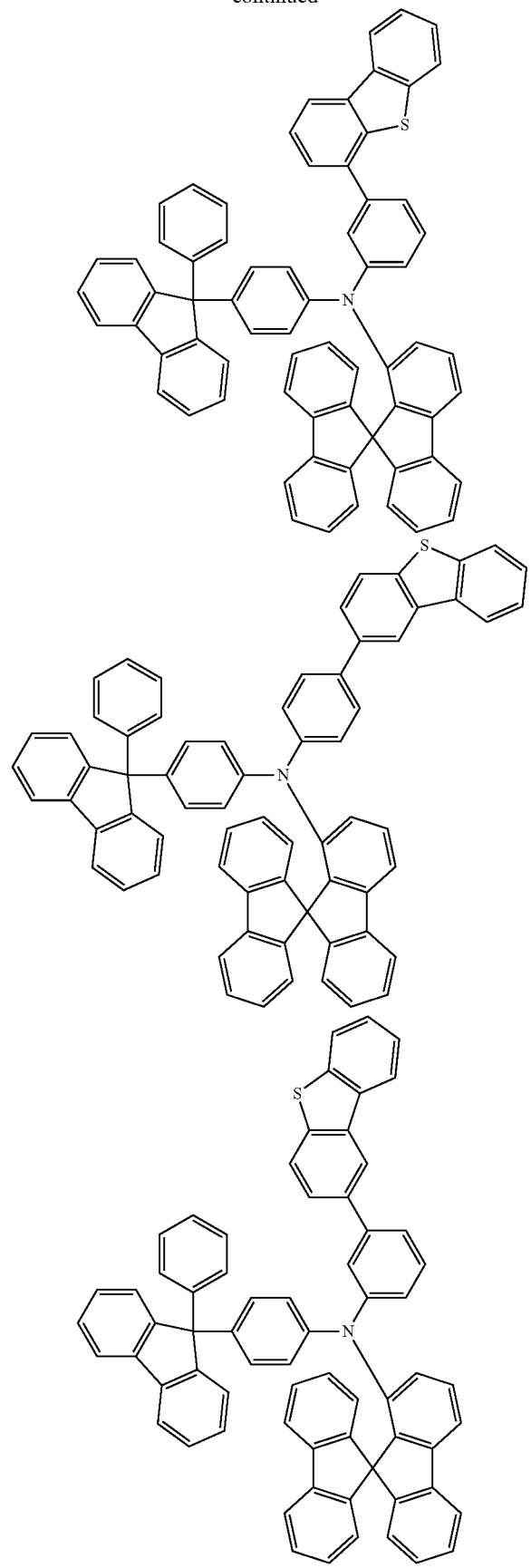
172
-continued
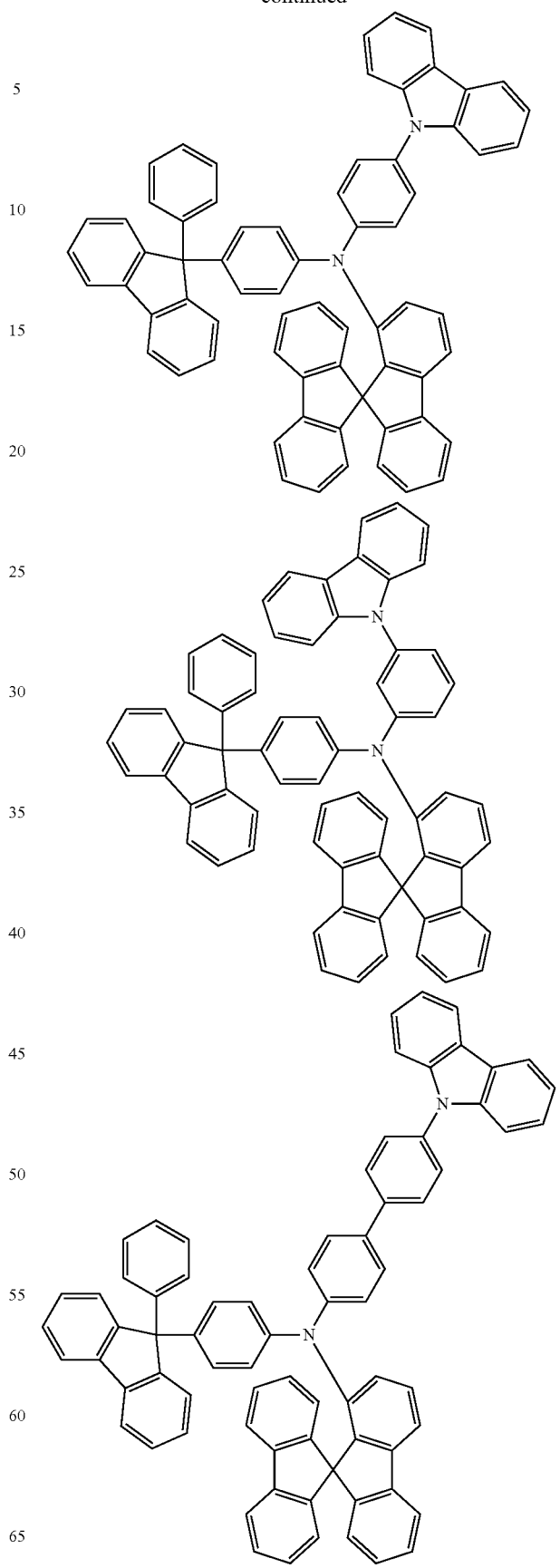

173
-continued
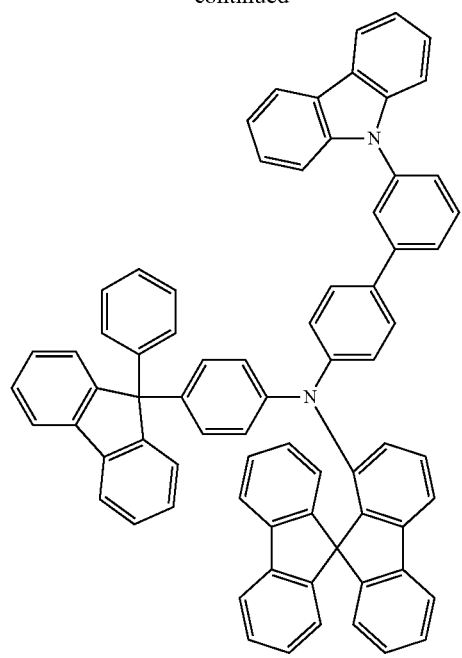
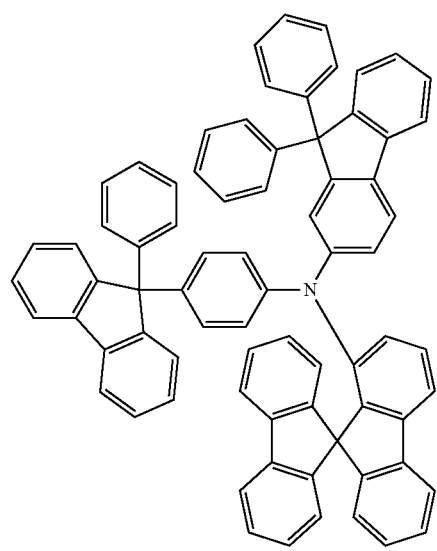
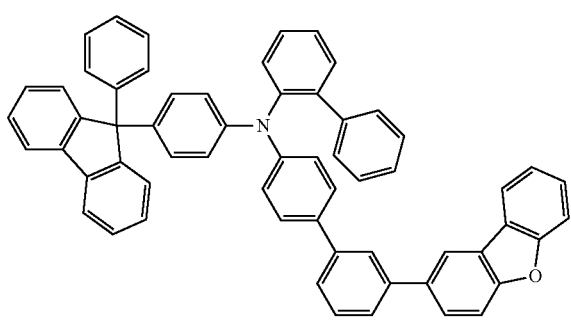
174
-continued
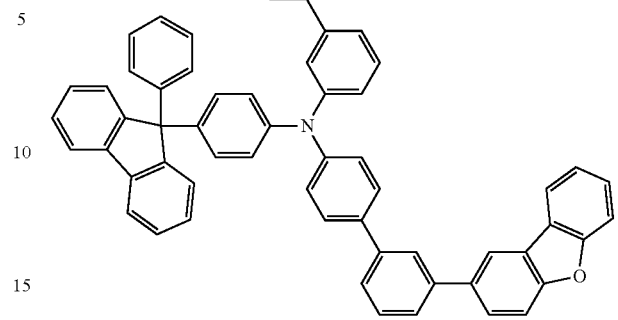
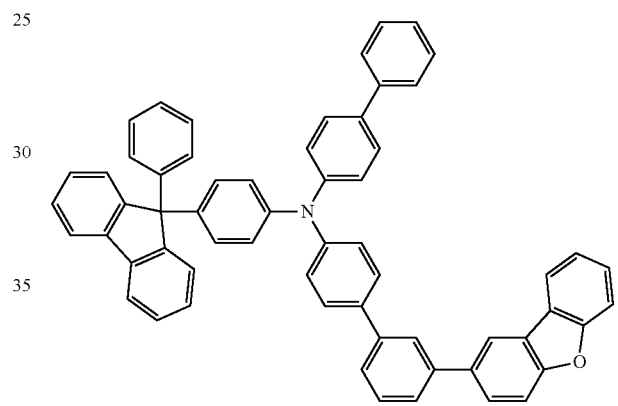
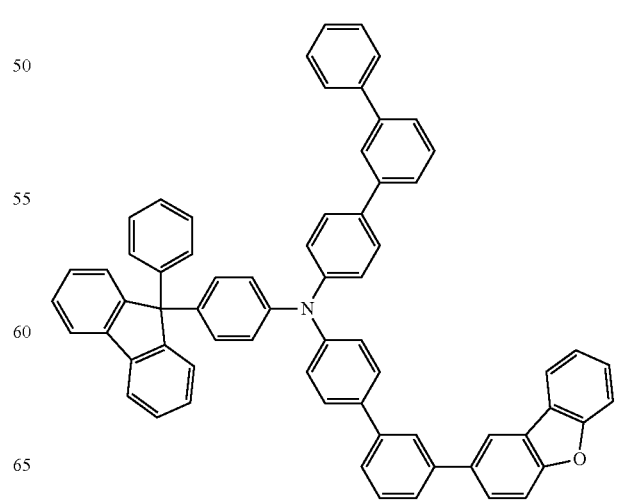

175
-continued
176
-continued
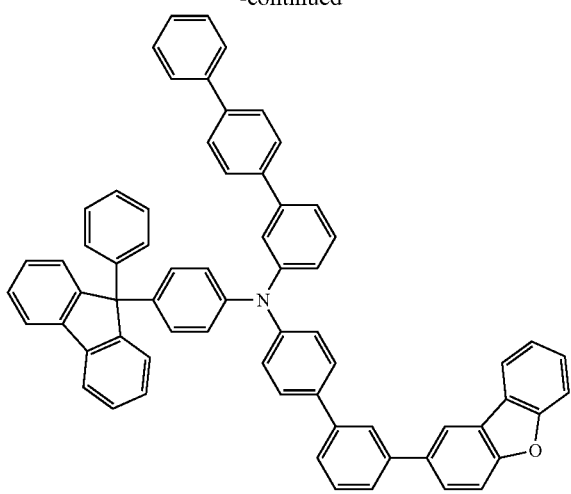
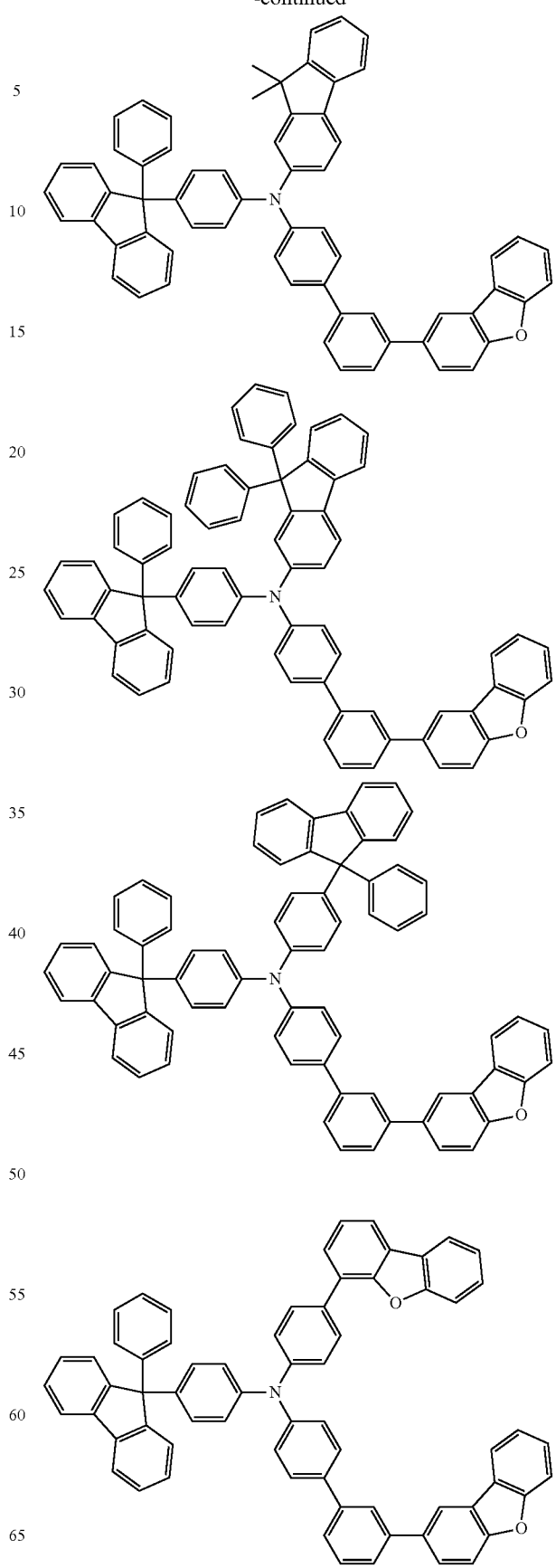

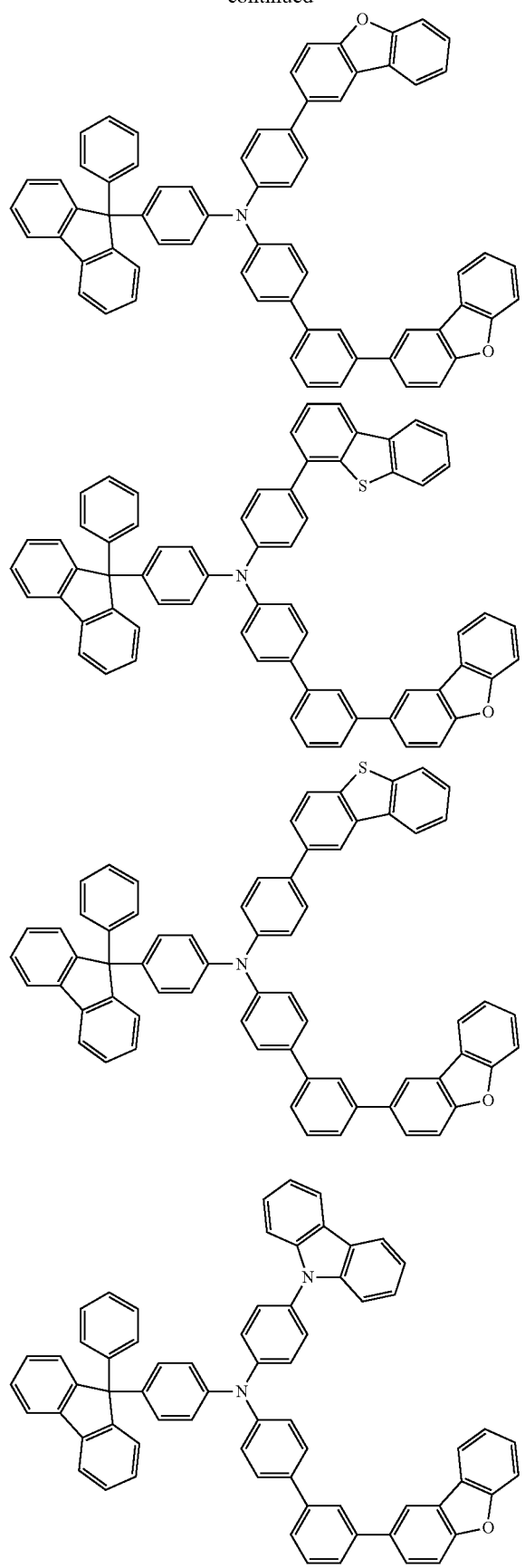
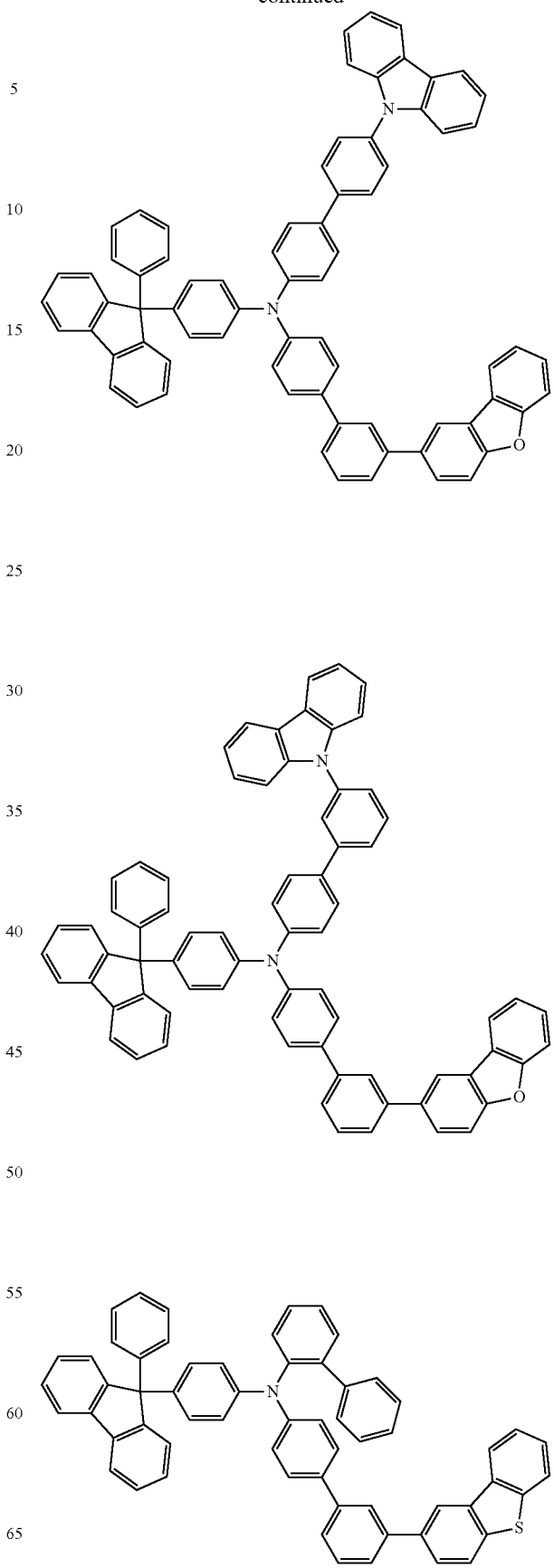

179
-continued
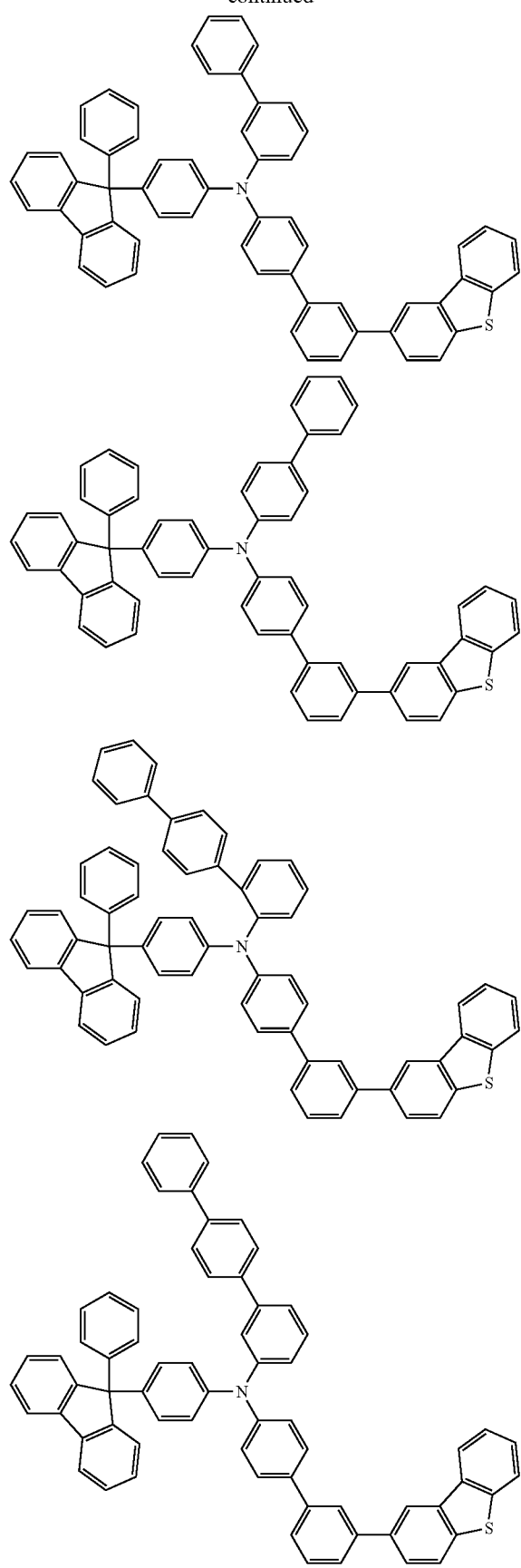
180
-continued
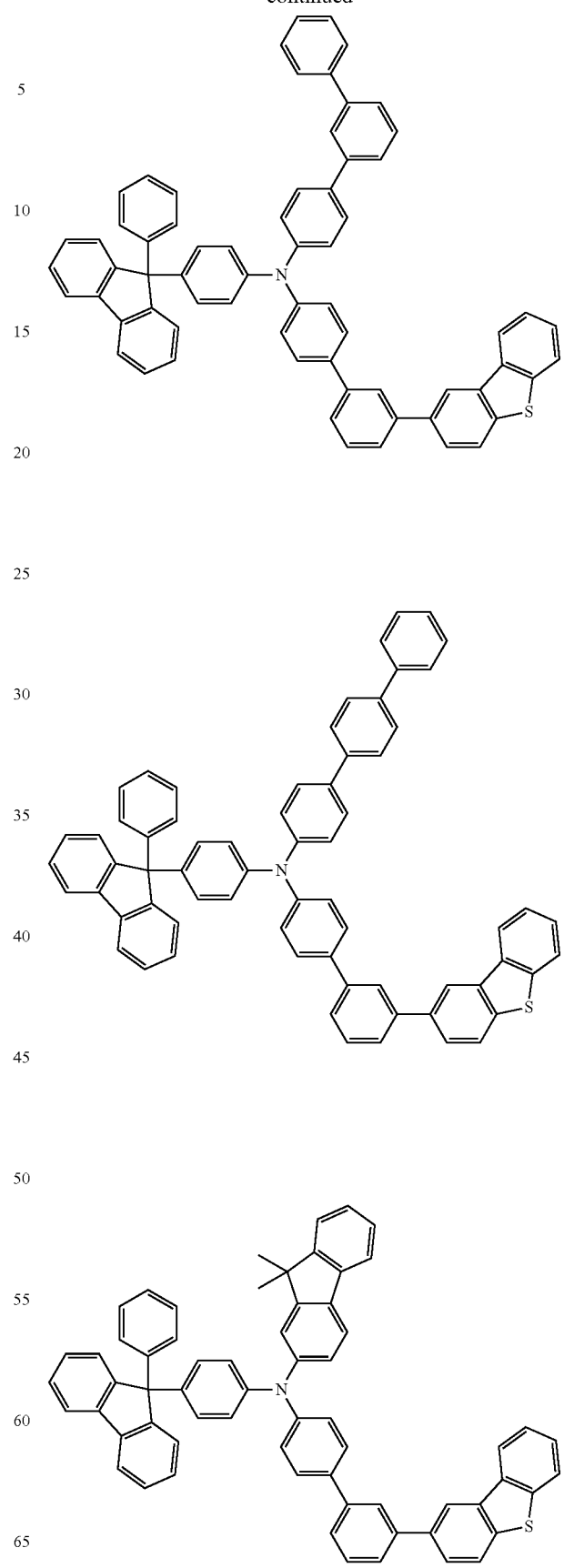

181
-continued
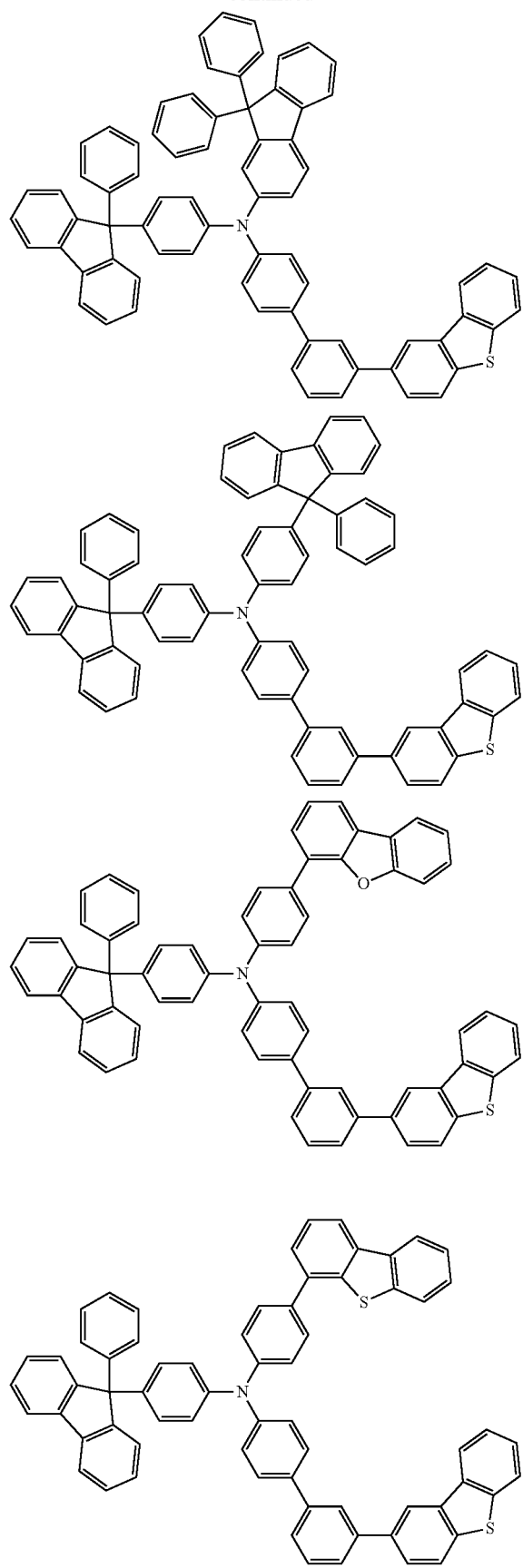
182
-continued
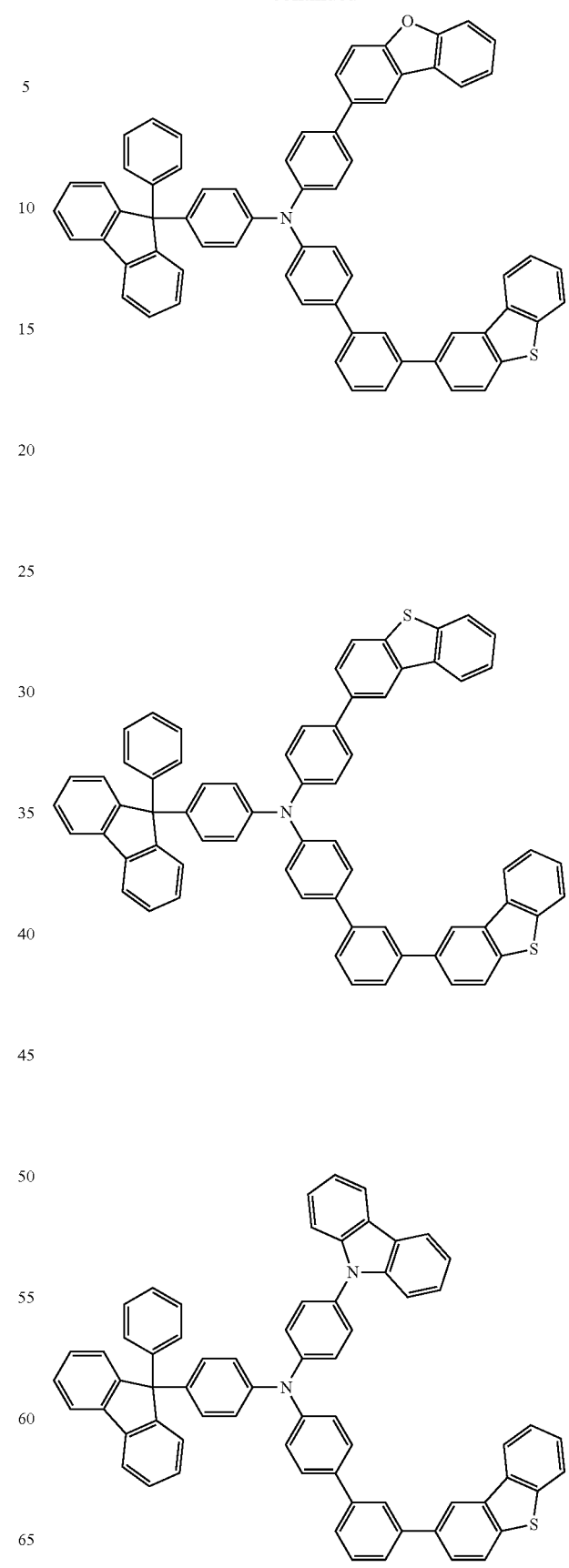

-continued
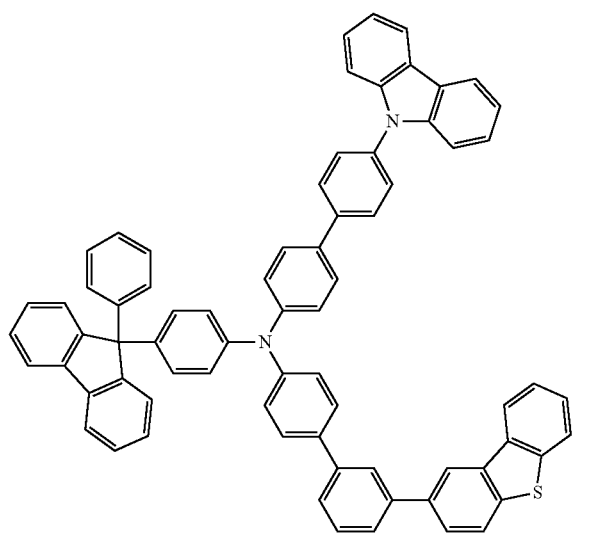
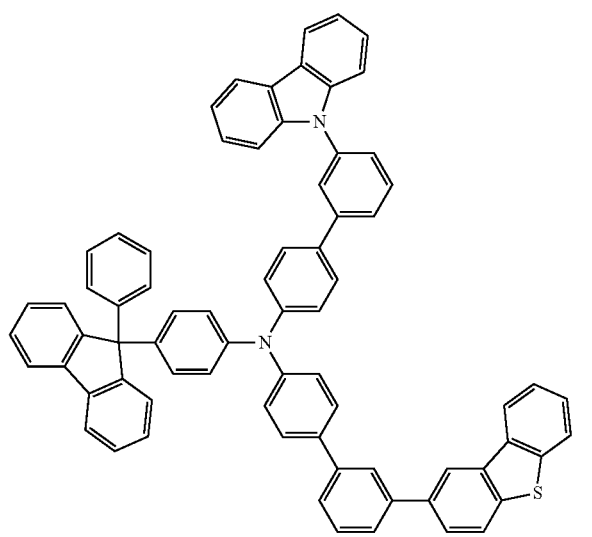
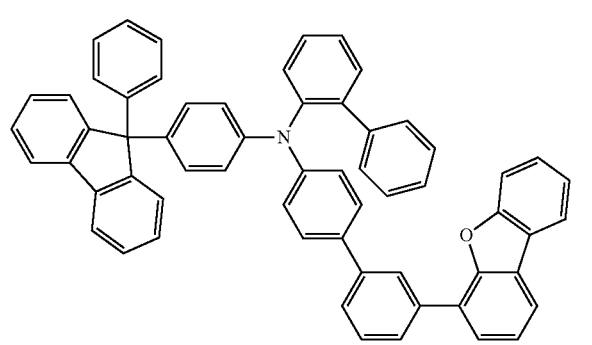
-continued
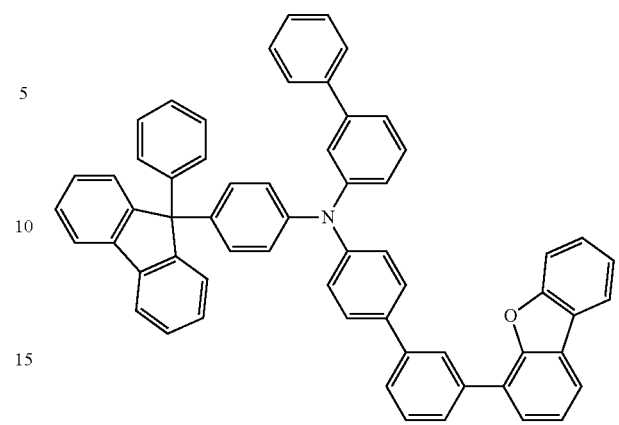
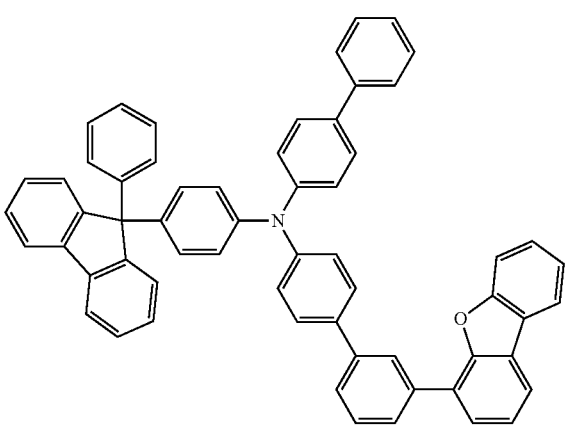
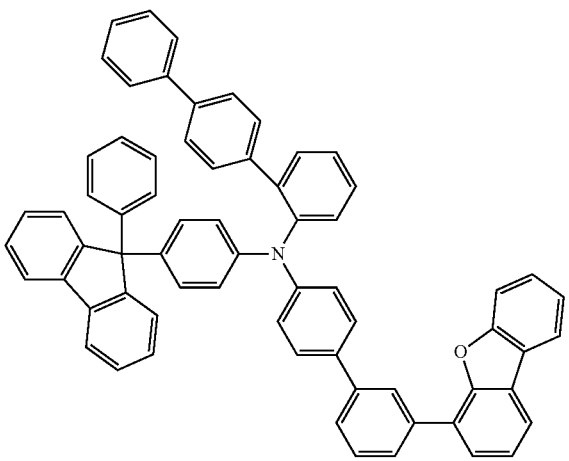

-continued
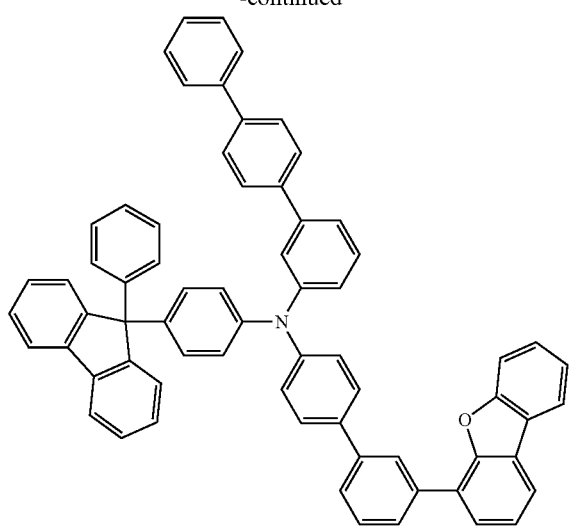
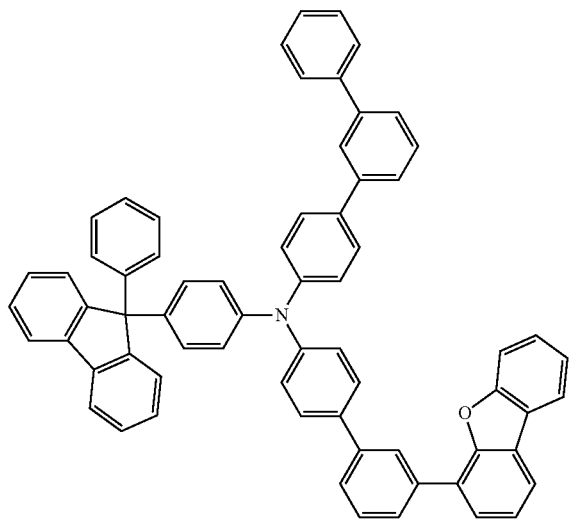
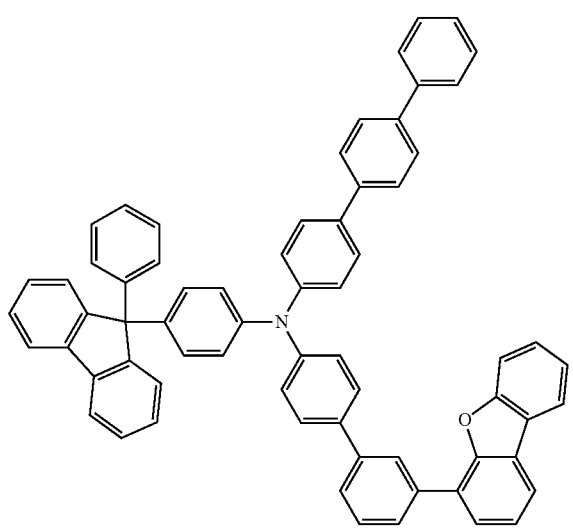
-continued
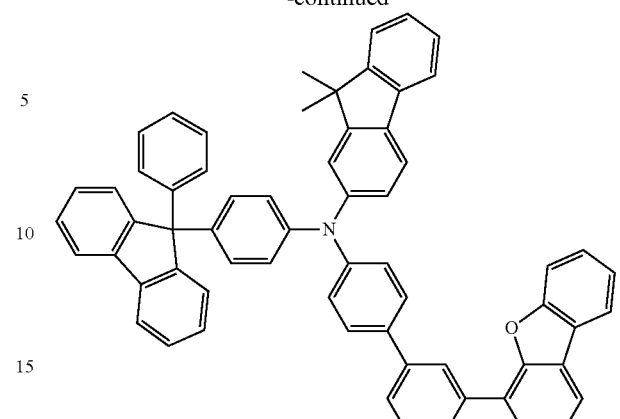
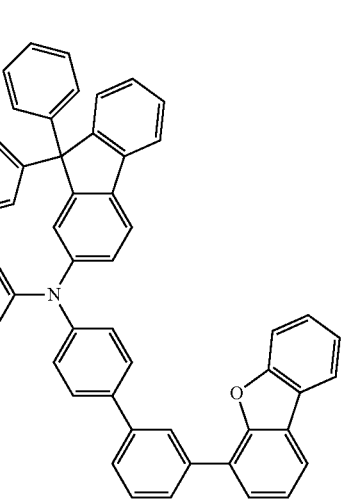
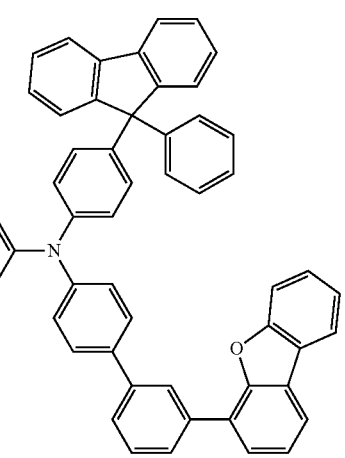

187
-continued
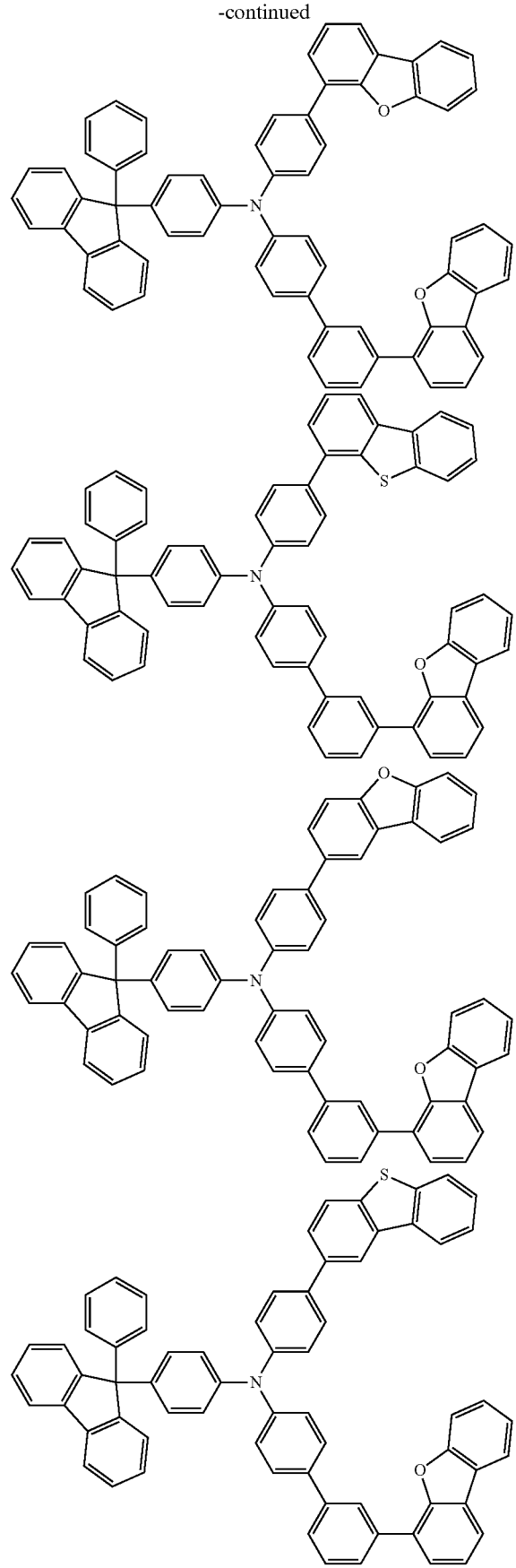
188
-continued
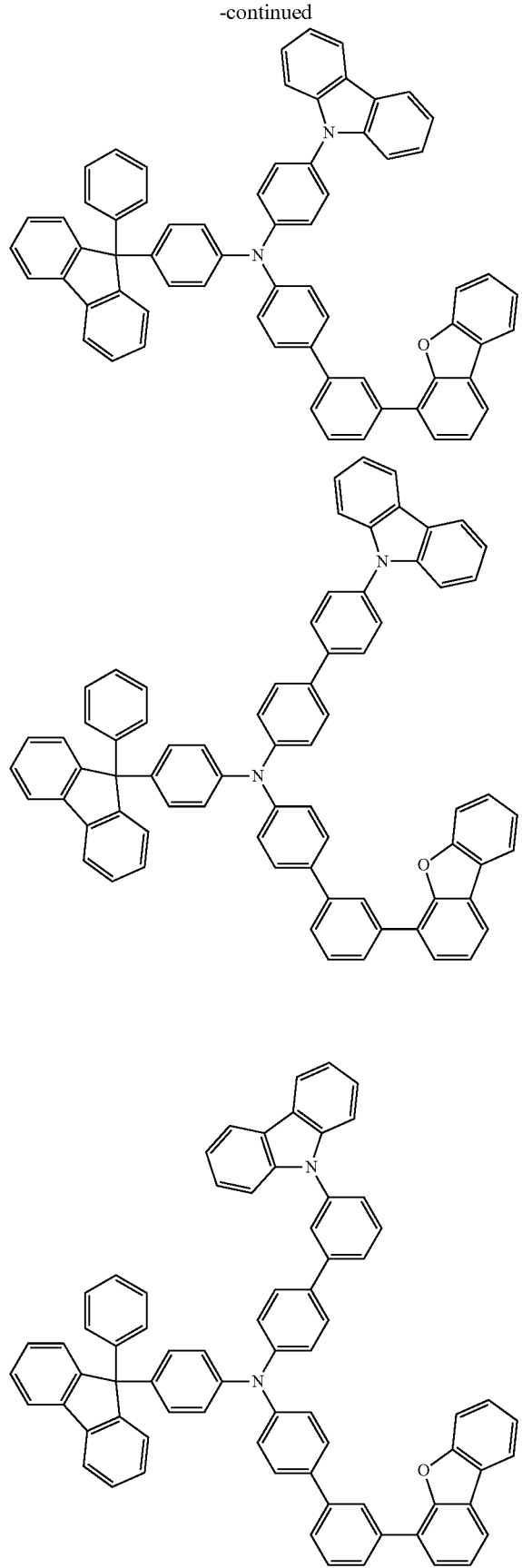

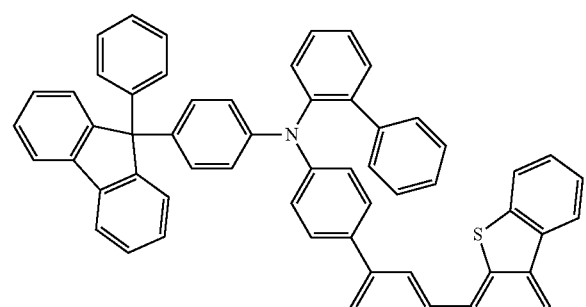
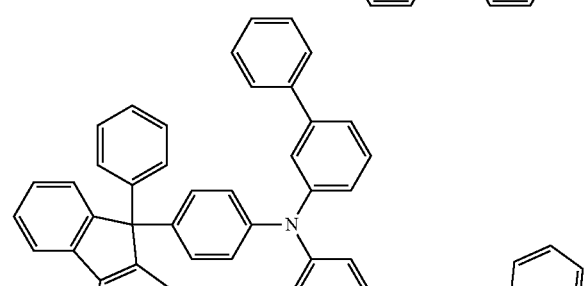
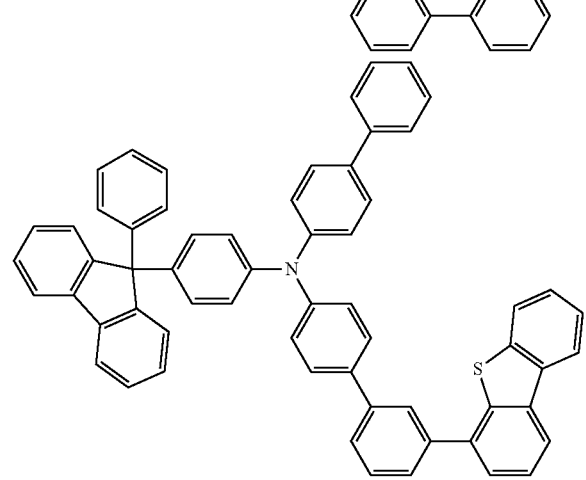
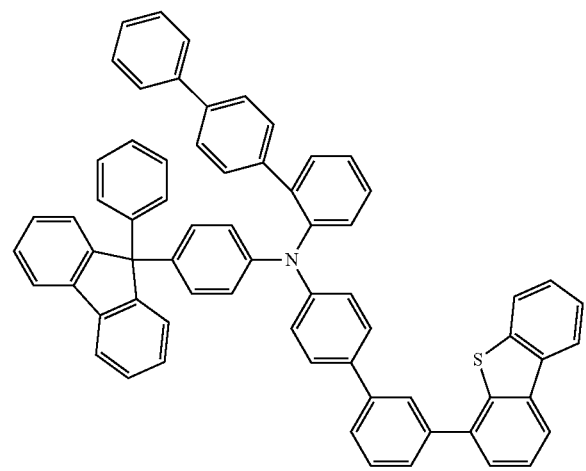

191
-continued
192
-continued
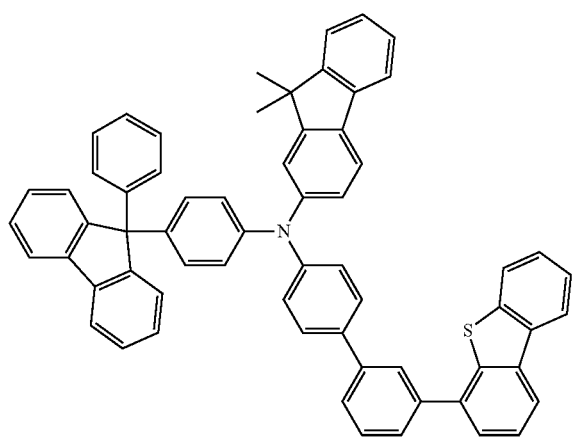
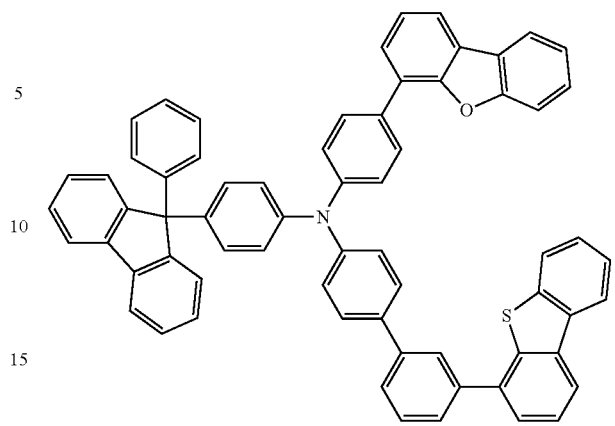

-continued
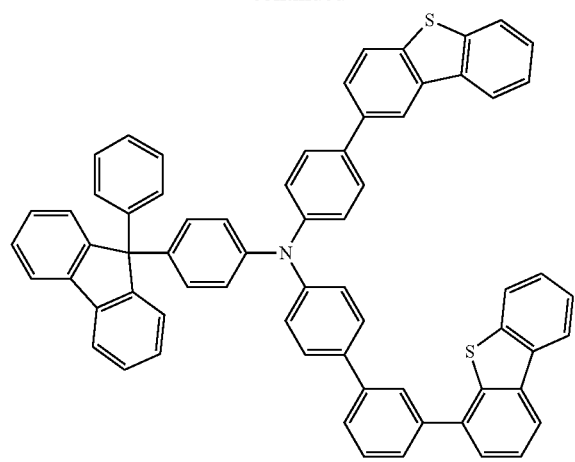
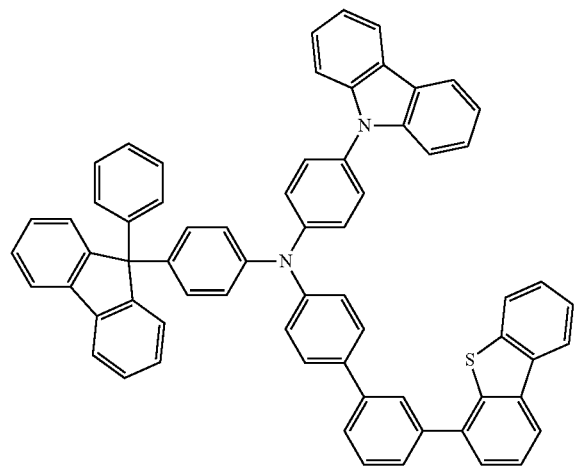
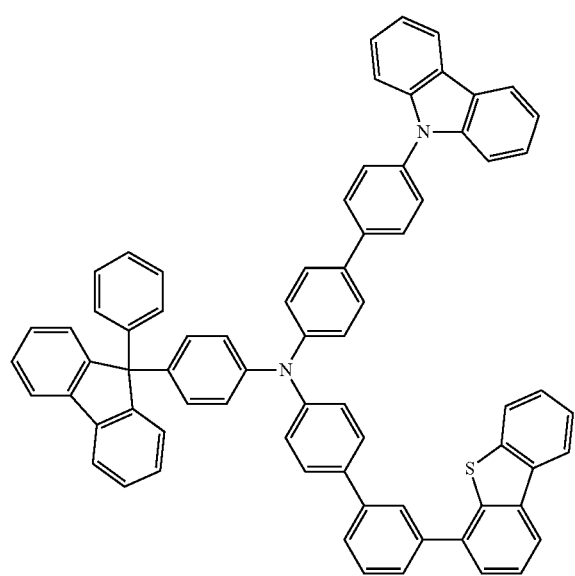
-continued
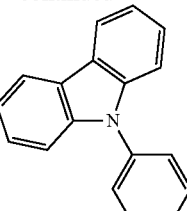
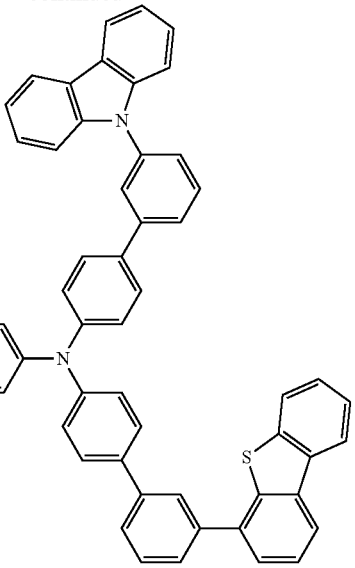
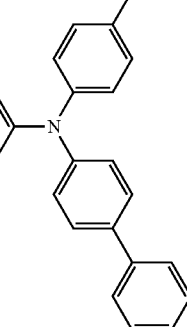
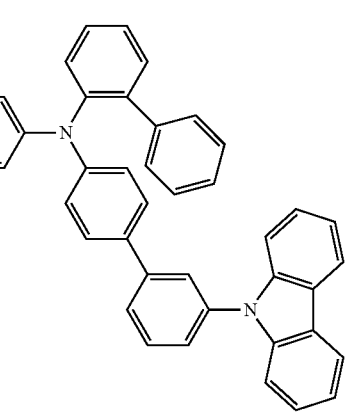
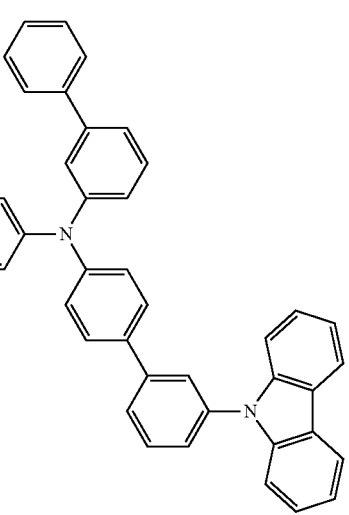

-continued
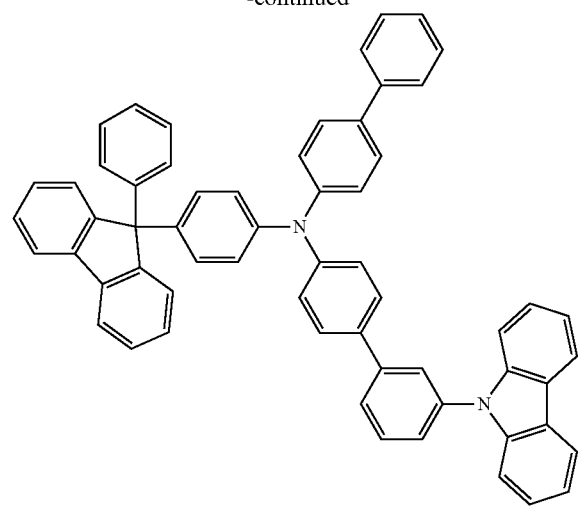
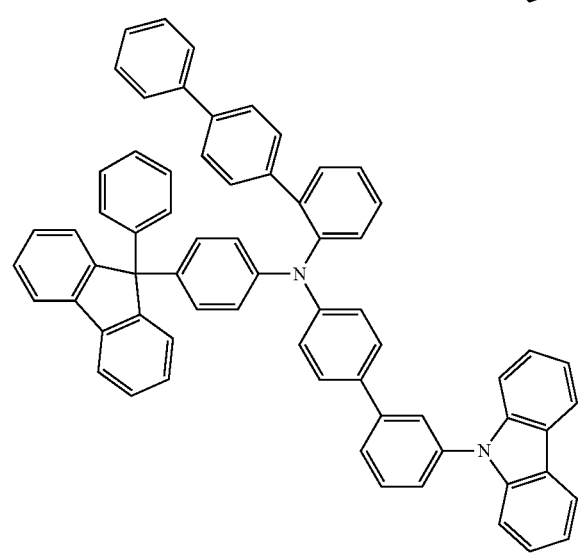
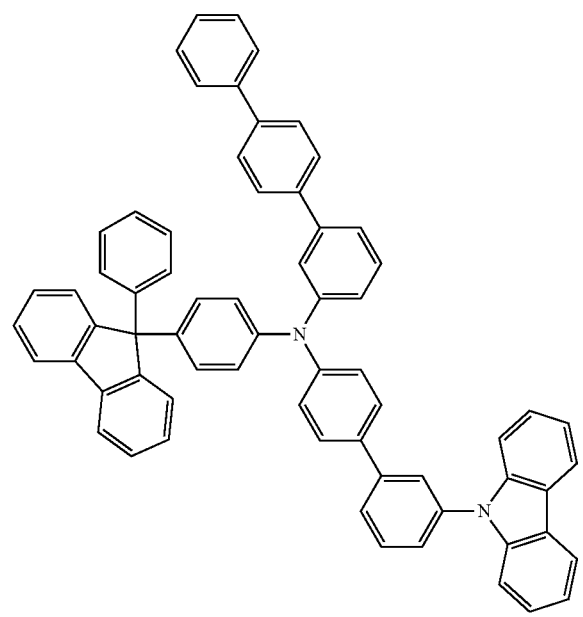
-continued
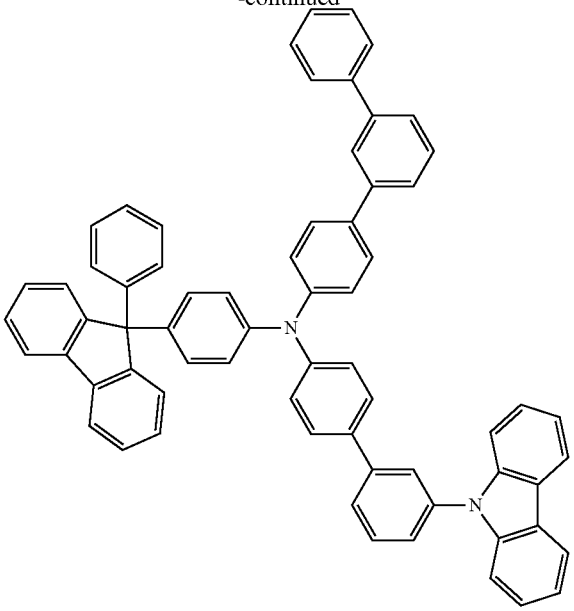
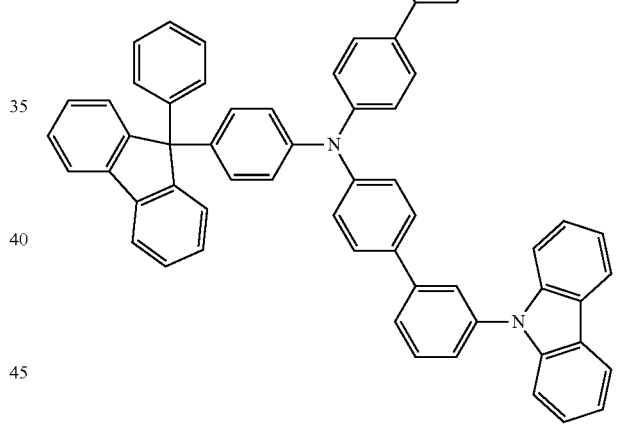

197
-continued
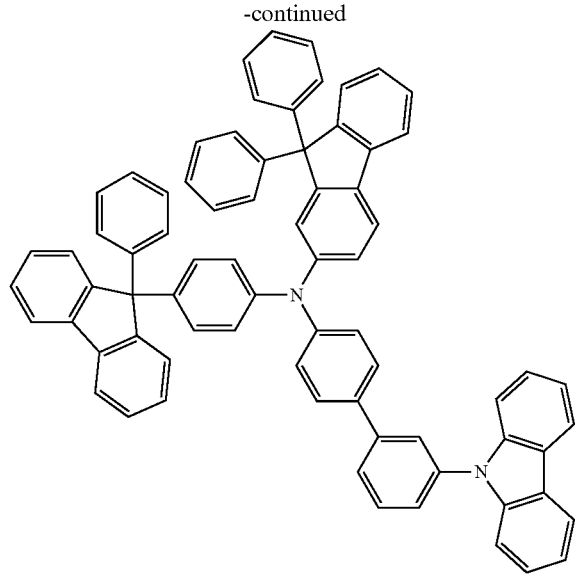
198
-continued
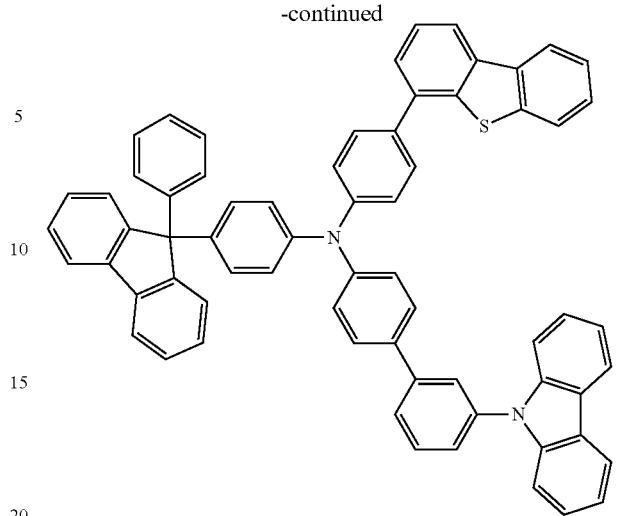
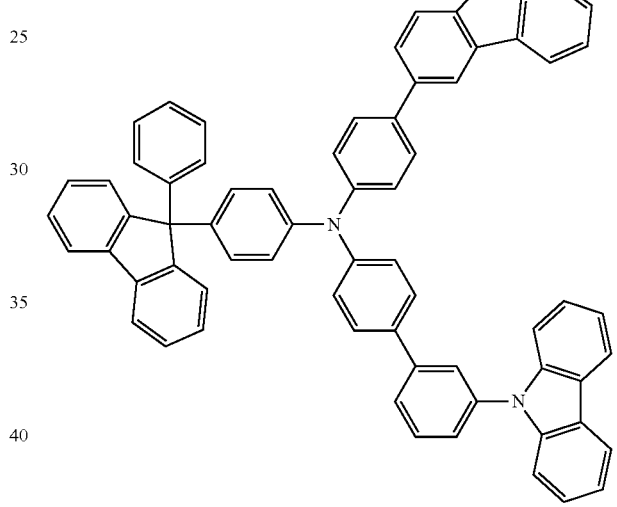
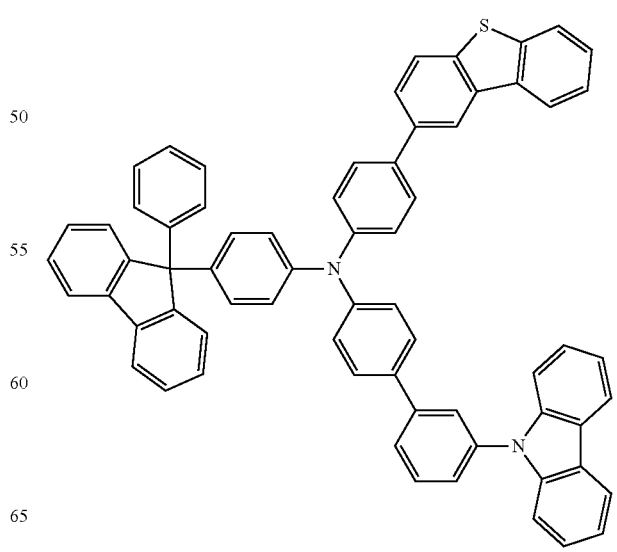

199
-continued
200
-continued
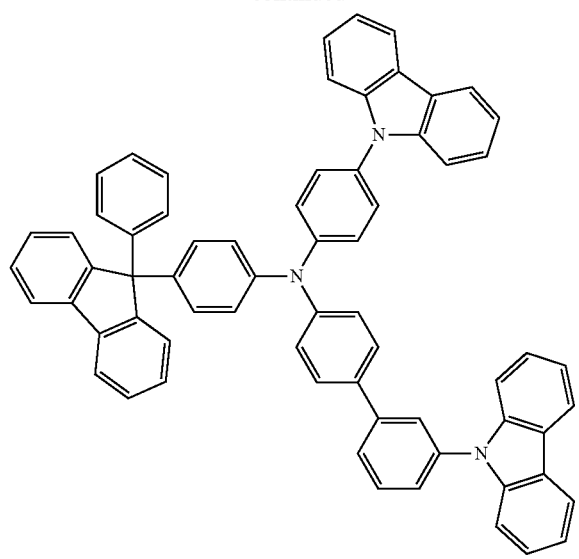
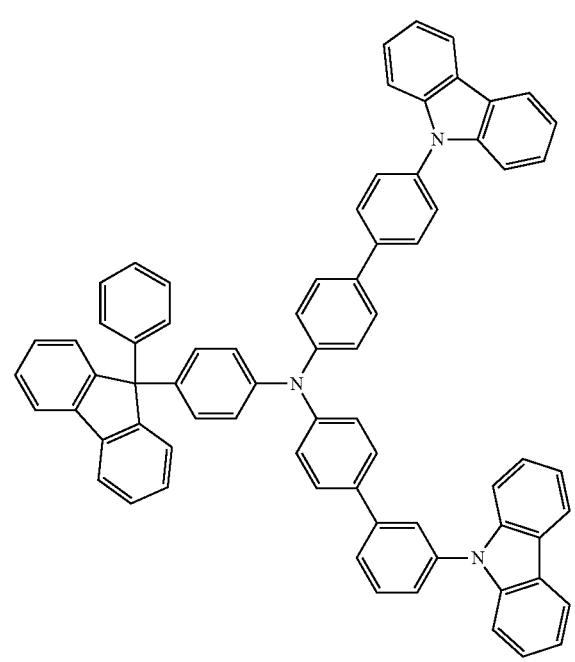
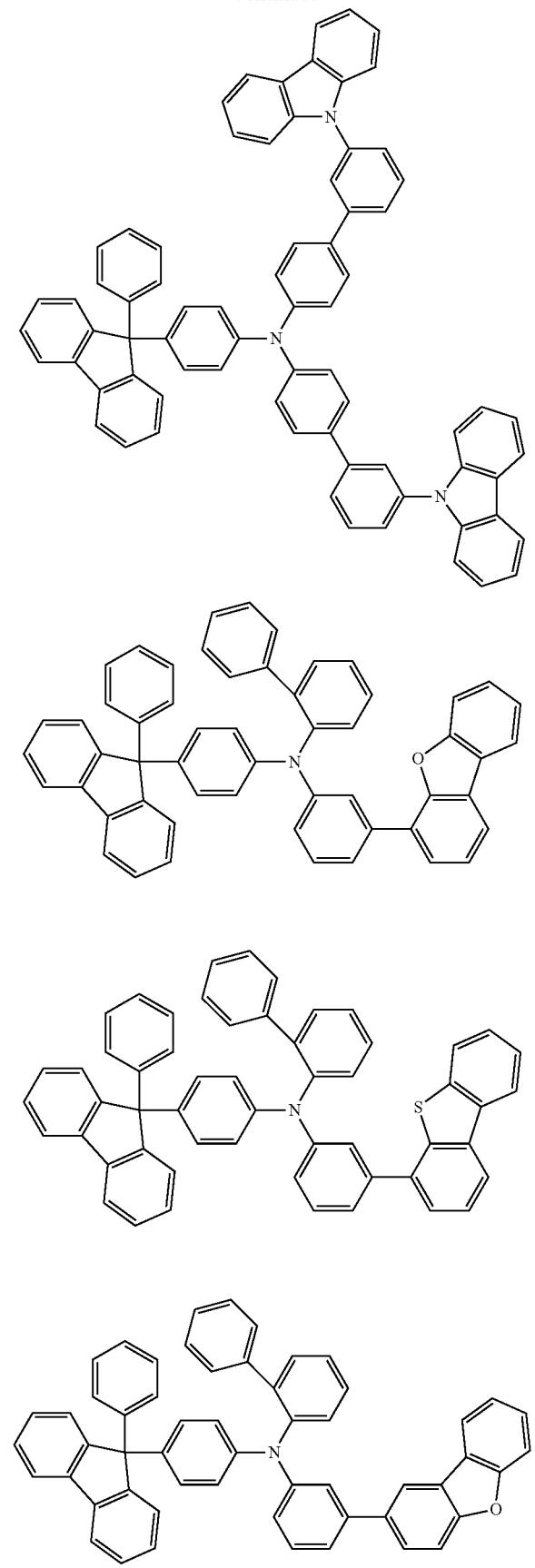

201
-continued
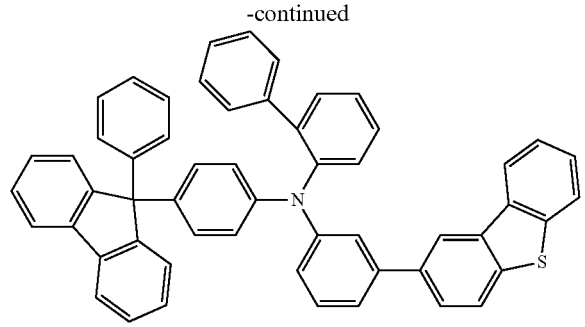
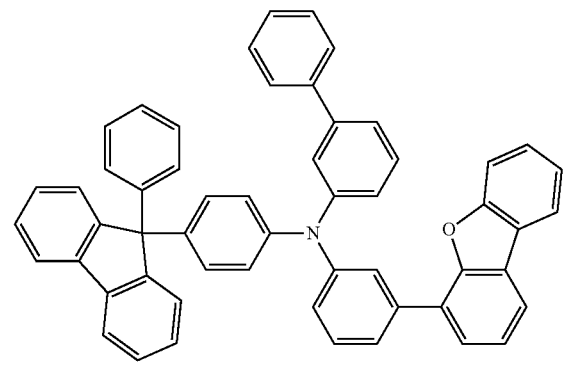
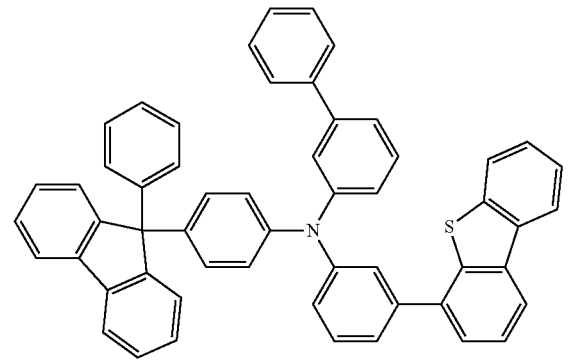
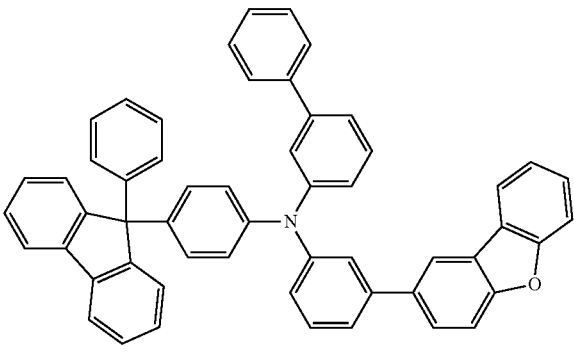
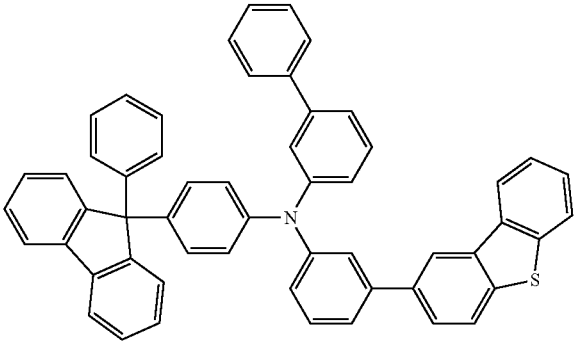
202
-continued
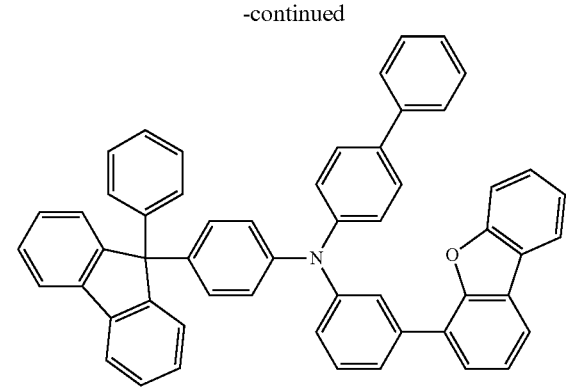
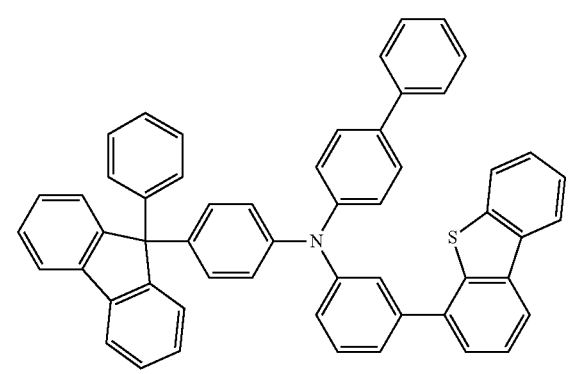
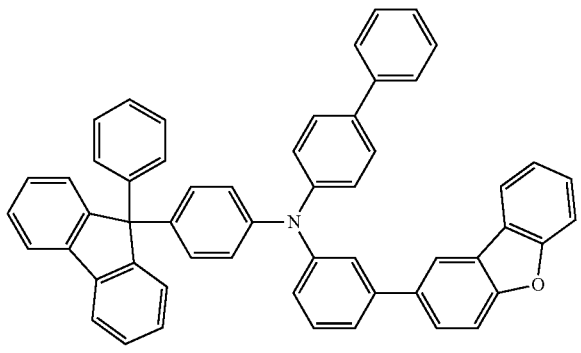
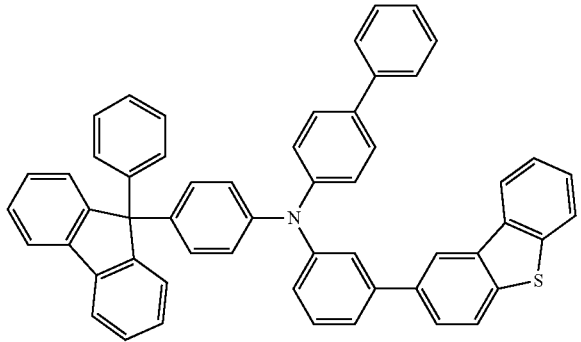

203
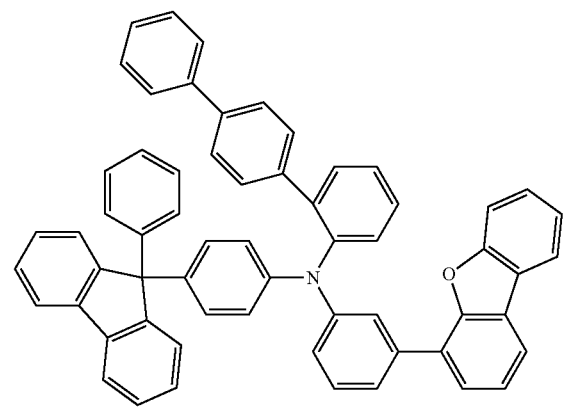
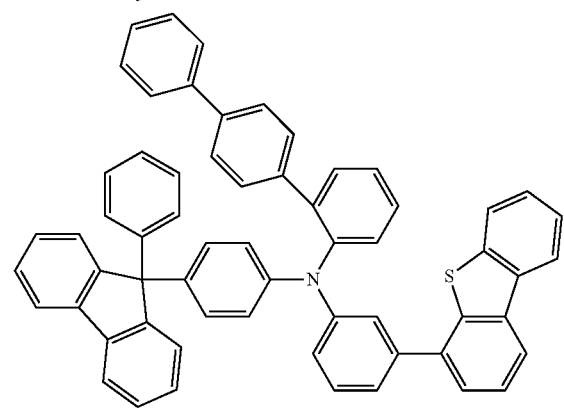
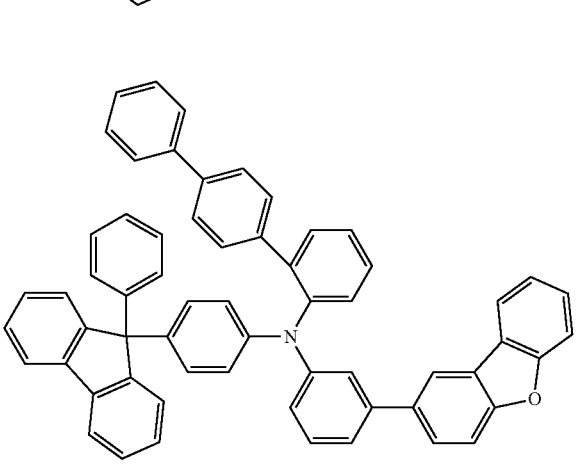
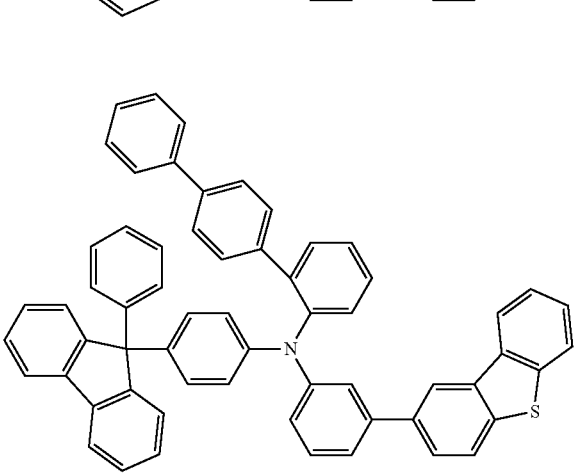
204
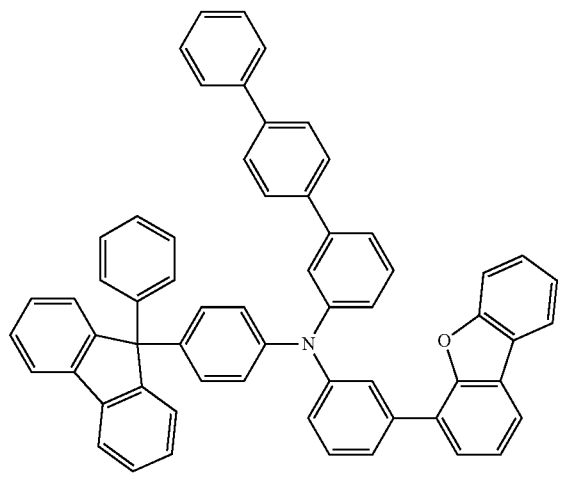
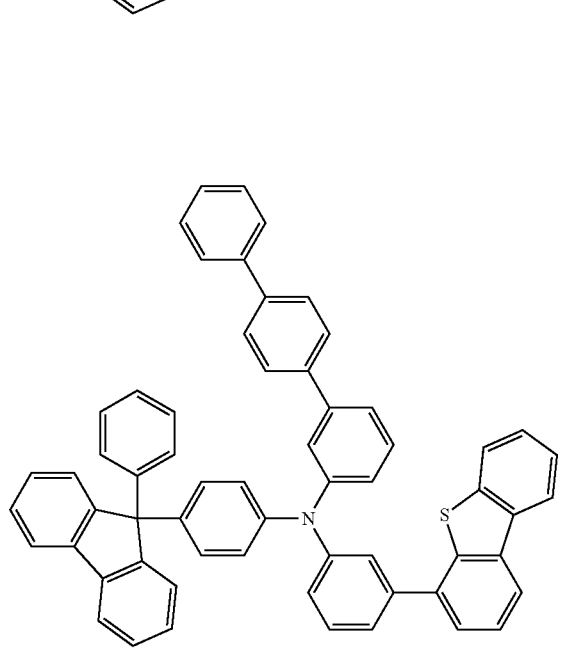
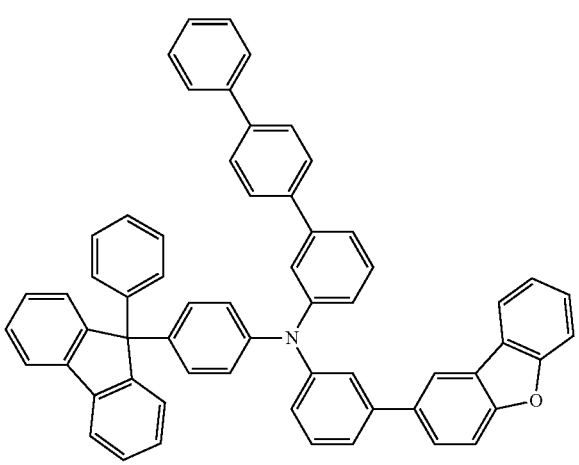

205
-continued
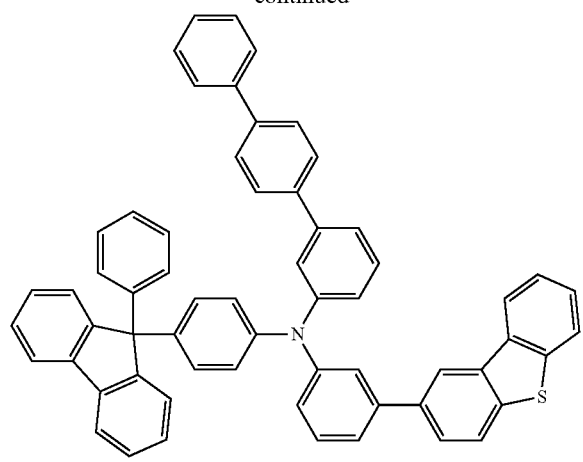
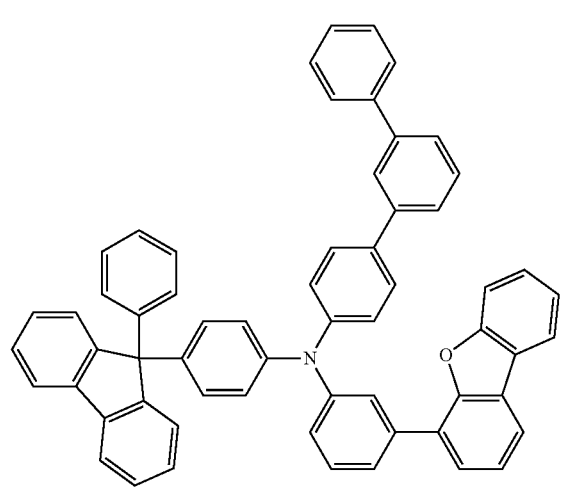
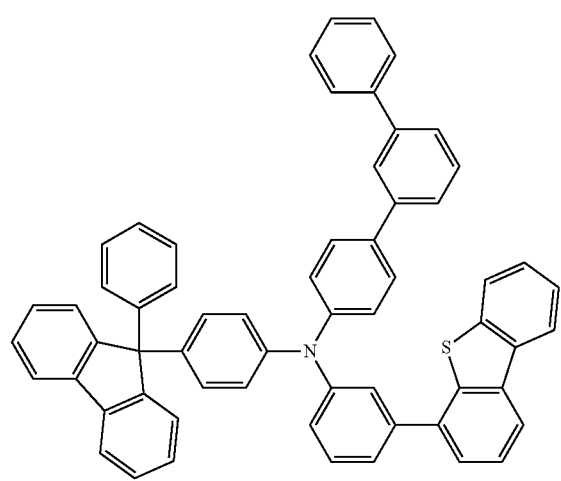
206
-continued
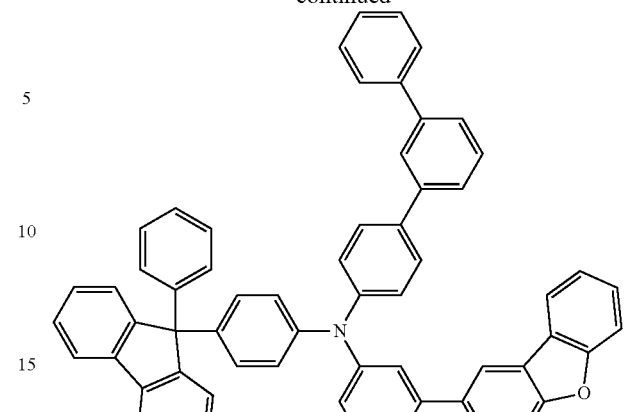
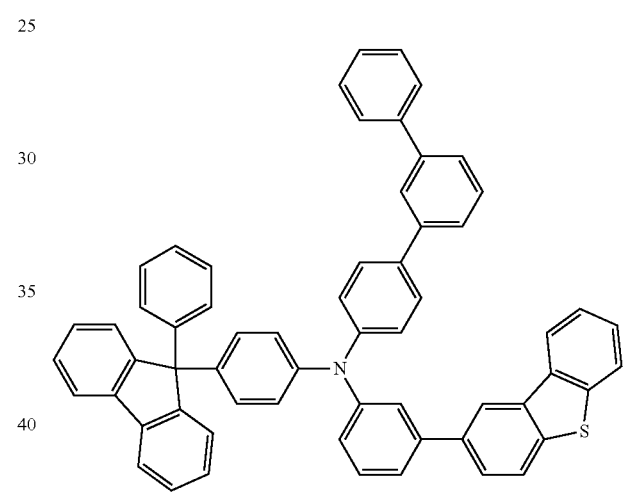
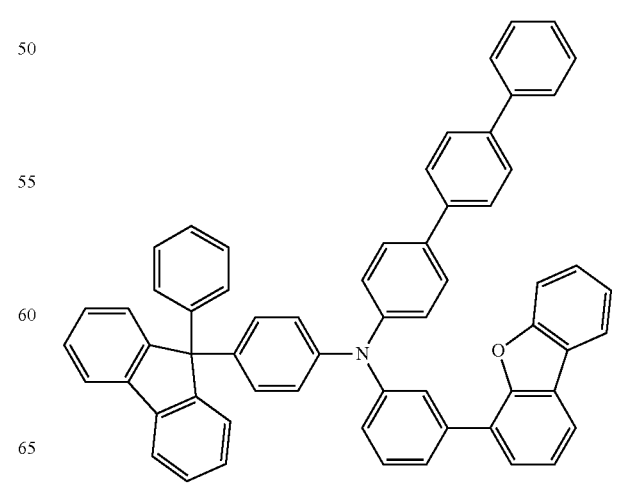

207
-continued
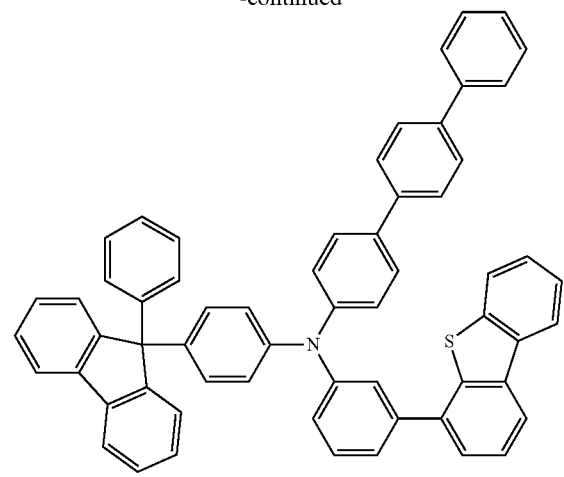
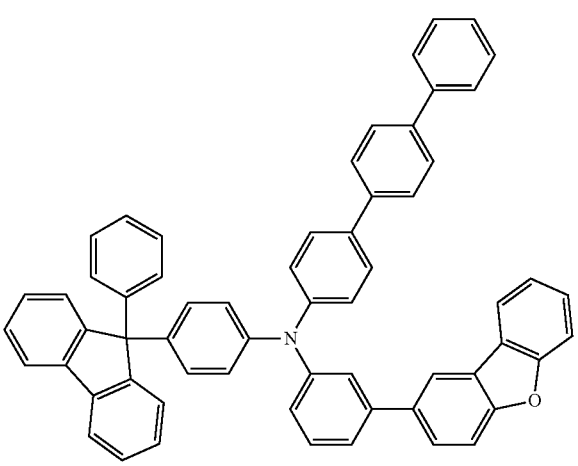
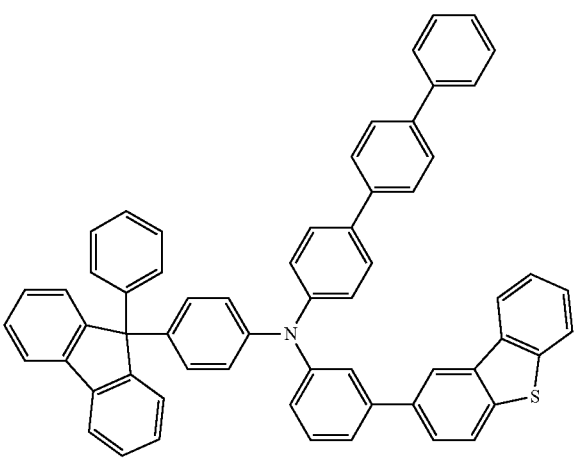
208
-continued
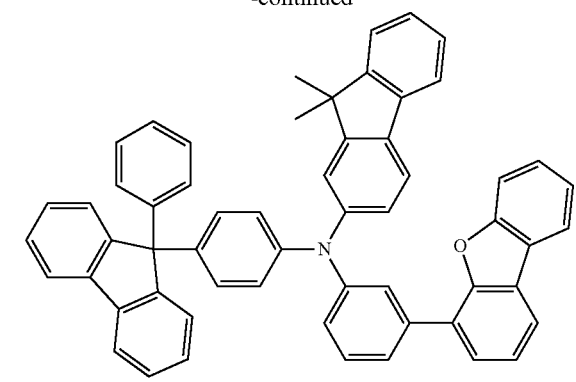
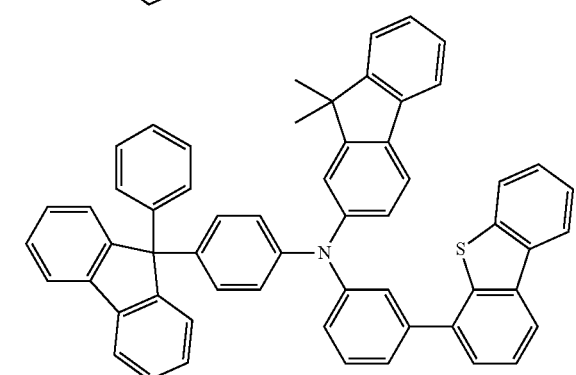
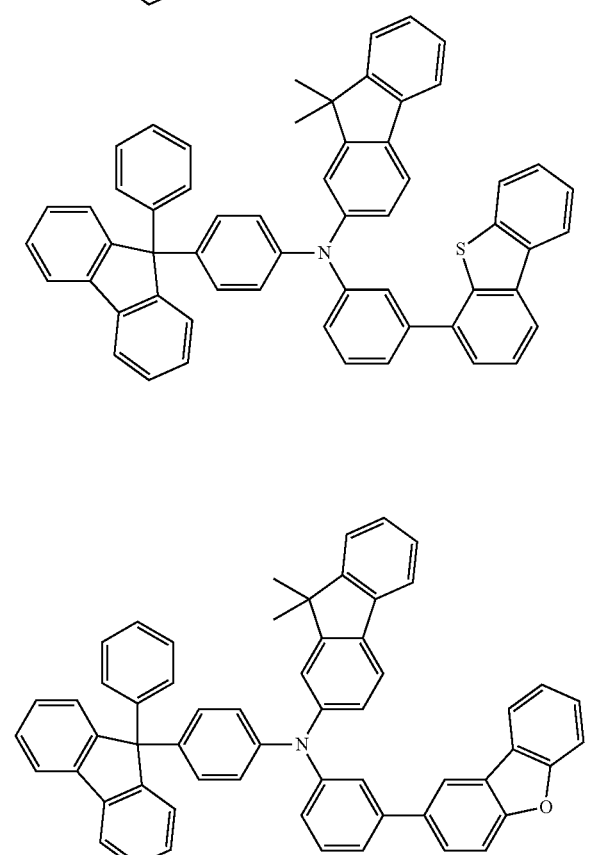
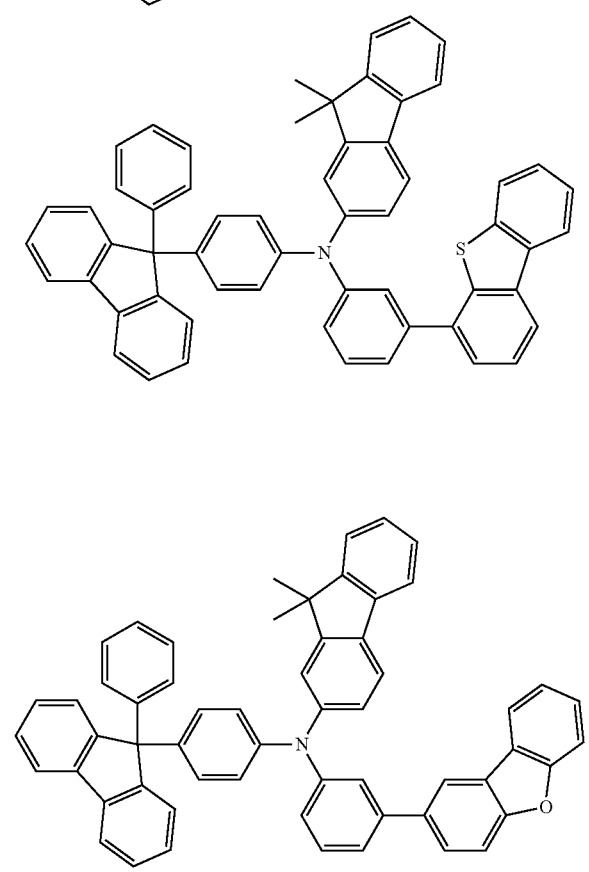

-continued
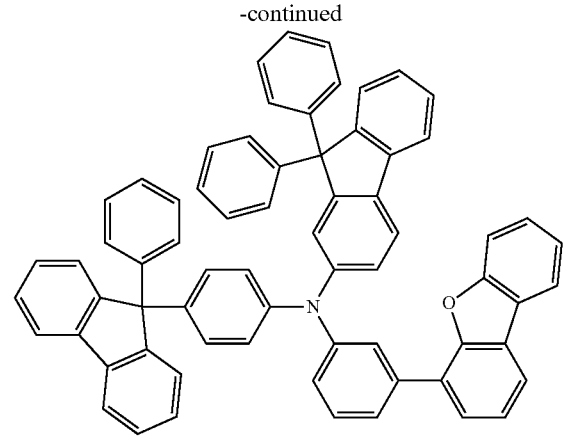
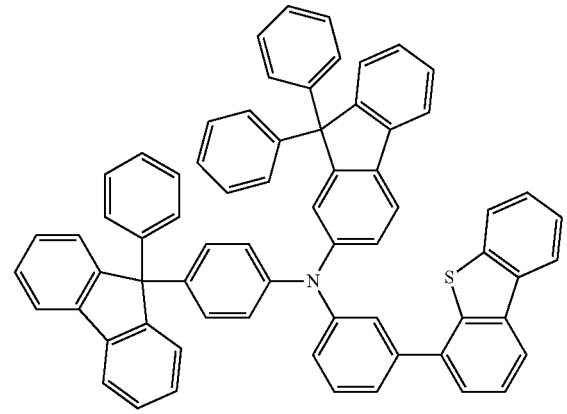
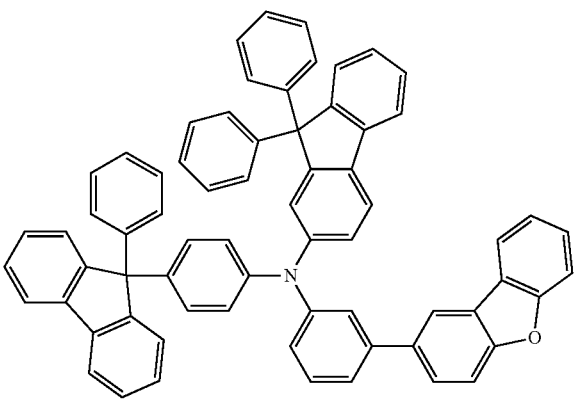
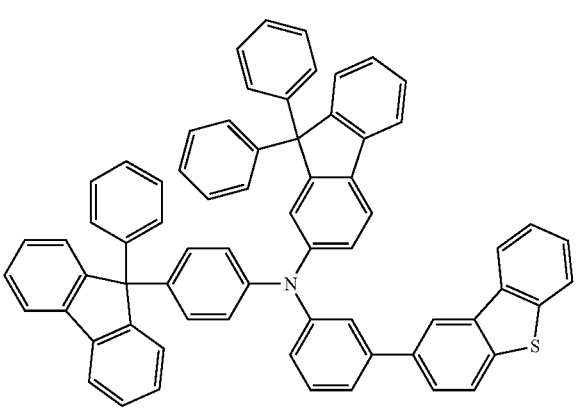
-continued
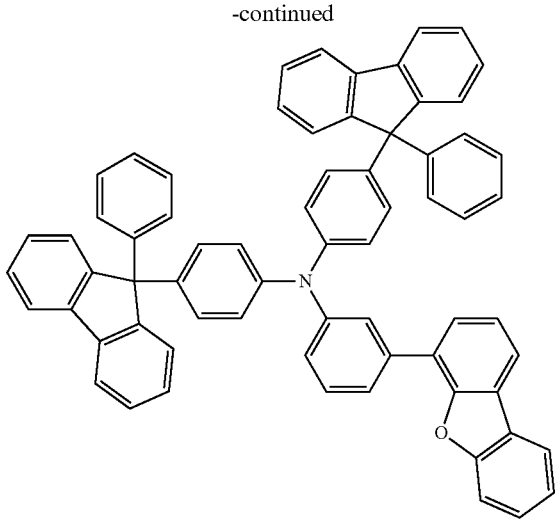
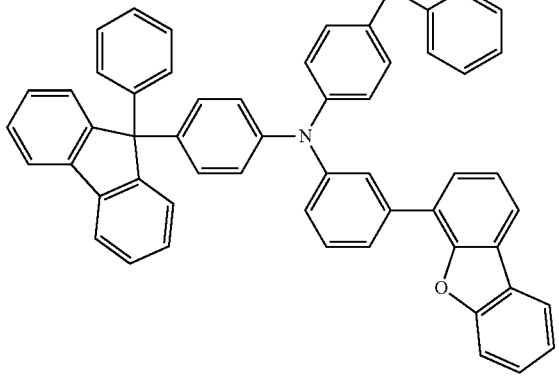
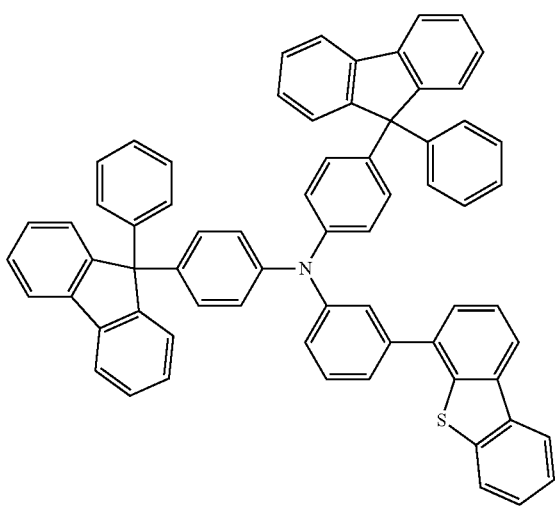
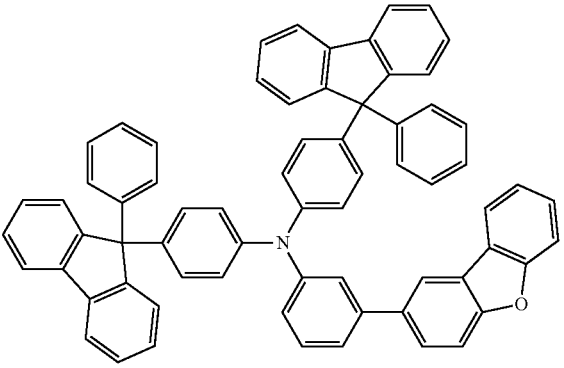

211
-continued
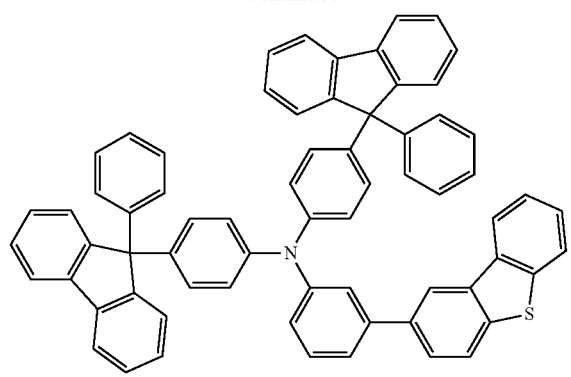
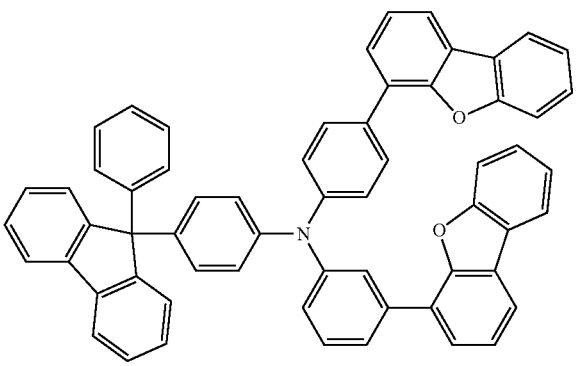
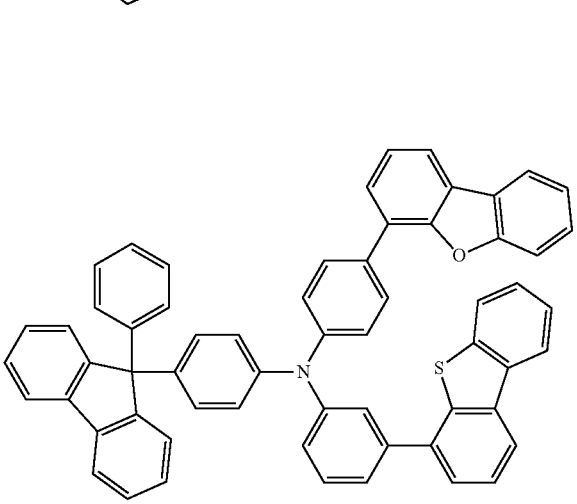
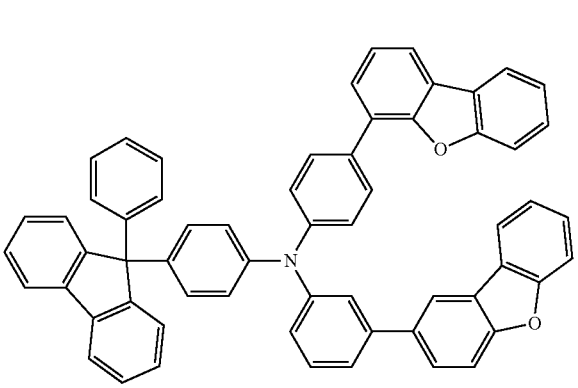
212
-continued
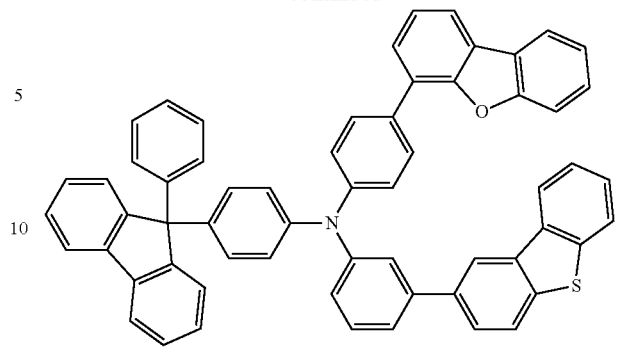
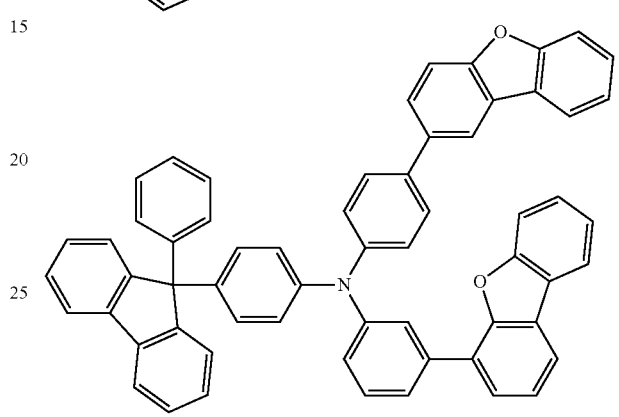
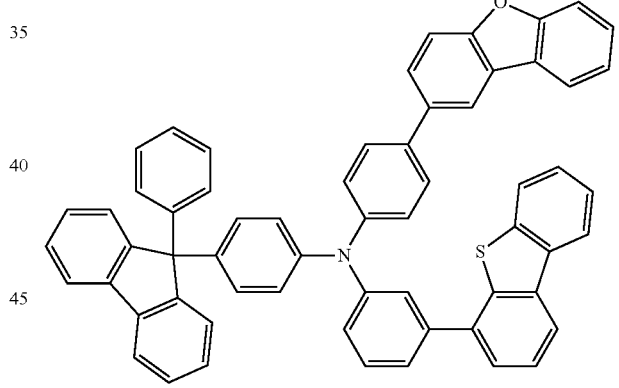
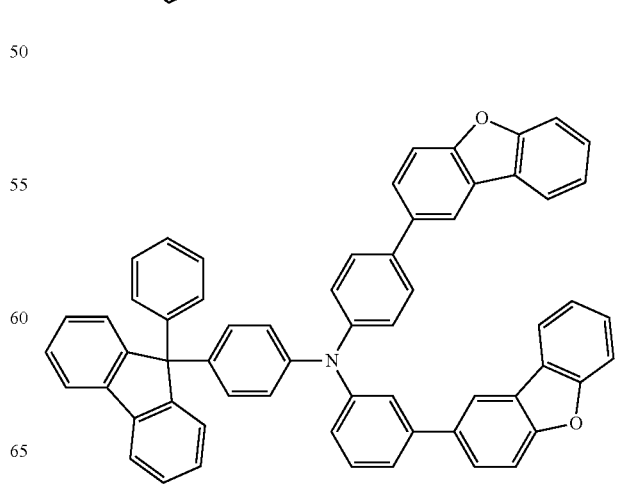

213
-continued
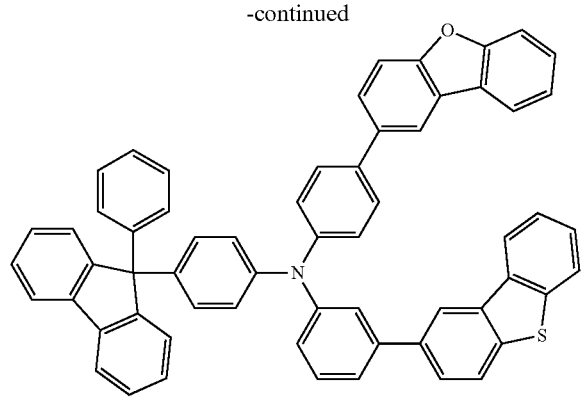
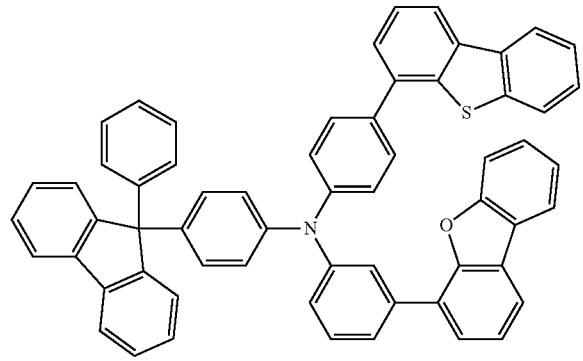
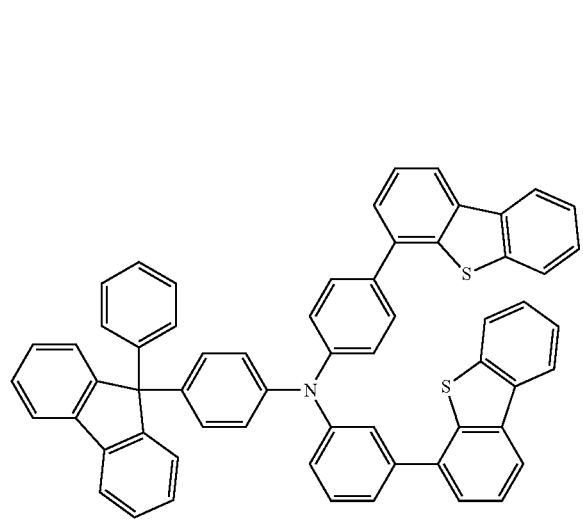
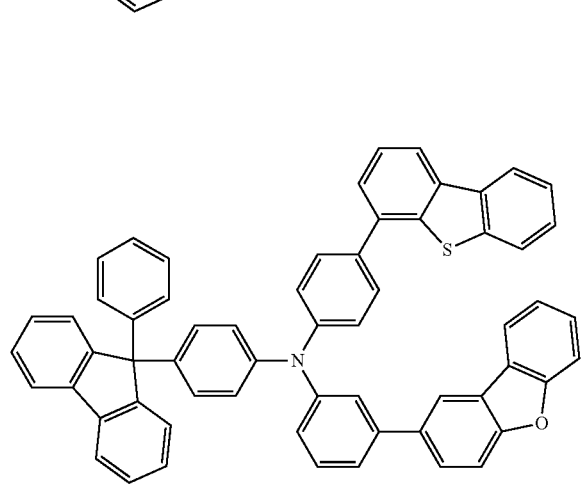
214
-continued
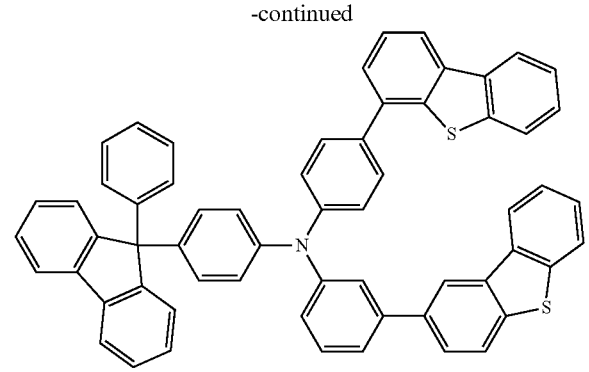
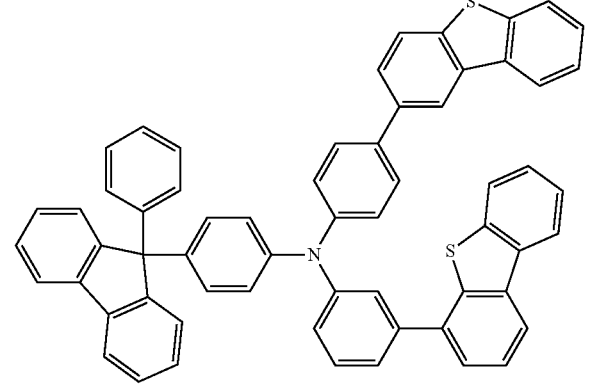
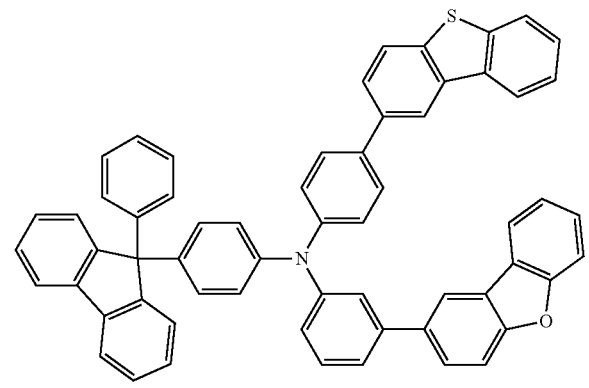

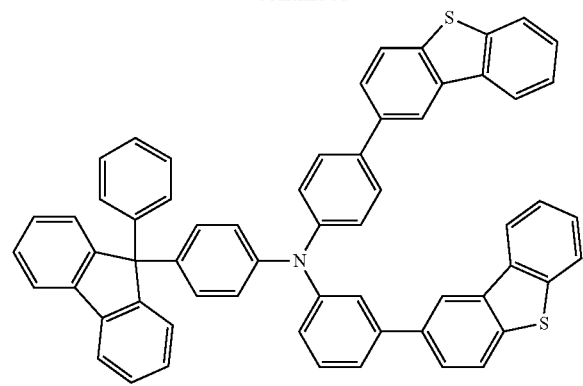
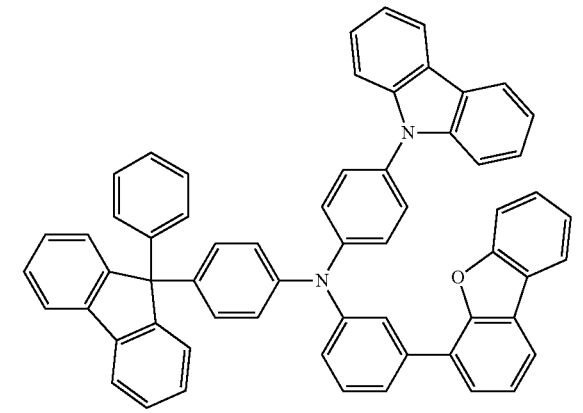
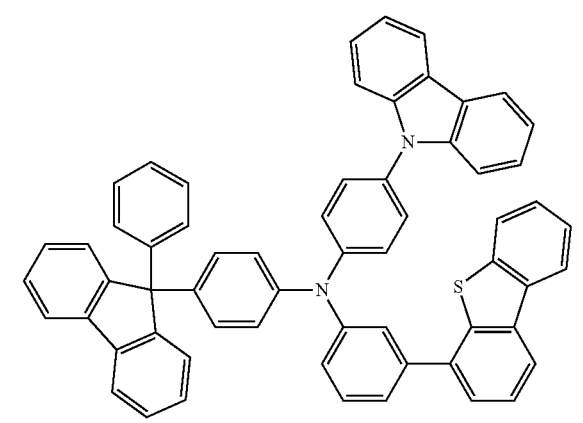
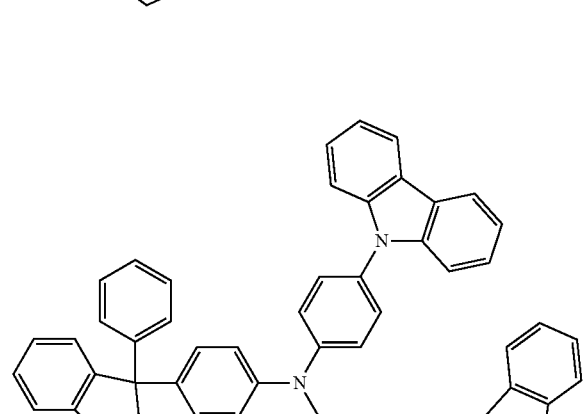
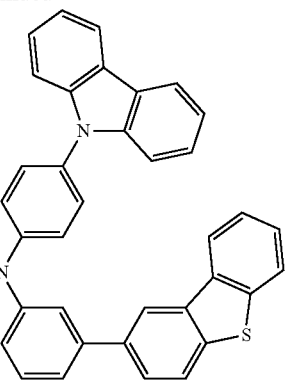
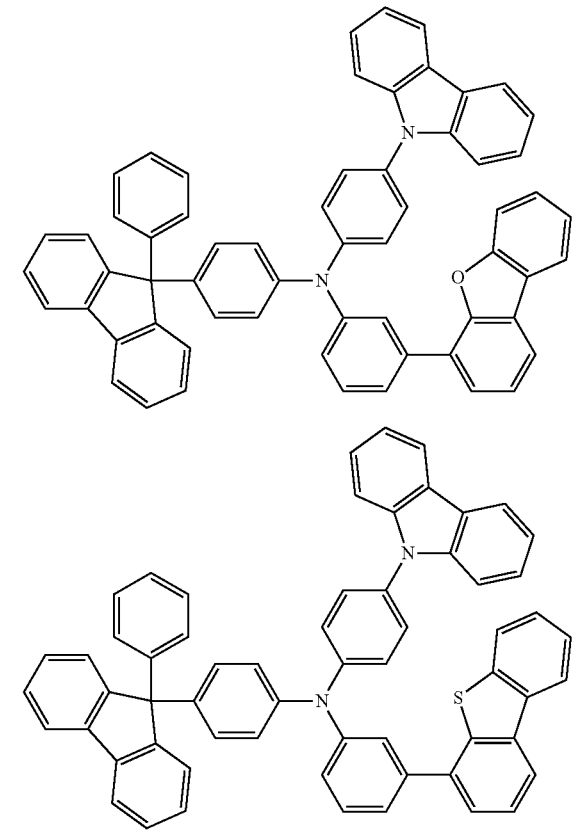
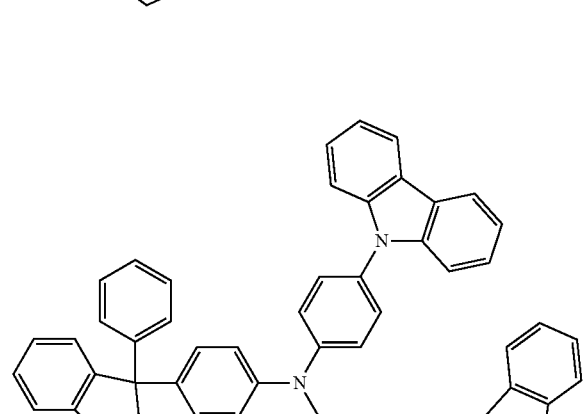

217
-continued
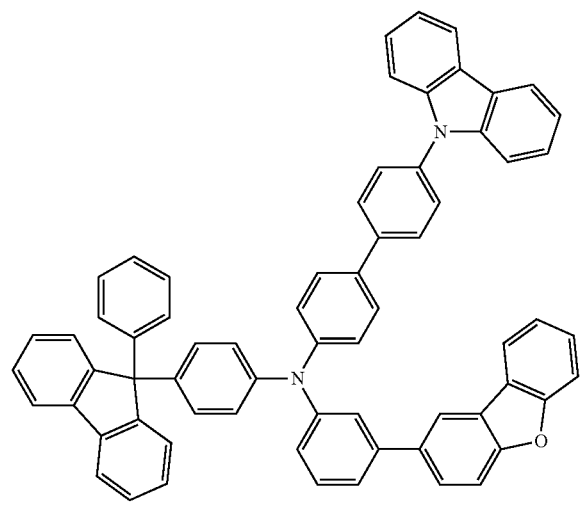
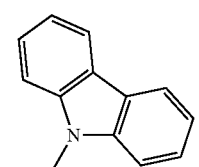
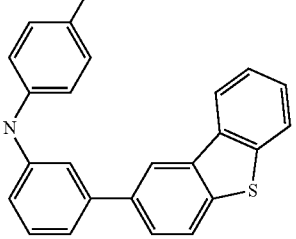
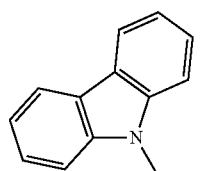
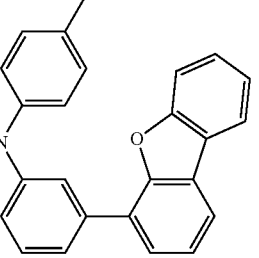
218
-continued
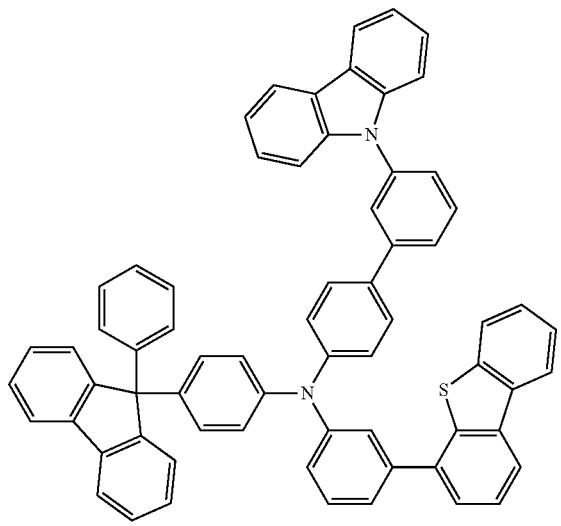
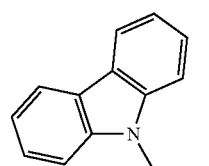
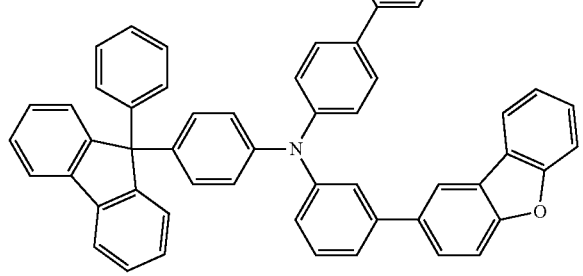
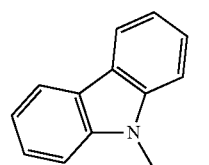
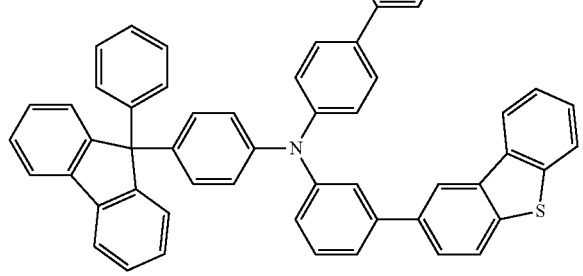

-continued
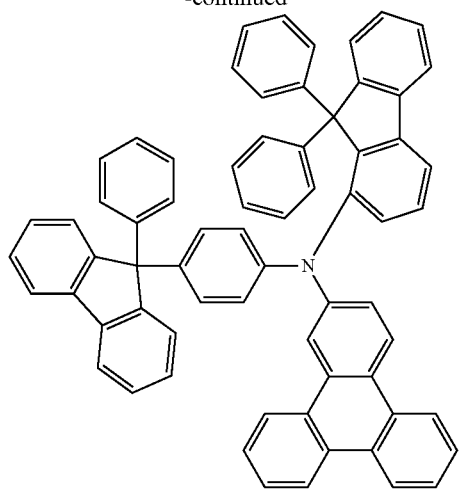
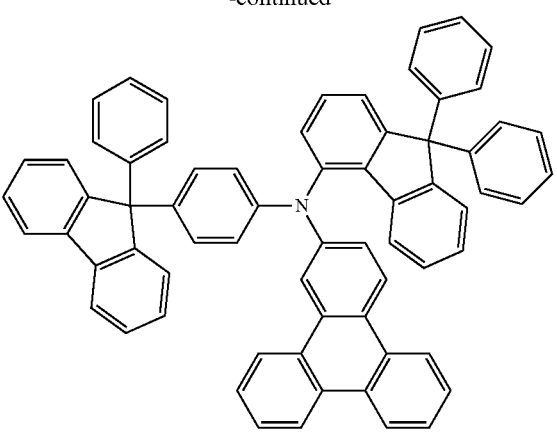
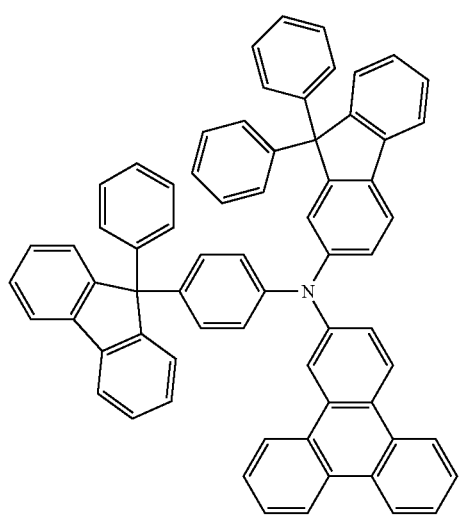
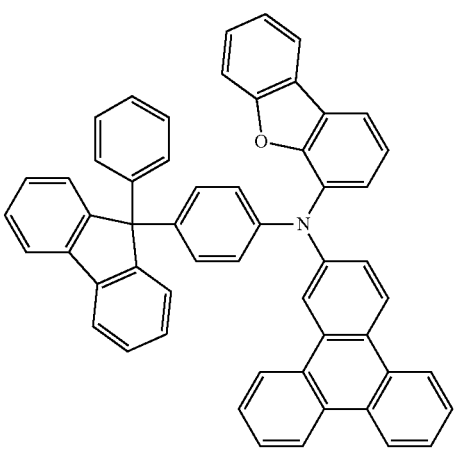
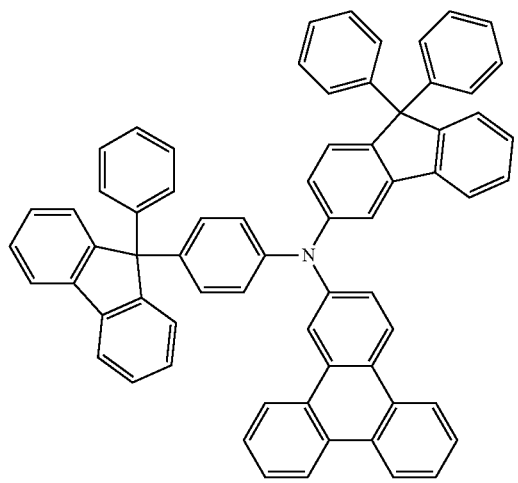
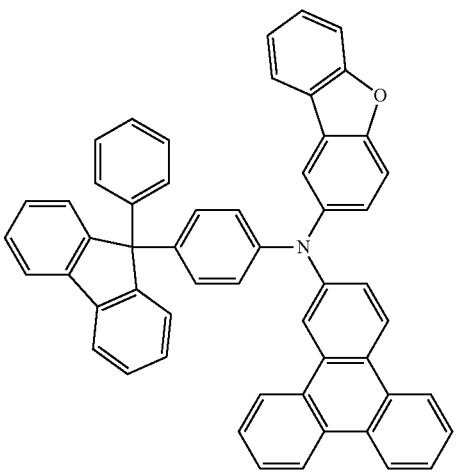

221
-continued
222
-continued
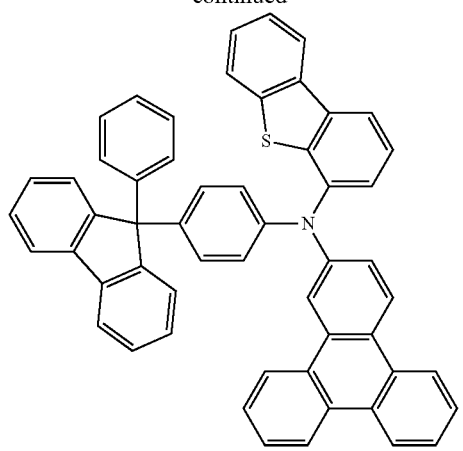
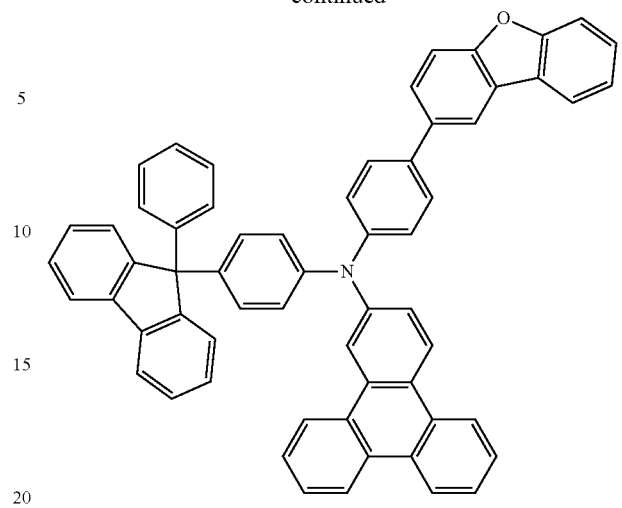
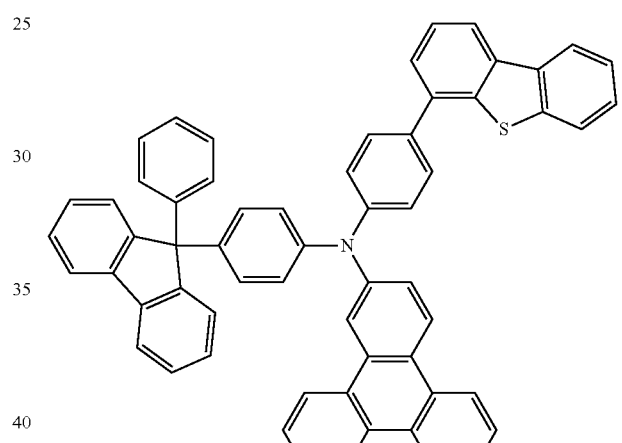
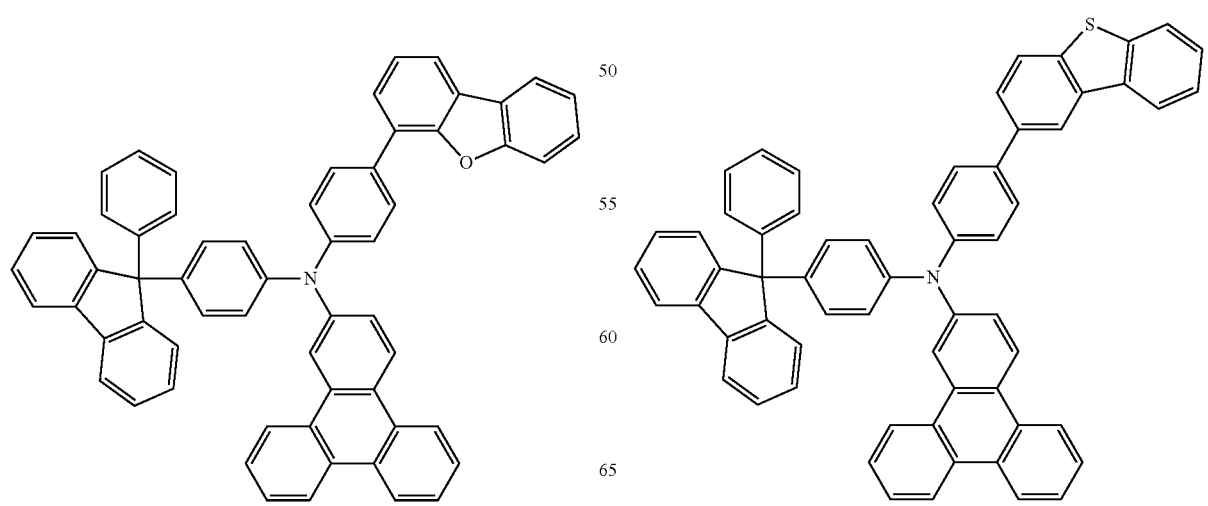

223
-continued
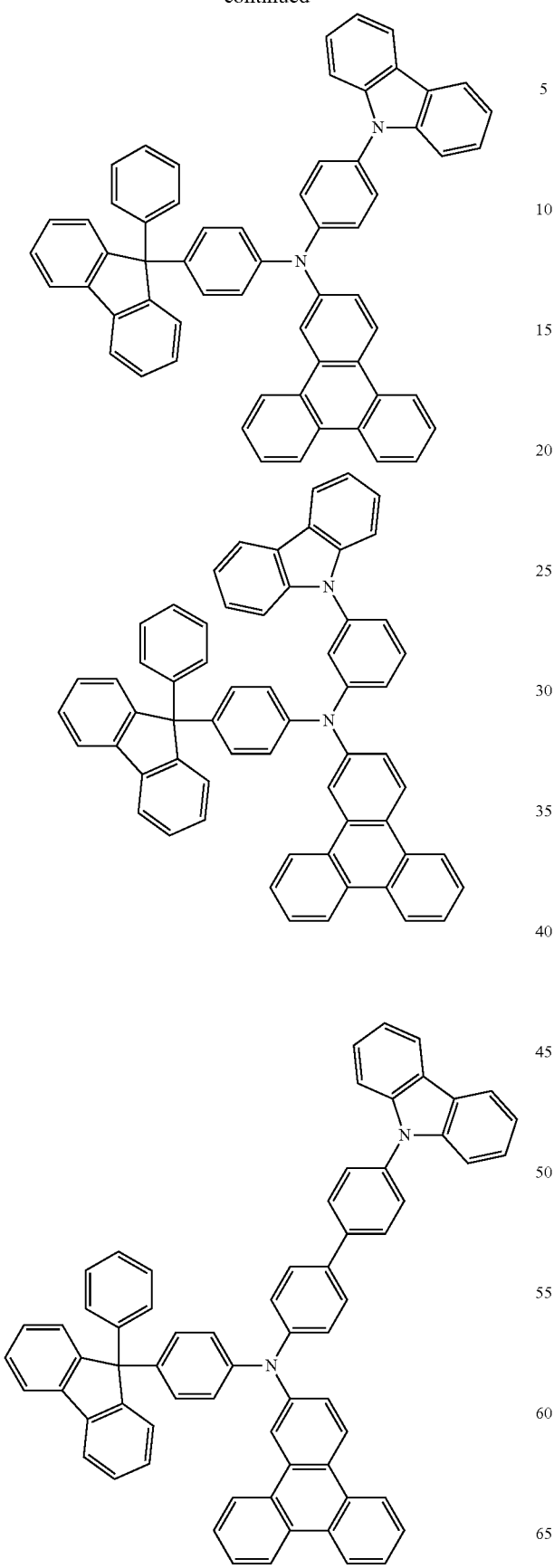
224
-continued
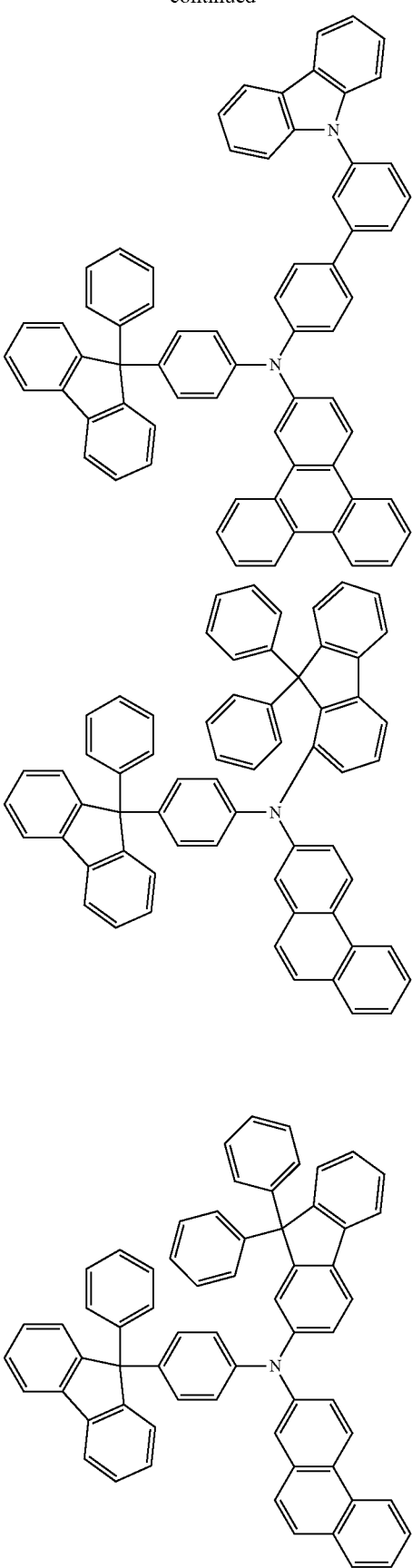

225
-continued
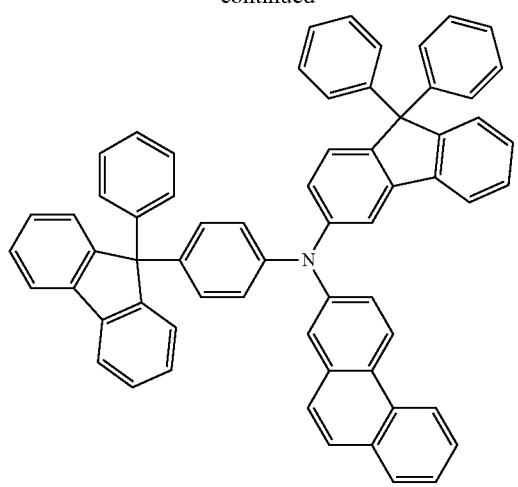
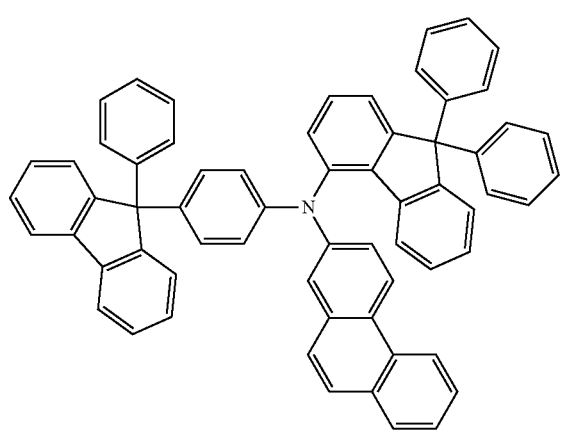
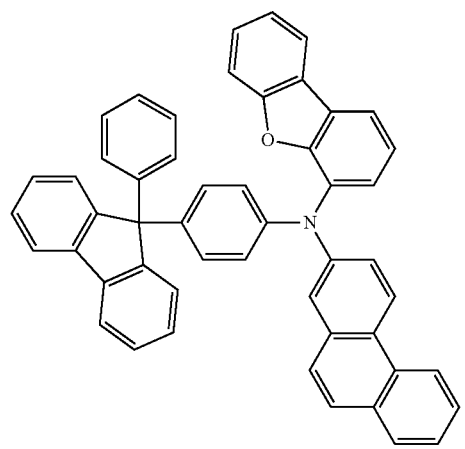
226
-continued
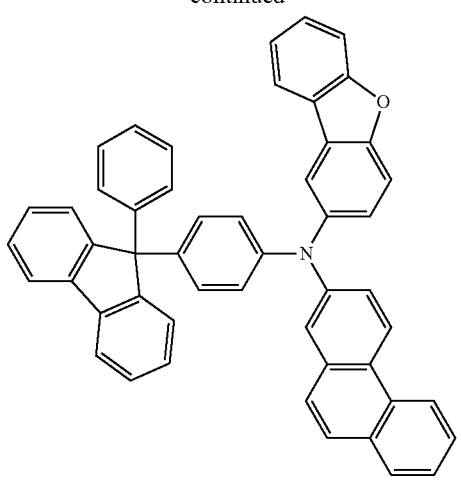
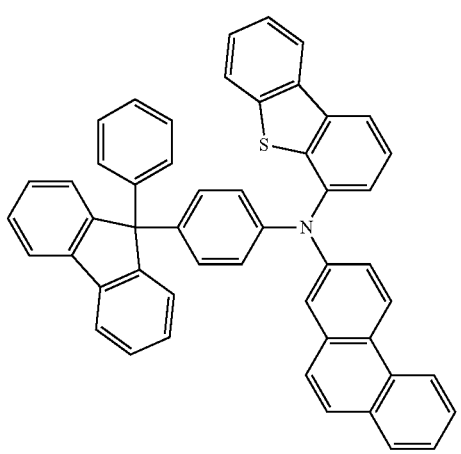
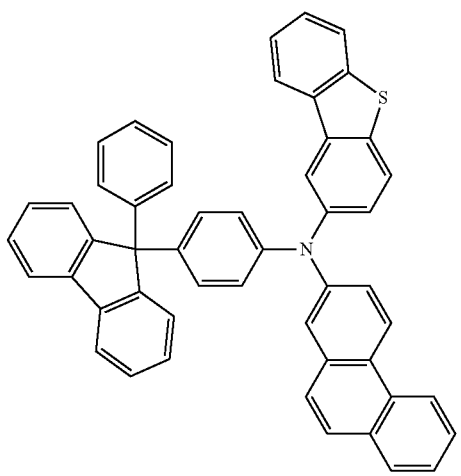

227
-continued
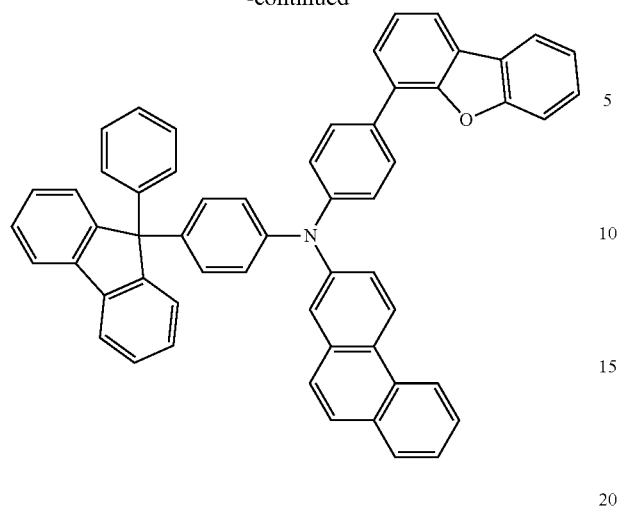
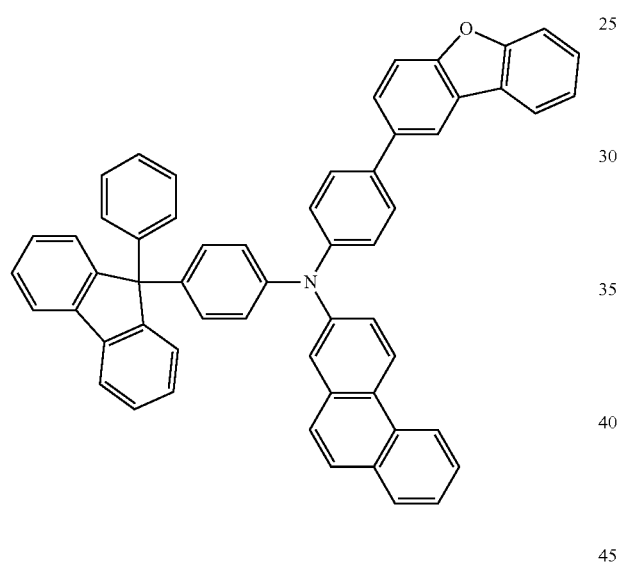
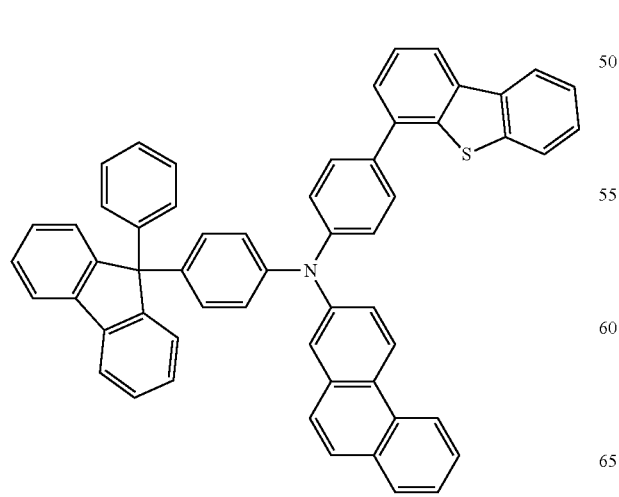
228
-continued
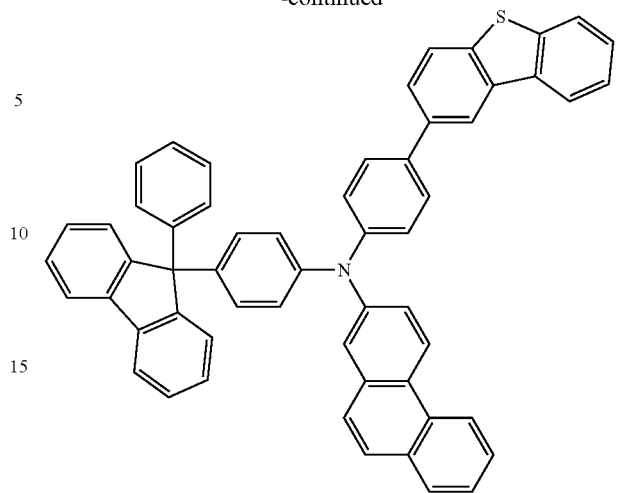
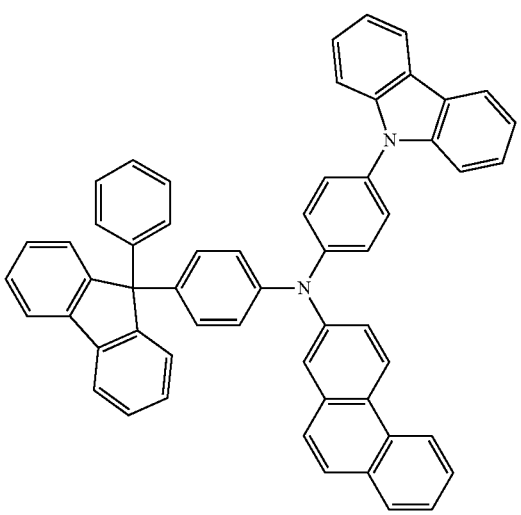
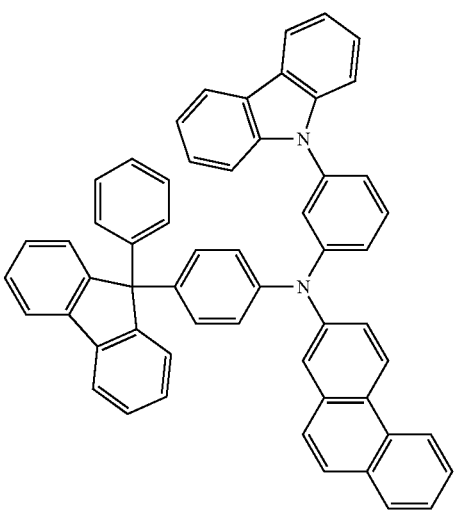

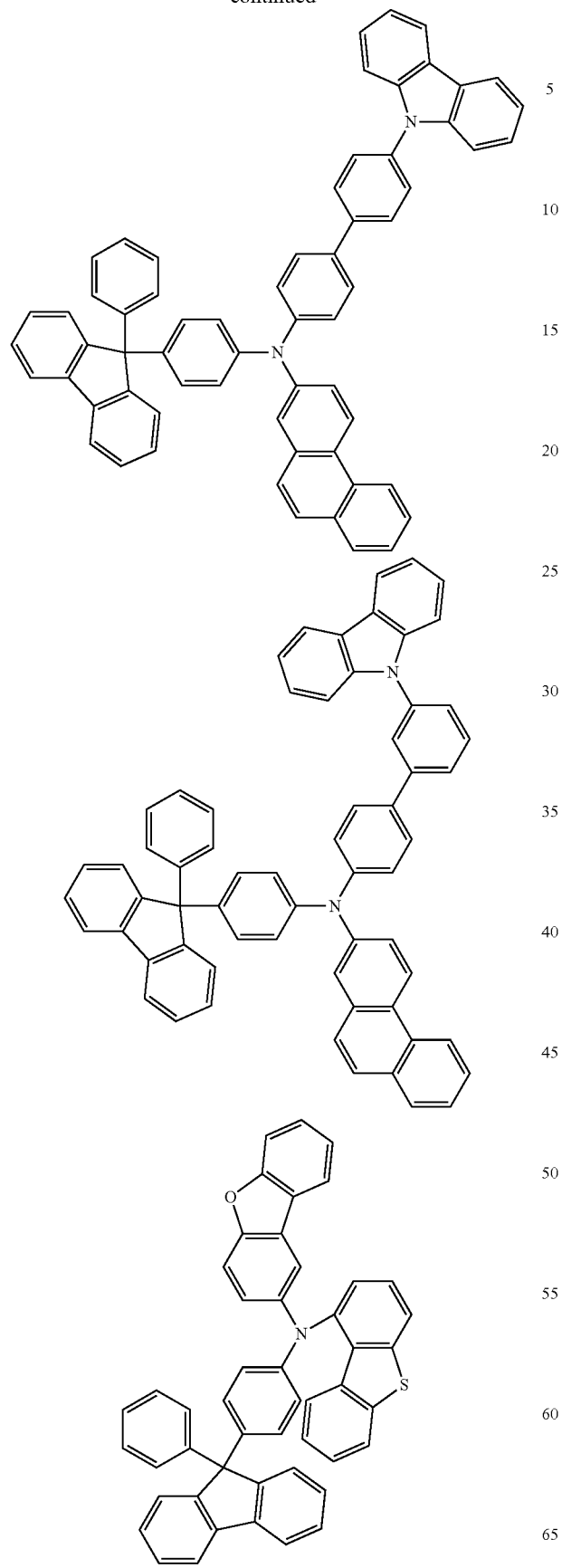
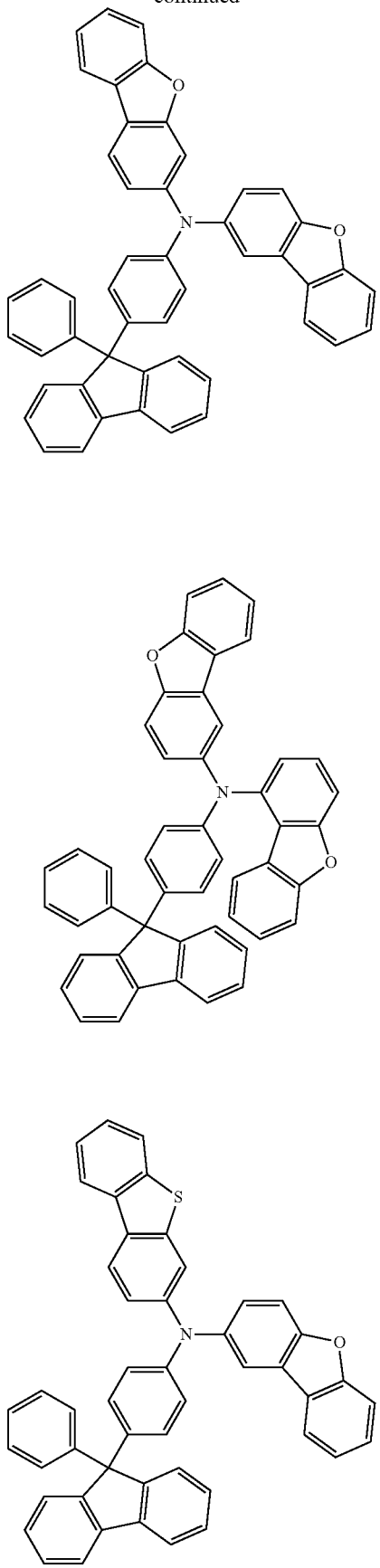

231
-continued
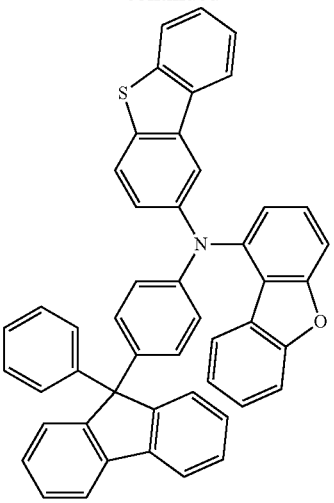
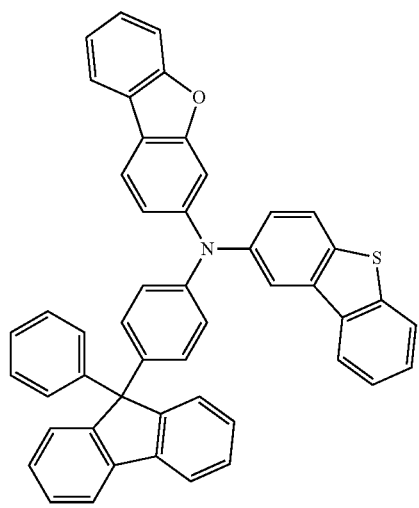
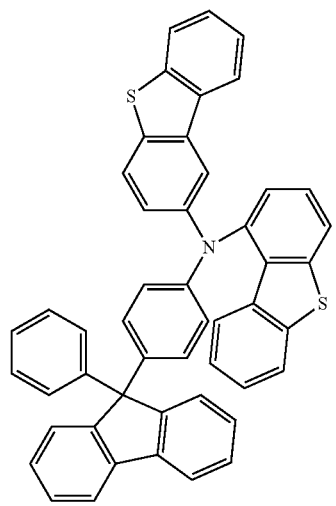
232
-continued
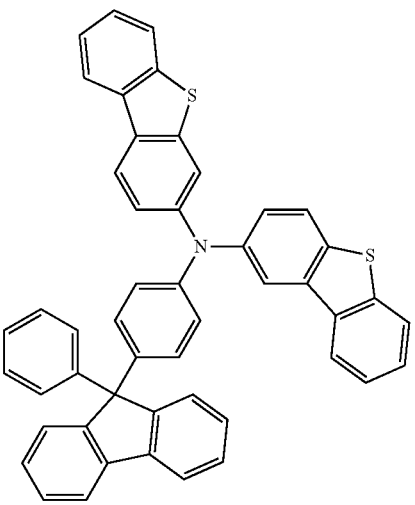
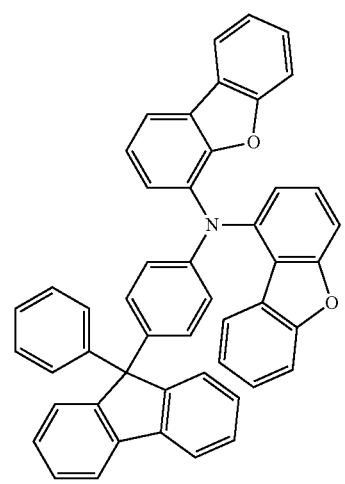
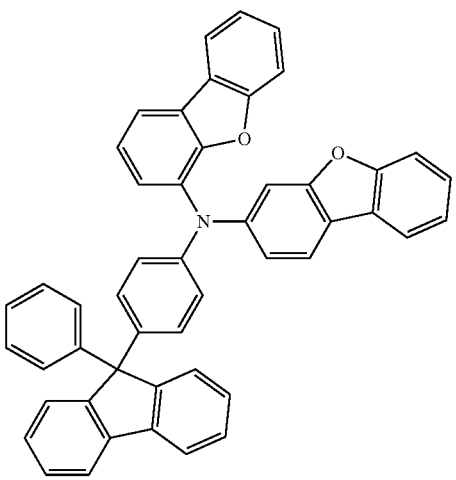

233
-continued
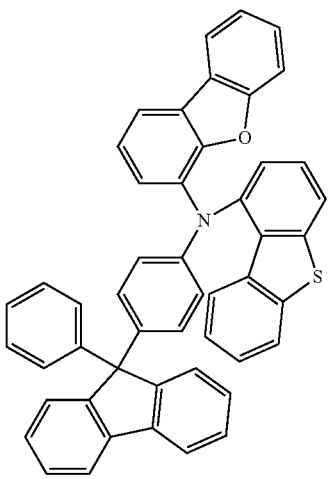
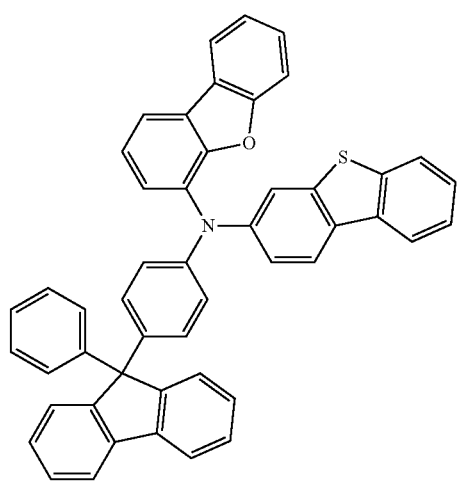
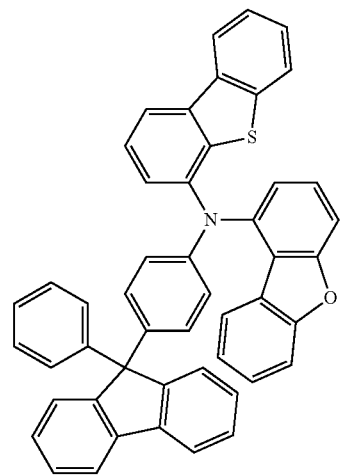
234
-continued
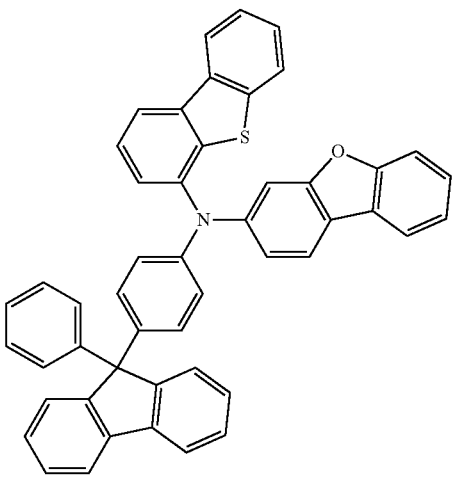
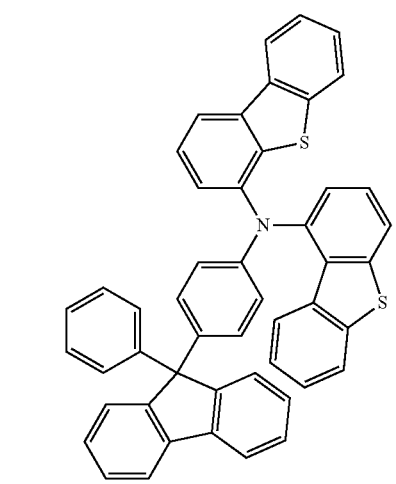
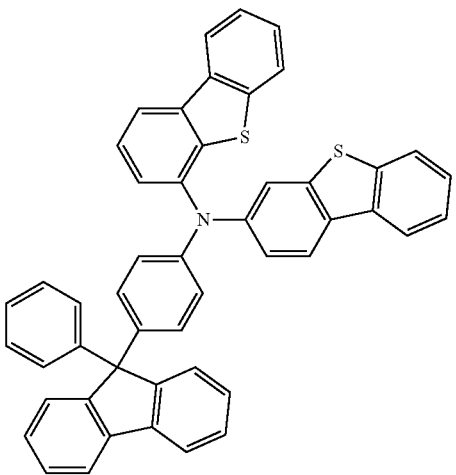

235
-continued
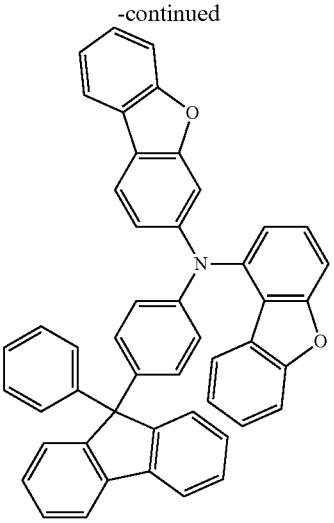
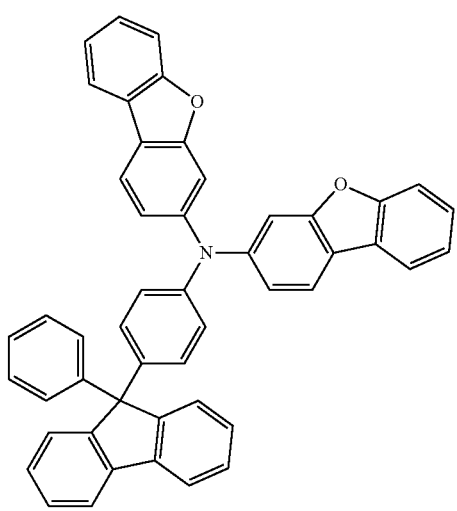
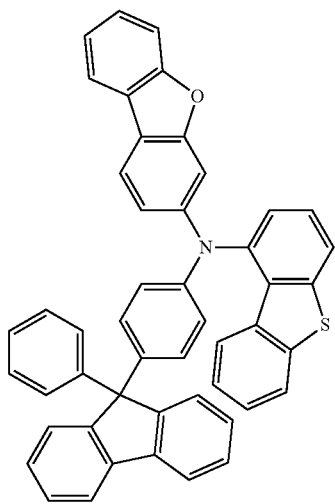
236
-continued
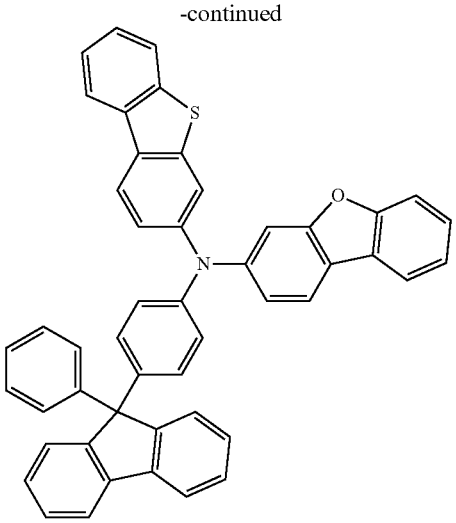
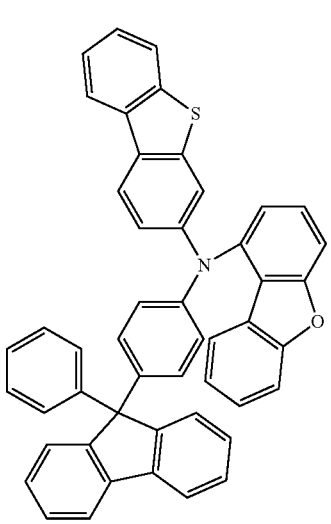
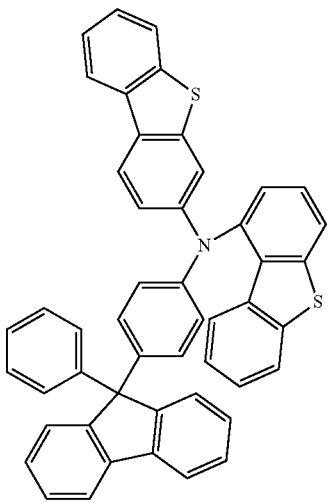

237
-continued
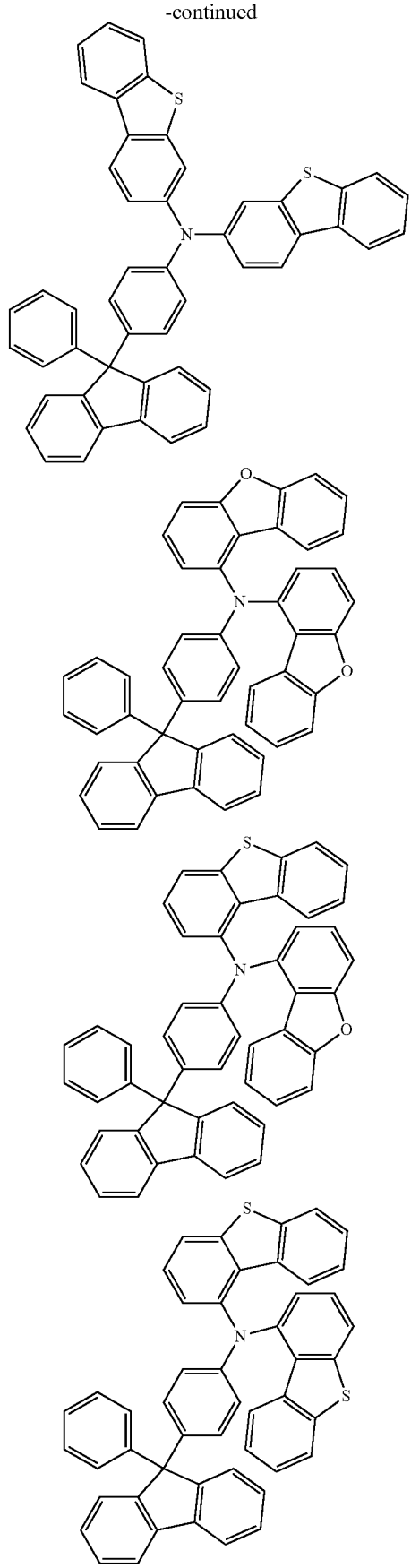
238
-continued
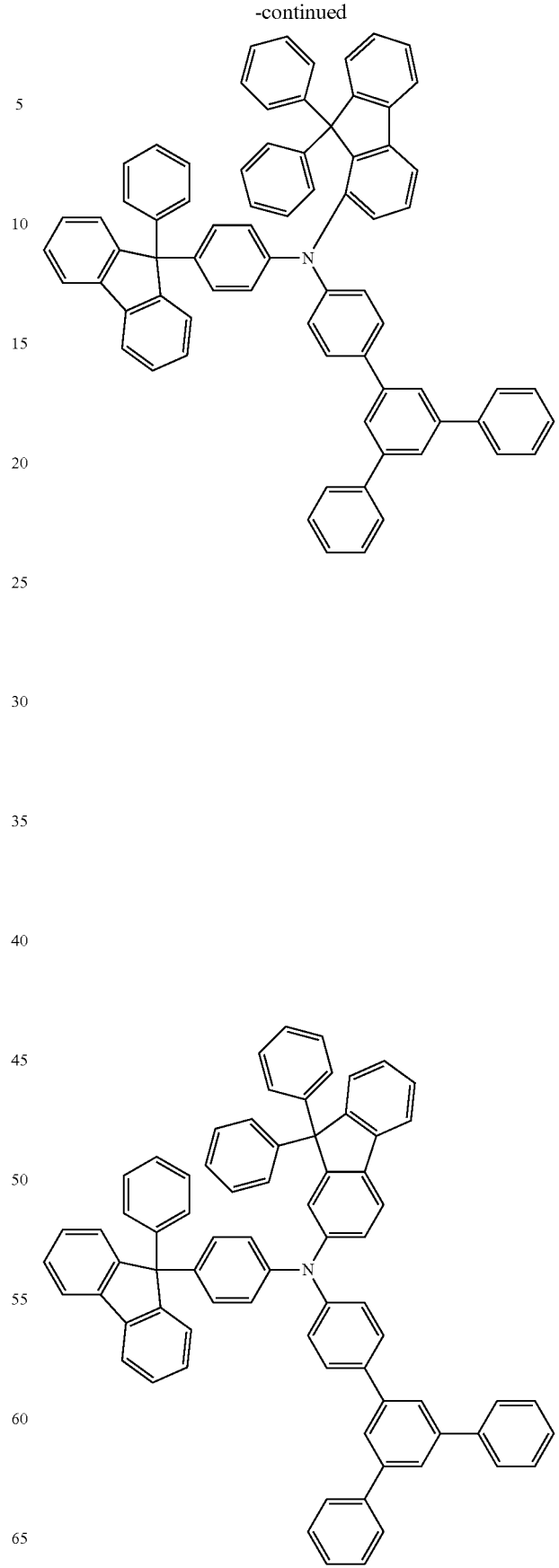

239
-continued
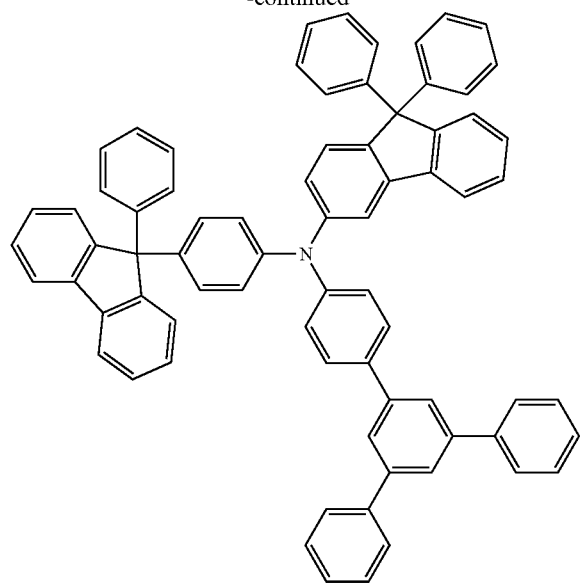
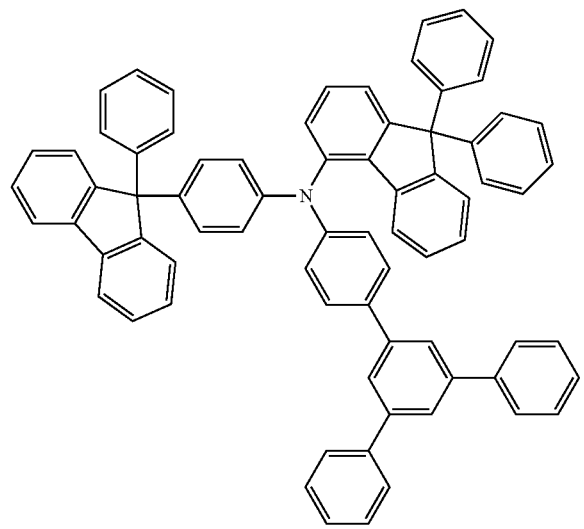
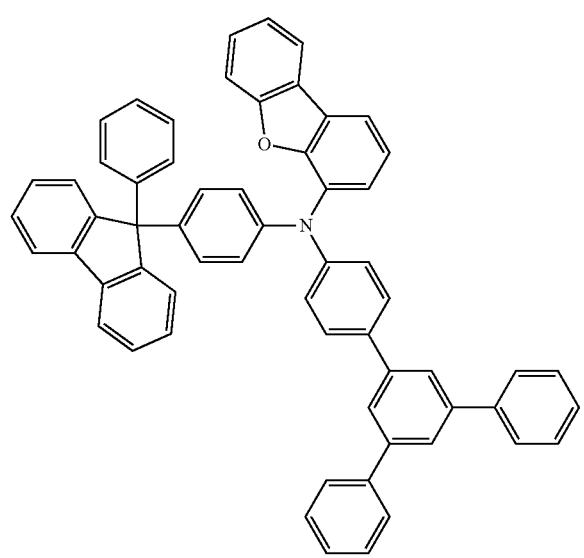
240
-continued
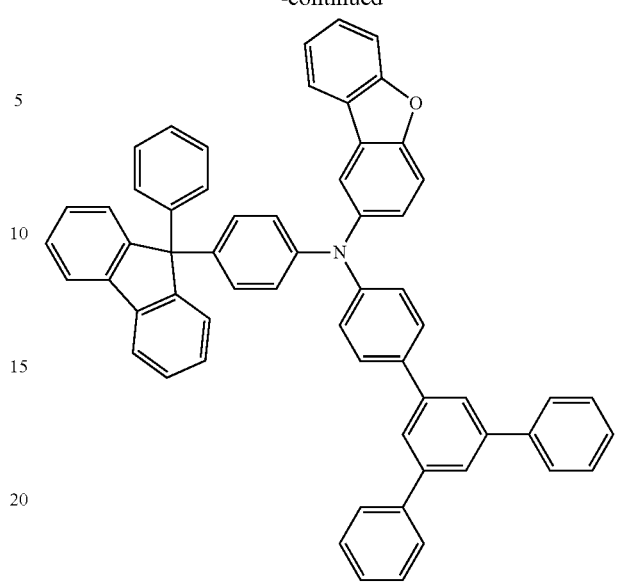
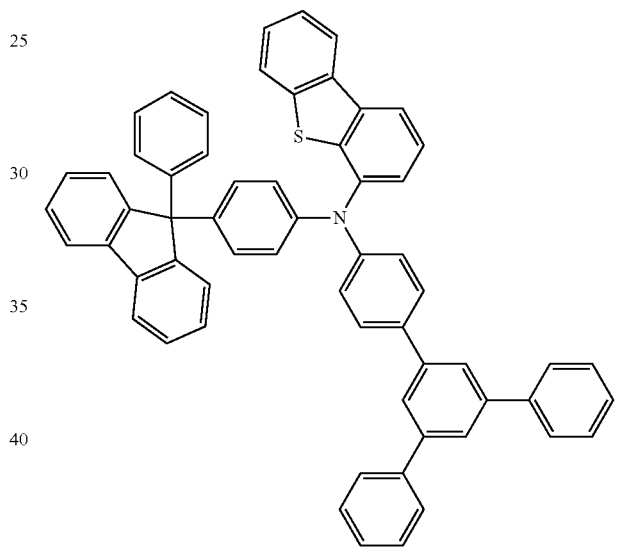
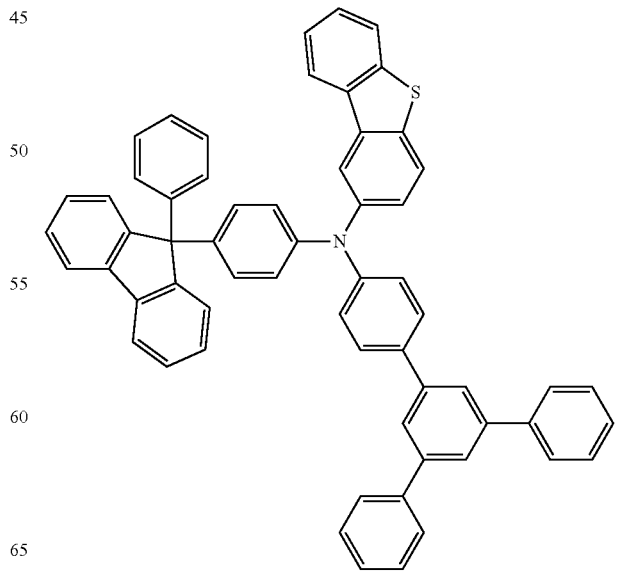

241
-continued
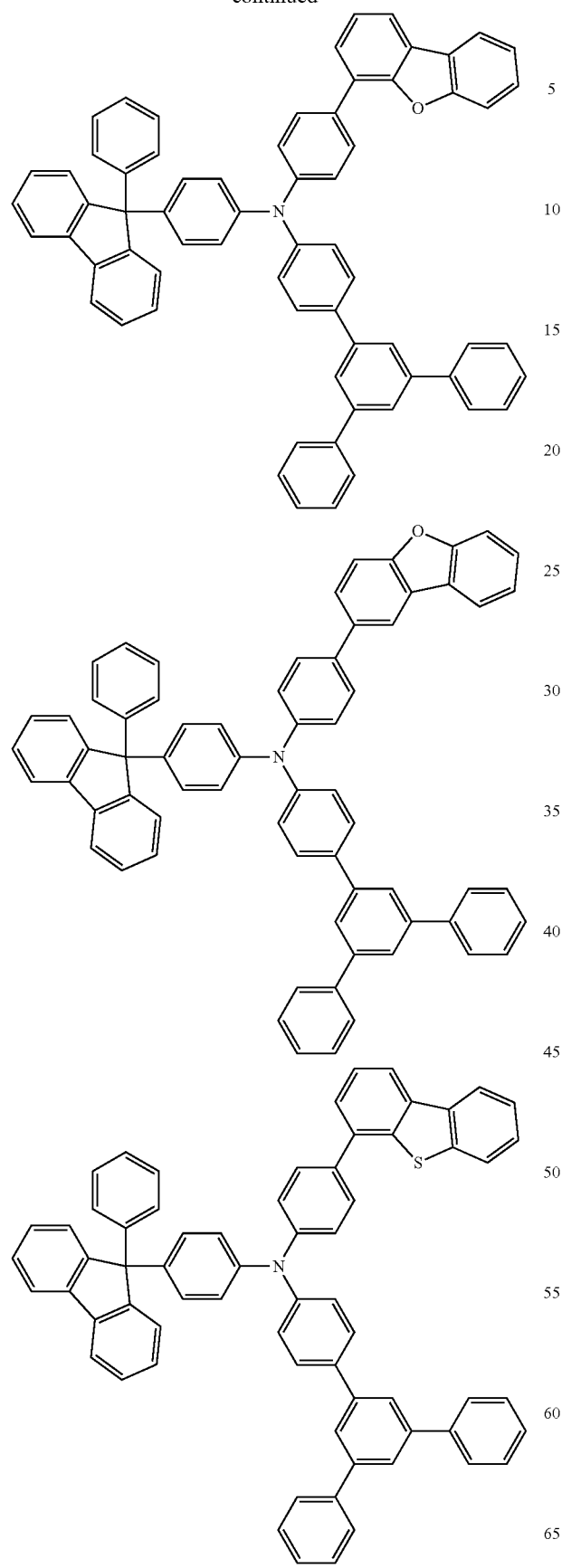
242
-continued
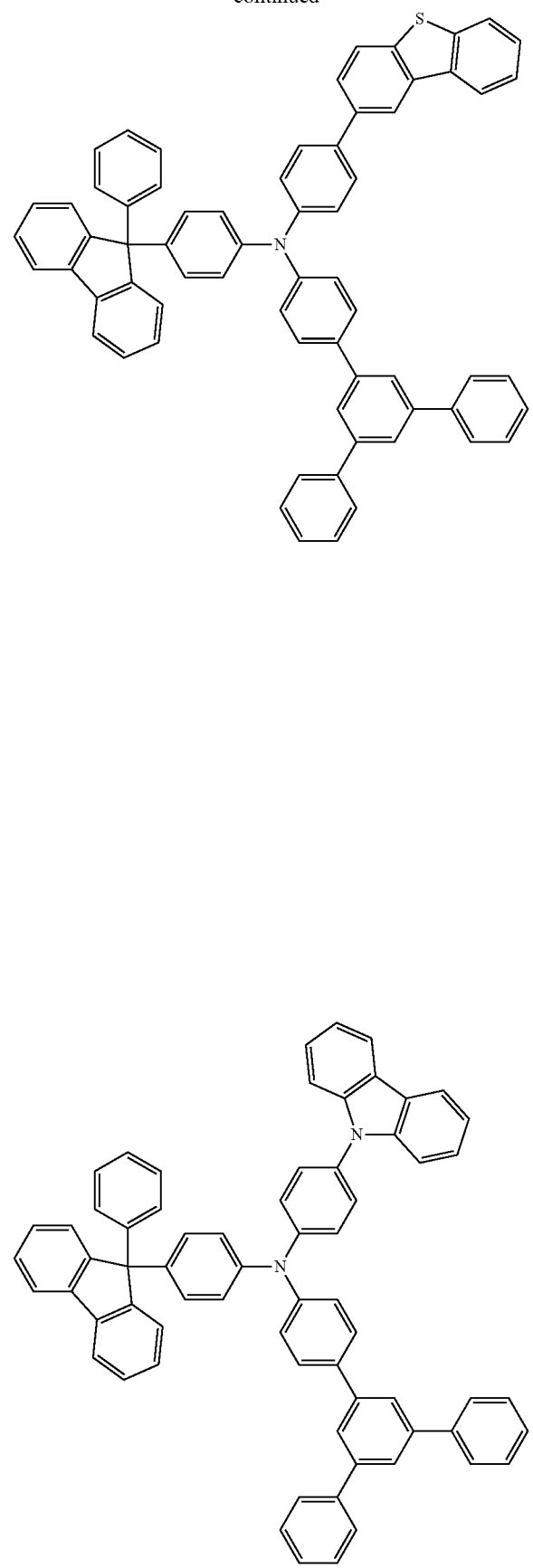

243
-continued
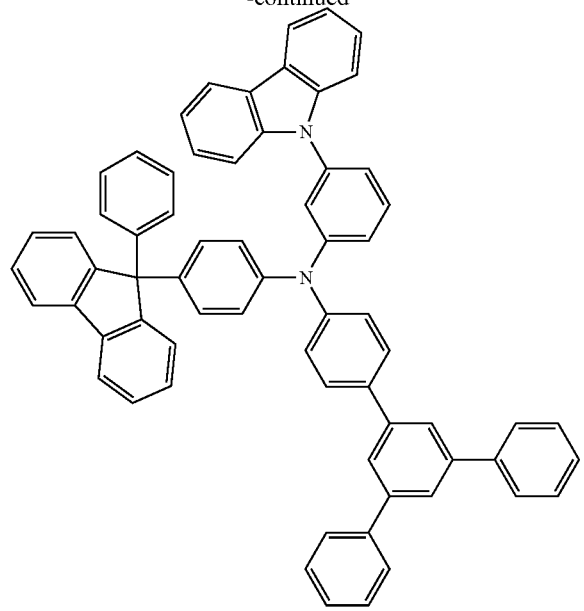
244
-continued
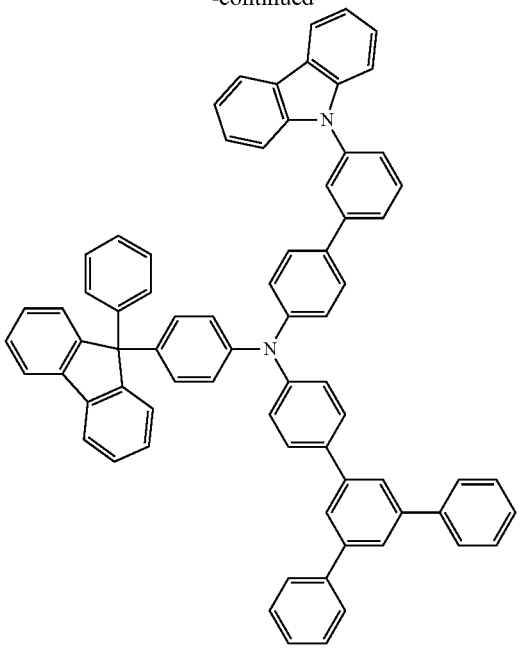
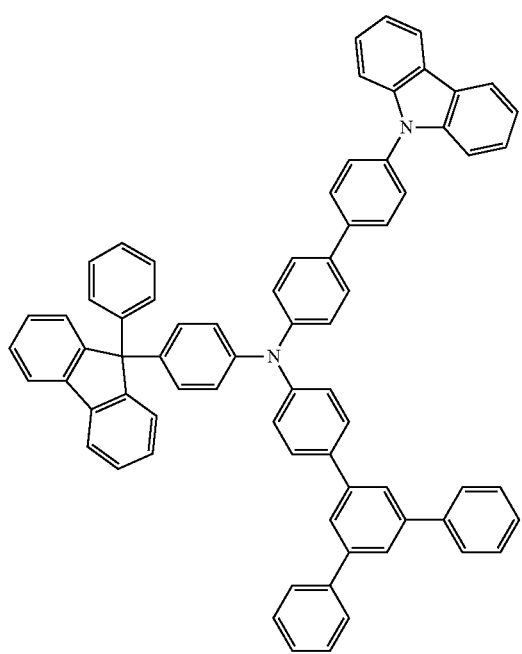

245
-continued
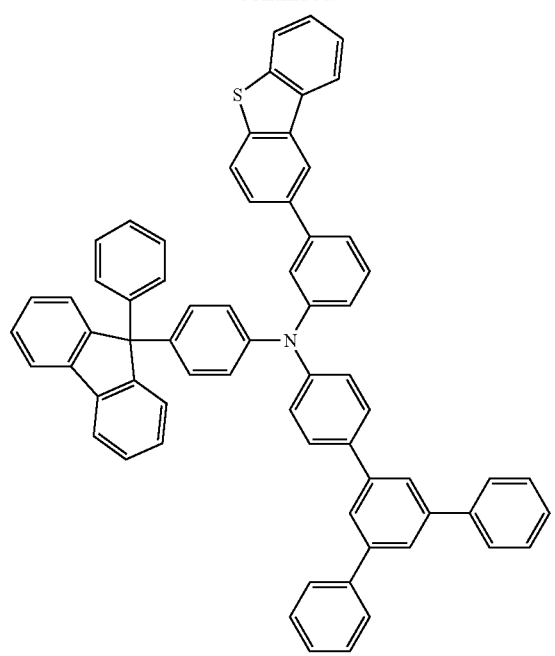
246
-continued
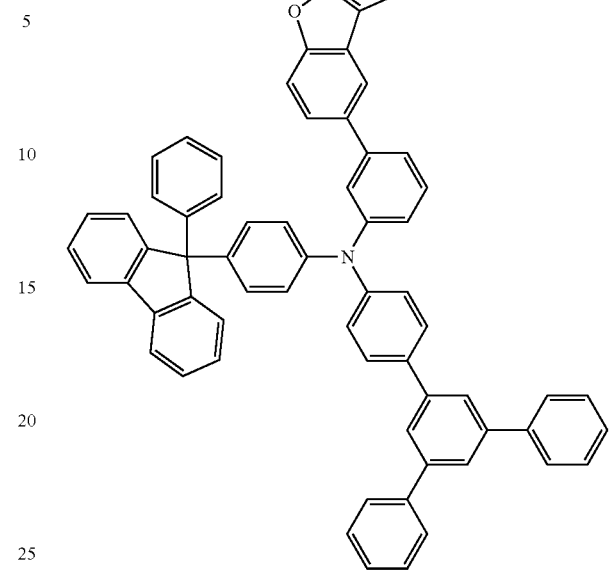
Of the above, the compound (1) in an aspect of the invention is preferably any of the following compounds (H1) to (H17).
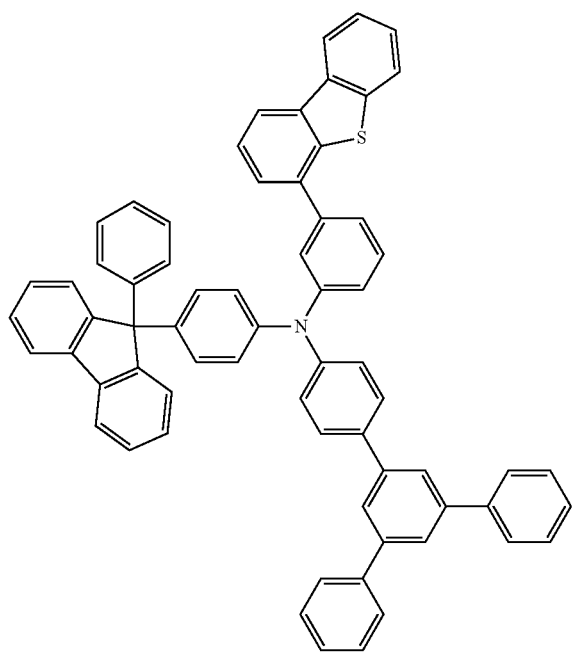
(H1)
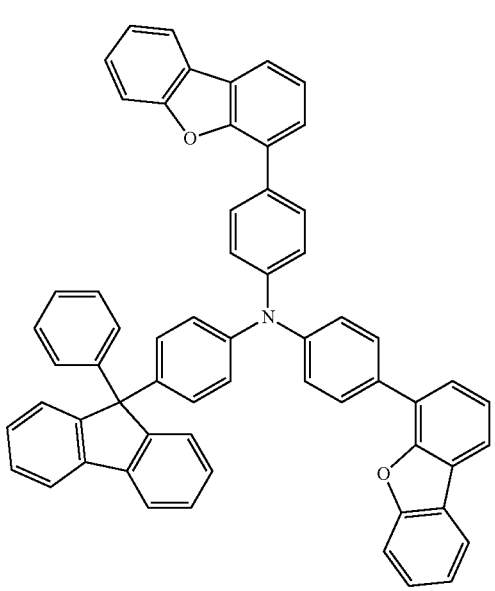

(H2)
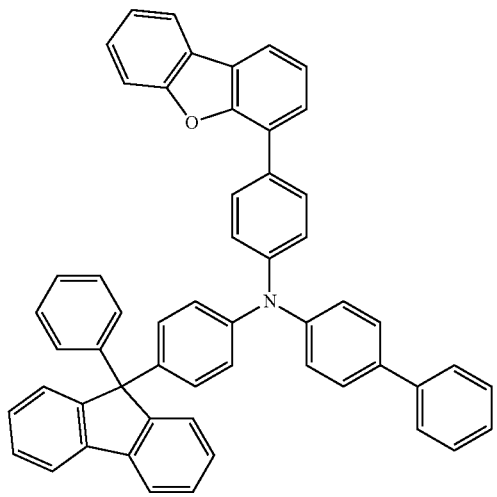
(H3)
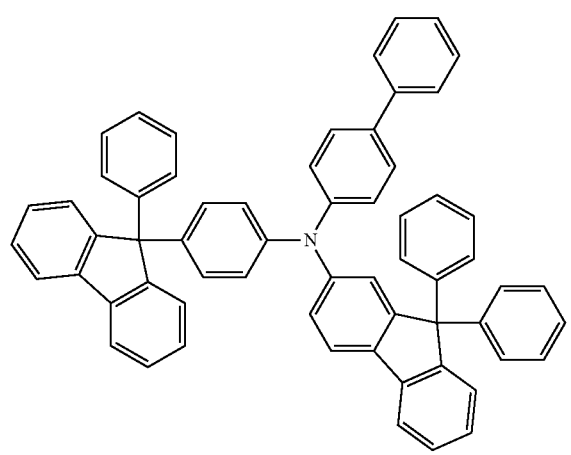
(H4)
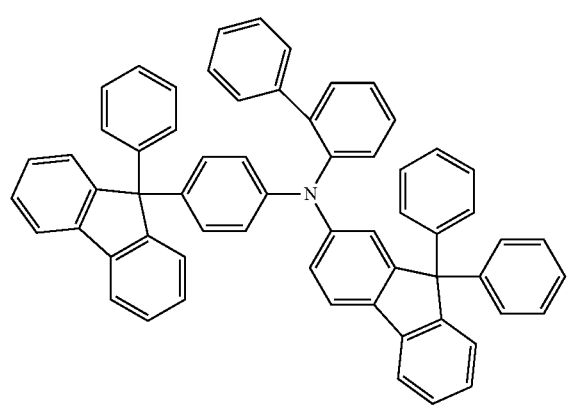
(H5)
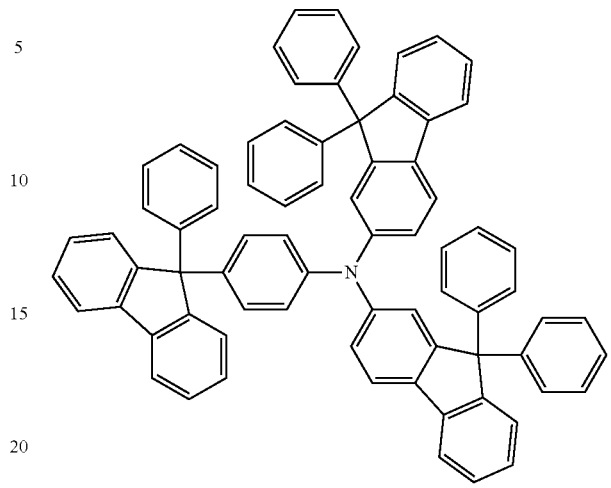
(H6)
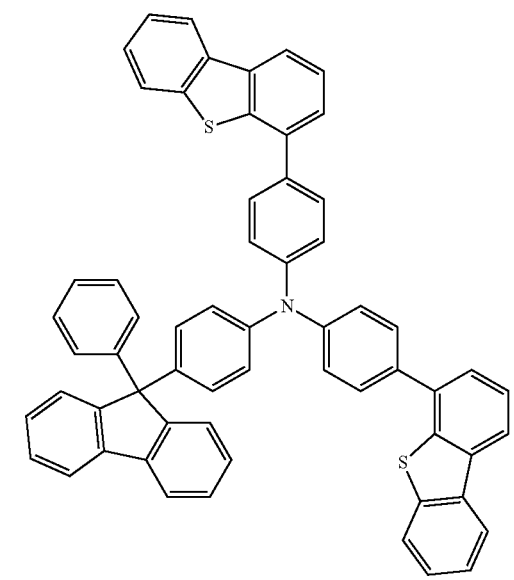
(H7)
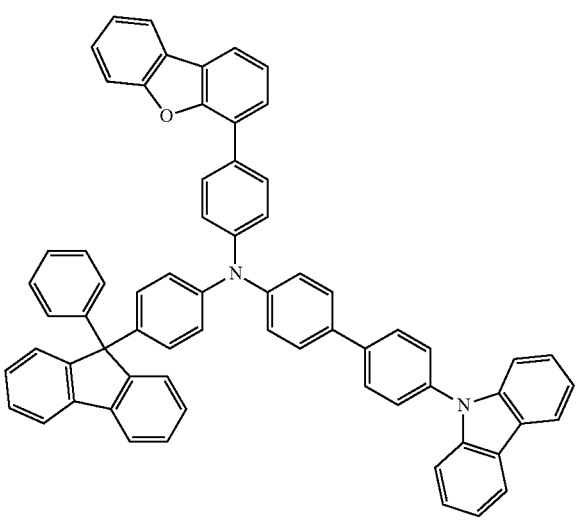

(H8)
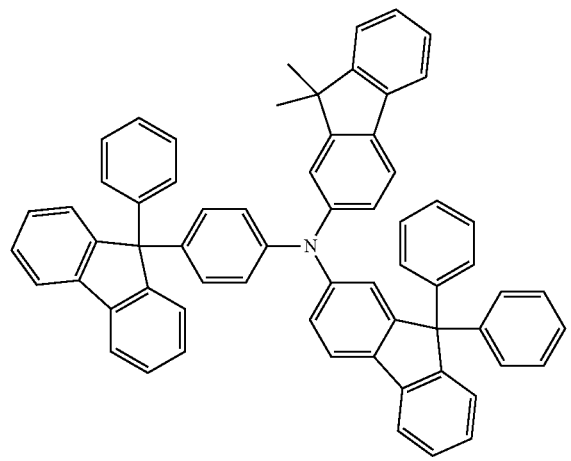
(H11)
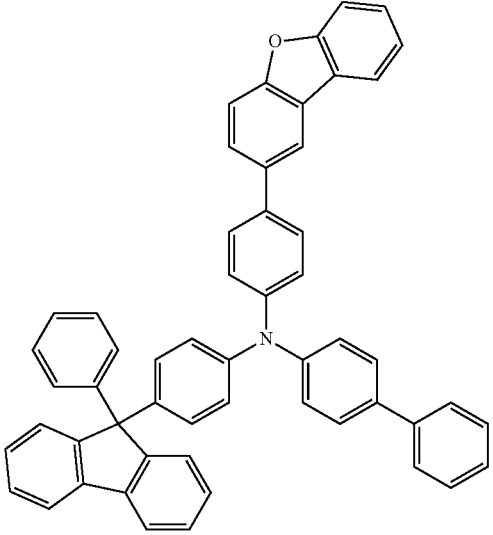
(H9)
(H12)
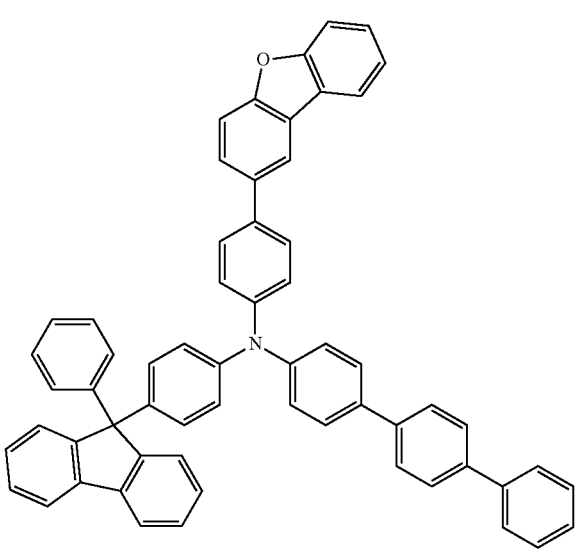
(H10)
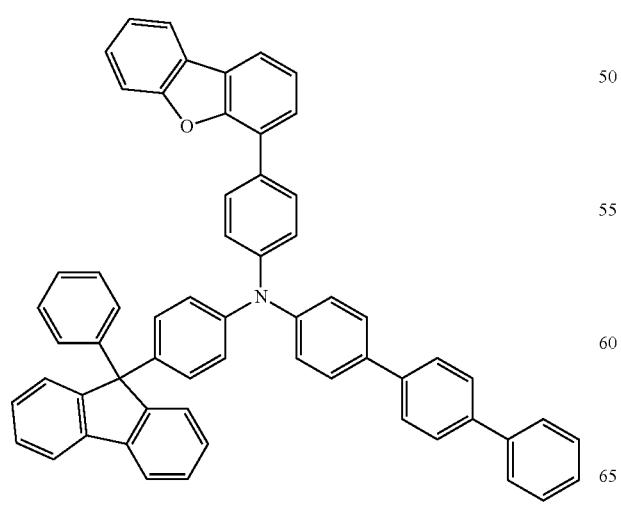
(H13)
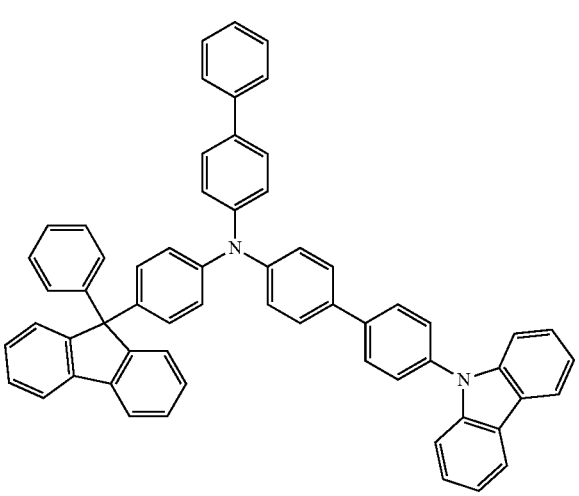

-continued (H14)

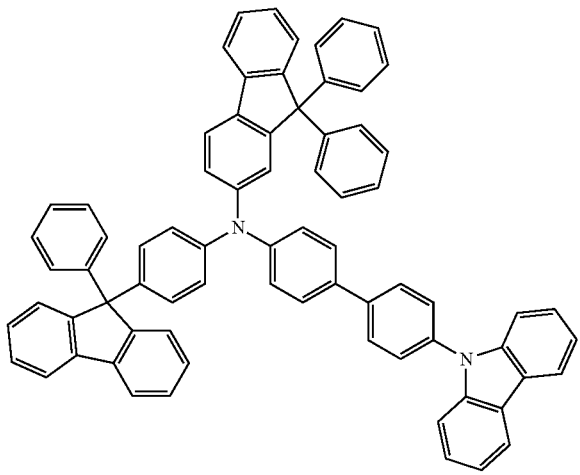

(H15)

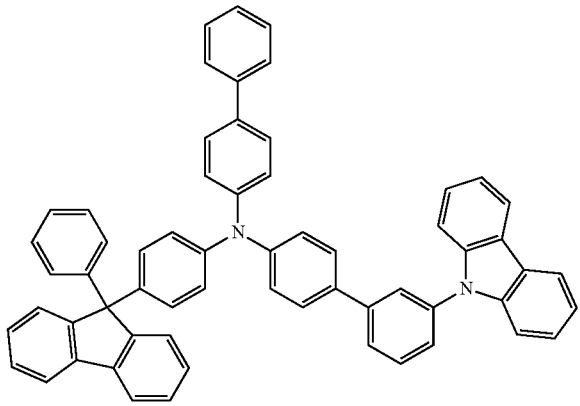

(H16)

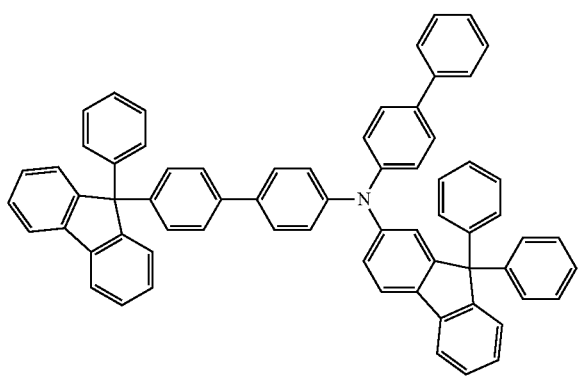

-continued (H17)

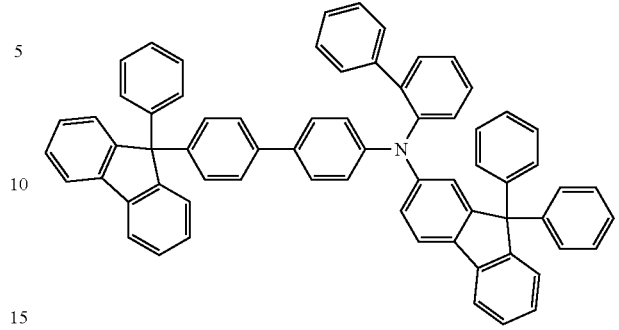

Material for Organic EL Devices

The material for organic EL devices in an aspect of the invention comprises the compound (1) and preferably comprises a compound selected from the compounds (1-1) to (1-7), (1-4-1), (1-5-1), (1-6-1), (1-7-1), and (1-7-2).

The following description with respect to the compound (1) is equally applicable to the compounds (1-1) to (1-7), (1-4-1), (1-5-1), (1-6-1), (1-7-1), and (1-7-2).

The material for organic EL devices in an aspect of the invention is useful as a material for producing an organic EL device, for example, as a material for at least one organic thin film layer disposed between an anode and a cathode, particularly as a material for a hole transporting layer or a hole injecting layer.

Organic EL Device

The organic EL device in an aspect of the invention will be described below.

Representative device structures (1) to (13) are shown below, although not limited thereto. The device structure (8) is preferably used.

(1) anode/light emitting layer/cathode;
(2) anode/hole injecting layer/light emitting layer/cathode;
(3) anode/light emitting layer/electron injecting layer/cathode;
(4) anode/hole injecting layer/light emitting layer/electron injecting layer/cathode;
(5) anode/organic semiconductor layer/light emitting layer/cathode;
(6) anode/organic semiconductor layer/electron blocking layer/light emitting layer/cathode;
(7) anode/organic semiconductor layer/light emitting layer/adhesion improving layer/cathode;
(8) anode/hole injecting layer/hole transporting layer/light emitting layer/(electron transporting layer/) electron injecting layer/cathode;
(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/hole injecting layer/hole transporting layer/light emitting layer/insulating layer/cathode; and
(13) anode/insulating layer/hole injecting layer/hole transporting layer/light emitting layer/(electron transporting layer/) electron injecting layer/cathode.

A schematic structure of an example of the organic EL device in an aspect of the invention is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5 which comprises a host material and a dopant (light emitting material). A hole injecting/transporting layer 6, etc. may be disposed between the light emitting layer 5 and the anode 3, and an electron injecting/transporting layer 7, etc. may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the exciton generation in the light emitting layer 5.

The organic EL device in an aspect of the invention comprises an anode, a cathode, and at least one organic thin film layer between the cathode and the anode. The at least one organic thin film layer comprises a light emitting layer and at least one layer of the at least one organic thin film layer comprise the compound represented by formula (1) (compound (1)).

Examples of the organic thin film layer comprising the compound (1) include an anode-side organic thin film layer formed between an anode and a light emitting layer (hole transporting layer, hole injecting layer, etc.), a light emitting layer, a cathode-side organic thin film layer formed between a cathode and a light emitting layer (electron transporting layer, electron injecting layer, etc.), a space layer, and a blocking layer, although not limited thereto.

The compound (1) may be used in any of the organic thin film layers of an organic EL device. In view of driving at a lower voltage, the compound (1) is preferably used in a hole injecting layer or a hole transporting layer, more preferably used in a hole transporting layer.

Namely, the organic EL device in an aspect of the invention is more preferably an organic EL device wherein the at least one organic thin film layer comprises a hole injecting layer comprising the compound (1), a hole transporting layer comprising the compound (1), or both.

The content of the compound (1) in the organic thin film layer, preferably in a hole injecting layer or a hole transporting layer, is preferably 30 to 100 mol %, more preferably 50 to 100 mol %, still more preferably 80 to 100 mol %, and further preferably 95 to 100 mol %, each based on the total molar amount (100 mol %) of the components in the organic thin film layer.

Substrate

The substrate is a support for the emitting device and made of, for example, glass, quartz, and plastics. The substrate may be a flexible substrate, for example, a plastic substrate made of, for example, polycarbonate, polyarylate, polyether sulfone, polypropylene, polyester, polyvinyl fluoride, and polyvinyl chloride. An inorganic deposition film is also usable.

Anode

The anode is formed on the substrate preferably from a metal, an alloy, an electrically conductive compound, and a mixture thereof, each having a large work function, for example, 4.5 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a metal nitride (for example, titanium nitride) are also usable.

These materials are made into a film generally by a sputtering method. For example, a film of indium oxide-zinc oxide is formed by sputtering an indium oxide target doped with 1 to 10% by mass of zinc oxide, and a film of indium oxide doped with tungsten oxide and zinc oxide is formed by sputtering an indium oxide target doped with 0.5 to 5% by mass of tungsten oxide and 0.1 to 1% by mass of zinc oxide. In addition, a vacuum vapor deposition method, a coating method, an inkjet method, and a spin coating method are usable.

A hole injecting layer to be formed in contact with the anode is formed from a composite material which is capable of easily injecting holes independently of the work function of the anode. Therefore a material, for example, a metal, an alloy, an electroconductive compound, a mixture thereof, and a group 1 element and a group 2 element of the periodic table are usable as the electrode material.

A material having a small work function, for example, the group 1 element and the group 2 element of the periodic table, i.e., an alkali metal, such as lithium (Li) and cesium (Cs), an alkaline earth metal, such as magnesium (Mg), calcium (Ca), and strontium (Sr), and an alloy thereof, such as MgAg and AlLi, are also usable. In addition, a rare earth metal, such as europium (Eu) and ytterbium (Yb), and an alloy thereof are also usable. The alkali metal, the alkaline earth metal, and the alloy thereof can be made into the anode by a vacuum vapor deposition or a sputtering method. When a silver paste, etc. is used, a coating method and an inkjet method are usable.

Hole Injecting Layer

The hole injecting layer comprises a highly hole-transporting material.

The hole injecting layer of the organic EL device in an aspect of the invention preferably comprises the compound (1) in an aspect of the invention alone or in combination with the following compound.

Examples of the highly hole-transporting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A polymeric compound, such as an oligomer, a dendrimer, a polymer, is also usable. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). An acid-added polymeric compound, such as poly(3,4-ethylenedioxythiophene)/poly(styrenesulfonic acid) (PEDOT/PSS) and polyalinine/poly(styrenesulfonic acid) (PAni/PSS), is also usable.

Hole Transporting Layer

The hole transporting layer comprises a highly hole-transporting material.

The hole transporting layer of the organic EL device in an aspect of the invention preferably comprises the compound (1) in an aspect of the invention alone or in combination with the following compound.

The hole transporting layer may contain an aromatic amine compound, a carbazole derivative, an anthracene derivative, etc., for examples, an aromatic amine compound, such as 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl)triphenylamine (BAFLP), 4,4'-bis[N-(9,9-dimethylfluorene-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of mainly $10^{-6}$ cm$^2$/Vs or more.

In addition, the hole transporting layer may contain a carbazole derivative, such as CBP, CzPA, and PCzPA, an anthracene derivative, such as t-BuDNA, DNA, and DPAnth, and a polymeric compound, such as poly(N-vinylcarbazole) (PVK) and poly(4-vinyltriphenylamine) (PVTPA).

Other materials are also usable if their hole transporting ability is higher than their electron transporting ability. The layer comprising a highly hole-transporting material may be a single layer or a laminate of two or more layers each comprising the material mentioned above. For example, the hole transporting layer may be made into a two-layered structure of a first hole transporting layer (anode side) and a second hole transporting layer (light emitting layer side). The compound (1) in an aspect of the invention may be used in either of the first hole transporting layer and the second hole transporting layer and preferably used in the second hole transporting layer.

In the organic EL device in an aspect of the invention, a layer comprising an electron-accepting compound (acceptor material) may be formed on the anode-side of the hole transporting layer or the first hole transporting layer, because it is expected that the driving voltage is lowered and the production cost is reduced.

A compound represented by formula (EA) is preferably used as the acceptor compound:

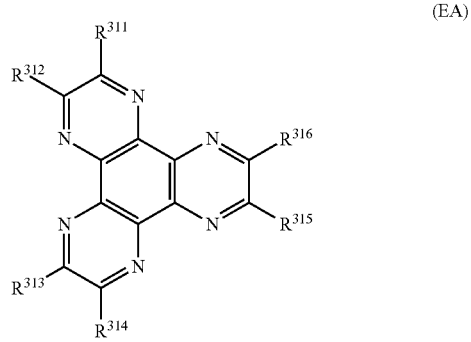

(EA)

wherein $R^{311}$ to $R^{316}$ may be the same or different and each independently represent a cyano group, —CONH$_2$, a carboxyl group, or —COOR$^{317}$ wherein $R^{317}$ represents an alkyl group having 1 to 20 carbon atoms or a cycloalkyl group having 3 to 20 carbon atoms; and $R^{311}$ and $R^{312}$, $R^{313}$ and $R^{314}$, or $R^{315}$ and $R^{316}$ may be bonded to each other to form a group represented by —CO—O—CO—.

Examples of alkyl group for $R^{317}$ include a methyl group, an ethyl group, a n-propyl group, an isopropyl group, a n-butyl group, an isobutyl group, and a t-butyl group. Examples of cycloalkyl group include a cyclopentyl group and a cyclohexyl group.

The thickness of the layer comprising the acceptor compound is preferably 5 to 20 nm, although not particularly limited thereto.

Guest Material of Light Emitting Layer

The light emitting layer comprises a highly light-emitting material and may be formed from a various kind of materials. For example, a fluorescent emitting compound and a phosphorescent emitting compound are usable as the highly light-emitting material. The fluorescent emitting compound is a compound capable of emitting light from a singlet excited state, and the phosphorescent emitting compound is a compound capable of emitting light from a triplet excited state.

Examples of blue fluorescent emitting material for use in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material for use in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material for use in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material for use in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2'] iridium(III) picolinato (FIrpic), bis[2-(3',5'-bistrifluoromethylphenyl)pyridinato-N,C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material for use in the light emitting layer include an iridium complex, such as tris(2-phenylpyridinato-N,C2')iridium(III) (Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)₂(acac)), bis(1-phenylisoquinolinato-N,C2')iridium(III) acetylacetonato (Ir(piq)₂(acac)), (acetylacetonato)bis[2,3-bis(4-fluorophenyl)quinoxalinato]iridium(III) (Ir(Fdpq)₂(acac)), and 2,3,7,8,12,13,17,18-octaethyl-21H,23H-porphyrin platinum(II) (PtOEP).

The following rare earth metal complex, such as tris(acetylacetonato) (monophenanthroline)terbium(III) (Tb(acac)₃(Phen)), tris(1,3-diphenyl-1,3-propanedionato)(monophenanthroline)europium(III) (Eu(DBM)₃(Phen)), and tris[1-(2-thenoyl)-3,3,3-trifluoroacetonato](monophenanthroline)europium(III) (Eu(TTA)₃(Phen)), emits light from the rare earth metal ion (electron transition between different multiple states), and therefore, usable as a phosphorescent emitting compound.

Host Material for Light Emitting Layer

The light emitting layer may be formed by dispersing the highly light-emitting material (guest material) mentioned above in another material (host material). The material in which the highly light-emitting material is to be dispersed may be selected from various kinds of materials and is preferably a material having a lowest unoccupied molecular orbital level (LUMO level) higher than that of the highly light-emitting material and a highest occupied molecular orbital level (HOMO level) lower than that of the highly light-emitting material.

The material in which the highly light-emitting material is to be dispersed may include, for example,
(1) a metal complex, such as an aluminum complex, a beryllium complex, and a zinc complex;
(2) a heterocyclic compound, such as an oxadiazole derivative, a benzimidazole derivative, and a phenanthroline derivative;
(3) a fused aromatic compound, such as a carbazole derivative, an anthracene derivative, a phenanthrene derivative, a pyrene derivative, and a chrysene derivative; and
(4) an aromatic amine compound, such as a triarylamine derivative and a fused aromatic polycyclic amine derivative.

Examples thereof include:
a metal complex, such as tris(8-quinolinolato)aluminum (III) (Alq), tris(4-methyl-8-quinolinolato)aluminum(III) (Almq₃), bis(10-hydroxybenzo[h]quinolinato)beryllium(II) (BeBq₂), bis(2-methyl-8-quinolinolato)(4-phenylphenolato)aluminum(III) (BAlq), bis(8-quinolinolato)zinc(H) (Znq), bis[2-(2-benzoxazolyl)phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene;

an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), NPB (or a-NPD), TPD, DFLDPBi, and BSPB.

The material (host material) for dispersing the highly light-emitting material (guest material) may be used alone or in combination of tow or more.

Electron Transporting Layer

The electron transporting layer comprises a highly electron-transporting material, for example,
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a polymeric compound.

Examples of the low molecular organic compound include a metal complex, such as Alq, tris(4-methyl-8-quinolinolato)aluminum (Almq₃), bis(10-hydroxybenzo[h]quinolinato)beryllium (BeBq2), BAlq, Znq, ZnPBO, and ZnBTZ; and a heteroaromatic compound, such as 2-(4-biphenylyl)-5-(4-tert-butylphenyl)-1,3,4-oxadiazole (PBD), 1,3-bis[5-(ptert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

The above compounds have an electron mobility of mainly $10^{-6}$ cm²/Vs or more. Other materials are also usable in the electron transporting layer if their electron transporting ability is higher than their hole transporting ability. The electron transporting layer may be a single layer or a laminate of two or more layers each comprising the material mentioned above.

A polymeric compound is also usable in the electron transporting layer. Examples there of include poly[(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

Electron Injecting Layer

The electron injecting layer comprises a highly electron-injecting material, for example, an alkali metal, an alkaline earth metal, and a compound of these metals, such as lithium (Li), cesium (Cs), calcium (Ca), lithium fluoride (LiF), cesium fluoride (CsF), calcium fluoride (CaF₂), and lithium oxide (LiOx). In addition, an electron transporting material which is incorporated with an alkali metal, an alkaline earth metal or a compound thereof, for example, Alq incorporated with magnesium (Mg), is also usable. By using such a material, electrons are efficiently injected from the cathode.

A composite material obtained by mixing an organic compound and an electron donor is also usable in the electron injecting layer. Such a composite material is excellent in the electron injecting ability and the electron transporting ability, because the electron donor donates electrons to the organic compound. The organic compound is preferably a material excellent in transporting the received electrons. Examples thereof are the materials for the electron transporting layer mentioned above, such as the metal complex and the aromatic heterocyclic compound. Any material capable of giving its electron to another organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, and a mixture thereof, each having a small work function, for example a work function of 3.8 eV or less. Examples of the material for the cathode include a metal of the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof can be made into the cathode by a vacuum vapor deposition or a sputtering method. When a silver paste, etc. is used, a coating method and an inkjet method are usable.

When the electron injecting layer is formed, the material for the cathode can be selected independently from the work function and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Each layer of the organic EL device is formed by a dry film-forming method, such as vacuum vapor deposition, sputtering, plasma, and ion plating, and a wet film-forming method, such as spin coating, dip coating, and flow coating. In the wet film-forming method, the material for each layer is dissolved or dispersed in a suitable solvent, such as ethanol, chloroform, tetrahydrofuran, and dioxane, and then the obtained solution or dispersion is made into a film. To improve the film-forming properties and prevent pin holes on the film, the solution and the dispersion may include a resin or an additive. Examples of the resin include an insulating resin and a copolymer thereof, such as polystyrene, polycarbonate, polyarylate, polyester, polyamide, polyurethane, polysulfone, polymethyl methacrylate, polymethyl acrylate, and cellulose; and a photoconductive resin, such as poly-N-vinylcarbazole and polysilane; and an electroconductive resin, such as polythiophene and polypyrrole. Examples of the additive include an antioxidant, an ultraviolet absorber, and a plasticizer.

The thickness of each layer is not particularly limited and selected so as to obtain a good device performance. If extremely thick, a large applied voltage is needed to obtain a desired emission output, thereby reducing the efficiency. If extremely thin, pinholes occur on the film to make it difficult to obtain a sufficient luminance even when applying an electric field. The thickness is generally 5 nm to 10 μm and preferably 10 nm to 0.2 μm.

The thickness of the light emitting layer is, but not particularly limited to, preferably 5 to 100 nm, more preferably 7 to 70 nm, and still more preferably 10 to 50 nm.

The thickness of the hole transporting layer is preferably 10 to 300 nm.

When the hole transporting layer is made into a two-layered structure as described above, the thickness of the first hole transporting layer is preferably 50 to 300 nm, more preferably 50 to 250 nm, still more preferably 50 to 200 nm, and further preferably 50 to 150 nm, and the thickness of the second hole transporting layer is preferably 5 to 100 nm, more preferably 5 to 50 nm, still more preferably 5 to 30 nm, and further preferably 5 to 20 nm, although not limited thereto.

Electronic Equipment

The electronic equipment in an aspect of the invention comprises the organic EL device in an aspect of the invention mentioned above.

Examples of the electronic equipment include display parts, such as organic EL panel module, display devices of television sets, mobile phones, personal computer, etc., and light emitting sources of lighting equipment and vehicle lighting equipment.

EXAMPLES

The present invention will be described in more detail with reference to the examples and comparative examples. However, it should be noted that the scope of the invention is not limited thereto.

The compounds recited in the claims of this application can be synthesized by referring to the following synthetic reactions while using a known synthetic reaction and a starting material in accordance with the target compound.

Synthesis of Compound (1)

Intermediate Synthesis 1-1 (Synthesis of Intermediate (1-1))

Under an argon atmosphere, into a mixture of 28.3 g (100.0 mmol) of 4-iodobromobenzene, 22.3 g (105.0 mmol) of dibenzofuran-4-boronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was refluxed for 10 h under heating and stirring.

After the reaction, the reaction mixture was cooled to room temperature and extracted with dichloromethane in a separating funnel. The organic layer was dried over MgSO$_4$, filtered, and concentrated. The residual concentrate was purified by column chromatography to obtain 26.2 g of a white solid (yield: 81%), which was identified by FD-MS analysis (field desorption mass spectrometric analysis) as the following intermediate (1-1).

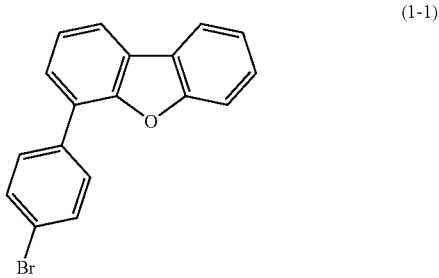 [SMILES: Brc1ccc(-c2cccc3c2oc2ccccc23)cc1]

(1-1)

Intermediate Synthesis 1-2 (Synthesis of Intermediate (1-2))

Under an argon atmosphere, into a mixture of 24.0 g (112.0 mmol) of 4'-bromoacetanilide, 28.6 g (135.0 mmol) of dibenzofuran-4-boronic acid, and 2.6 g (2.24 mmol) of Pd[PPh$_3$]$_4$, 450 ml of toluene, 100 ml of dimethoxyethane, and 110 ml (220.0 mmol) of a 2 M aqueous solution of Na$_2$CO$_3$ were added, and the resultant mixture was refluxed for 10 h under heating and stirring.

After the reaction, the reaction mixture was cooled to room temperature and the precipitated crystal was collected by filtration. The obtained crystal was dissolved in tetrahydrofuran. The obtained solution was filtered through celite/silica gel, and the filtrate was concentrated under reduced pressure. The obtained residue was washed with methanol/hexane and dried to obtain 18.0 g of a white solid (yield: 53%), which was identified by FD-MS analysis as the following intermediate (1-2).

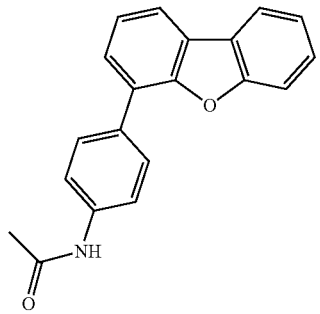

(1-2)

Intermediate Synthesis 1-3 (Synthesis of Intermediate (1-3))

A mixture of 18.0 g (59.7 mmol) of the intermediate (1-2) in 120 ml of xylene, 1200 ml of water, and 60 ml of ethanol was stirred. After adding 20.0 g (360.0 mmol) of potassium hydroxide, the resultant mixture was refluxed for 10 h under heating and stirring.

After the reaction, the reaction mixture was cooled to room temperature and extracted with toluene in a separating funnel. The organic layer was dried over MgSO$_4$, filtered, and concentrated. The obtained residue was recrystallized from xylene, and the precipitated crystal was collected by filtration and dried to obtain 14.7 g of a white crystal (yield: 95%), which was identified by FD-MS analysis as the following intermediate (1-3).

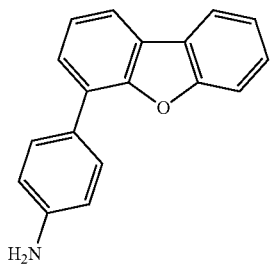

(1-3)

Intermediate Synthesis 1-4 (Synthesis of Intermediate (1-4))

Under an argon atmosphere, into a mixture of 28.3 g (100.0 mmol) of 4-iodobromobenzene, 23.9 g (105.0 mmol) of dibenzothophene-4-boronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was refluxed for 10 h under heating and stirring.

After the reaction, the reaction mixture was cooled to room temperature and extracted with dichloromethane in a separating funnel. The organic layer was dried over MgSO$_4$, filtered, and concentrated. The residual concentrate was purified by column chromatography to obtain 27.1 g of a white solid (yield: 80%), which was identified by FD-MS analysis as the following intermediate (1-4).

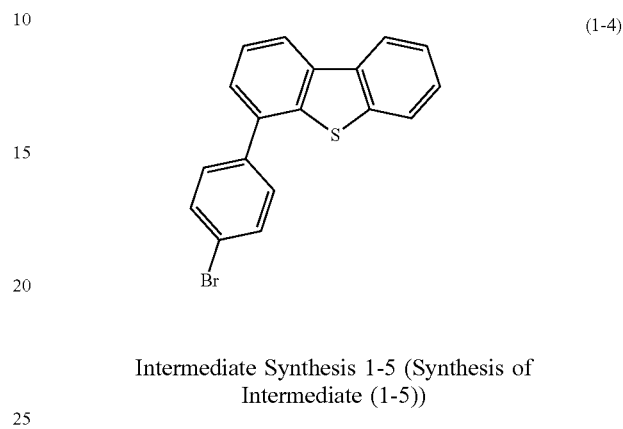

(1-4)

Intermediate Synthesis 1-5 (Synthesis of Intermediate (1-5))

Under an argon atmosphere, into a mixture of 24.0 g (112.0 mmol) of 4'-bromoacetanilide, 30.8 g (135.0 mmol) of dibenzothophene-4-boronic acid, and 2.6 g (2.24 mmol) of Pd[PPh$_3$]$_4$, 450 ml of toluene, 100 ml of dimethoxyethane, and 110 ml (220.0 mmol) of a 2 M aqueous solution of Na$_2$CO$_3$ were added, and the resultant mixture was refluxed for 10 h under heating and stirring.

After the reaction, the reaction mixture was cooled to room temperature and the precipitated crystal was collected by filtration. The obtained crystal was dissolved in tetrahydrofuran. The obtained solution was filtered through celite/silica gel, and the filtrate was concentrated under reduced pressure. The obtained residue was washed with methanol/hexane and dried to obtain 17.8 g of a white solid (yield: 50%), which was identified by FD-MS analysis as the following intermediate (1-5).

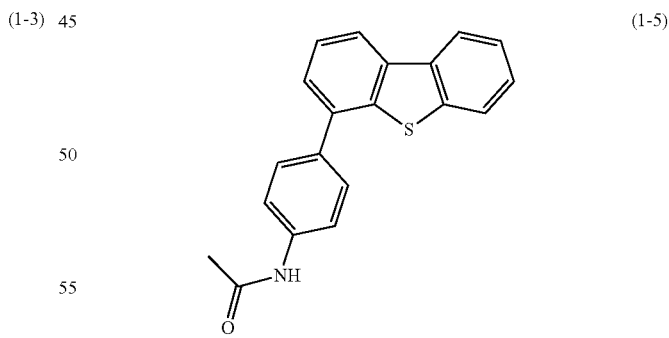

(1-5)

Intermediate Synthesis 1-6 (Synthesis of Intermediate (1-6))

A mixture of 18.0 g (56.1 mmol) of the intermediate (1-5) in 120 ml of xylene, 1200 ml of water, and 60 ml of ethanol was stirred. After further adding 20.0 g (360.0 mmol) of potassium hydroxide, the resultant mixture was refluxed for 10 h under heating and stirring.

After the reaction, the reaction mixture was cooled to room temperature and extracted with toluene in a separating funnel. The organic layer was dried over MgSO₄, filtered, and concentrated. The obtained residue was recrystallized from xylene, and the precipitated crystal was collected by filtration and dried to obtain 14.7 g of a white crystal (yield: 95%), which was identified by FD-MS analysis as the following intermediate (1-6).

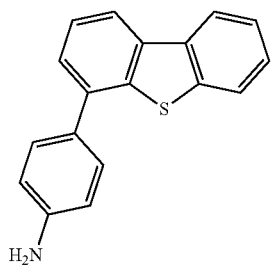

(1-6)

Intermediate Synthesis 1-7 (Synthesis of Intermediate (1-7))

Under an argon atmosphere, into a mixture of 47.0 g (201.6 mmol) of 4-bromobiphenyl, 23 g (90.6 mmol) of iodine, and 9.4 g (41.2 mmol) of periodic acid dihydrate, 42 ml of water, 360 ml of acetic acid, and 11 ml of sulfuric acid were added, and the resultant mixture was stirred at 65° C. for 30 min and further stirred at 90° C. for 6 h.

After the reaction, the reaction mixture was poured into an iced water and filtered. The collected solid was washed with water and then methanol to obtain 67.0 g of a white solid (yield: 93%), which was identified by FD-MS analysis as the following intermediate (1-7).

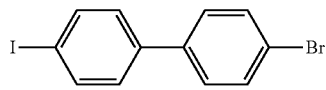

(1-7)

Intermediate Synthesis 1-8 (Synthesis of Intermediate (1-8))

Under an argon atmosphere, into a mixture of 35.9 g (100.0 mmol) of the intermediate (1-7), 16.7 g (100.0 mmol) of carbazole, 0.2 g (1.00 mmol) of copper iodide (CuI), and 42.4 g (210.0 mmol) of tripotassium phosphate, 2 ml of trans-1,2-cyclohexane diamine and 300 ml of 1,4-dioxane were added, and the resultant mixture was stirred at 100° C. for 20 h.

After the reaction, the reaction mixture was liquid-liquid separated after adding 300 ml of water, and the aqueous layer was removed. The organic layer was dried over sodium sulfate and concentrated. The obtained residue was purified by silica gel column chromatography to obtain 23.1 g of a white solid (yield: 58%), which was identified by FD-MS analysis as the following intermediate (1-8).

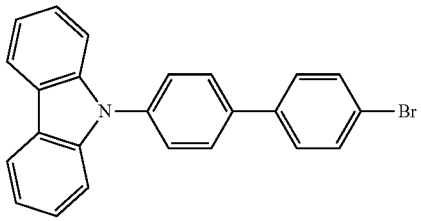

(1-8)

Intermediate Synthesis (1-9) (Synthesis of Intermediate (1-9))

Under an argon atmosphere, into a mixture of 28.3 g (100.0 mmol) of 4-iodobromobenzene, 22.3 g (105.0 mmol) of dibenzofuran-2-boronic acid, and 2.31 g (2.00 mmol) of Pd[PPh₃]₄, 150 ml of toluene, 150 ml of dimethoxyethane, and 150 ml (300.0 mmol) of a 2 M aqueous solution of Na₂CO₃ were added, and the resultant mixture was refluxed for 10 h under heating and stirring.

After the reaction, the reaction mixture was cooled to room temperature and extracted with dichloromethane in a separating funnel. The organic layer was dried over MgSO₄, filtered, and concentrated. The residual concentrate was purified by column chromatography to obtain 27.4 g of a white solid (yield: 85%), which was identified by FD-MS analysis as the following intermediate (1-9).

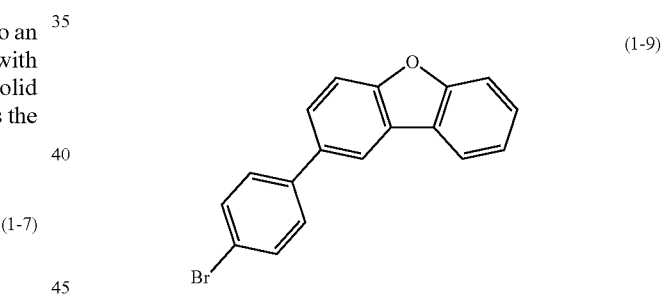

(1-9)

Intermediate Synthesis 1-10 (Synthesis of Intermediate (1-10))

Under an argon atmosphere, into a mixture of 28.3 g (100.0 mmol) of 4-iodobromobenzene, 30.1 g (105.0 mmol) of 3-(911-carbazole-9-yl)phenylboronic acid, and 2.31 g (2.00 mmol) of Pd[PPh₃]₄, 150 ml of toluene, 150 ml of dimethoxyethane, and 150 ml (300.0 mmol) of a 2 M aqueous solution of Na₂CO₃ were added, and the resultant mixture was refluxed for 10 h under heating and stirring.

After the reaction, the reaction mixture was cooled to room temperature and extracted with dichloromethane in a separating funnel. The organic layer was dried over MgSO₄, filtered, and concentrated. The residual concentrate was purified by column chromatography to obtain 27.2 g of a white solid (yield: 68%), which was identified by FD-MS analysis as the following intermediate (1-10).

(1-10)

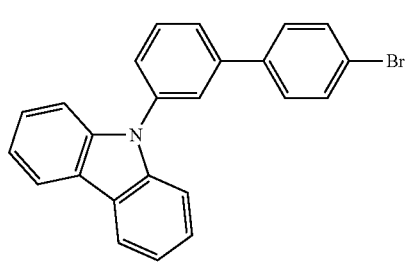

Intermediate Synthesis 1-11 (Synthesis of Intermediate (1-11))

Under an argon atmosphere, into a mixture of 39.7 g (100.0 mmol) of 9-(4-bromophenyl)-9-phenylfluorene, 16.4 g (105.0 mmol) of 4-chlorophenylboronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was refluxed for 10 h under heating and stirring.

After the reaction, the reaction mixture was cooled to room temperature and extracted with dichloromethane in a separating funnel. The organic layer was dried over MgSO$_4$, filtered, and concentrated. The residual concentrate was purified by column chromatography to obtain 30.0 g of a white solid (yield: 70%), which was identified by FD-MS analysis as the following intermediate (1-11).

(1-11)

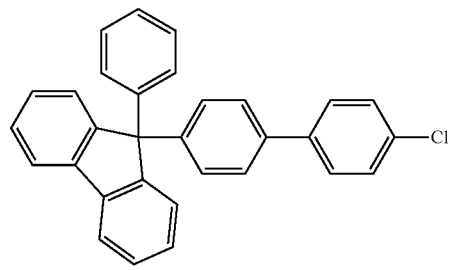

Intermediate Synthesis 2-1 (Synthesis of Intermediate (2-1))

Under an argon atmosphere, into a mixture of 19.9 g (50.0 mmol) of 9-(4-bromophenyl)-9-phenylfluorene, 13.0 g (50.0 mmol) of the intermediate (1-3), and 9.6 g (100.0 mmol) of sodium t-butoxide, 250 ml of dehydrated toluene was added, and the resultant mixture was stirred. After further adding 225 mg (1.0 mmol) of palladium acetate and 202 mg (1.0 mmol) of tri-t-butylphosphine, the mixture was allowed to react at 80° C. for 8 h.

After cooling, the reaction mixture was filtered through celite/silica gel, and the filtrate was concentrated under reduced pressure. The obtained residue was recrystallized from toluene, and the precipitated crystal was collected by filtration and dried to obtain 23.0 g of a white crystal (yield: 80%), which was identified by FD-MS analysis as the following intermediate (2-1).

(2-1)

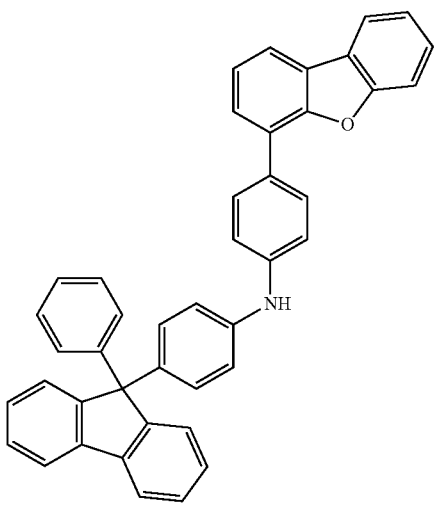

Intermediate Synthesis 2-2 (Synthesis of Intermediate (2-2))

In the same manner as in Intermediate Synthesis 2-1 except for using 16.7 g of 2-amino-9,9'-diphenylfluorene in place of the intermediate (1-3), 25.3 g of a white crystal was obtained (yield: 78%), which was identified by FD-MS analysis as the following intermediate (2-2).

(2-2)

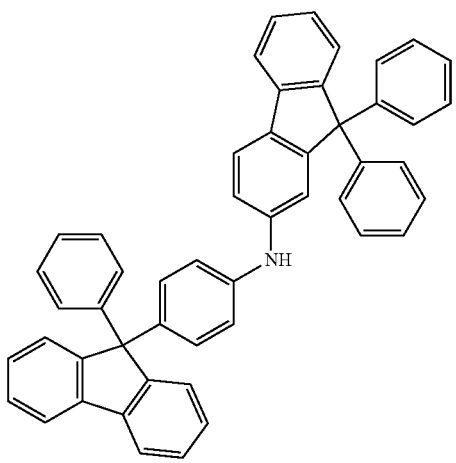

Intermediate Synthesis 2-3 (Synthesis of Intermediate (2-3))

In the same manner as in Intermediate Synthesis 2-1 except for using 13.8 g of the intermediate (1-6) in place of the intermediate (1-3), 23.7 g of a white crystal was obtained (yield: 80%), which was identified by FD-MS analysis as the following intermediate (2-3).

(2-3)

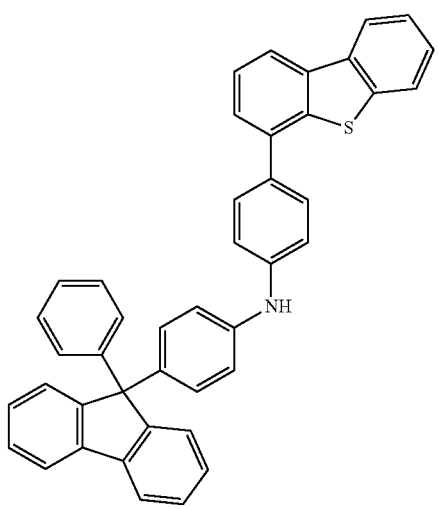

Intermediate Synthesis 2-4 (Synthesis of Intermediate (2-4))

In the same manner as in Intermediate Synthesis 2-1 except for using 24.5 g of 4-aminoterphenyl in place of the intermediate (1-3), 22.5 g of a white crystal was obtained (yield: 80%), which was identified by FD-MS analysis as the following intermediate (2-4).

(2-4)

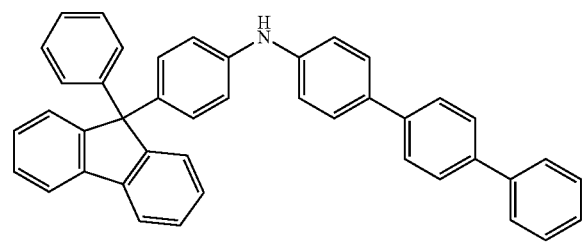

Intermediate Synthesis 2-5 (Synthesis of Intermediate (2-5))

Under an argon atmosphere, into a mixture of 11.4 g (54.0 mmol) of 4-biphenylacetamide, 25.8 g (65.0 mmol) of 9-(4-bromophenyl)-9-phenylfluorene, 4.1 g (21.6 mmol) of CuI, 0.95 g (10.8 mmol) of N,N-dimethylethylenediamine, and 24.0 g (114.0 mmol) of $K_3PO_4$, 300 ml of xylene was added, and the resultant mixture was refluxed for 10 h under heating and stirring.

After the reaction, the reaction mixture was filtered through celite/silica gel, and the filtrate was concentrated under reduced pressure. The residual concentrate was purified by column chromatography and recrystallized from toluene to obtain 15.1 g of a white crystal (yield: 53%), which was identified by FD-MS analysis as the following intermediate (2-5).

(2-5)

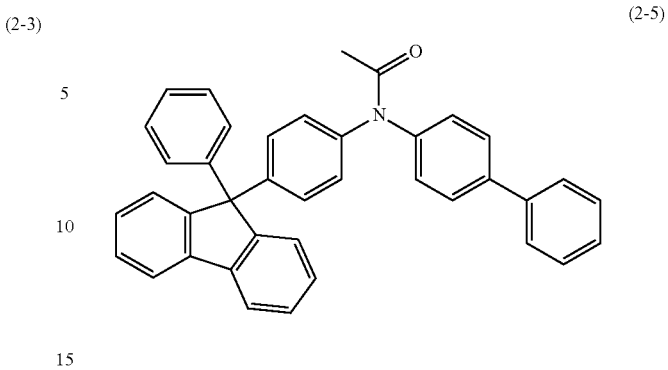

Intermediate Synthesis 2-6 (Synthesis of Intermediate (2-6))

Into a mixture of 30.1 g (57.0 mmol) of the intermediate (2-5) and 20.0 g (352.0 mmol) of potassium hydroxide, 1140 ml of water, 57 ml of ethanol, and 114 ml of xylene were added, and the resultant mixture was refluxed for 10 h under heating and stirring.

After the reaction, the reaction mixture was cooled to room temperature and the precipitated crystal was collected by filtration. The collected crystal was washed with water and then methanol. The filtrate was extracted with toluene in a separating funnel, and the organic layer was dried over $MgSO_4$, filtered, and concentrated. The obtained residue together with the collected crystal was recrystallized from xylene. The precipitated crystal was collected by filtration and dried to obtain 24.9 g of a white crystal (yield: 90%), which was identified by FD-MS analysis as the following intermediate (2-6).

(2-6)

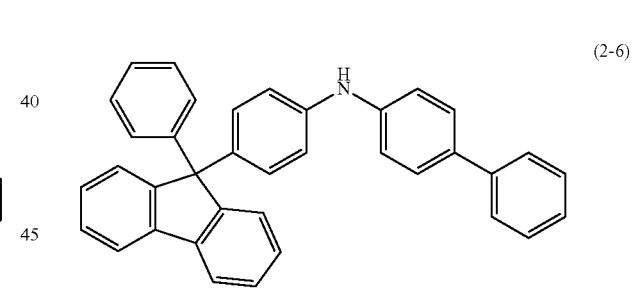

Intermediate Synthesis 2-7 (Synthesis of Intermediate (2-7))

Under an argon atmosphere, into a mixture of 21.4 g (50.0 mmol) of the intermediate (1-11), 16.7 g (50.0 mmol) of 2-amino-9,9'-diphenylfluorene, and 9.6 g (100.0 mmol) of sodium t-butoxide, 250 ml of dehydrated toluene was added, and the resultant mixture was stirred. After further adding 225 mg (1.0 mmol) of palladium acetate and 202 mg (1.0 mmol) of tri-t-butylphosphine, the mixture was allowed to react at 80° C. for 8 h.

After cooling, the reaction mixture was filtered through celite/silica gel, and the filtrate was concentrated under reduced pressure. The obtained residue was recrystallized from toluene, and the precipitated crystal was collected by filtration and dried to obtain 26.1 g of a white crystal (yield: 72%), which was identified by FD-MS analysis as the following intermediate (2-7).

(2-7)

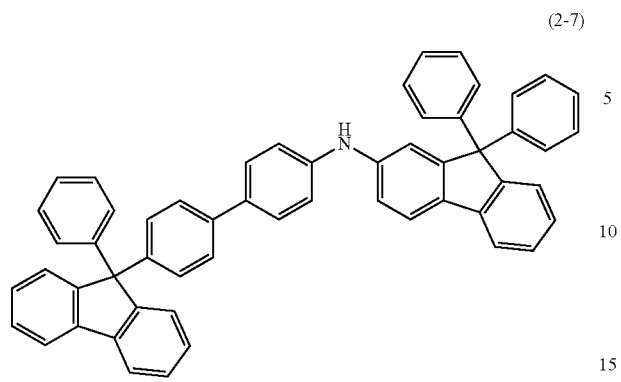

Synthesis Example 1 (Synthesis of Compound (H1))

Under an argon atmosphere, into a mixture of 3.2 g (10.0 mmol) of the intermediate (1-1), 5.8 g (10.0 mmol) of the intermediate (2-1), 0.14 g (0.15 mmol) of $Pd_2(dba)_3$, 0.087 g (0.3 mmol) of $P(tBu)_3HBF_4$, and 1.9 g (20.0 mmol) of sodium t-butoxide, 50 ml of dehydrated xylene was added, and the resultant mixture was refluxed for 8 h under heating.

After the reaction, the reaction mixture was cooled to 50° C. and filtered through celite/silica gel. The filtrate was concentrated, and the residual concentrate was purified by column chromatography and recrystallized from toluene to obtain 3.7 g of a white crystal (yield: 45%), which was identified by FD-MS analysis as the following compound (H1).

(H1)

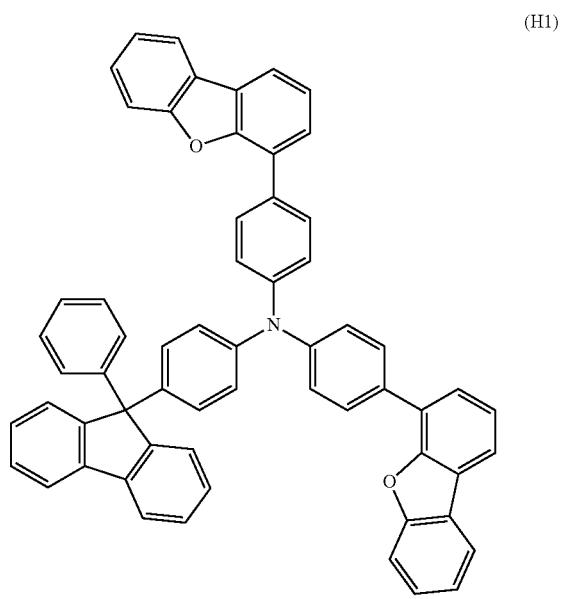 [SMILES: c1ccc(C2(c3ccc(N(c4ccc(-c5cccc6c5oc5ccccc56)cc4)c4ccc(-c5cccc6c5oc5ccccc56)cc4)cc3)c3ccccc3-c3ccccc32)cc1]

Synthesis Example 2 (Synthesis of Compound (H2))

In the same manner as in Synthesis Example 1 except for using 2.3 g (10.0 mmol) of 4-bromobiphenyl in place of the intermediate (1-1), 4.0 g of a white crystal was obtained (yield: 55%), which was identified by FD-MS analysis as the following compound (H2).

(H2)

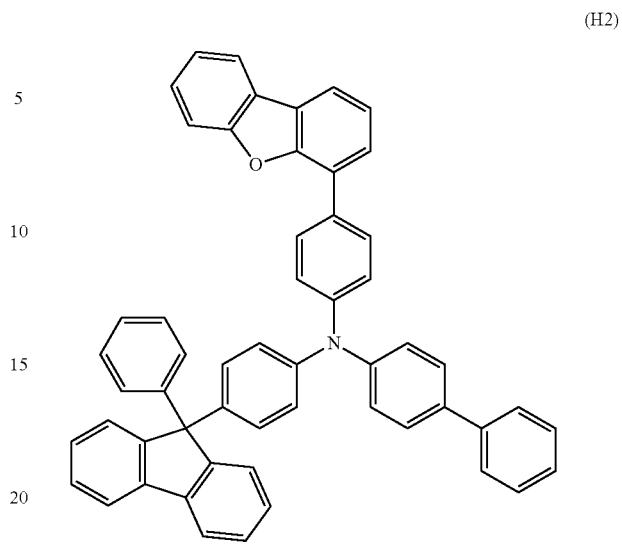

Synthesis Example 3 (Synthesis of Compound (H3))

Under an argon atmosphere, into a mixture of 2.3 g (10.0 mmol) of 4-bromobiphenyl, 6.5 g (10.0 mmol) of the intermediate (2-2), 0.14 g (0.15 mmol) of $Pd_2(dba)_3$, 0.087 g (0.3 mmol) of $P(tBu)_3HBF_4$, and 1.9 g (20.0 mmol) of sodium t-butoxide, 50 ml of dehydrated xylene was added, and the resultant mixture was refluxed for 8 h under heating.

After the reaction, the reaction mixture was cooled to 50° C. and filtered through celite/silica gel. The filtrate was concentrated, and the residual concentrate was purified by column chromatography and recrystallized from toluene to obtain 4.4 g of a white crystal (yield: 55%), which was identified by FD-MS analysis as the following compound (H3).

(H3)

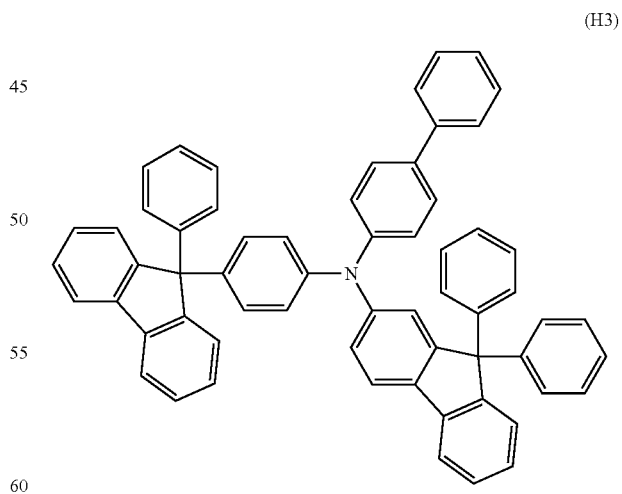

Synthesis Example 4 (Synthesis of Compound (H4))

In the same manner as in Synthesis Example 3 except for using 2.3 g (10.0 mmol) of 2-bromobiphenyl in place of 4-bromobiphenyl, 3.2 g of a white crystal was obtained (yield: 40%), which was identified by FD-MS analysis as the following compound (H4).

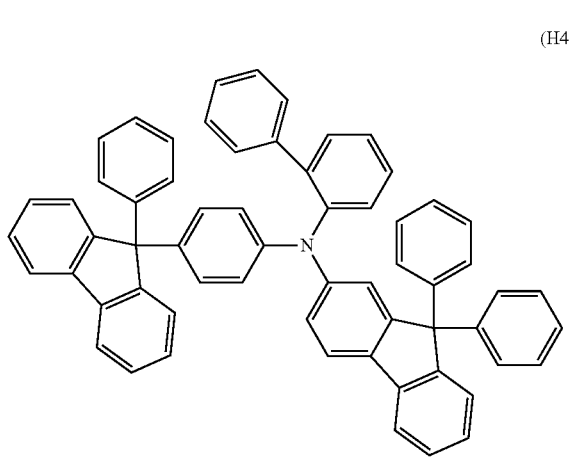 [SMILES: c1ccc(-c2ccccc2N(c2ccc(C3(c4ccccc4)c4ccccc4-c4ccccc43)cc2)c2ccc3c(c2)C(c2ccccc2)(c2ccccc2)c2ccccc2-3)cc1]

(H4)

Synthesis Example 5 (Synthesis of Compound (H5))

In the same manner as in Synthesis Example 3 except for using 4.0 g (10.0 mmol) of 2-bromo-9,9'-diphenylfluorene in place of 4-bromobiphenyl, 4.4 g of a white crystal was obtained (yield: 46%), which was identified by FD-MS analysis as the following compound (H5).

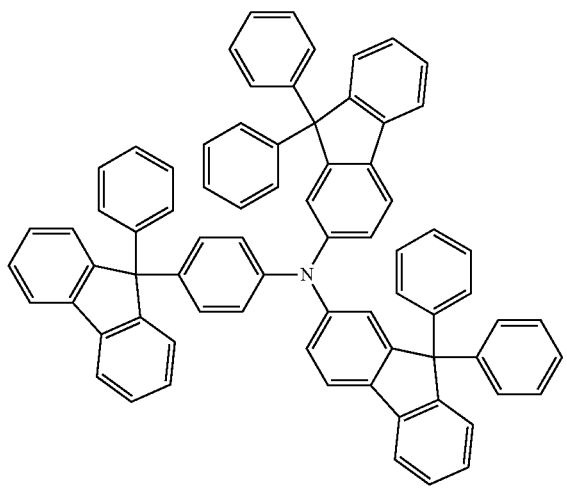

(H5)

Synthesis Example 6 (Synthesis of Compound (H6))

In the same manner as in Synthesis Example 1 except for using 3.4 g (10.0 mmol) of the intermediate (1-4) in place of the intermediate (1-1) and using 5.9 g (10.0 mmol) of the intermediate (2-3) in place of the intermediate (2-1), 4.7 g of a white crystal was obtained (yield: 55%), which was identified by FD-MS analysis as the following compound (H6).

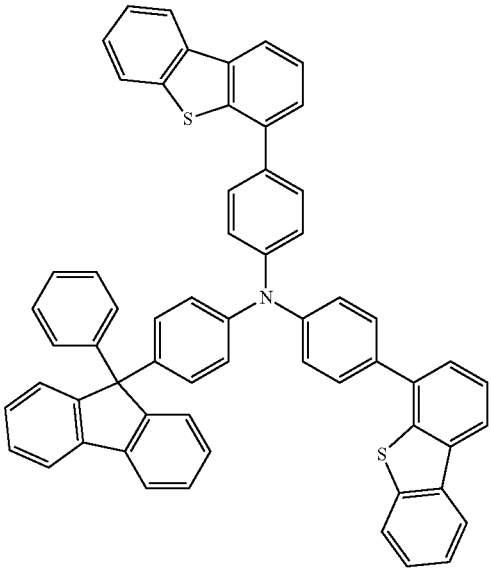

(H6)

Synthesis Example 7 (Synthesis of Compound (H7))

In the same manner as in Synthesis Example 1 except for using 4.0 g (10.0 mmol) of the intermediate (1-8) in place of the intermediate (1-1), 4.3 g of a white crystal was obtained (yield: 50%), which was identified by FD-MS analysis as the following compound (H7).

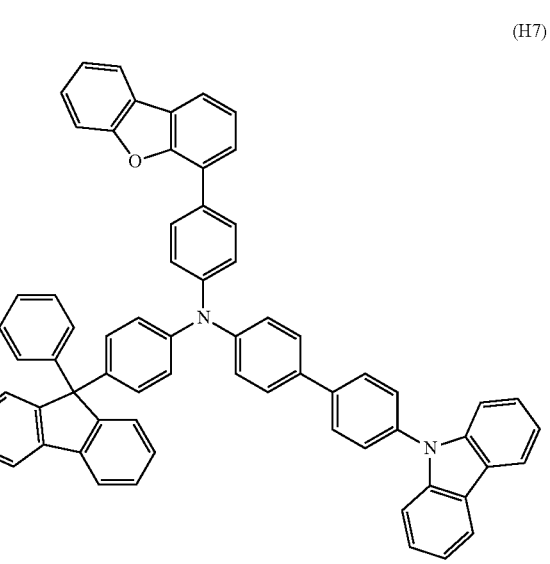

(H7)

Synthesis Example 8 (Synthesis of Compound (H8))

In the same manner as in Synthesis Example 3 except for using 2.7 g (10.0 mmol) of 2-bromo-9,9'-dimethylfluorene in place of 4-bromobiphenyl, 3.2 g of a white crystal was obtained (yield: 38%), which was identified by FD-MS analysis as the following compound (H8).

(H8)

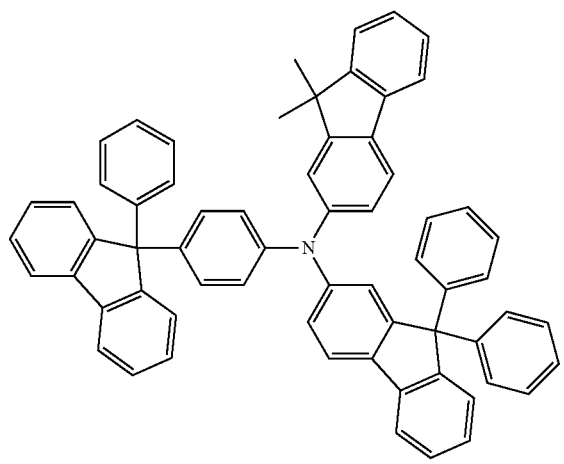

Synthesis Example 9 (Synthesis of Compound (119))

In the same manner as in Synthesis Example 3 except for using 3.1 g (10.0 mmol) of 4-bromoterphenyl in place of 4-bromobiphenyl, 3.5 g of a white crystal was obtained (yield: 40%), which was identified by FD-MS analysis as the following compound (H9).

(H9)

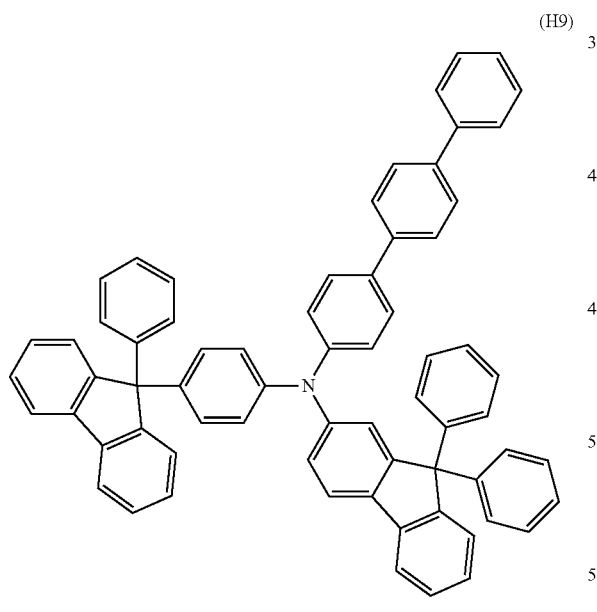

Synthesis Example 10 (Synthesis of Compound (1110))

In the same manner as in Synthesis Example 1 except for using 3.1 g (10.0 mmol) of 4-bromoterphenyl in place of the intermediate (1-1), 3.2 g of a white crystal was obtained (yield: 40%), which was identified by FD-MS analysis as the following compound (H10).

(H10)

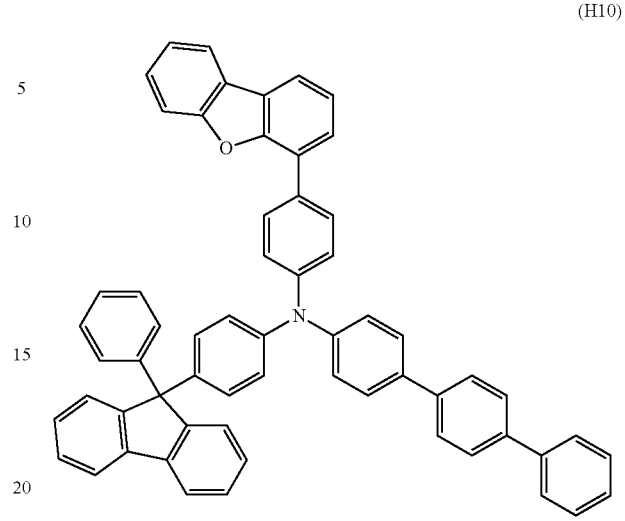

Synthesis Example 11 (Synthesis of Compound (H11))

In the same manner as in Synthesis Example 1 except for using 3.2 g (10.0 mmol) of the intermediate (1-9) in place of the intermediate (1-1) and using 4.9 g (10.0 mmol) of the intermediate (2-6) in place of the intermediate (2-1), 2.5 g of a white crystal was obtained (yield: 35%), which was identified by FD-MS analysis as the following compound (H11).

(H11)

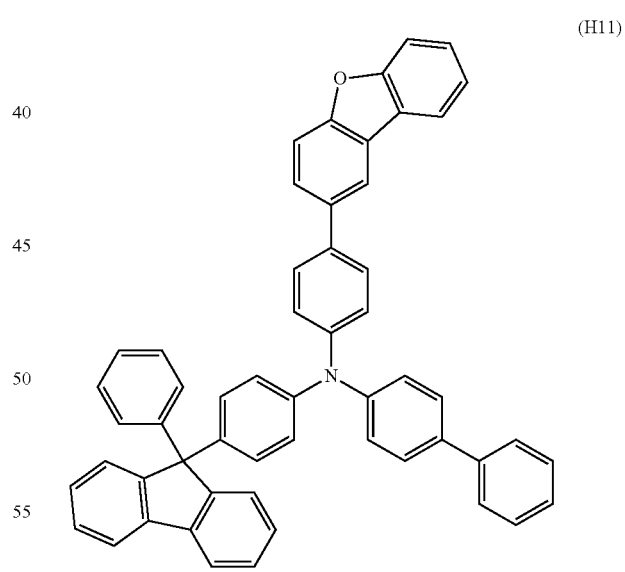

Synthesis Example 12 (Synthesis of Compound (H12))

In the same manner as in Synthesis Example 1 except for using 3.2 g (10.0 mmol) of the intermediate (1-9) in place of the intermediate (1-1) and using 5.6 g (10.0 mmol) of the intermediate (2-4) in place of the intermediate (2-1), 3.5 g of a white crystal was obtained (yield: 43%), which was identified by FD-MS analysis as the following compound (H12).

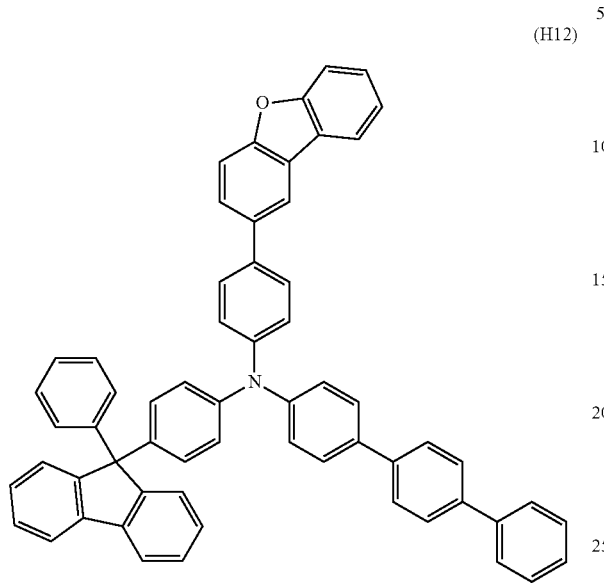

(H12)

Synthesis Example 13 (Synthesis of Compound (H13))

In the same manner as in Synthesis Example 1 except for using 4.0 g (10.0 mmol) of the intermediate (1-8) in place of the intermediate (1-1) and using 4.9 g (10.0 mmol) of the intermediate (2-6) in place of the intermediate (2-1), 3.5 g of a white crystal was obtained (yield: 43%), which was identified by FD-MS analysis as the following compound (H13).

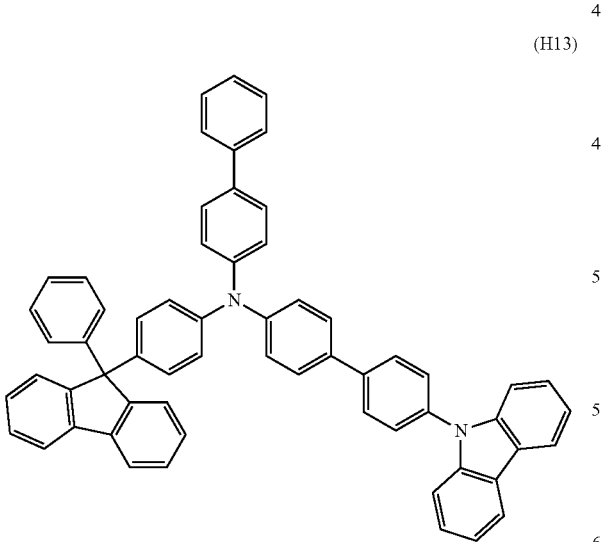

(H13)

Synthesis Example 14 (Synthesis of Compound (H14))

In the same manner as in Synthesis Example 3 except for using 4.0 g (10.0 mmol) of the intermediate (1-8) in place of 4-bromobiphenyl, 3.8 g of a white crystal was obtained (yield: 39%), which was identified by FD-MS analysis as the following compound (H14).

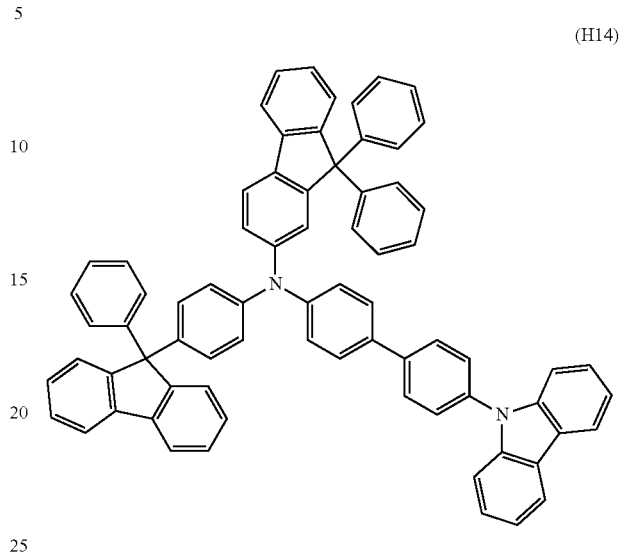

(H14)

Synthesis Example 15 (Synthesis of Compound (H15))

In the same manner as in Synthesis Example 1 except for using 4.0 g (10.0 mmol) of the intermediate (1-10) in place of the intermediate (1-1) and using 4.9 g (10.0 mmol) of the intermediate (2-6) in place of the intermediate (2-1), 2.4 g of a white crystal was obtained (yield: 30%), which was identified by FD-MS analysis as the following compound (H15).

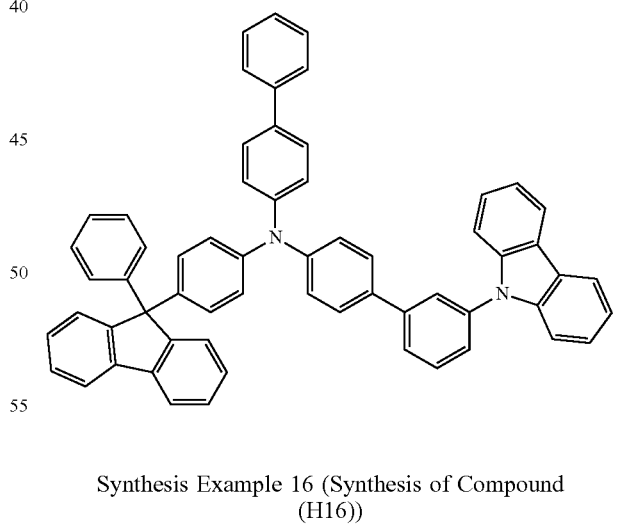

(H15)

Synthesis Example 16 (Synthesis of Compound (H16))

In the same manner as in Synthesis Example 1 except for using 2.3 g (10.0 mmol) of 4-bromobiphenyl in place of the intermediate (1-1) and using 7.3 g (10.0 mmol) of the intermediate (2-7) in place of the intermediate (2-1), 2.9 g of a white crystal was obtained (yield: 33%), which was identified by FD-MS analysis as the following compound (H16).

(H16)

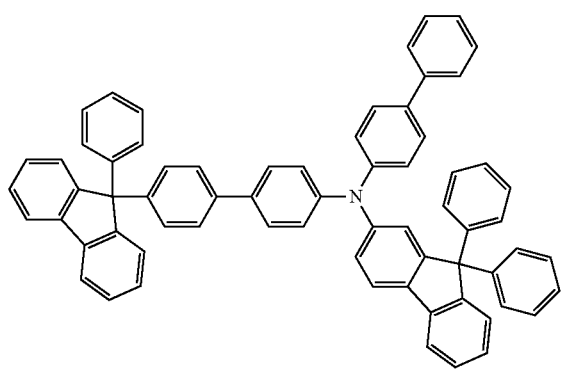

Synthesis Example 17 (Synthesis of Compound (H17))

In the same manner as in Synthesis Example 1 except for using 2.3 g (10.0 mmol) of 2-bromobiphenyl in place of the intermediate (1-1) and using 7.3 g (10.0 mmol) of the intermediate (2-7) in place of the intermediate (2-1), 2.6 g of a white crystal was obtained (yield: 30%), which was identified by FD-MS analysis as the following compound (H17).

(H17)

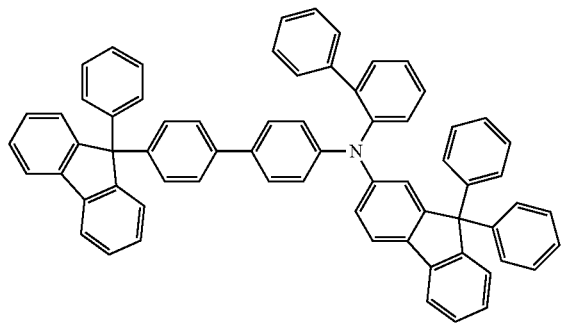

Production of Organic EL Device Using Compound (1)

Examples 1-1 to 1-17 (Production of Organic EL Device)

A glass substrate of 25 mm×75 mm×1.1 mm having an ITO transparent electrode (product of Geomatec Company) was cleaned by ultrasonic cleaning in isopropyl alcohol for 5 min and then UV (ultraviolet) ozone cleaning for 30 rain.

The cleaned glass substrate having a transparent electrode line was mounted to a substrate holder of a vacuum vapor deposition apparatus. First, the following electron-accepting compound (EA1) was vapor-deposited so as to cover the transparent electrode to form a film (EA1) with a thickness of 10 nm.

On the film (EA1), the following aromatic amine derivative (X1) as a first hole transporting material was vapor-deposited to form a first hole transporting layer with a thickness of 80 nm. Successively after forming the first hole transporting layer, each of the compounds (H1) to (H17) obtained in Synthesis Examples 1 to 17 as a second hole transporting material was vapor-deposited to form a second hole transporting layer with a thickness of 10 nm.

On the second hole transporting layer, the following host compound (BH) and dopant compound (BD) as fluorescent emitting materials were vapor co-deposited to form a light emitting layer with a thickness of 25 nm. The concentration of the dopant compound (BD) in the light emitting layer was 4% by mass.

Thereafter, on the light emitting layer, the following compound (ET1), compound (ET2), and LiF were vapor co-deposited into a thickness of 25 nm, 10 nm, and 1 nm, respectively to form an electron transporting/injecting layer.

Further, metallic Al was deposited into a thickness of 80 nm to form a cathode, thereby producing an organic EL device.

(EA1)

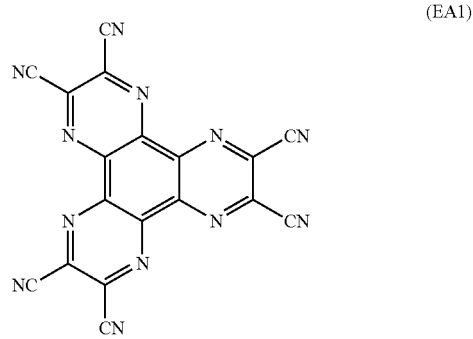

(X1)

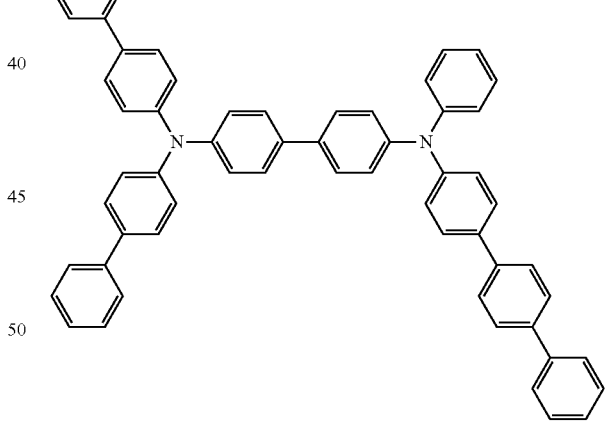

(BH)

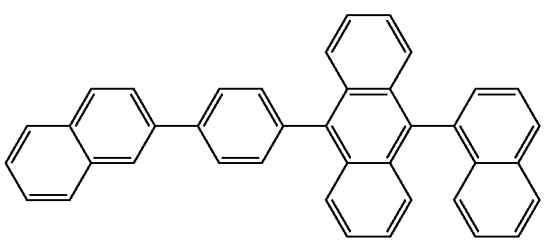

(BD)
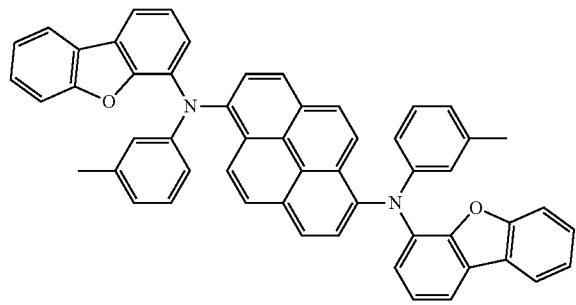
(H1)
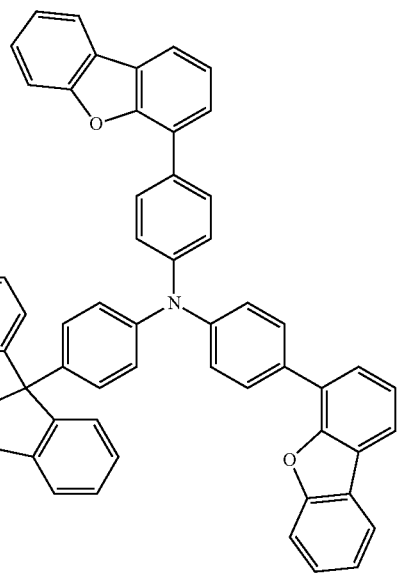
(ET1)
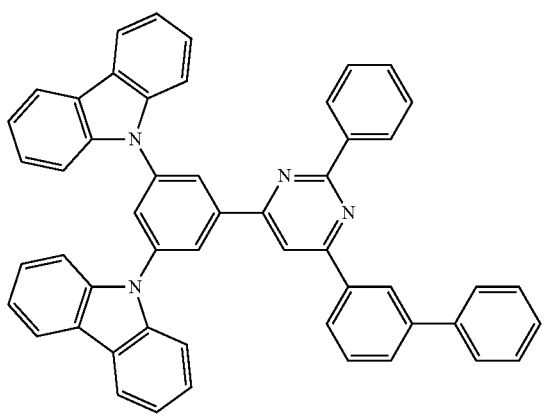
(H2)
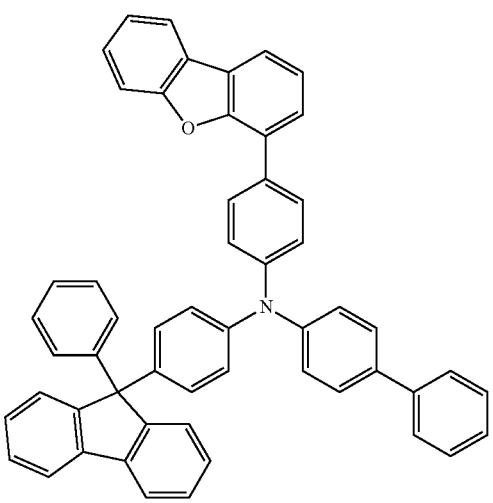
(ET2)
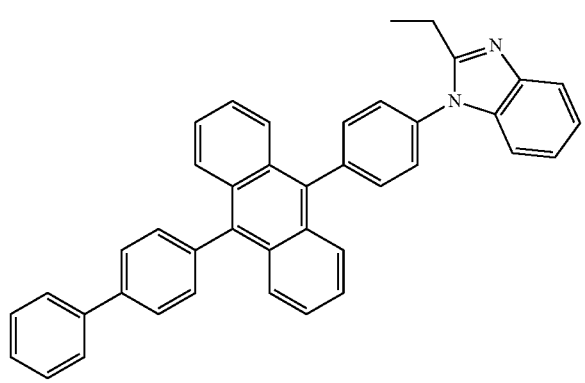
(H3)
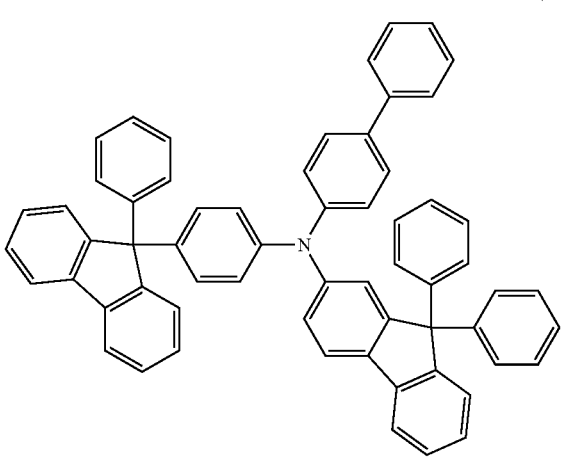
The compounds (H1) to (H17) obtained in Synthesis Examples 1 to 17 which were used as the second hole transporting materials are shown below.

(H4)
(H5)
(H6)
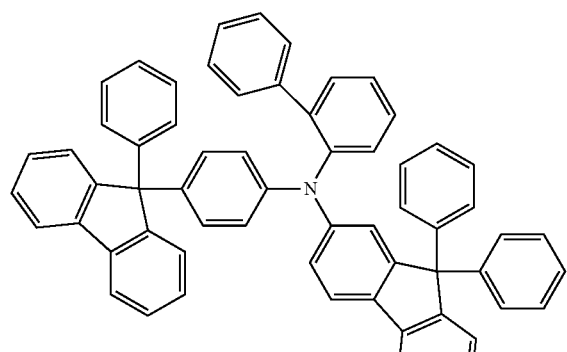
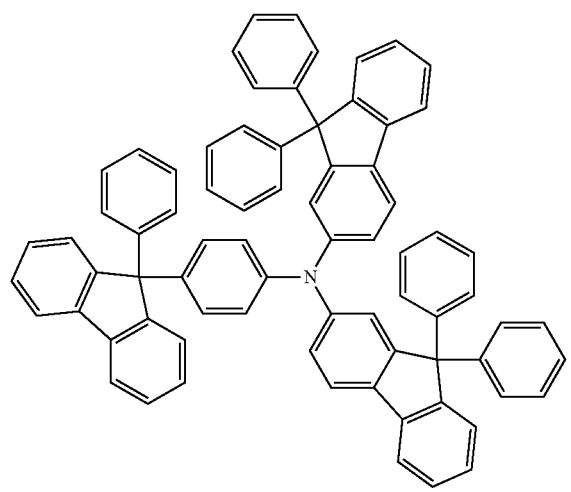
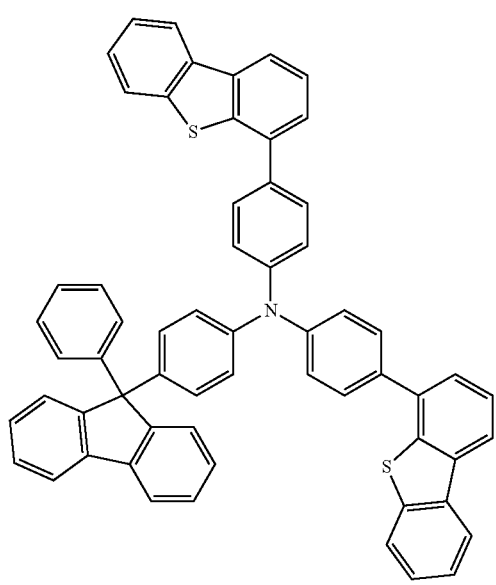
(H7)
(H8)
(H9)
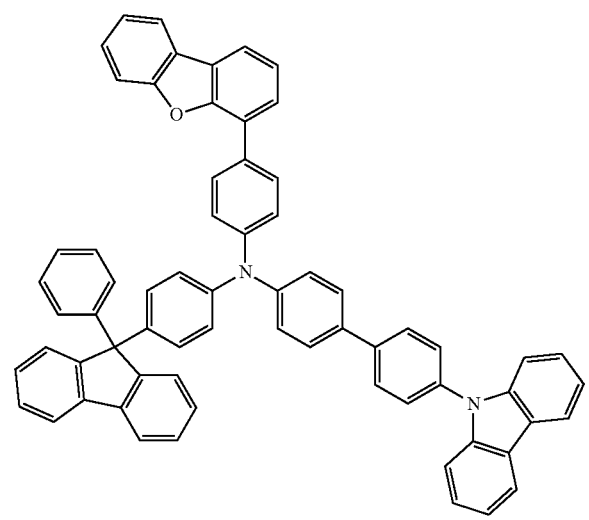

(H10)
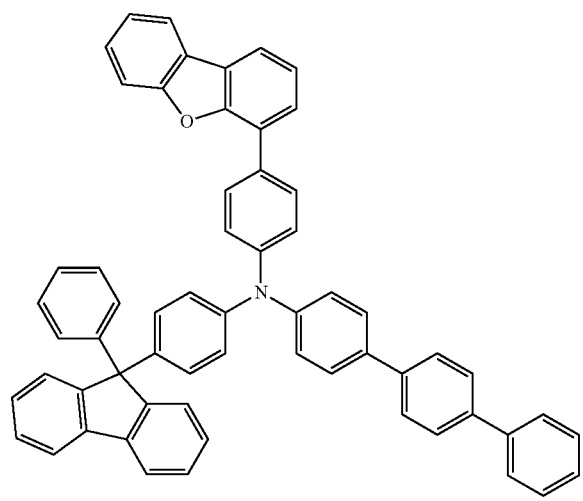
(H11)
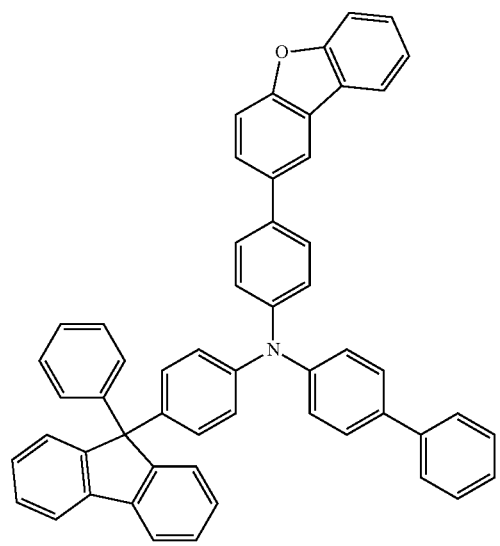
(H12)
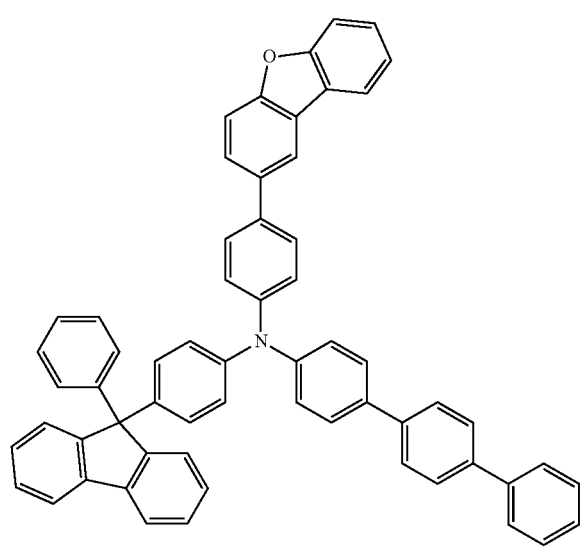
(H13)
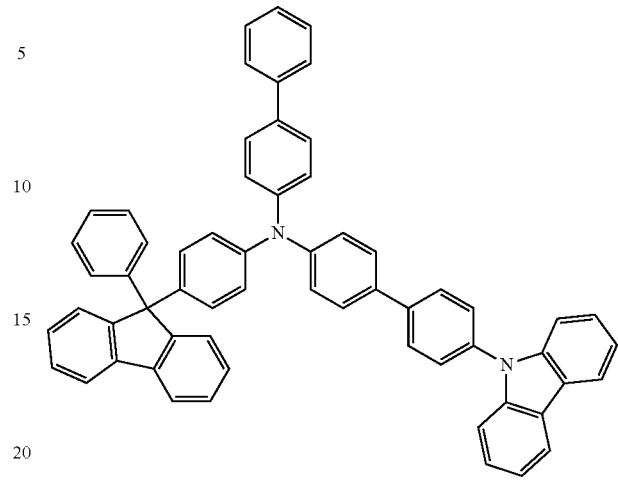
(H14)
(H15)
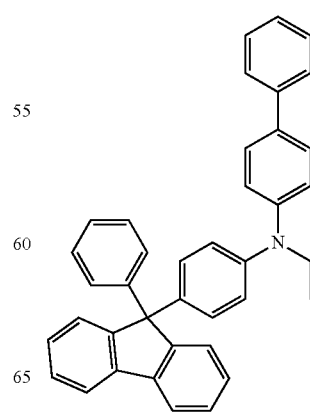

(H16)
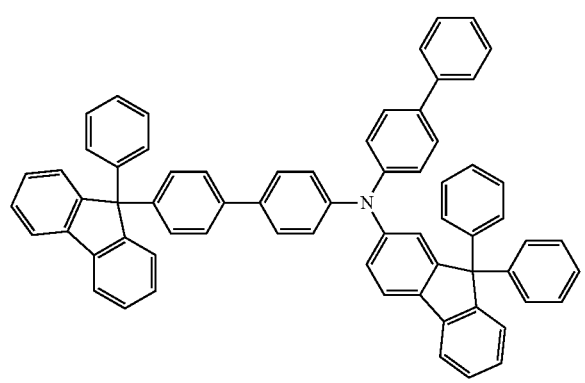

(H17)
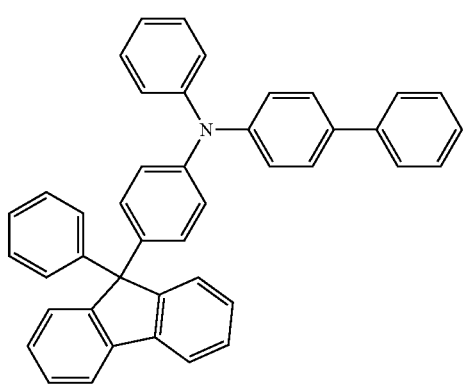

Comparative Examples 1-1 to 1-4

Each organic EL device of Comparative Examples 1 to 4 was produced in the same manner as in Example 1 except for forming the second hole transporting layer by using each of the following comparative compounds (a1) to (a4) as the second hole transporting material.

(a1)

(a2)
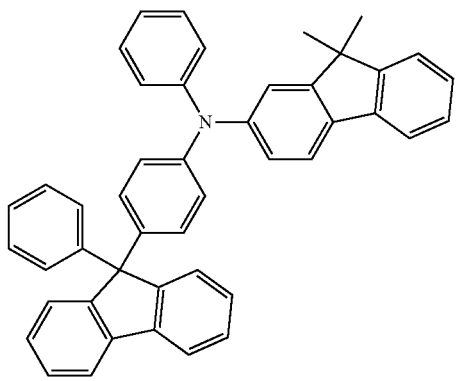

(a3)
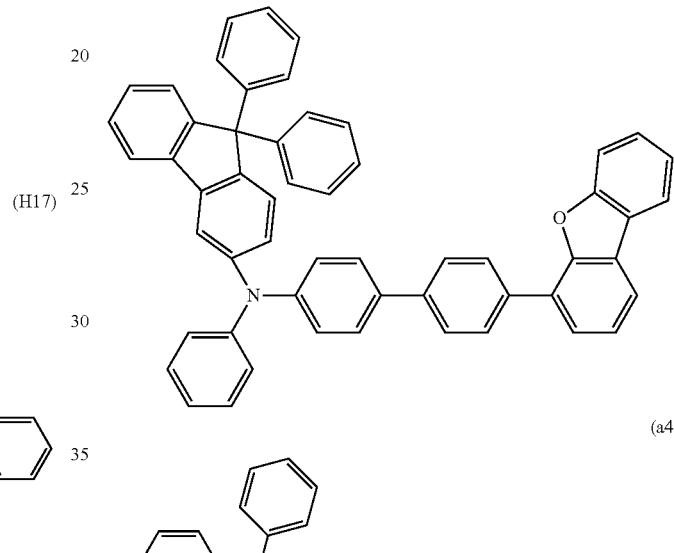

(a4)
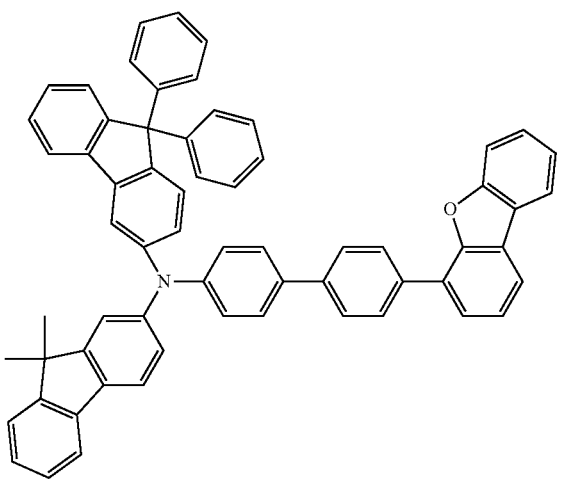

Evaluation of Emission Performance of Organic EL Device

Each organic EL device thus produced was allowed to emit light by driving at a constant current to measure the luminance (L) and a current density. From the measured results, the emission efficiency (cd/A) and the driving voltage (V) at a current density of 10 mA/cm² were determined. In addition, the 80% lifetime at a current density of 50 mA/cm² was determined. The 80% lifetime is the time taken until the luminance is reduced to 80% of the initial luminance when driving at a constant current. The results are shown in Table 1.

TABLE 1

| | First hole transporting material | Second hole transporting material | Emission efficiency (cd/A) @10 mA/cm² | Driving voltage (V) @10 mA/cm² | 80% lifetime (h) @50 mA/cm² |
|---|---|---|---|---|---|
| | | | Measured results | | |
| | | Examples | | | |
| 1-1 | X1 | H1 | 9.9 | 4.7 | 300 |
| 1-2 | X1 | H2 | 9.7 | 4.7 | 280 |
| 1-3 | X1 | H3 | 9.6 | 4.5 | 260 |
| 1-4 | X1 | H4 | 9.8 | 4.5 | 270 |
| 1-5 | X1 | H5 | 9.5 | 4.4 | 280 |
| 1-6 | X1 | H6 | 9.8 | 4.7 | 280 |
| 1-7 | X1 | H7 | 9.9 | 4.5 | 280 |
| 1-8 | X1 | H8 | 9.5 | 4.3 | 270 |
| 1-9 | X1 | H9 | 9.6 | 4.4 | 300 |
| 1-10 | X1 | H10 | 9.8 | 4.6 | 310 |
| 1-11 | X1 | H11 | 9.9 | 4.6 | 280 |
| 1-12 | X1 | H12 | 9.8 | 4.6 | 300 |
| 1-13 | X1 | H13 | 9.9 | 4.5 | 280 |
| 1-14 | X1 | H14 | 9.8 | 4.5 | 280 |
| 1-15 | X1 | H15 | 10.1 | 4.9 | 280 |
| 1-16 | X1 | H16 | 9.5 | 4.4 | 280 |
| 1-17 | X1 | H17 | 9.7 | 4.4 | 270 |
| | | Comparative Examples | | | |
| 1-1 | X1 | a1 | 9.9 | 4.9 | 60 |
| 1-2 | X1 | a2 | 9.6 | 4.5 | 80 |
| 1-3 | X1 | a3 | 8.2 | 4.5 | 220 |
| 1-4 | X1 | a4 | 7.8 | 4.3 | 250 |

As seen from Table 1, it can be found that an organic EL device capable of driving at low voltage and having high emission efficiency and long lifetime is obtained by using each of the compounds (H1) to (H17) within the compound (1) in an aspect of the invention as the second hole transporting material.

Examples 2-1 to 2-4 (Production of Organic EL Device)

Each organic EL device of Examples 2-1 to 2-4 was produced in the same manner as in Example 1-1 except for forming a film (EA2) with a thickness of 10 nm by vapor-depositing the following electron-accepting compound (EA2) so as to cover the transparent electrode; forming the first hole transporting layer with a thickness of 80 nm on the film (EA1) by using each of the compounds (H3), (H4), (H5), and (H8) obtained in Synthesis Examples 3, 4, 5, and 8 as the first hole transporting material; and forming the second hole transporting layer with a thickness of 10 nm on the first hole transporting layer by using the following aromatic amine derivative (Y1) as the second hole transporting material.

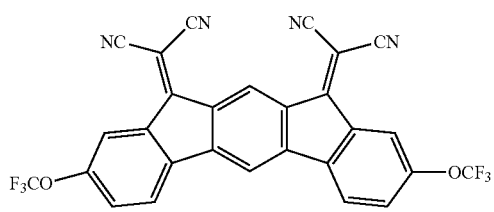

(EA2)

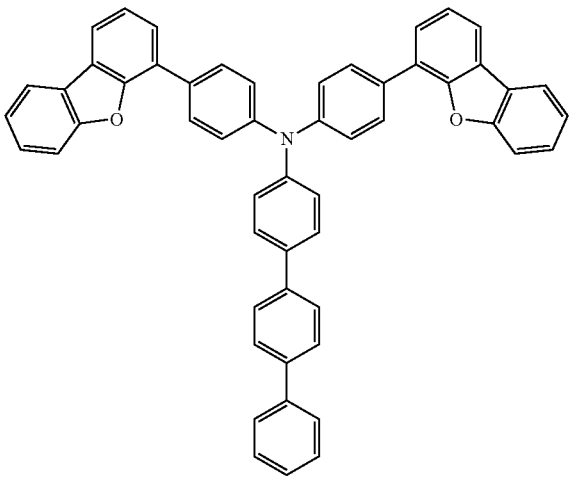

(Y1)

Comparative Examples 2-1 to 2-2 (Production of Organic EL Device)

Each organic EL device of Comparative Examples 2-1 to 2-2 was produced in the same manner as in Example 2-1 except for forming the first hole transporting layer by using the above comparative compound (a1) or (a2) as the first hole transporting material.

Evaluation of Emission Performance of Organic EL Device

Each organic EL device thus produced was allowed to emit light by driving at a constant current to measure the luminance (L) and a current density. From the measured results, the current efficiency (L/J) and the driving voltage (V) at a current density of 10 mA/cm² were determined. In addition, the 80% lifetime at a current density of 50 mA/cm² was determined. The 80% lifetime is the time taken until the luminance is reduced to 80% of the initial luminance when driving at a constant current. The results are shown in Table 2.

TABLE 2

| | First hole transporting material | Second hole transporting material | Emission efficiency (cd/A) @10 mA/cm² | Driving voltage (V) @10 mA/cm² | 80% lifetime (h) @50 mA/cm² |
|---|---|---|---|---|---|
| | | | Measured results | | |
| | | Examples | | | |
| 2-1 | H3 | Y1 | 9.5 | 4.5 | 350 |
| 2-2 | H4 | Y1 | 9.6 | 4.5 | 450 |
| 2-3 | H5 | Y1 | 9.6 | 4.6 | 420 |
| 2-4 | H8 | Y1 | 9.5 | 4.6 | 380 |
| | | Comparative Examples | | | |
| 2-1 | a1 | Y1 | 8.2 | 5.6 | 120 |
| 2-2 | a2 | Y1 | 9.5 | 4.5 | 250 |

As seen from Table 2, it can be found that an organic EL device capable of driving at low voltage and having high emission efficiency and long lifetime is obtained by using each of the compounds (H3), (1-14), (H5), and (118) within the compound (1) in an aspect of the invention as the first hole transporting material.

REFERENCE SIGNS LIST

1: Organic EL device
2: Substrate
3: Anode
4: Cathode
5: Light emitting layer
6: Anode-side organic thin film layer
7: Cathode-side organic thin film layer
10: Emission unit

What is claimed is:
1. A compound represented by formula (1):

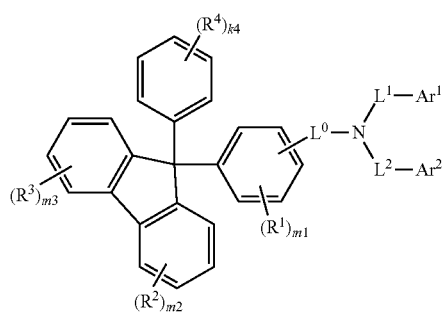

(1)

wherein
$R^1$ and $R^4$ each independently represent a substituted or unsubstituted alkyl group having 1 to 20 carbon atoms, a substituted or unsubstituted aryl group having 6 to 50 ring carbon atoms, a substituted or unsubstituted heteroaryl group having 5 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group, and when $R^1$ and $R^4$ are each plural in number, groups $R^1$ and groups $R^4$ may be the same or different, respectively;

$R^2$ and $R^3$ are each independently represent a substituted or unsubstituted alkyl group having 1 to 20 carbon atoms, a substituted or unsubstituted aryl group having 6 to 50 ring carbon atoms, a substituted or unsubstituted heteroaryl group having 5 to 50 ring atoms, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group, and when $R^2$ and $R^3$ are each plural in number, groups $R^2$ and $R^3$ may be the same or different, respectively;

m1 to m3 each independently represent an integer of 0 to 4, and k4 represents an integer of 0 to 5;

$L^0$ to $L^2$ each independently represent a single bond, a substituted or unsubstituted arylene group having 6 to 50 ring carbon atoms, or a substituted or unsubstituted heteroarylene group having 5 to 50 ring atoms;

$Ar^1$ represents a monovalent residue of a compound represented by formula (2):

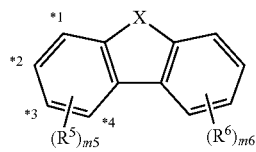

(2)

wherein X represents $—C(R^A)R^B)—$;

$R^A$ and $R^B$ may be the same or different and each independently represent a substituted or unsubstituted aryl group having 6 to 50 ring carbon atoms or a substituted or unsubstituted heteroaryl group having 5 to 50 ring atoms;

$R^5$ and $R^6$ are each independently the same as defined with respect to $R^1$;

m5 and m6 each independently represent an integer of 0 to 4;

two selected from $R^5$ and $R^6$ may be bonded to each other to form a ring structure;

the hydrogen atom or $R^5$ attached to one of carbon atoms *1 to *4 is eliminated and a remaining carbon atom is bonded to $L^1$ or the nitrogen atom in formula (1);

$Ar^2$ is a group represented by any of the formulae selected from the group consisting of (b), (c), (d), (f), (g), and (h):

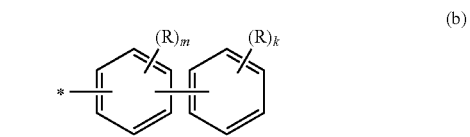

(b)

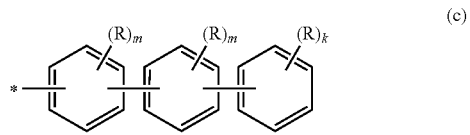

(c)

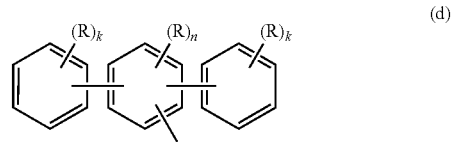

(d)

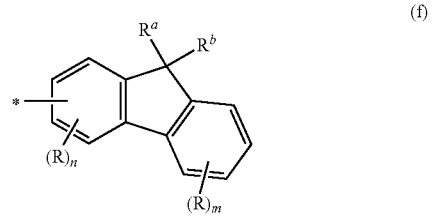

(f)

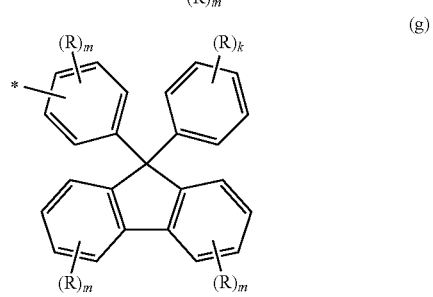

(g)

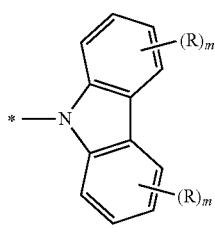

(h)

wherein R, R$^a$, and R$^b$ are each independently the same as defined with respect to R$^1$, when more than one R occurs, groups R may be the same or different, two selected from groups R may be bonded to each other to form a ring structure, and two selected from groups R, R$^a$, and R$^b$ in formula (f) may be bonded to each other to form a ring structure;

each k independently represents an integer of 0 to 5, each m independently represents an integer of 0 to 4, and each n independently represents an integer of 0 to 3; and

* represents a bonding site to L$^2$ or the nitrogen atom in formula (1).

2. The compound according to claim 1, wherein the compound is represented by formula (1-1):

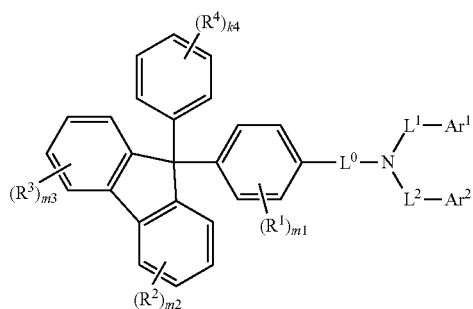

(1-1)

wherein R$^1$ to R$^4$, m1 to m3, k4, L$^0$ to L$^2$, Ar$^1$, and Ar$^2$ are as defined in claim 1.

3. The compound according to claim 1, wherein the compound is represented by formula (1-2):

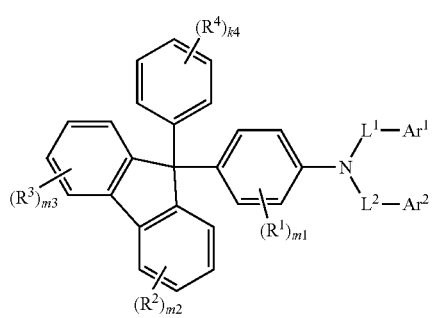

(1-2)

wherein R$^1$ to R$^4$, m1 to m3, k4, L$^1$ to L$^2$, Ar$^1$, and Ar$^2$ are as defined in claim 1.

4. The compound according to claim 1, wherein the compound is represented by formula (1-3):

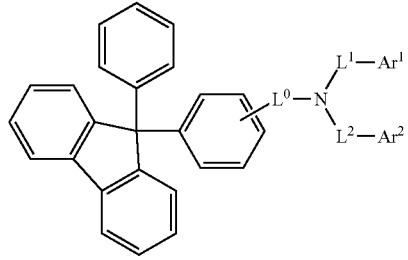

(1-3)

wherein L$^0$ to L$^2$, Ar$^1$, and Ar$^2$ are as defined in claim 1.

5. The compound according to claim 1, wherein Ar$^2$ is a group represented by a formula selected from the group of formulae consisting of (b-1), (b-2), (c-1), (c-2), and (d-1):

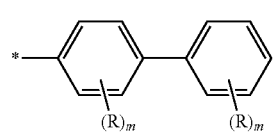

(b-1)

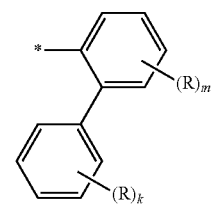

(b-2)

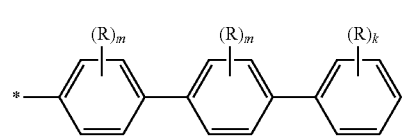

(c-1)

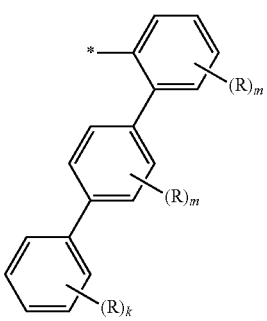

(c-2)

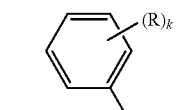

(d-1)

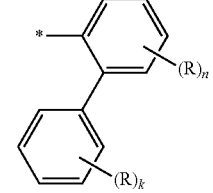

wherein R, k, m, n, and * are as defined in claim 1.

6. The compound according to claim 1, wherein $L^0$ to $L^2$ each independently represent a single bond or a group represented by formula (i) or (ii):

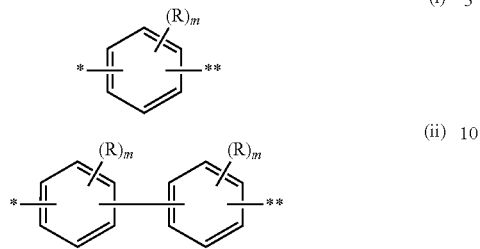

wherein each R is independently the same as defined with respect to $R^1$ in claim 1, when more than one R occurs, groups R may be the same or different, two selected from groups R may be bonded to each other to form a ring structure, each m independently represents an integer of 0 to 4, and * and ** each represent a bonding site.

7. The compound according to claim 1, wherein the compound is represented by formula (1-4):

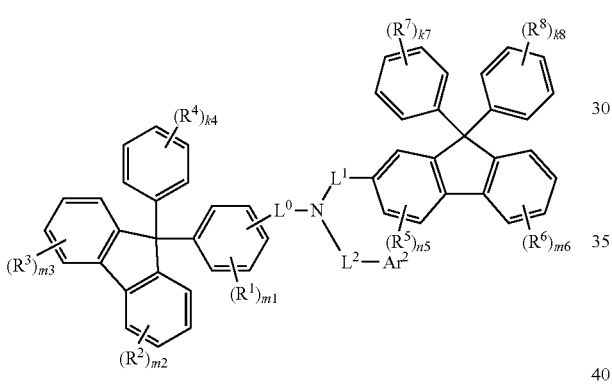

wherein $R^1$ to $R^6$, m1 to m3, k4, m6, $L^0$ to $L^2$, and $Ar^2$ are as defined in claim 1, $R^7$ and $R^8$ are each independently the same as defined with respect to $R^1$ in claim 1, n5 represents an integer of 0 to 3, and k7 and k8 each independently represent an integer of 0 to 5.

8. The compound according to claim 7, wherein the compound is represented by formula (1-4-1):

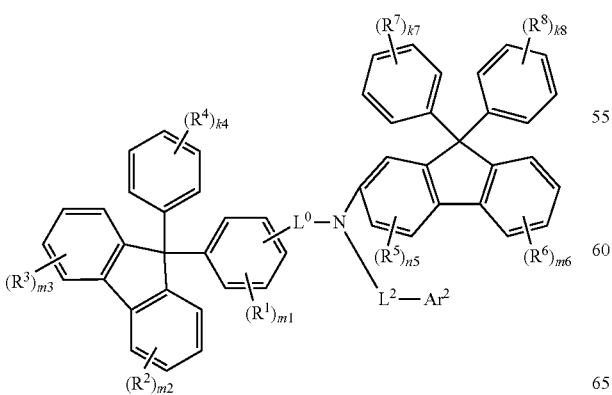

wherein $R^1$ to $R^8$, m1 to m3, k4, n5, m6, k7, k8, $L^0$, $L^2$, and $Ar^2$ are as defined in claim 7.

9. The compound according to claim 7, wherein $Ar^2$ is a group represented by a formula selected from the group of formulae (b), (c), (d), (f) and (g):

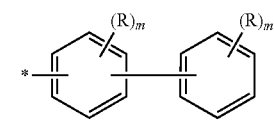

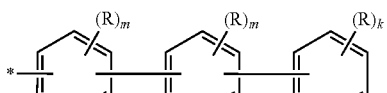

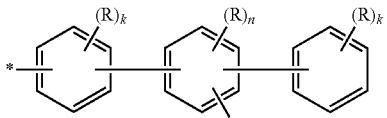

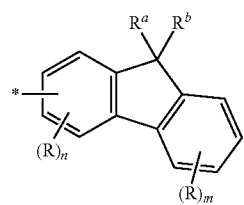

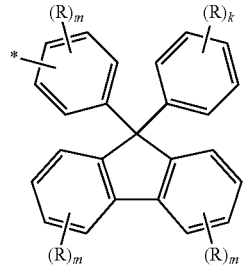

wherein R, $R^a$, $R^b$, k, m, n and * are as defined in claim 1.

10. A material for organic electroluminescence devices comprising the compound according to claim 1.

11. An organic electroluminescence device which comprises a cathode, an anode, and at least one organic thin film layer disposed between the cathode and the anode, wherein the at least one organic thin film layer comprises a light emitting layer and at least one layer of the at least one organic thin film layer comprises the compound according to claim 1.

12. The organic electroluminescence device according to claim 11, wherein the at least one organic thin film layer comprises at least one selected from a hole injecting layer comprising the compound and a hole transporting layer comprising the compound.

13. An electronic equipment comprising the organic electroluminescence device according to claim 11.

14. The compound according to claim 8, wherein $Ar^2$ is a group represented by a formula selected from the group of formulae (b), (c), (d), (f) and (g):

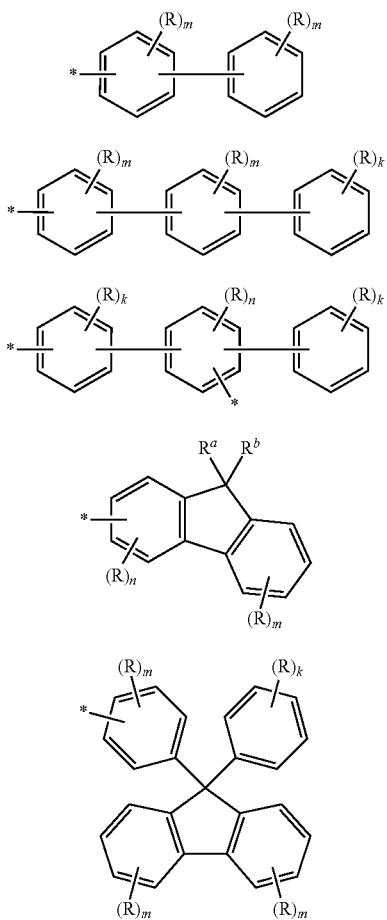

wherein R, $R^a$, $R^b$, k, m, n and * are as defined in claim 1.

15. The compound according to claim 1, wherein the group $-L^2-Ar^2$ is a group of a formula selected from the group consisting of the following formulae:

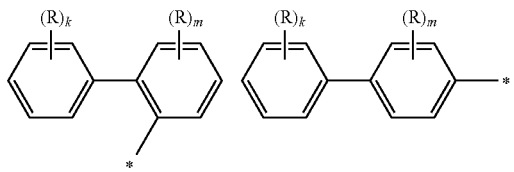

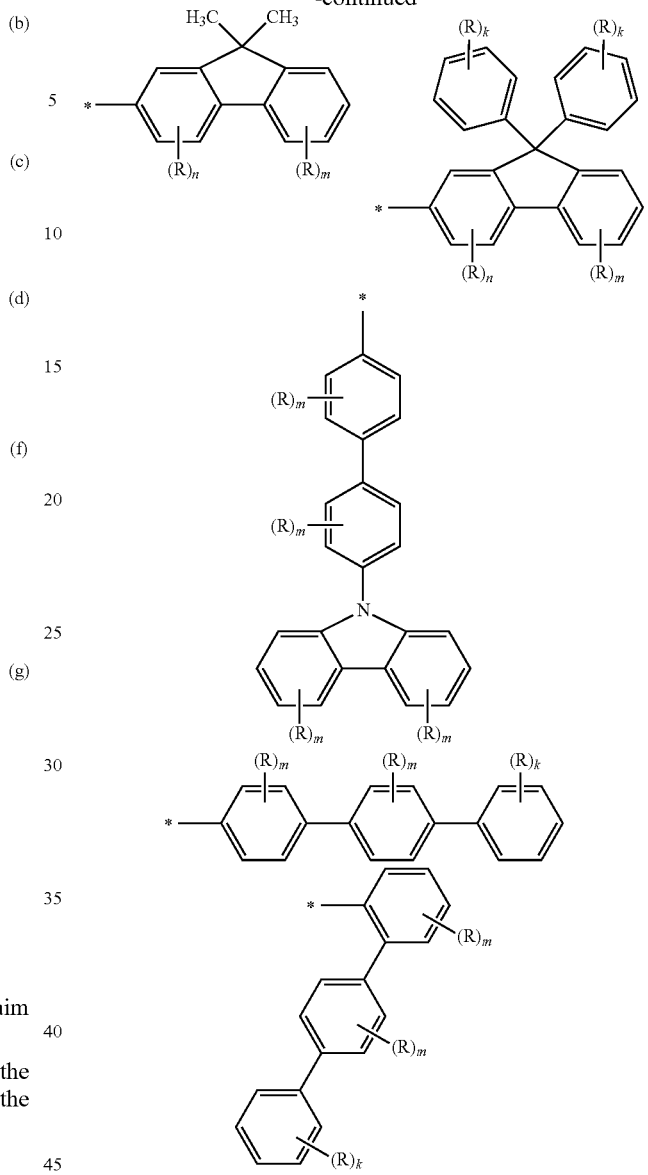

wherein R, k, m and n are as defined in claim 1 and * represents a bonding site the nitrogen atom in formula (1).

16. The compound according to claim 1, wherein $Ar^2$ is a group represented by a formula selected from the group of formulae (b), (c), (d), (f), and (g).

* * * * *

UNITED STATES PATENT AND TRADEMARK OFFICE
CERTIFICATE OF CORRECTION

PATENT NO. : 10,756,275 B2
APPLICATION NO. : 14/910596
DATED : August 25, 2020
INVENTOR(S) : Tomoki Kato et al.

Page 1 of 3

It is certified that error appears in the above-identified patent and that said Letters Patent is hereby corrected as shown below:

In the Claims

In Column 290, Line 25, Claim 1, delete "(1);", and insert -- (1); and --, therefor.

In Column 294, approximately Line 10, delete "

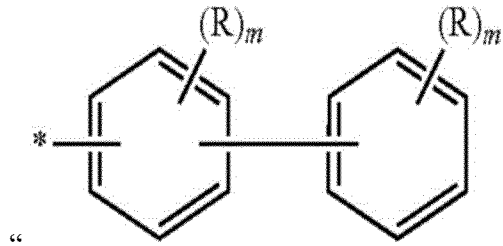

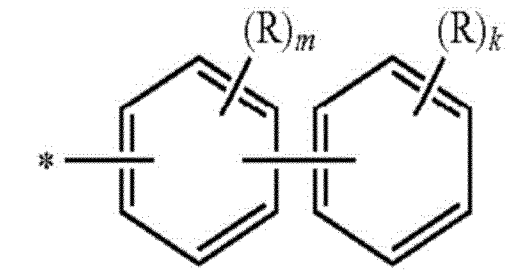

", and insert --

(b)

(b)

--, therefor.

In Column 294, approximately Line 20, delete

Signed and Sealed this
Seventeenth Day of November, 2020

Andrei Iancu
*Director of the United States Patent and Trademark Office*

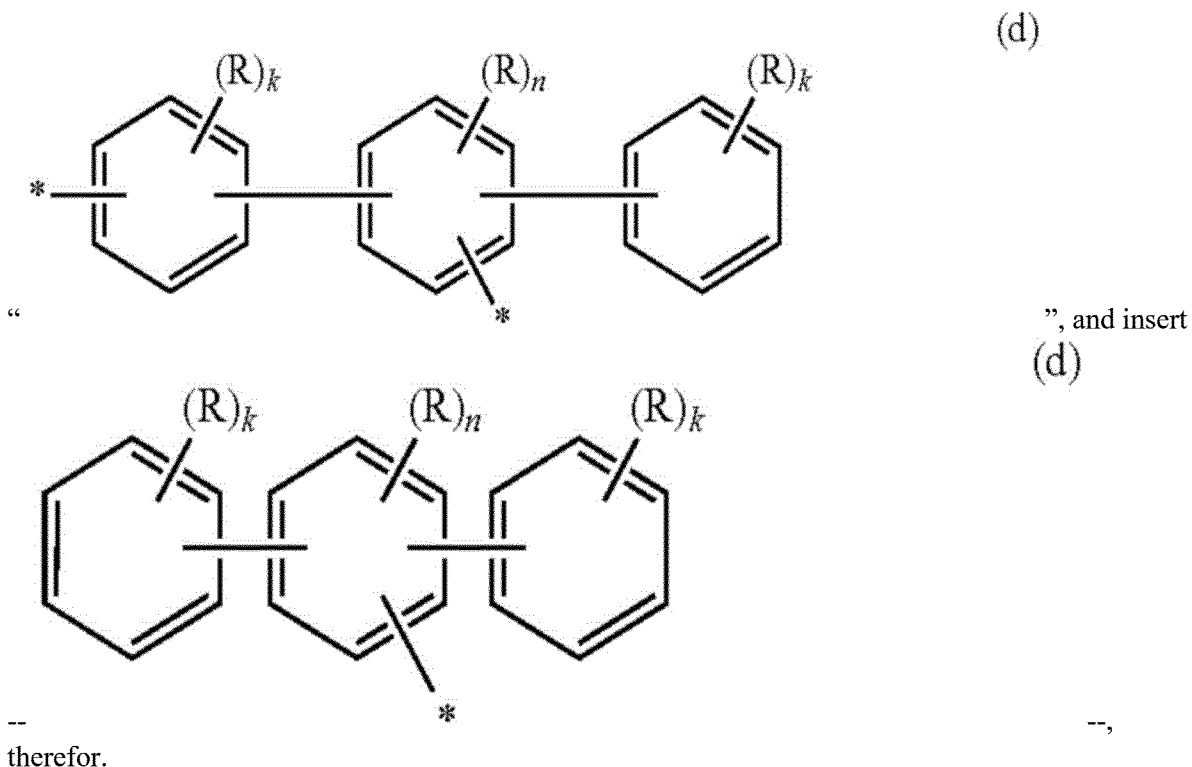
" ", and insert  --, therefor.
In Column 295, approximately Line 5, delete
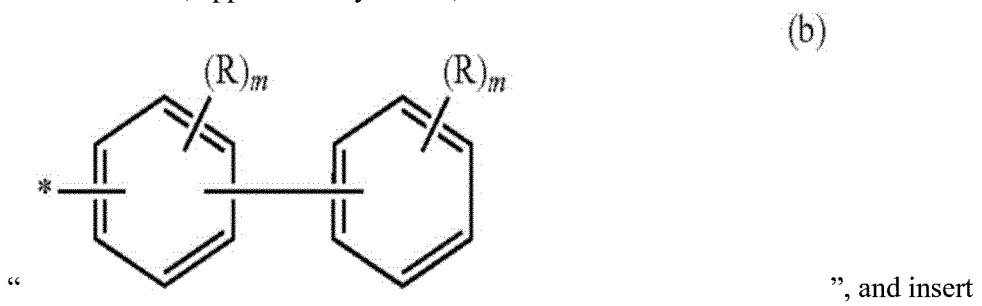
" ", and insert  --, therefor.
In Column 295, approximately Line 15, delete
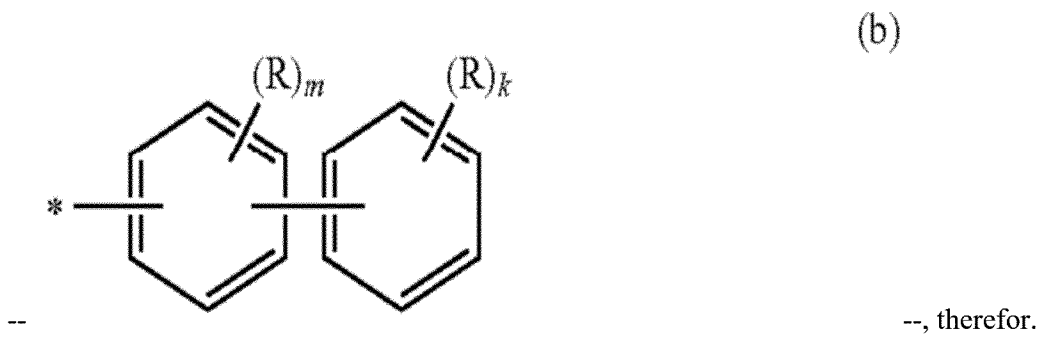

CERTIFICATE OF CORRECTION (continued)
U.S. Pat. No. 10,756,275 B2

(d)

"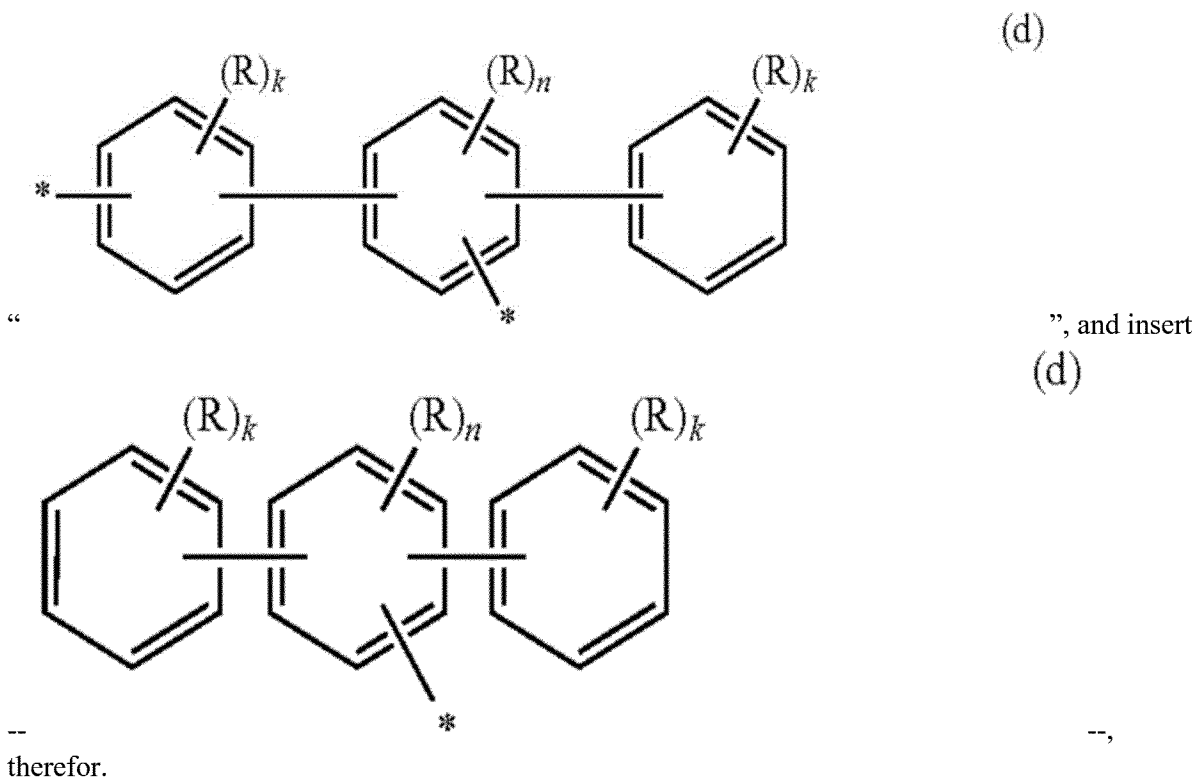", and insert (d)

--
therefor.

--,